United States Patent
Park et al.

(10) Patent No.: US 9,583,715 B2
(45) Date of Patent: Feb. 28, 2017

(54) ANTHRACENE-BASED COMPOUNDS AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Jun-Ha Park, Yongin (KR); Seok-Hwan Hwang, Yongin (KR); Young-Kook Kim, Yongin (KR); Hye-Jin Jung, Yongin (KR); Eun-Young Lee, Yongin (KR); Jong-Woo Kim, Yongin (KR); Jin-O Lim, Yongin (KR); Sang-Hyun Han, Yongin (KR); Kwang-Hyun Kim, Yongin (KR); Eun-Jae Jeong, Yongin (KR); Soo-Yon Kim, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 441 days.

(21) Appl. No.: 14/283,335

(22) Filed: May 21, 2014

(65) Prior Publication Data

US 2015/0041773 A1 Feb. 12, 2015

(30) Foreign Application Priority Data

Aug. 9, 2013 (KR) ........................ 10-2013-0094888

(51) Int. Cl.
*H01L 51/00* (2006.01)
*H01L 51/50* (2006.01)
(Continued)

(52) U.S. Cl.
CPC ........ *H01L 51/0058* (2013.01); *C07D 401/10* (2013.01); *C07D 401/14* (2013.01);
(Continued)

(58) Field of Classification Search
None
See application file for complete search history.

(56) References Cited

U.S. PATENT DOCUMENTS

| | | |
|---|---|---|
| 5,645,948 A | 7/1997 | Shi et al. |
| 9,178,001 B2 | 11/2015 | Kwak et al. |

(Continued)

FOREIGN PATENT DOCUMENTS

| | | |
|---|---|---|
| JP | 10-017860 A | 1/1998 |
| JP | 11-087067 A | 3/1999 |

(Continued)

OTHER PUBLICATIONS

Shigehiro Yamaguchi et al.; Diphenylamino-Substituted 2,5-Diarylsiloles for Single-Layer Organic Electroluminescent Devices; Chemistry Letters 2001; pp. 98-99.

(Continued)

*Primary Examiner* — Dawn Garrett

(74) *Attorney, Agent, or Firm* — Lee & Morse, P.C.

(57) ABSTRACT

An anthracene-based compound is represented by Formula 1 as below:

(Continued)

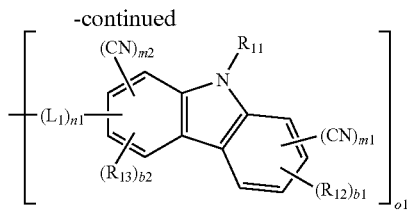

wherein Ar, $R_1$ to $R_3$, $R_{11}$ to $R_{13}$, $L_1$, $L_2$, a1 to a3, b1, b2, n1, n2, m1, m2, o1 and o2 are as defined in the specification. An organic light-emitting device includes the anthracene-based compound.

20 Claims, 1 Drawing Sheet

(51) Int. Cl.
| | |
|---|---|
| C09K 11/06 | (2006.01) |
| C07D 401/14 | (2006.01) |
| C07D 401/10 | (2006.01) |
| C07D 403/10 | (2006.01) |
| C07D 405/10 | (2006.01) |
| C07D 409/12 | (2006.01) |
| C07D 413/12 | (2006.01) |
| C07D 471/04 | (2006.01) |

(52) U.S. Cl.
CPC ......... *C07D 403/10* (2013.01); *C07D 405/10* (2013.01); *C07D 409/12* (2013.01); *C07D 413/12* (2013.01); *C07D 471/04* (2013.01); *C09K 11/06* (2013.01); *H01L 51/0052* (2013.01); *H01L 51/0067* (2013.01); *H01L 51/0072* (2013.01); *H01L 51/5072* (2013.01)

(56) References Cited

U.S. PATENT DOCUMENTS

| | | | |
|---|---|---|---|
| 9,425,407 B2 | 8/2016 | Hwang et al. | |
| 2002/0132134 A1 | 9/2002 | Hu et al. | |
| 2010/0155714 A1 | 6/2010 | Seo et al. | |
| 2011/0121268 A1 | 5/2011 | Nagao et al. | |
| 2012/0056165 A1 | 3/2012 | Kawamura et al. | |
| 2012/0256172 A1 | 10/2012 | Ito et al. | |
| 2013/0001526 A1 | 1/2013 | Kwak et al. | |
| 2015/0069355 A1* | 3/2015 | Hwang | H01L 51/0058 257/40 |

FOREIGN PATENT DOCUMENTS

| | | |
|---|---|---|
| JP | 2004-083507 B | 3/2004 |
| JP | 2011-012190 A | 1/2011 |
| KR | 10-0525408 B1 | 10/2005 |
| KR | 10-2011-0040874 A | 4/2011 |
| KR | 10-2011-0094271 A | 8/2011 |
| KR | 10-2012-0051598 A | 5/2012 |
| KR | 10-2012-0104087 A | 9/2012 |

OTHER PUBLICATIONS

Youichi Samamoto et al.; Synthesis, Characterization, and Electron-Transport Property of Perfluorinated Phenylene Dendrimers; Journal American Chemical Society 2000, 122, pp. 1832-1833.

Nicklas Johansson et al.; Solid-State Amplified Spontaneous Emission in Some Spiro-Type Molecules: A New concept for the Design of Solid-State Lasing Molecules; Advanced Material 1998, 10, No. 14; pp. 1136-1141.

C. W. Tang et al.; Organic Electroluminescent Diodes; Applied Physics Letter vol. 51 No. 12, Sep. 21, 1987; pp. 913-915.

Chihaya Adachi et al.; "Confinement of Charge Carriers and Molecular Excitons Within 5nmthick Emitter Layer in Organic Electroluminescent Devices With a Double Heterostructure"; Applied Physics Letter vol. 57 No. 6, Aug. 6, 1990; pp. 531-533.

Y.T. Tae et al.; Sharp Green Electroluminescence From 1H-Pyrazolo [3,4-b] Quinoline-Based Light-Emitting Diodes; Applied Physics Letter vol. 77 No. 11, Sep. 11, 2000; pp. 1575-1577.

USPTO Action mailed Nov. 4, 2016, in U.S. Appl. No. 14/251,754, wherein claims were provisionally rejected on the ground of nonstatutory double patenting over claims of the captioned application.

* cited by examiner

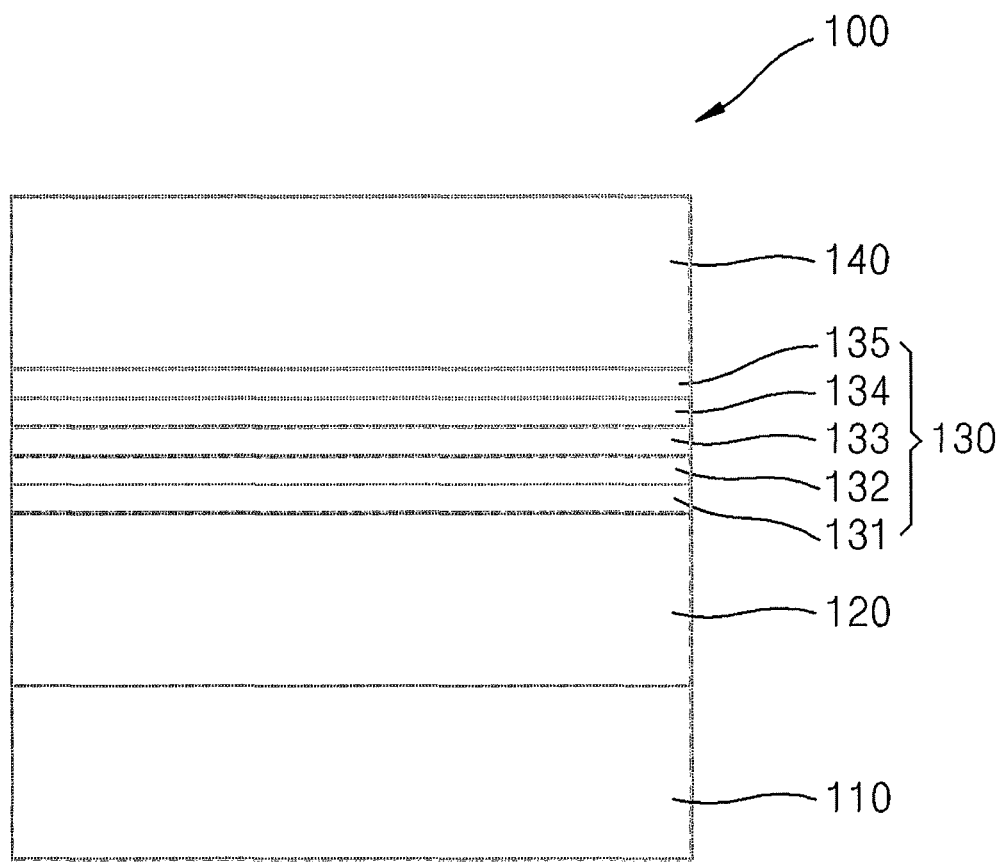

ANTHRACENE-BASED COMPOUNDS AND ORGANIC LIGHT-EMITTING DEVICE INCLUDING THE SAME

CROSS-REFERENCE TO RELATED APPLICATION

Korean Patent Application No. 10-2013-0094888, filed on Aug. 9, 2013, in the Korean Intellectual Property Office, and entitled: "Anthracene-Based Compounds and Organic Light-Emitting Device Including The Same," is incorporated by reference herein in its entirety.

BACKGROUND

1. Field

Embodiments relate to an anthracene-based compound and an organic light-emitting device including the anthracene-based compound.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

Embodiments are directed to an anthracene-based compound represented by Formula 1 below:

<Formula 1>

$$[Ar-(L_2)_{n2}]_{o2} - [\text{anthracene}] - [(L_1)_{n1} - [\text{carbazole with } (CN)_{m1}, (CN)_{m2}, R_{11}, (R_{12})_{b1}, (R_{13})_{b2}]]_{o1}$$

with $(R_1)_{a1}$, $(R_2)_{a2}$, $(R_3)_{a3}$ substituents wherein, in Formula 1, Ar is an electron transport moiety selected from a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{60}$ heteroaryl group, excluding a substituted or unsubstituted carbazolyl group;

$R_1$ to $R_3$, and $R_{11}$ to $R_{13}$ are each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{30}$ heteroaryl group;

a1 to a3 are each independently an integer of 0 or 2;

b1 is an integer from 0 to 3;

b2 is an integer from 0 to 4;

$L_1$ and $L_2$ are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted $C_2$-$C_{10}$ heterocycloalkylene group, a substituted or unsubstituted $C_2$-$C_{10}$ heterocycloalkenylene group, and a substituted or unsubstituted $C_2$-$C_{60}$ heteroarylene group;

n1 and n2 are each independently an integer from 0 to 3;

m1 and m2 are each independently an integer from 0 to 3, where m1+m2 is equal to an integer of 1 or greater;

m1+b1=4, and m2+b2=3; and o1 and o2 are each independently an integer from 1 to 3.

Ar may be selected from:

i) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group;

ii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a deuterium atom, —F, a hydroxyl group, a cyano group, a nitro group, a methyl group, an ethyl group, an n-propyl group, and a t-butyl group;

iii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group; and iv) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group that are substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group.

Ar may be selected from:
i) a pyridyl group, a pyrimidyl group, a quinolinyl group, a phenanthrolinyl group, a benzoimidazolyl group, a dibenzofuranyl group, a dibenzothiophenyl group, and a triazinyl group;
ii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group; and
iii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group that are substituted with at least one of a phenyl group, a naphthyl group, a pyridyl group, and a quinolinyl group.

Ar may be selected from the groups represented by Formulae 2-1 to 2-12 below:

2-1

2-2

2-3

2-4

2-5

2-6

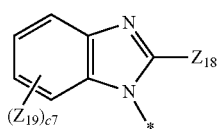

2-7

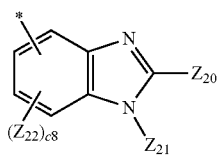

2-8

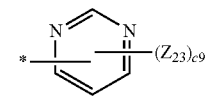

2-9

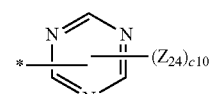

2-11

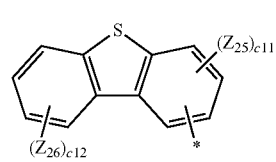

2-12

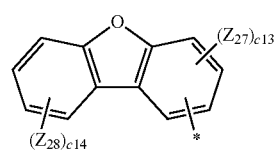

wherein, in Formulae 2-1 to 2-12,
$Z_{11}$ to $Z_{28}$ are each independently selected from:
i) a phenyl group, a 1-naphthyl group, a 2-naphthyl group, a pyridyl group, and a quinolinyl group; and
ii) a phenyl group, a 1-naphthyl group, a 2-naphthyl group, a pyridyl group, and a quinolinyl group, each substituted with at least one of a phenyl group, a 1-naphthyl group, a 2-naphthyl group, a pyridyl group, and a quinolinyl group,
c1 to c14 are each independently an integer from 0 to 2, and
* indicates a binding site to $L_2$ or an anthracene core.

Ar may be selected from the groups represented by Formulae 3-1 to 3-14 below:

3-1

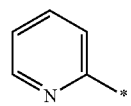

3-2

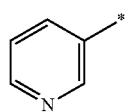

3-3 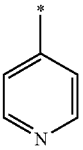

3-4 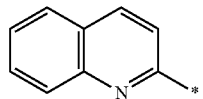

3-5 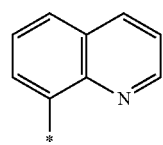

3-6 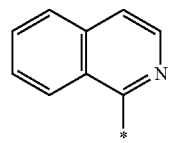

3-7 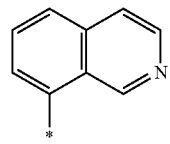

3-8 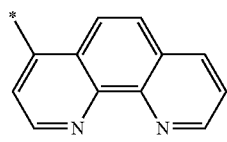

3-9 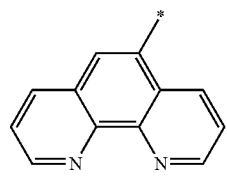

3-10 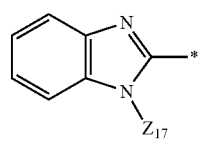

3-11 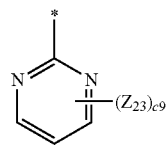

3-12 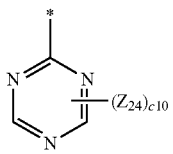

3-13 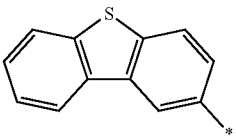

3-14 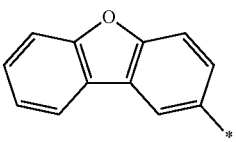

wherein, in Formulae 3-1 to 3-14, $Z_{17}$, $Z_{23}$, and $Z_{24}$ are each independently selected from:
i) a phenyl group, a 1-naphthyl group, a 2-naphthyl group, a pyridyl group, and a quinolinyl group; and
ii) a phenyl group, a 1-naphthyl group, a 2-naphthyl group, a pyridyl group, and a quinolinyl group, each substituted with a phenyl group, c9 and c10 are each independently an integer from 0 to 2, and

* indicates a binding site to $L_2$ or an anthracene core.

$R_1$ to $R_3$ in Formula 1 may each be independently selected from:
i) a hydrogen atom, a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and
ii) a phenyl group, a naphthyl group, a pyridyl group, and a quinolinyl group, each substituted with at least one of a deuterium atom, —F, a hydroxyl group, a cyano group, a nitro group, a methyl group, an ethyl group, an n-propyl group, and a t-butyl group.

$R_1$ to $R_3$ in Formula 1 may be each independently selected from a deuterium atom, —F, a cyano group, a nitro group, a methyl group, a t-butyl group, a phenyl group, a naphthyl group, a pyridyl group, and a quinolinyl group.

$R_{11}$ to $R_{13}$ in Formula 1 may each be independently selected from:
i) a phenyl group, a naphthyl group, a fluorenyl group, a pyridyl group, a quinolinyl group, an isoquinolinyl group, a dibenzofuranyl group, and a dibenzothiophenyl group;
ii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and
iii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a methyl group, a t-butyl group, a phenyl group, a naphthyl group, a pyridyl group, and a quinolinyl group that are substituted with at least one of a deuterium atom, —F, a hydroxyl group, a cyano group, a nitro group, a methyl group, and a t-butyl group.

$R_{11}$ to $R_{13}$ in Formula 1 may each be independently selected from the groups represented by Formulae 2-1 to 2-12 and Formulae 4-1 to 4-3 below:

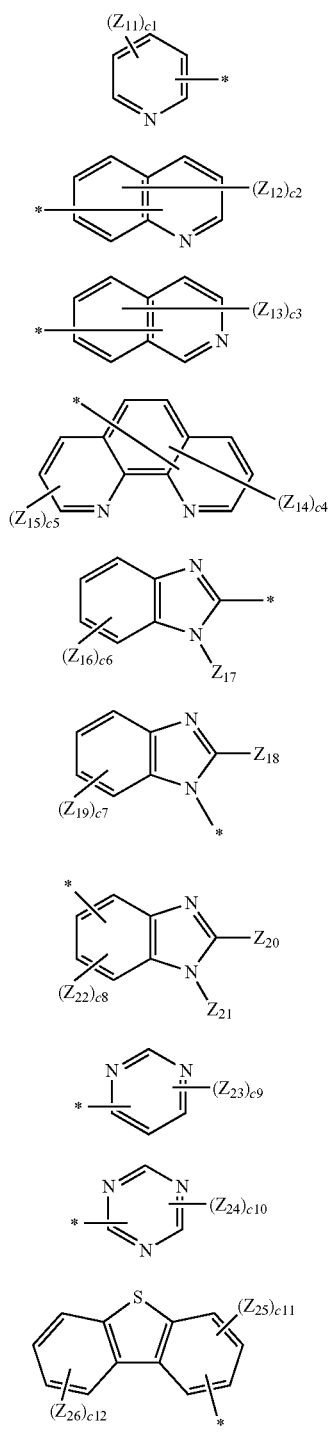

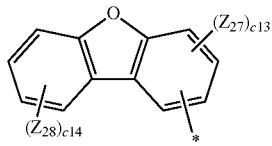

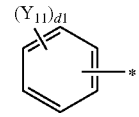

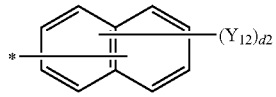

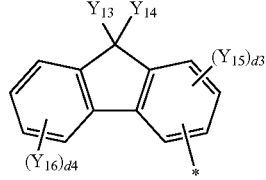

wherein, in Formulae 2-1 to 2-12, and Formulae 4-1 to 4-3, $Z_{11}$ to $Z_{28}$, and $Y_{11}$ to $Y_{16}$ are each independently selected from:

i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 are each independently an integer from 0 to 2, and

* indicates a binding site to $L_1$ or an anthracene core.

$R_{11}$ to $R_{13}$ in Formula 1 may each be independently selected from groups represented by Formulae 3-1 to 3-14 and Formulae 5-1 to 5-4 below:

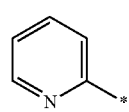

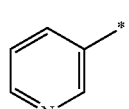

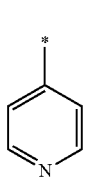

3-4 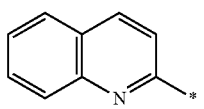

3-5 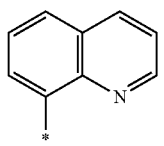

3-6 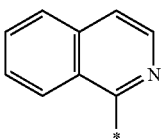

3-7 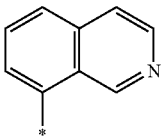

3-8 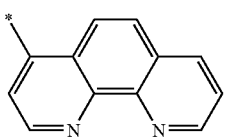

3-9 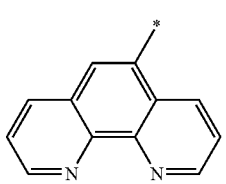

3-10 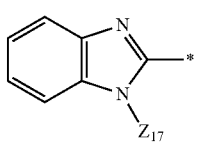

3-11 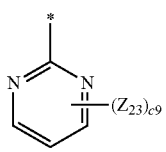

3-12 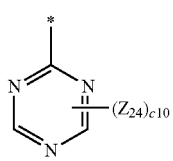

3-13 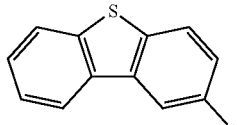

3-14 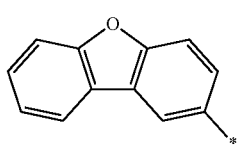

5-1 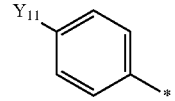

5-2 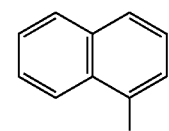

5-3 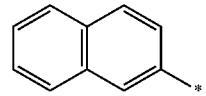

5-4 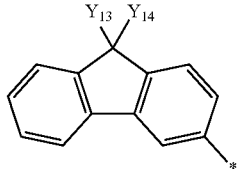

wherein, in Formulae 3-1 to 3-14 and Formulae 5-1 to 5-4, $Z_{17}$, $Z_{23}$, $Z_{24}$, $Y_{13}$, and $Y_{14}$ are each independently selected from:
i) —F, a cyano group, a nitro group, a methyl group, a t-butyl group, a phenyl group, and a pyridyl group; and
ii) a methyl group, a phenyl group, and a pyridyl group, each substituted with at least one of —F, a cyano group, a nitro group, a methyl group, a t-butyl group, a phenyl group, and a pyridyl group, c9 and c10 are each independently an integer from 0 to 2, and

* indicates a binding site to $L_1$ or an anthracene core.

$L_1$ and $L_2$ in Formula 1 may each be independently selected from:
i) a phenylene group, a naphthylene group, an anthracenyl group, a chrysenylene group, and a pyrenylene group; and
ii) a phenylene group, a naphthylene group, an anthracenyl group, a chrysenylene group, and a pyrenylene group, each substituted with at least one selected from:
a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, and a $C_1$-$C_{10}$ alkyl group;
a $C_1$-$C_{10}$ alkyl group substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof;

a $C_6$-$C_{16}$ aryl group, and a $C_2$-$C_{16}$ heteroaryl group; and a $C_6$-$C_{16}$ aryl group, and a $C_2$-$C_{16}$ heteroaryl group, each substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

$L_1$ and $L_2$ in Formula 1 may each be independently selected from:

i) a phenylene group, an anthracenyl group, a chrysenylene group, and a pyrenylene group; and ii) a phenylene group, an anthracenyl group, a chrysenylene group, and a pyrenylene group, each substituted with at least one selected from:

a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group; a phenyl group, a naphthyl group, a pyridyl group, and a triazinyl group; and a phenyl group, a naphthyl group, a pyridyl group, and a triazinyl group, each substituted with at least one of a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group.

n1 and n2 may both be 0.

m1 may be 1, and m2 may be 0.

o1 and o2 may each be independently 1 or 2.

The anthracene-based compound of Formula 1 is a compound represented by one of

Formulae 1a(1) to 1a(5), 1b(1) to 1b(3), 1c(1) to 1c(3) and 1d(1) below:

<Formula 1a(1)>

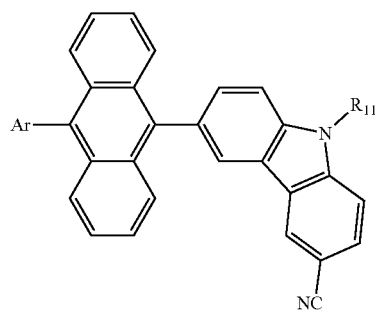

<Formula 1a(2)>

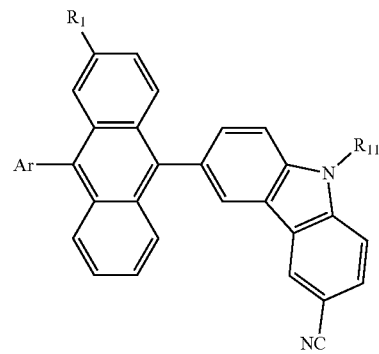

<Formula 1a(3)>

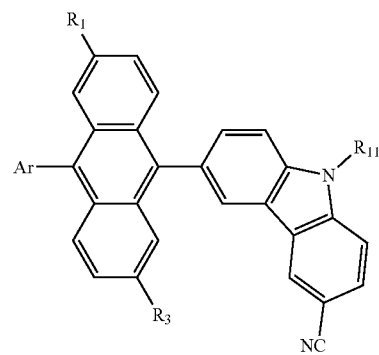

<Formula 1a(4)>

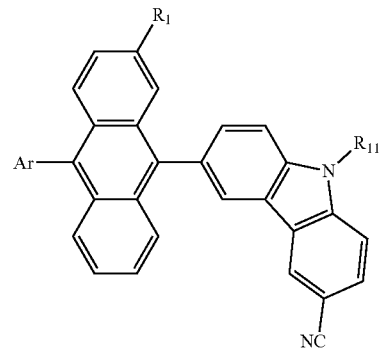

<Formula 1a(5)>

<Formula 1b(1)>
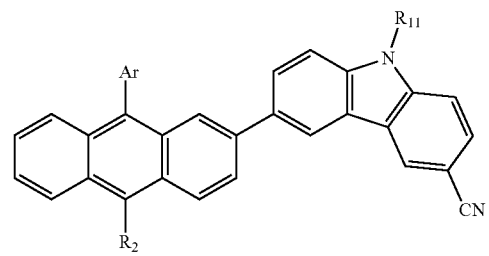
<Formula 1b(2)>
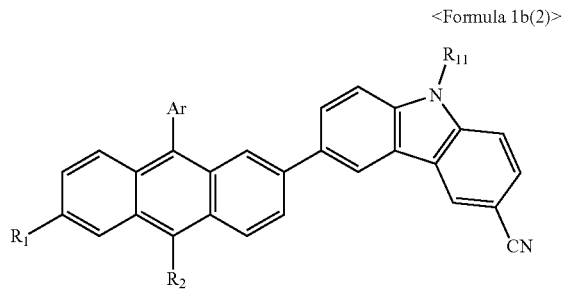
<Formula 1b(3)>
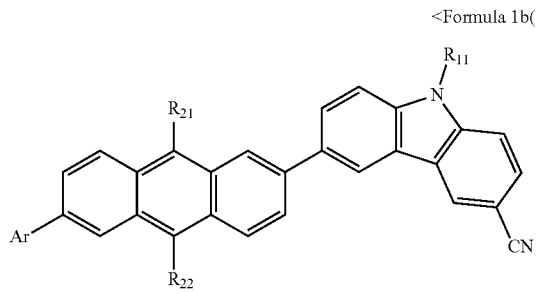
<Formula 1c(1)>
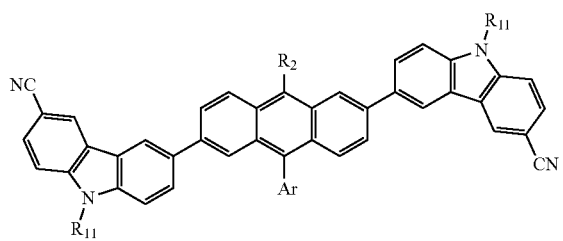
<Formula 1c(2)>
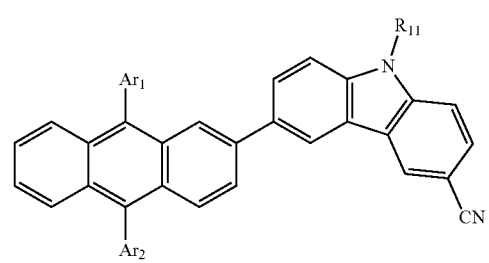
<Formula 1c(3)>
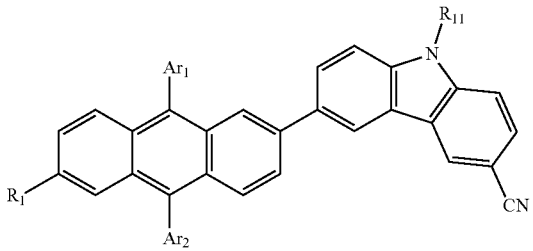
<Formula 1d(1)>
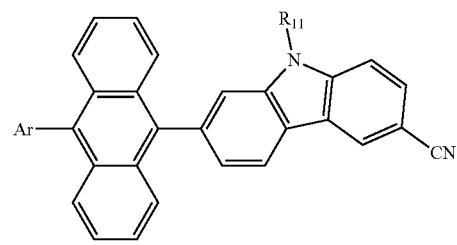
wherein, in Formulae 1a(1) to 1a(5), 1b(1) to 1b(3), 1c(1) to 1c(3), and 1d(1),
Ar, $Ar_1$, and $Ar_2$ are each independently selected from the groups represented by Formulae 3-1 to 3-14:
3-1
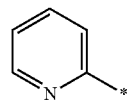
3-2
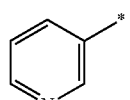
3-3
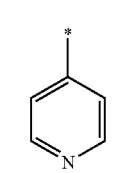
3-4
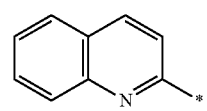
3-5
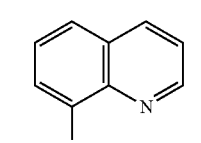
3-6
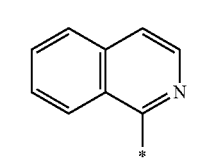

-continued 3-7
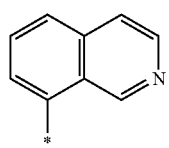

3-8
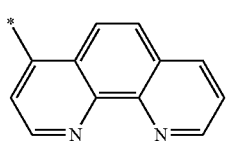

3-9
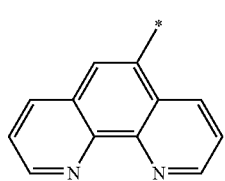

3-10
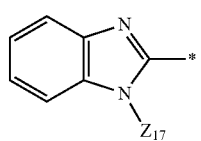

3-11
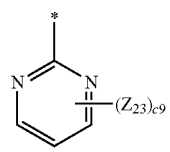

3-12
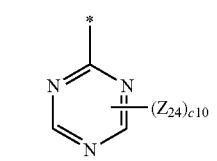

3-13
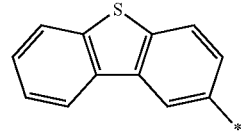

3-14
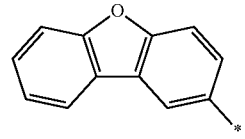

$Z_{17}$, $Z_{23}$, and $Z_{24}$ are each independently selected from:
i) a phenyl group, a 1-naphthyl group, a 2-naphthyl group, a pyridyl group, and a quinolinyl group; and
ii) a phenyl group, a 1-naphthyl group, a 2-naphthyl group, a pyridyl group, and a quinolinyl group, each substituted with a phenyl group, c9 and c10 are each independently an integer from 0 to 2,
* indicates a binding site to an anthracene core,
$R_1$ to $R_3$, $R_{21}$, and $R_{22}$ are each independently selected from a deuterium atom, —F, a cyano group, a nitro group, a methyl group, a t-butyl group, a phenyl group, a naphthyl group, a pyridyl group, and a quinolinyl group, and $R_{11}$ is selected from the groups represented by Formulae 2-1 to 2-12, and Formulae 4-1 to 4-3 below:

2-1
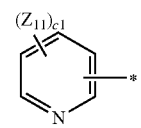

2-2
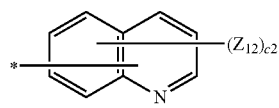

2-3
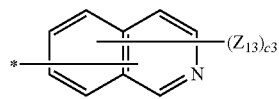

2-4
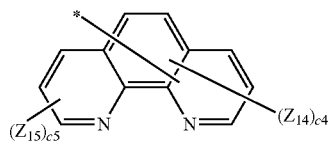

2-5
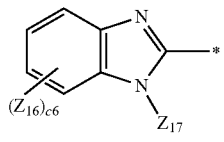

2-6
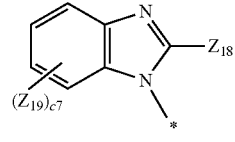

2-7
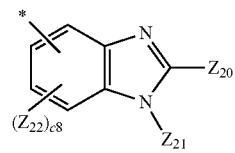

2-8
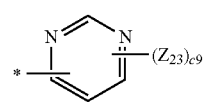

2-9
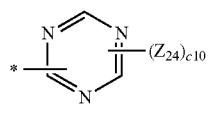

2-11
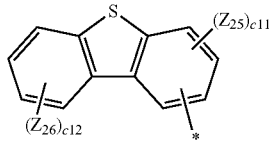

-continued 2-12

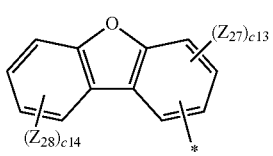

4-1

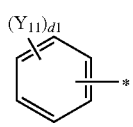

4-2

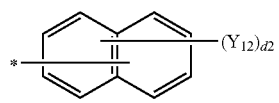

-continued 4-3

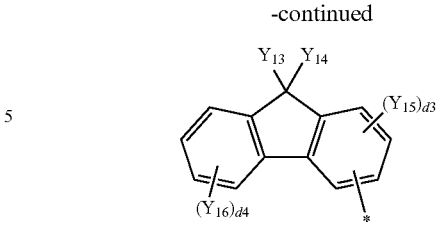

wherein, in Formulae 2-1 to 2-12, and Formulae 4-1 to 4-3, $Z_{11}$ to $Z_{28}$, and $Y_{11}$ to $Y_{16}$ are each independently selected from:

i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 are each independently an integer from 0 to 2, and

* indicates a binding site to an anthracene core.

The anthracene-based compound of Formula 1 may be one selected from Compounds 1 to 102 below:

1

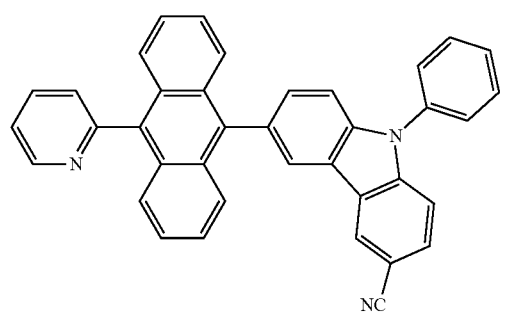

2

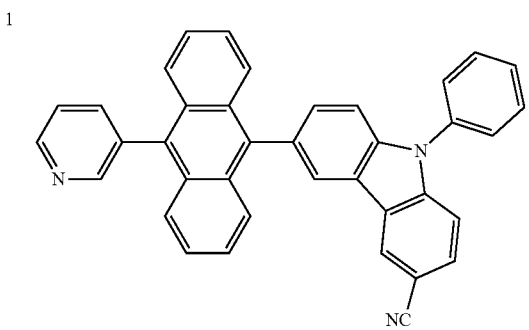

3

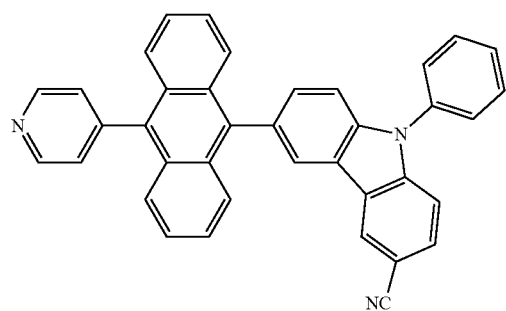

4

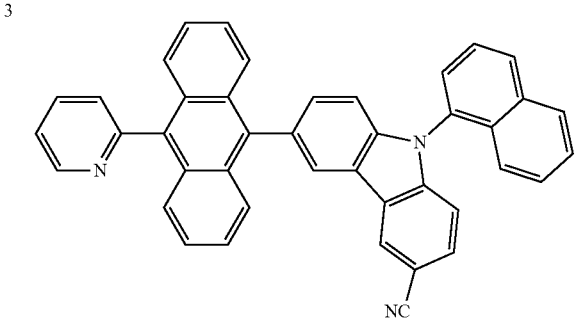

5

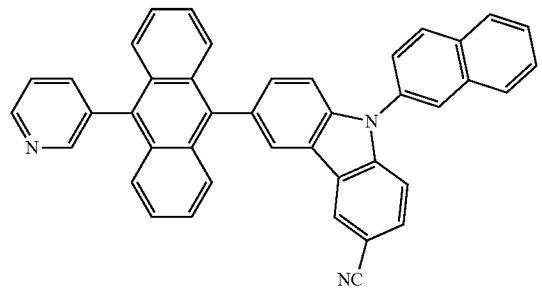

6

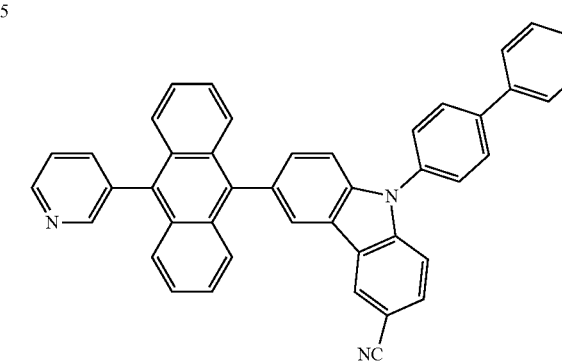

-continued
7
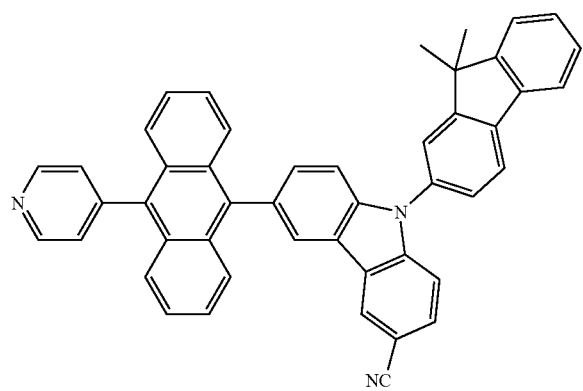
8
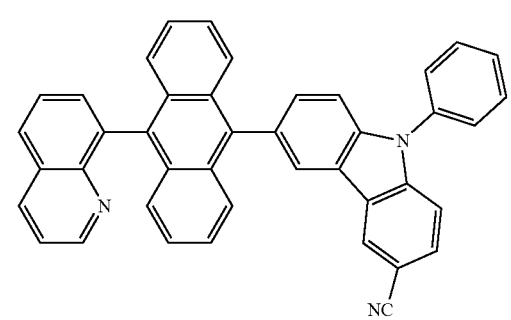
9
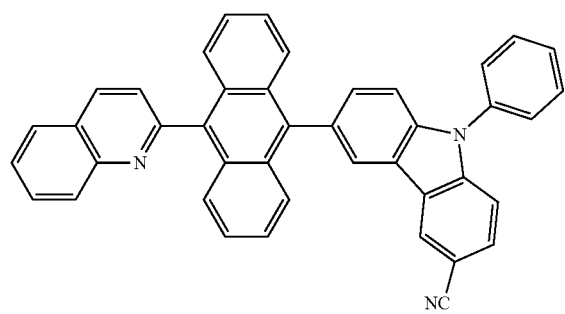
10
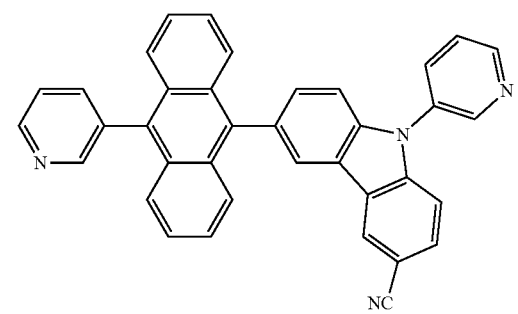
11
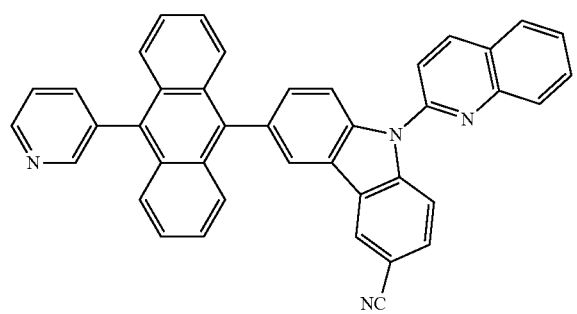
12
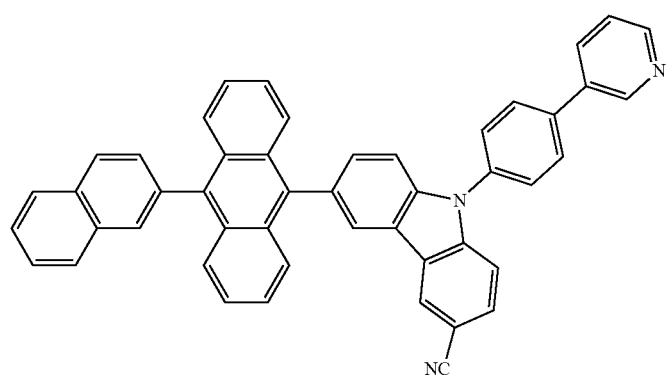

-continued
13
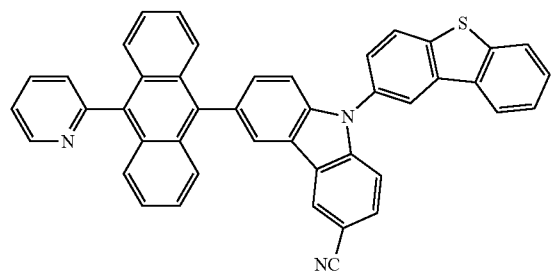
14
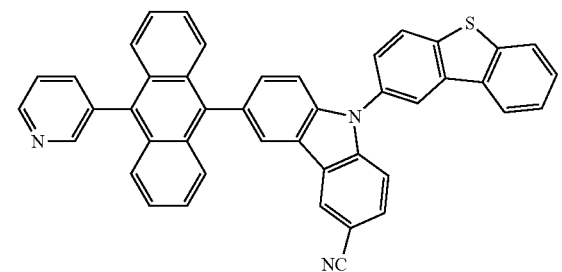
15
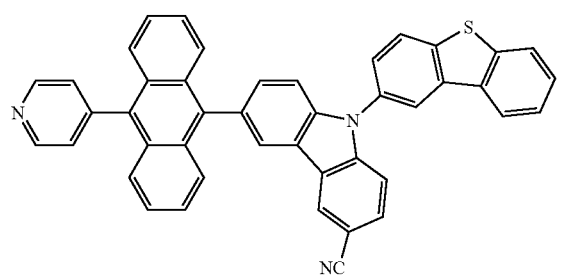
16
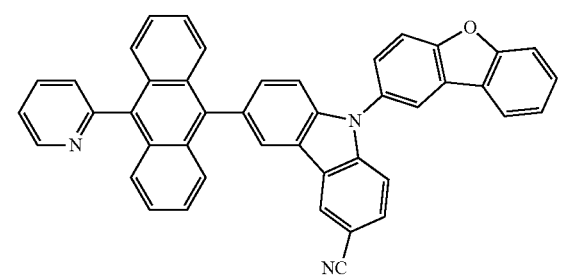
17
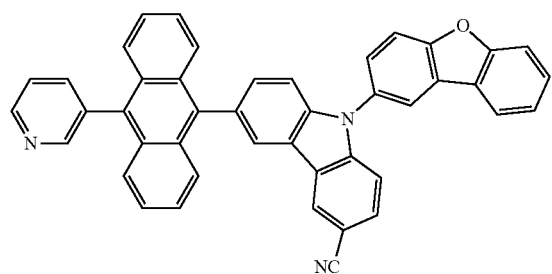
18
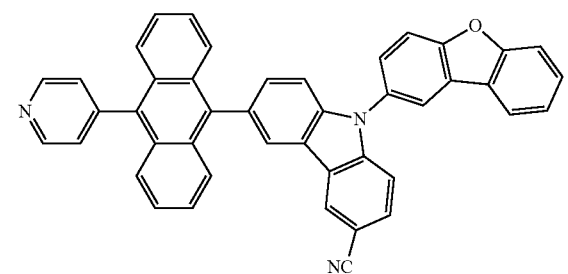
19
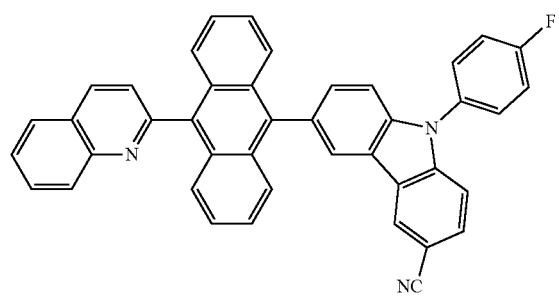
20
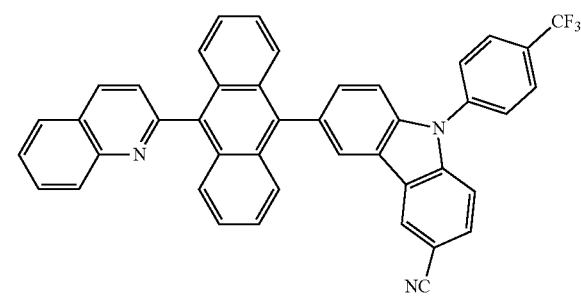
21
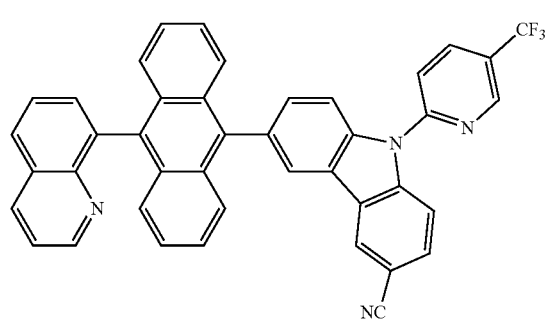
22
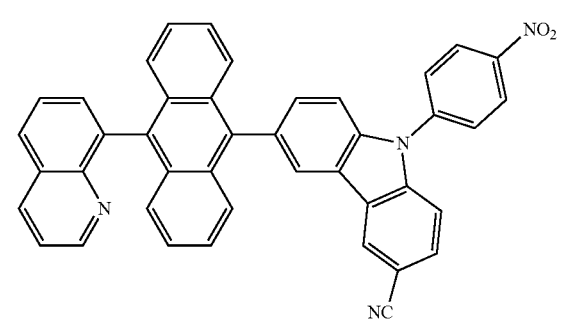

-continued
23
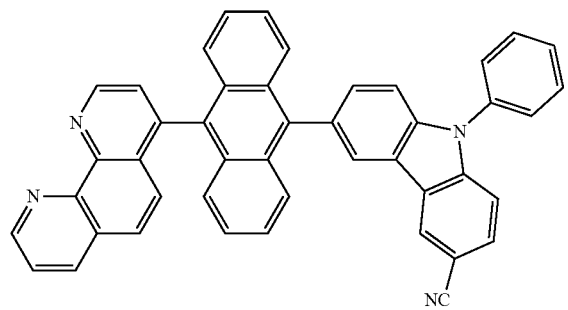
24
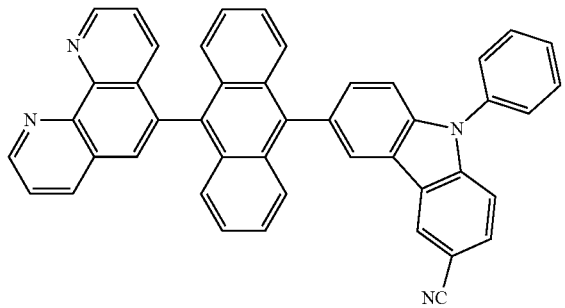
25
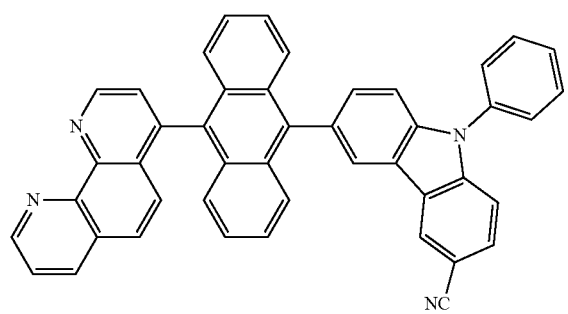
26
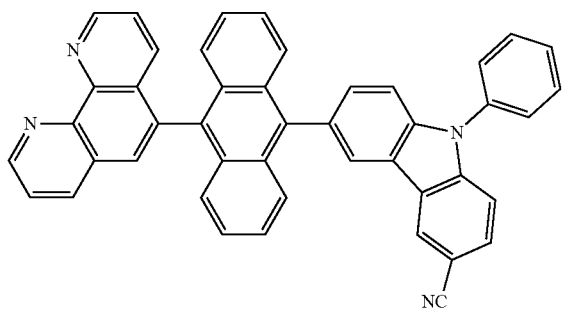
27
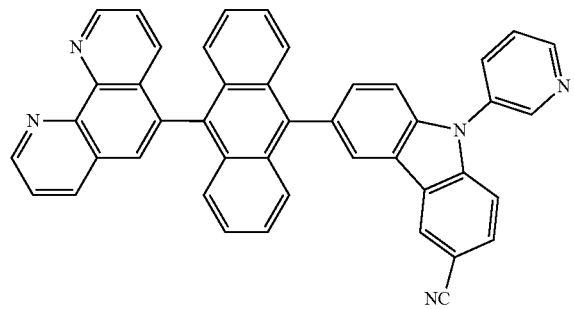
28
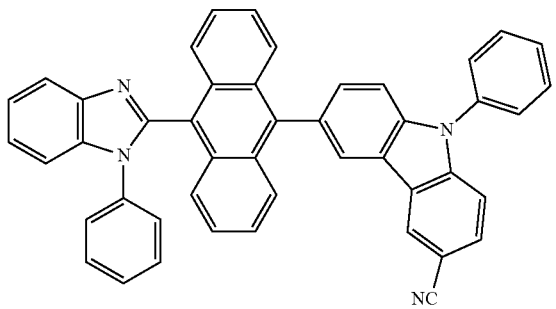
29
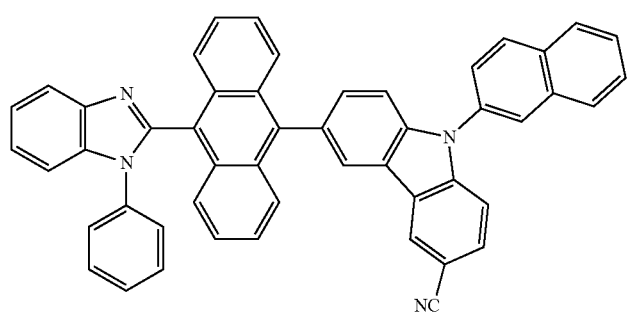

30
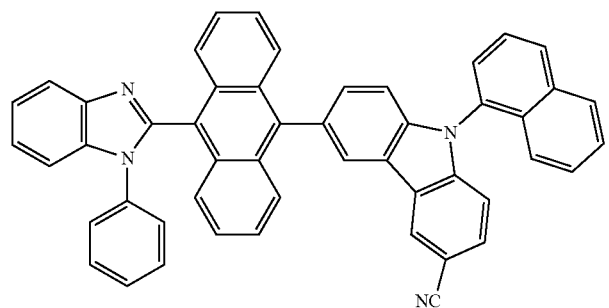
31
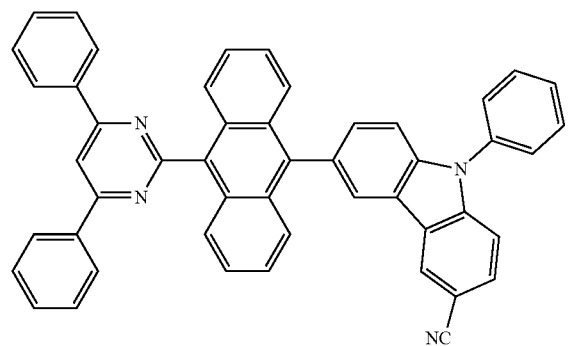
32
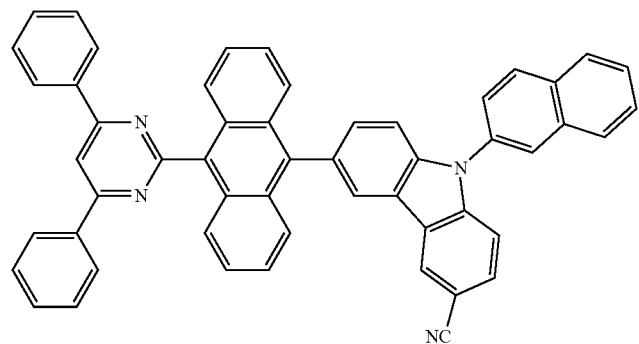
33
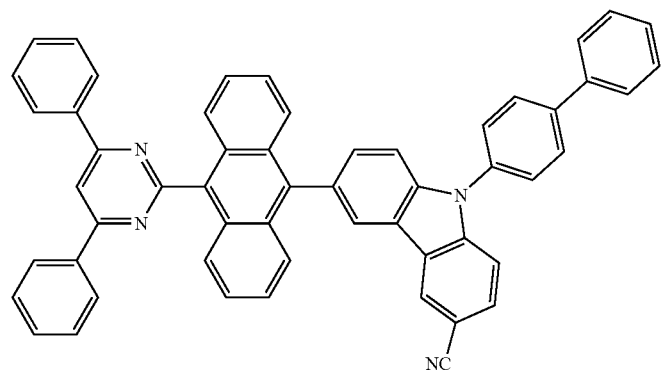

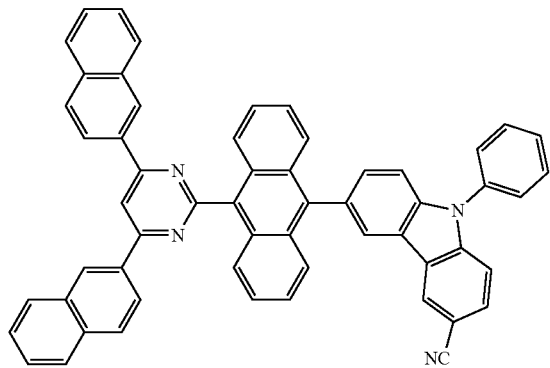
34
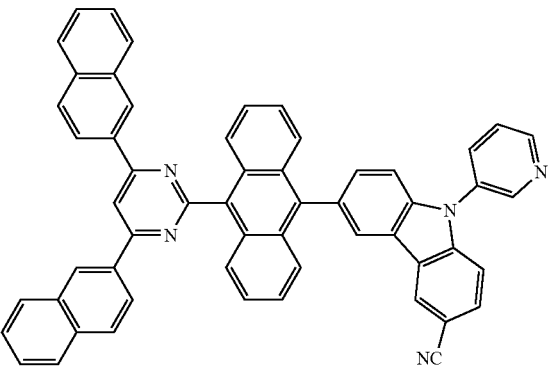
35
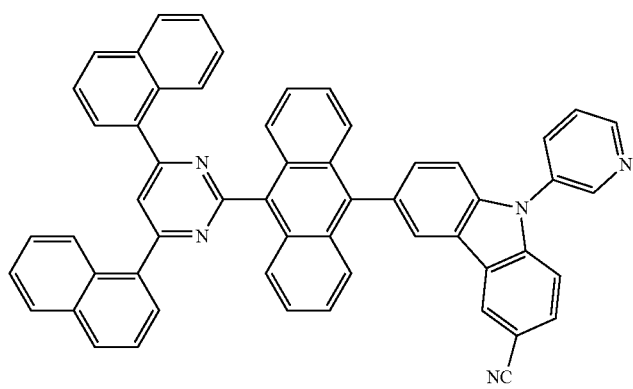
36
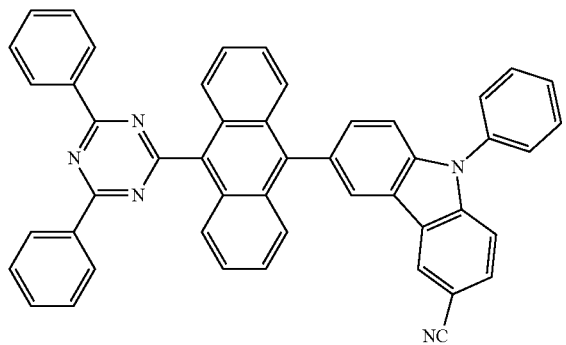
37
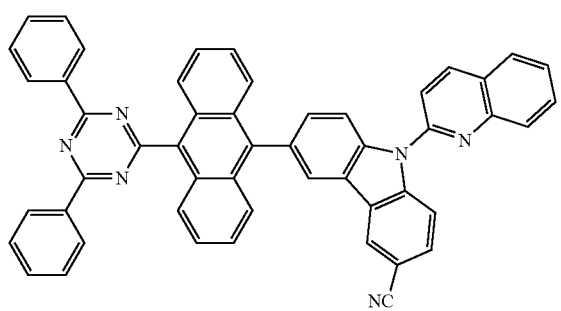
38
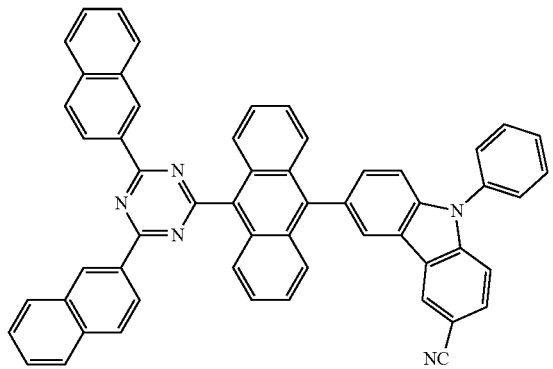
39

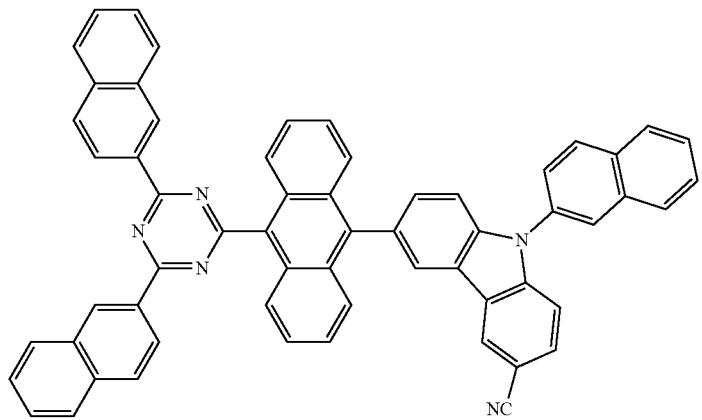
40
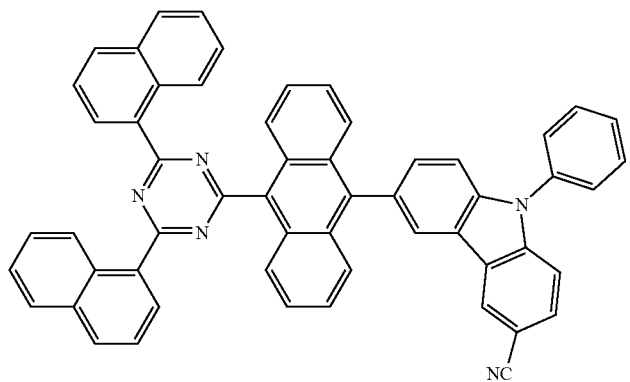
41
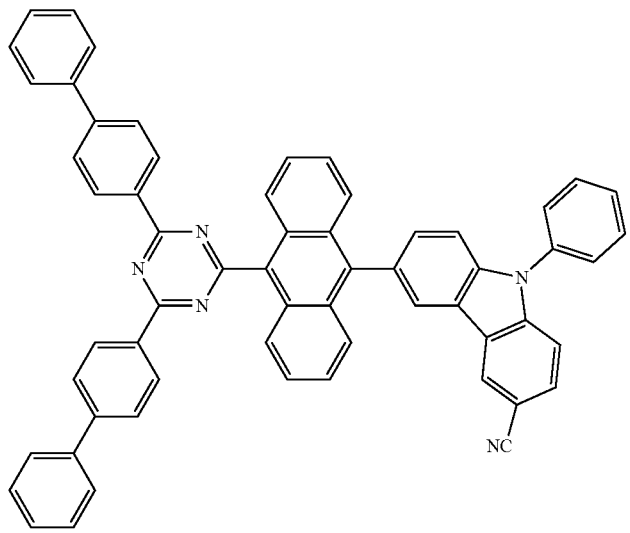
42

-continued
43
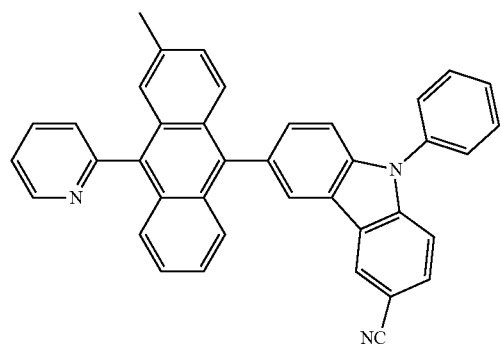
44
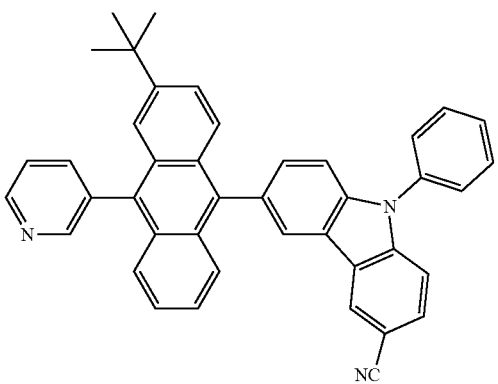
45
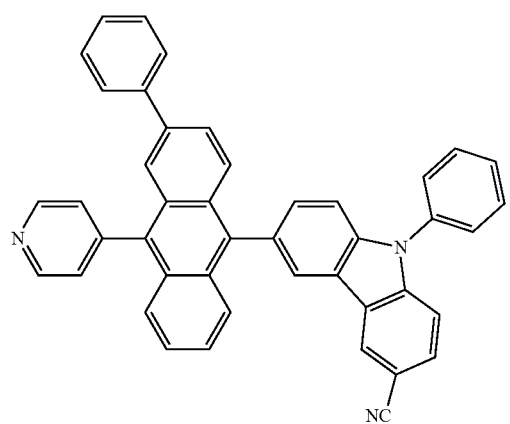
46
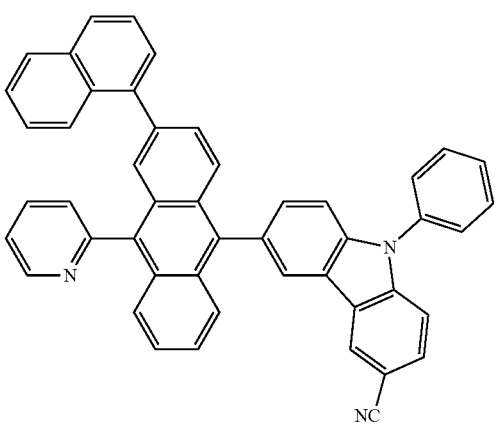
47
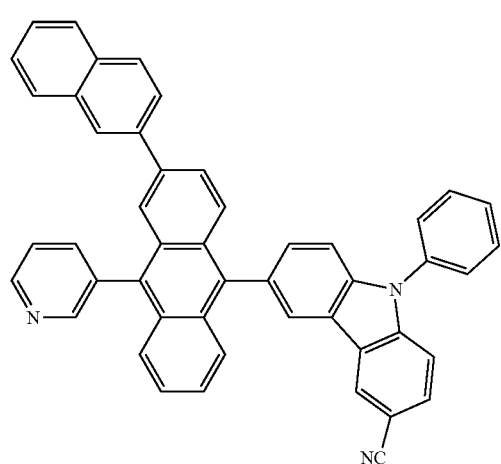
48
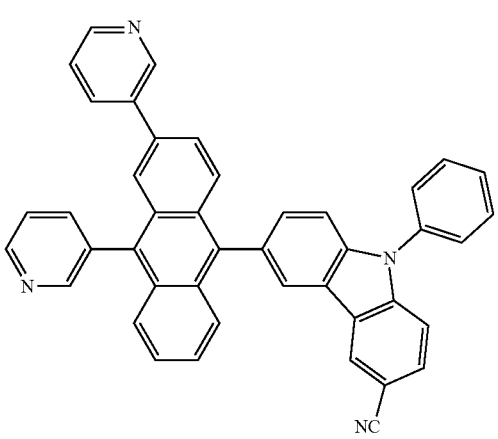
49
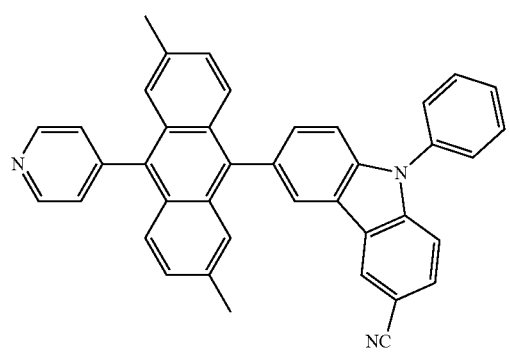
50
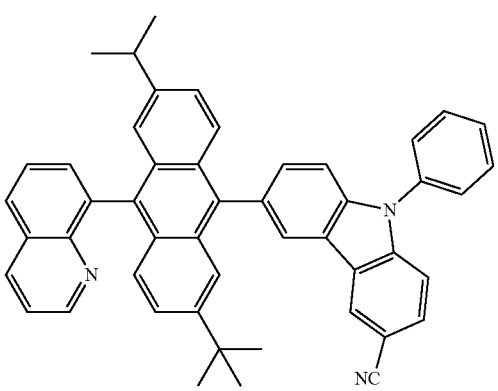

-continued
51
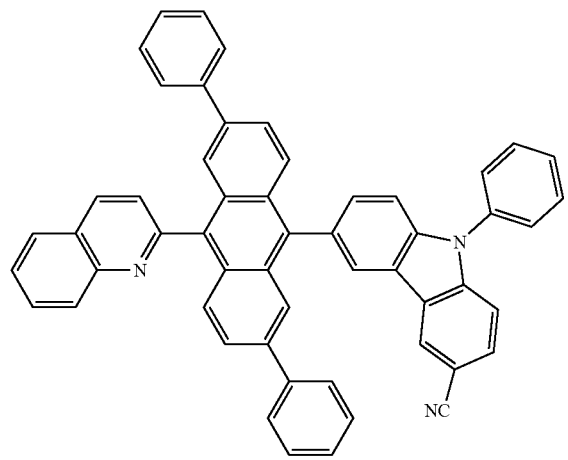
52
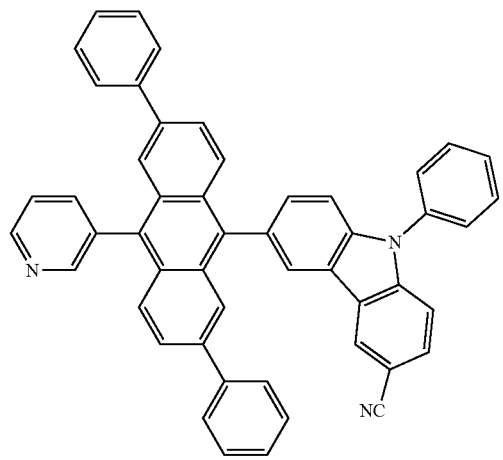
53
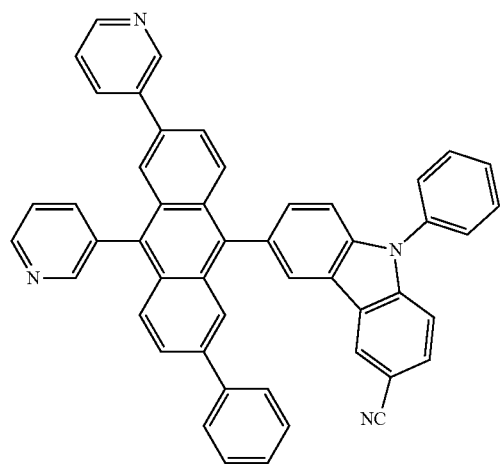
54
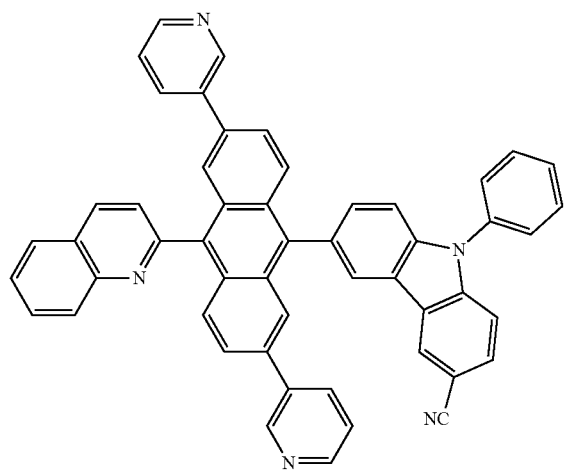
55
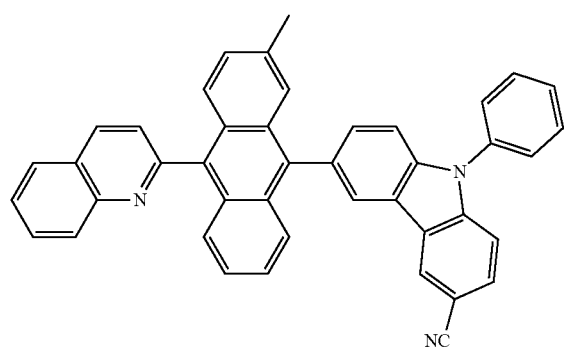
56
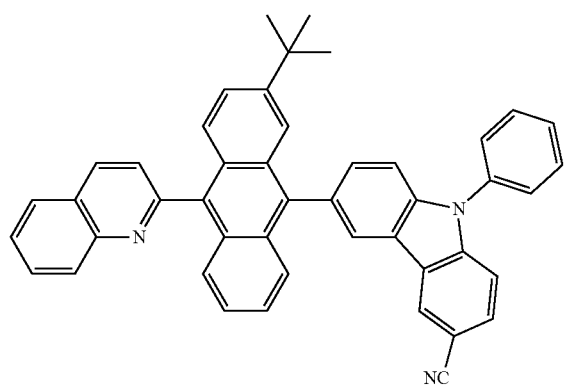

57
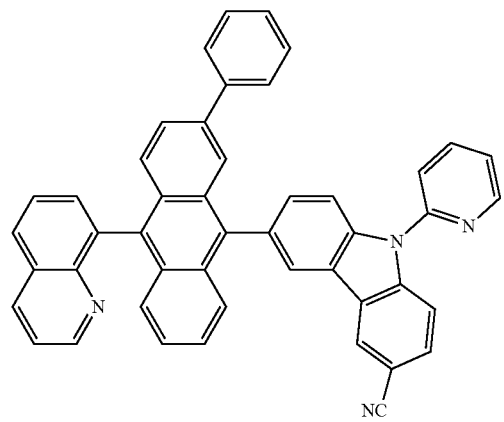
58
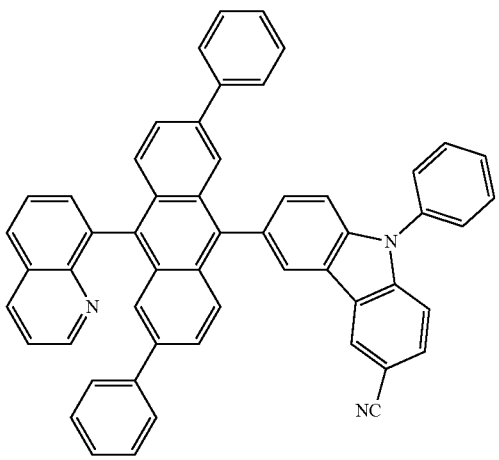
59
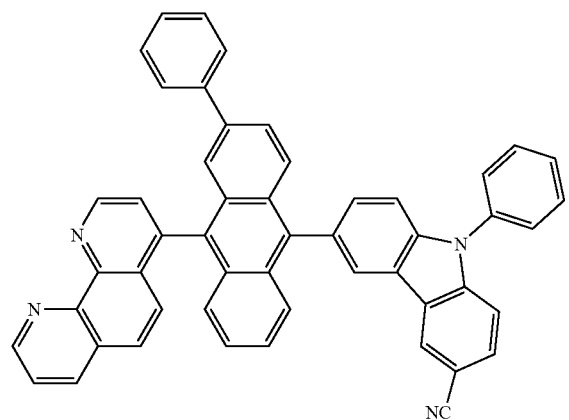
60
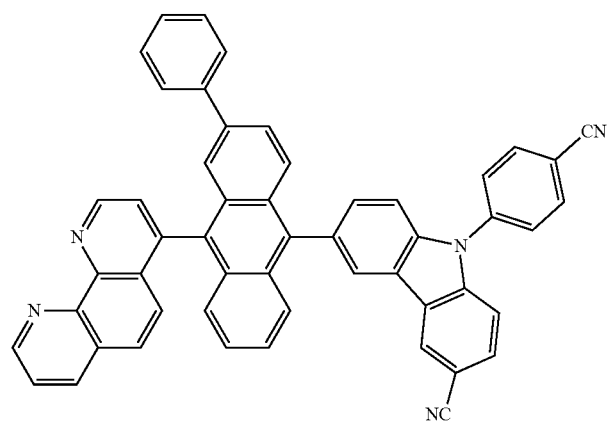

-continued
61
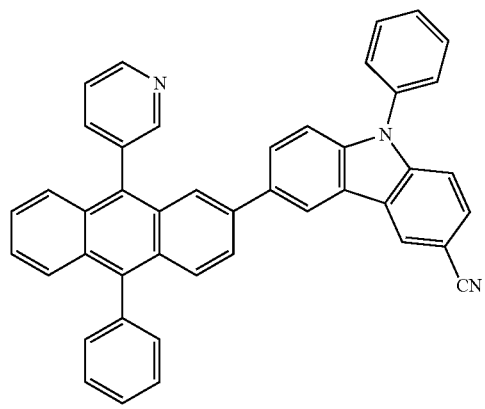
62
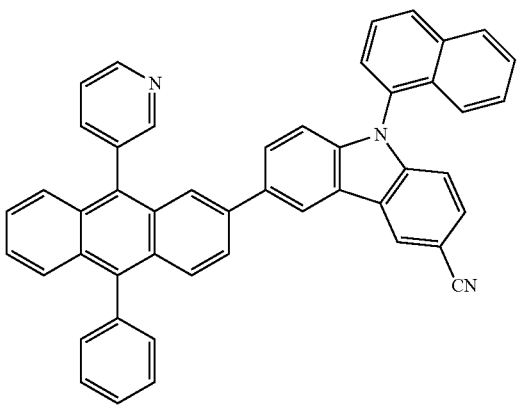
63
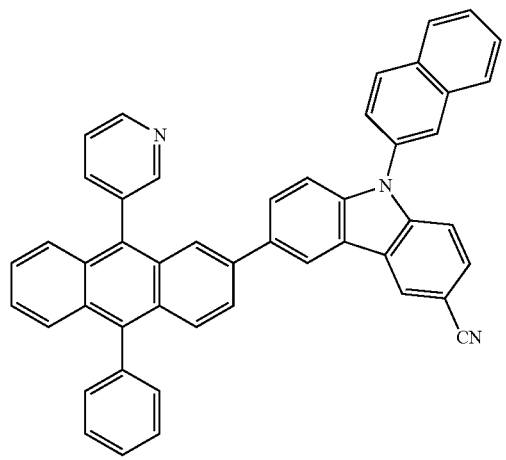
64
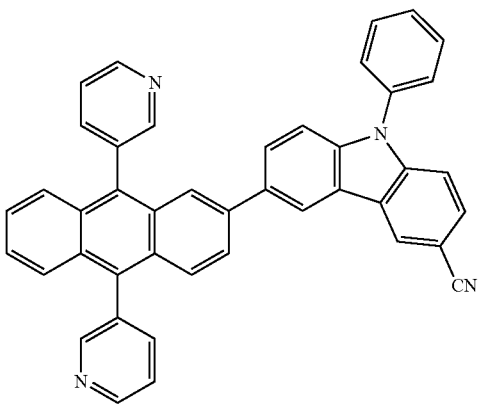
65
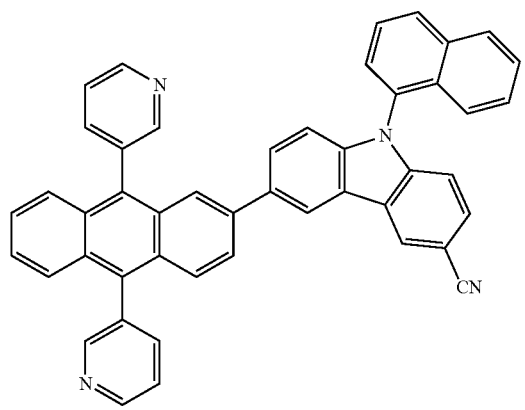
66
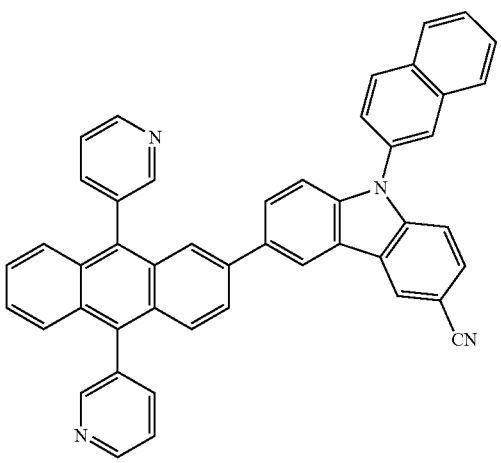

-continued
67
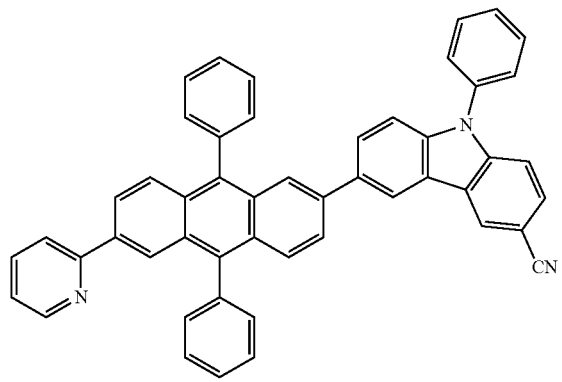
68
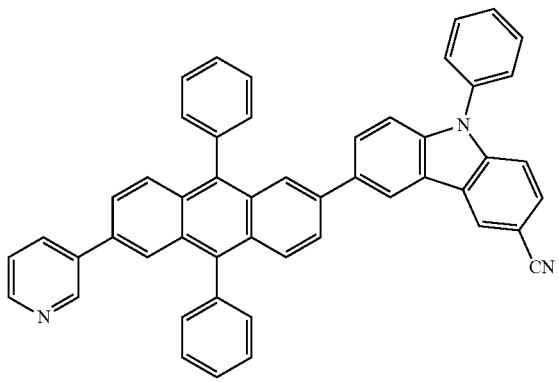
69
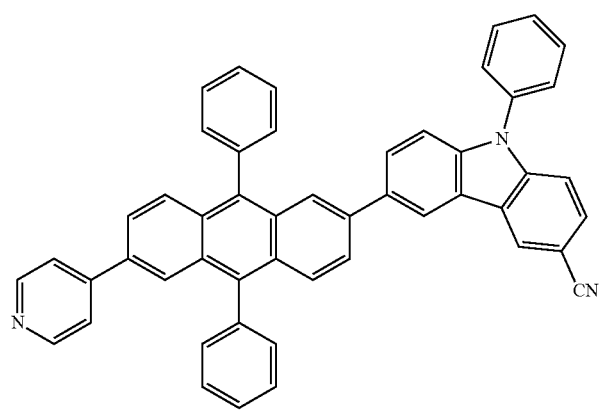
70
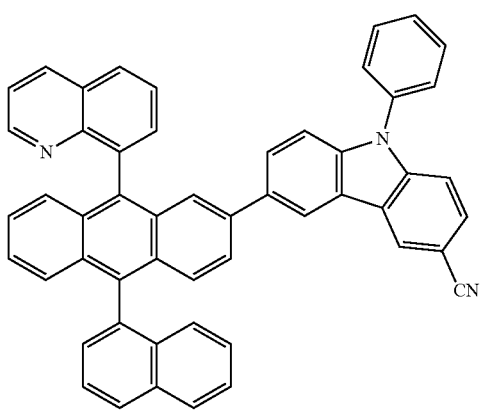
71
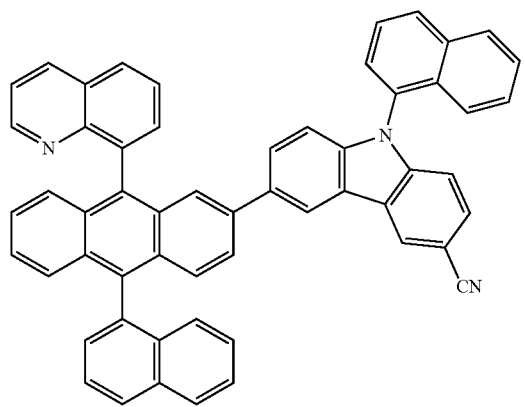
72
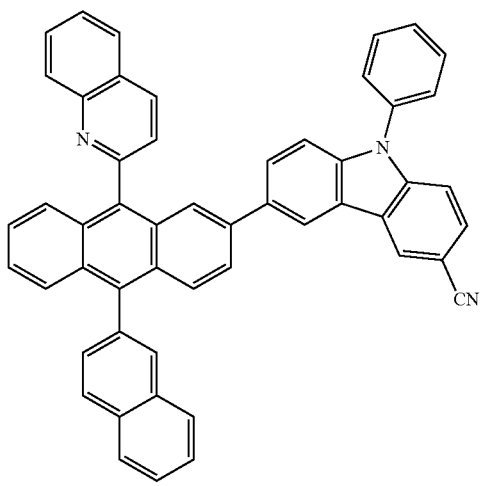

-continued
73
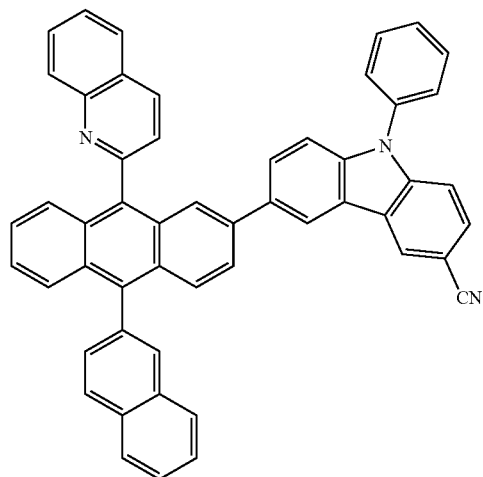
74
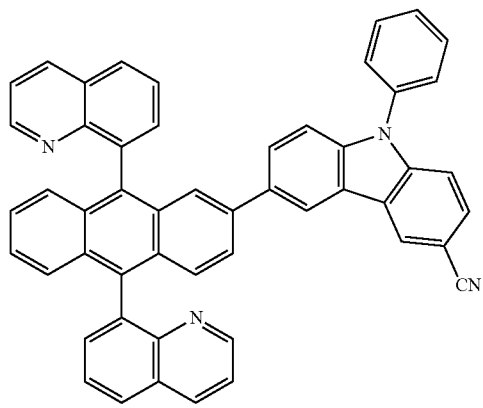
75
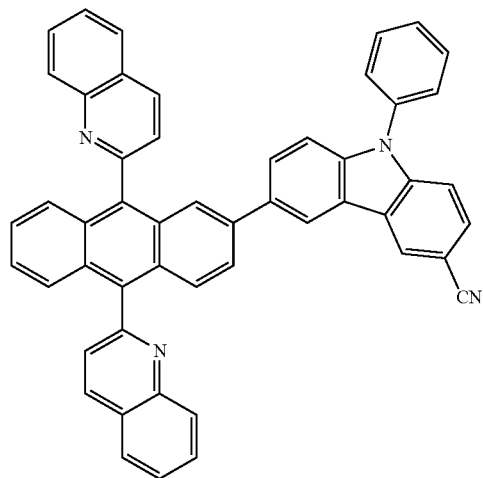
76
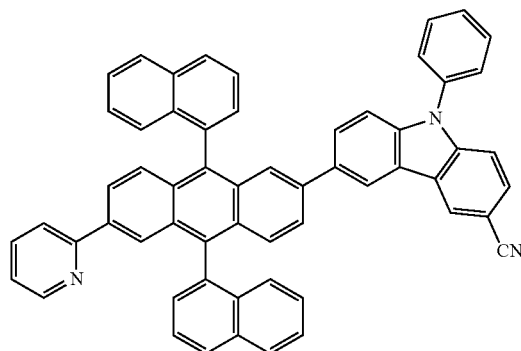
77
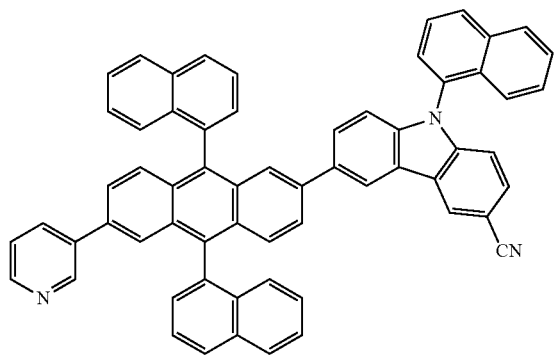

-continued
78
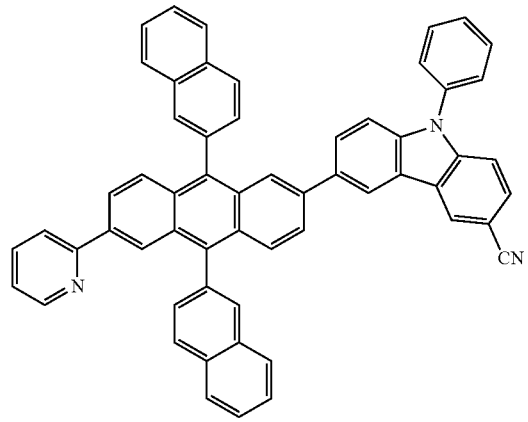
79
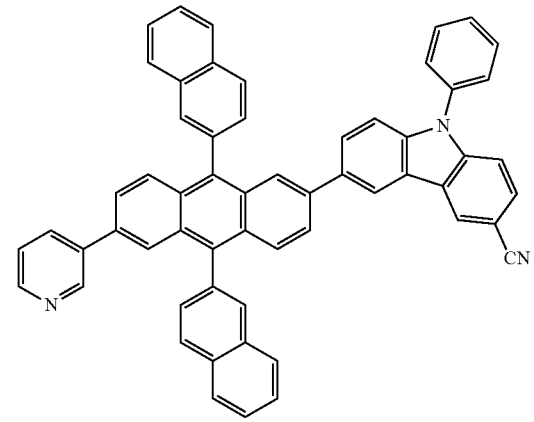
80
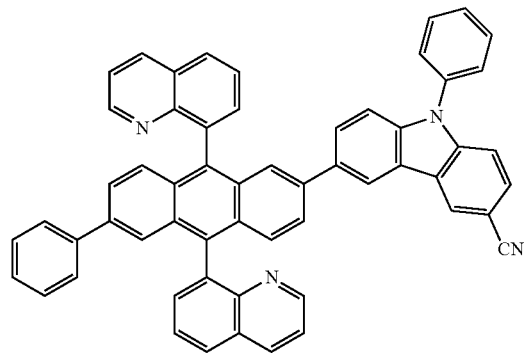
81
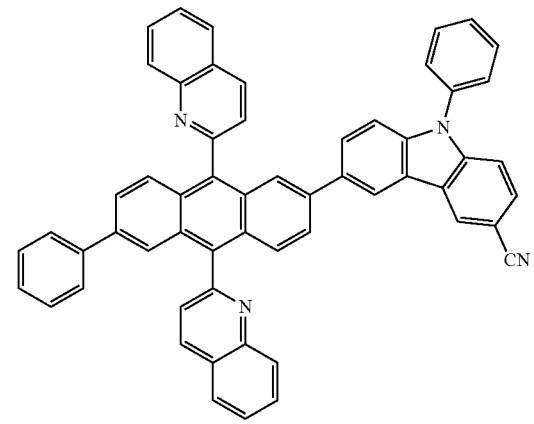
82
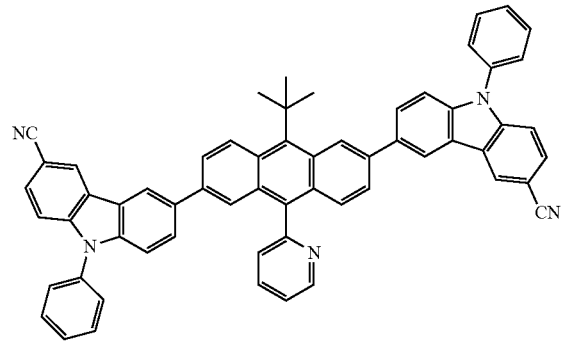
83
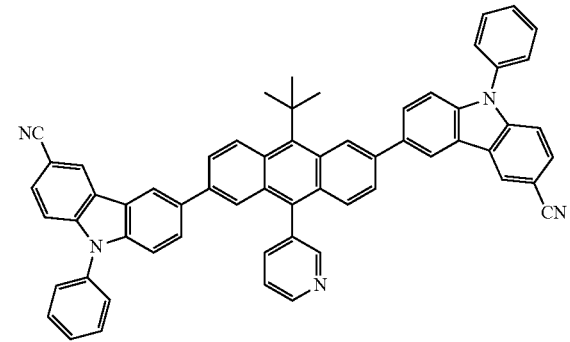
84
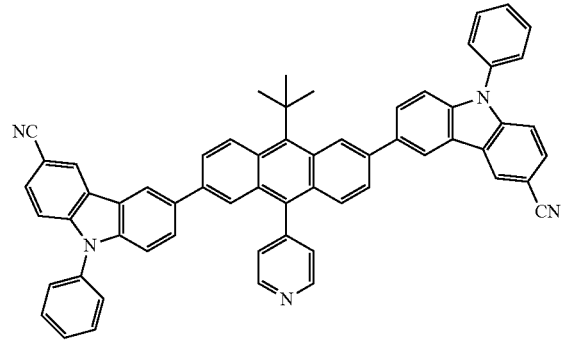
85
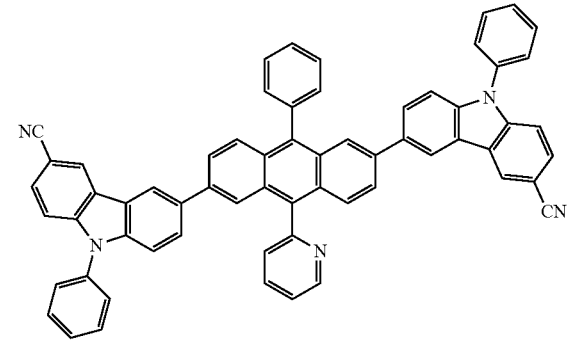

-continued
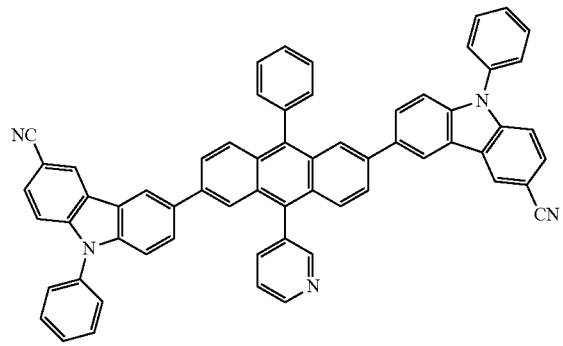
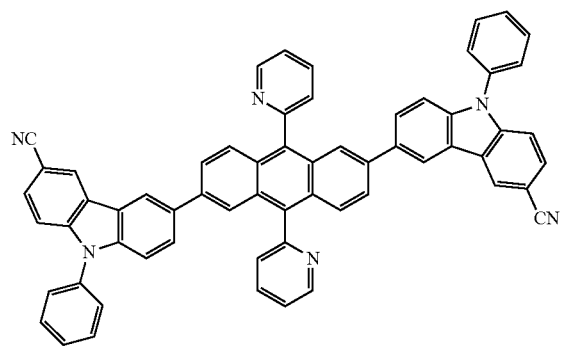
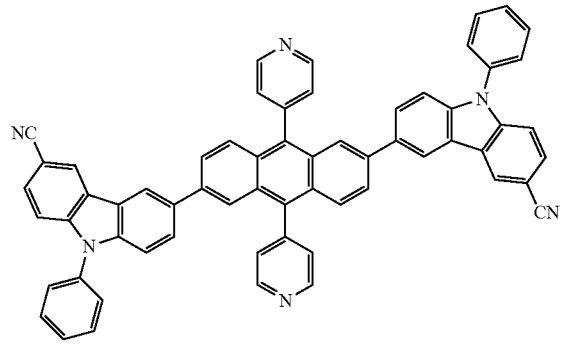
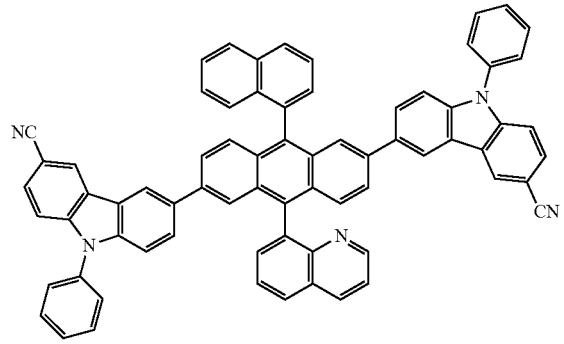

-continued
94
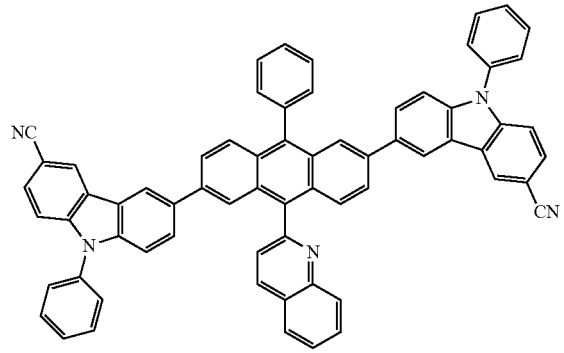
95
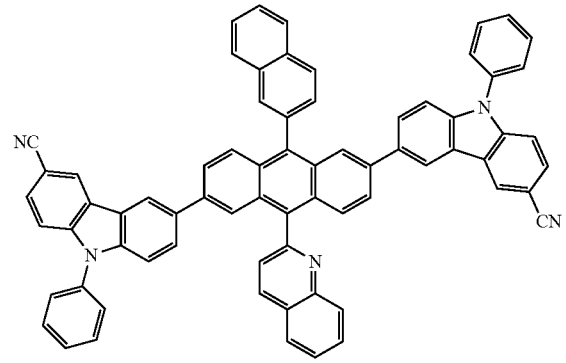
96
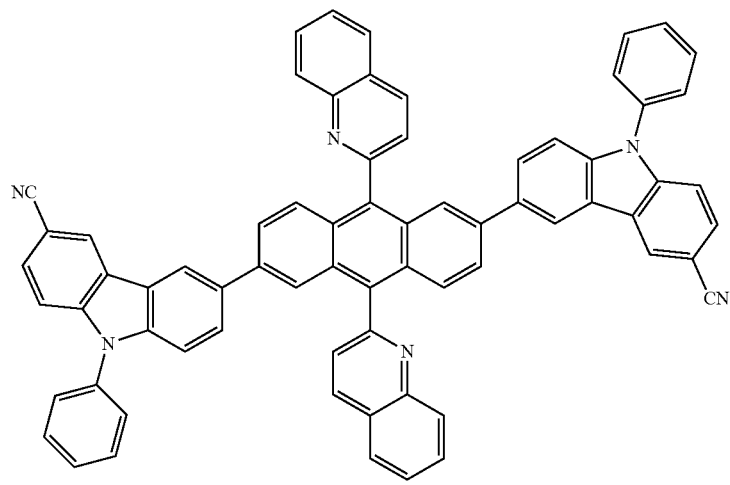
97
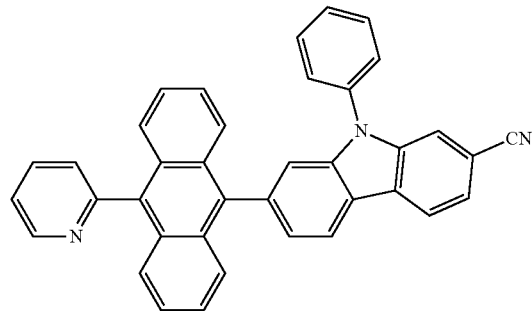
98
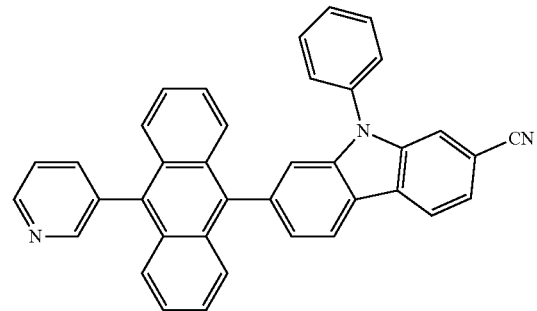
99
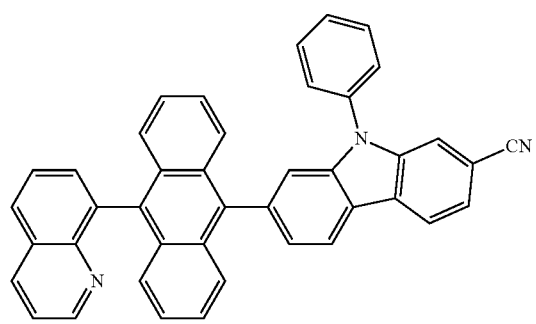
100
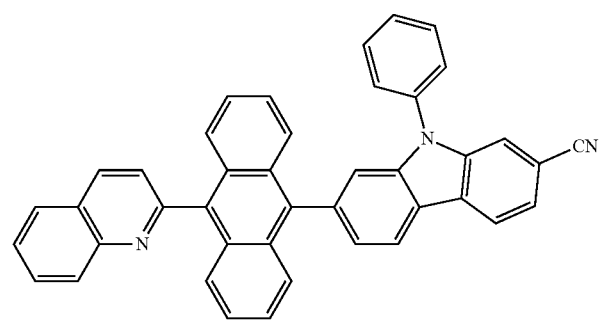

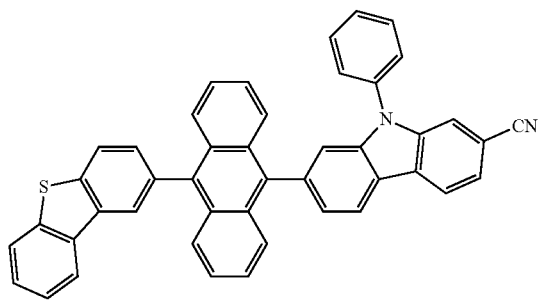

101

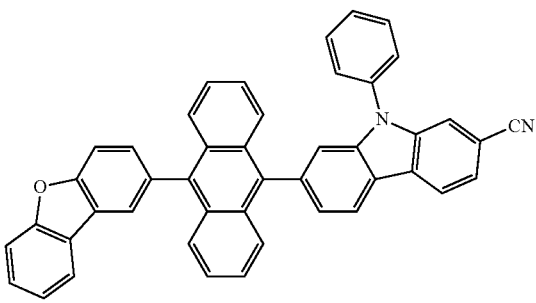

102

Embodiments are also directed to an organic light-emitting device including a first electrode, a second electrode disposed opposite to the first electrode, and an organic layer disposed between the first electrode and the second electrode and including an emission layer, wherein the organic layer includes at least one of the anthracene-based compounds of Formula 1 above.

The organic layer may include a hole transport region between the first electrode and the emission layer, and an electron transport region between the emission layer and the second electrode. The hole transport region may include at least one of a hole injection layer, a hole transport layer, a functional layer having both hole injection and hole transport capabilities, a buffer layer, an electron blocking layer. The electron transport region includes at least one of a hole blocking layer, an electron transport layer, and an electron injection layer.

The anthracene-based compound may be present in the electron transport region.

BRIEF DESCRIPTION OF THE DRAWING

Features will become apparent to those of skill in the art by describing in detail exemplary embodiments with reference to the attached drawings in which:

FIG. 1 illustrates a schematic cross-sectional view of a structure of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURES, the dimensions of layers and regions may be exaggerated for clarity of illustration. Like reference numerals refer to like elements throughout.

According to an embodiment, there is provided an anthracene-based compound represented by Formula 1 below:

<Formula 1>

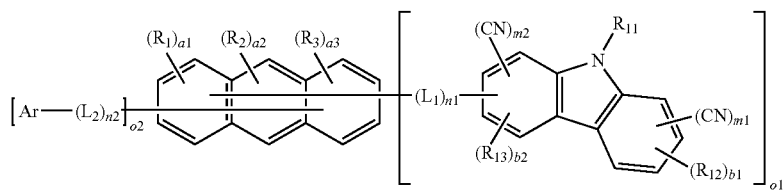

In Formula 1, Ar is an electron transport moiety selected from a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{60}$ heteroaryl group, excluding a substituted or unsubstituted carbazolyl group.

Ar in Formula 1 above excludes a substituted or unsubstituted carbazolyl group. According to some embodiments, the anthracene-based compound of Formula 1 may be a compound in which only one carbazolyl group is linked to an anthracene core directly or via $L_1$ and $L_2$. For example, such a compound may be provided where $R_1$ to $R_3$ are groups other than carbazolyl groups and o1 is 1.

In some embodiments, Ar in Formula 1 may be selected from a substituted or unsubstituted pyrrolyl group, a substituted or unsubstituted imidazolyl group, a substituted or unsubstituted pyrazolyl group, a substituted or unsubstituted pyridyl group, a substituted or unsubstituted pyrazinyl group, a substituted or unsubstituted pyrimidyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted isoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, and a substituted or unsubstituted benzoxazolyl group, but is not limited thereto.

In some other embodiments, Ar in Formula 1 may be selected from:

i) a pyrrolyl group, an imidazolyl group, a pyridyl group, a pyrazinyl group, a pyrimidyl group, an isoindolyl group, an indolyl group, a quinolinyl group, an isoquinolinyl group, a benzoquinolinyl group, a naphthyridinyl group, a quinoxalinyl group, a quinazolinyl group, a phenanthridinyl group, an acridinyl group, a phenanthrolinyl group, a phenazinyl group, a benzoimidazolyl group, a furanyl group, a benzofuranyl group, a dibenzofuranyl group, a thiophenyl group, a benzothiophenyl group, a dibenzothiophenyl group, and a triazinyl group; and ii) a pyrrolyl group, an imidazolyl group, a pyridyl group, a pyrazinyl group, a pyrimidyl group, an isoindolyl group, an indolyl group, a quinolinyl group, an isoquinolinyl group, a benzoquinolinyl group, a naphthyridinyl group, a quinoxalinyl group, a quinazolinyl group, a phenanthridinyl group, an acridinyl group, a phenanthrolinyl group, a phenazinyl group, a benzoimidazolyl group, a furanyl group, a benzofuranyl group, a dibenzofuranyl group, a thiophenyl group, a benzothiophenyl group, a dibenzothiophenyl group, and a triazinyl group, each substituted with at least one of a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{30}$ heteroaryl group.

For example, Ar in Formula 1 may be selected from:

i) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group;

ii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a deuterium atom, —F, a hydroxyl group, a cyano group, a nitro group, a methyl group, an ethyl group, an n-propyl group, and a t-butyl group;

iii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group; and iv) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group that are substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group.

As another example, Ar in Formula 1 may be selected from:

i) a pyridyl group, a pyrimidyl group, a quinolinyl group, a phenanthrolinyl group, a benzoimidazolyl group, a dibenzofuranyl group, a dibenzothiophenyl group, and a triazinyl group;

ii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group; and iii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group that are substituted with at least one of a phenyl group, a naphthyl group, a pyridyl group, and a quinolinyl group.

As another example, Ar in Formula 1 may be selected from the groups represented by Formulae 2-1 to 2-12 below:

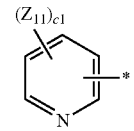

2-1

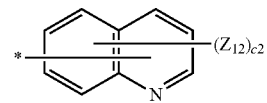

2-2

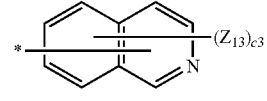

2-3

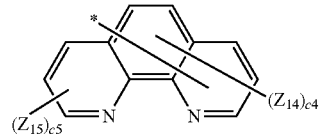

2-4

-continued 2-5
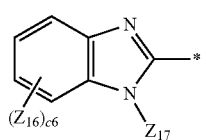

2-6
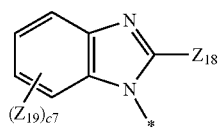

2-7
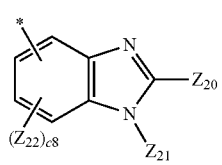

2-8
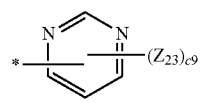

2-9
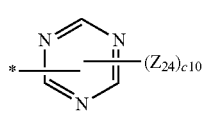

2-11
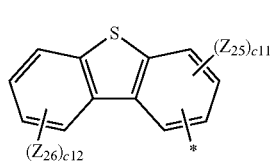

2-12
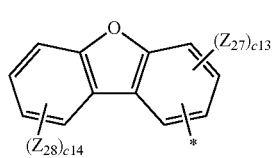

In Formulae 2-1 to 2-12, $Z_{11}$ to $Z_{28}$ may be each independently selected from i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with at least one of a phenyl group, a 1-naphthyl group, a 2-naphthyl group, a pyridyl group, and a quinolinyl group, c1 to c14 may be each independently an integer from 0 to 2, and \* may indicate a binding site to $L_2$ or an anthracene core.

As still another example, Ar in Formula 1 may be selected from the groups represented by Formulae 3-1 to 3-14 below:

3-1
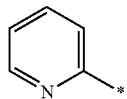

3-2
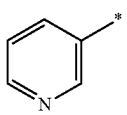

3-3
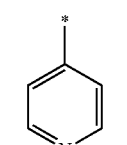

3-4
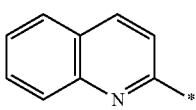

3-5
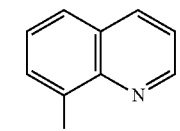

3-6
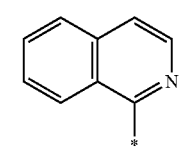

3-7
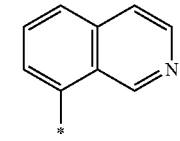

3-8
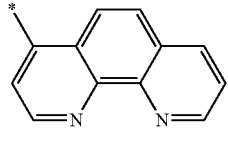

3-9
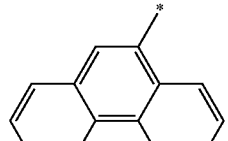

3-10
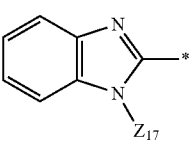

-continued 3-11

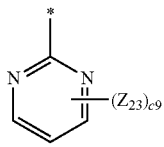

3-12

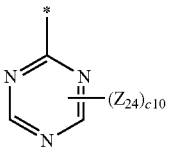

3-13

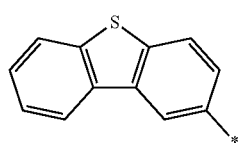

3-14

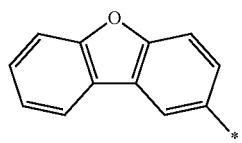

In Formulae 3-1 to 3-14, $Z_{17}$, $Z_{23}$, and $Z_{24}$ may be each independently selected from i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with a phenyl group, c9 and c10 may be each independently an integer from 0 to 2, and

* may indicate a binding site to $L_2$ or an anthracene core.

In Formula 1 above, $R_1$ to $R_3$, and $R_{11}$ to $R_{13}$ may be each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{30}$ heteroaryl group.

In some embodiments, $R_1$ to $R_3$ in Formula 1 may be each independently selected from:

i) a hydrogen atom, a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and ii) a phenyl group, a naphthyl group, a pyridyl group, and a quinolinyl group, each substituted with at least one of a deuterium atom, —F, a hydroxyl group, a cyano group, a nitro group, a methyl group, an ethyl group, an n-propyl group, and a t-butyl group.

In some other embodiments, $R_1$ to $R_3$ in Formula 1 may be each independently selected from a deuterium atom, —F, a cyano group, a nitro group, a methyl group, a t-butyl group, a phenyl group, a naphthyl group, a pyridyl group, and a quinolinyl group.

For example, $R_{11}$ to $R_{13}$ in Formula 1 may be each independently selected from:

i) a phenyl group, a naphthyl group, a fluorenyl group, a spiro-fluorenyl group, an anthryl group, a pyrrolyl group, an imidazolyl group, a pyridyl group, a pyrazinyl group, a pyrimidyl group, an isoindolyl group, an indolyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a benzoimidazolyl group, a furanyl group, a benzofuranyl group, a dibenzofuranyl group, a thiophenyl group, a benzothiophenyl group, a dibenzothiophenyl group, and a triazinyl group;

ii) a phenyl group, a naphthyl group, a fluorenyl group, a spiro-fluorenyl group, an anthryl group, a pyrrolyl group, an imidazolyl group, a pyridyl group, a pyrazinyl group, a pyrimidyl group, an isoindolyl group, an indolyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a benzoimidazolyl group, a furanyl group, a benzofuranyl group, a dibenzofuranyl group, a thiophenyl group, a benzothiophenyl group, a dibenzothiophenyl group, and a triazinyl group, each substituted with at least one of a deuterium atom, a halogen atom, a hydroxyl group, a cyano group, a nitro group, a $C_1$-$C_{30}$ alkyl group, a $C_6$-$C_{30}$ aryl group, and a $C_2$-$C_{30}$ heteroaryl group; and iii) a phenyl group, a naphthyl group, a fluorenyl group, a spiro-fluorenyl group, an anthryl group, a pyrrolyl group, an imidazolyl group, a pyridyl group, a pyrazinyl group, a pyrimidyl group, an isoindolyl group, an indolyl group, a quinolinyl group, an isoquinolinyl group, a benzoquinolinyl group, a naphthyridinyl group, a quinoxalinyl group, a quinazolinyl group, a carbazolyl group, a phenanthridinyl group, an acridinyl group, a phenanthrolinyl group, a phenazinyl group, a benzoimidazolyl group, a furanyl group, a benzofuranyl group, a dibenzofuranyl group, a thiophenyl group, a benzothiophenyl group, a dibenzothiophenyl group, and a triazinyl group, each substituted with at least one of a $C_1$-$C_{30}$ alkyl group, a $C_6$-$C_{30}$ aryl group, and a $C_2$-$C_{30}$ heteroaryl group that are each substituted with at least one of a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{30}$ heteroaryl group.

As another example, $R_{11}$ to $R_{13}$ in Formula 1 may be each independently selected from:

i) a phenyl group, a naphthyl group, a fluorenyl group, a pyridyl group, a quinolinyl group, an isoquinolinyl group, a dibenzofuranyl group, and a dibenzothiophenyl group;

ii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and iii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a methyl group, a t-butyl group, a phenyl group, a naphthyl group, a pyridyl group, and a quinolinyl group that are substituted with at least one of a deuterium atom, —F, a hydroxyl group, a cyano group, a nitro group, a methyl group, and a t-butyl group.

As still another example, $R_{11}$ to $R_{13}$ in Formula 1 may be each independently selected from groups represented by Formulae 2-1 to 2-12 and Formulae 4-1 to 4-3 below:

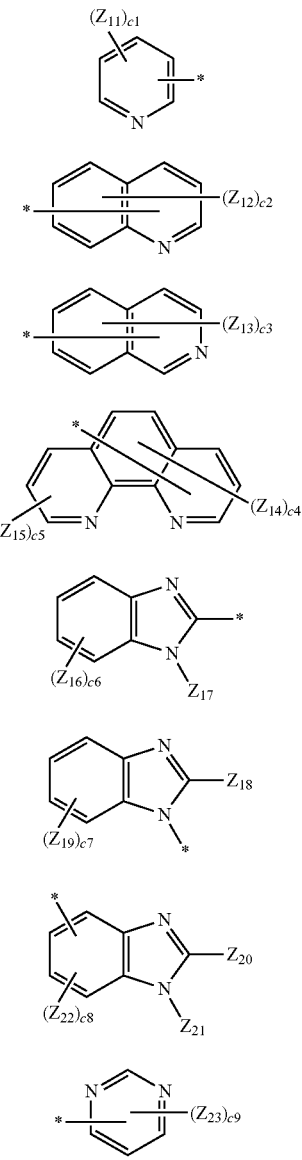

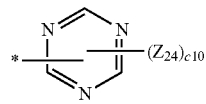

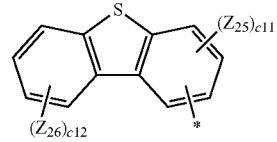

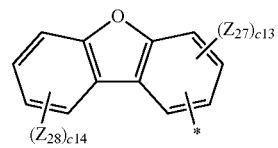

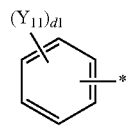

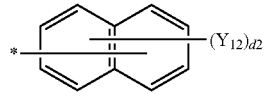

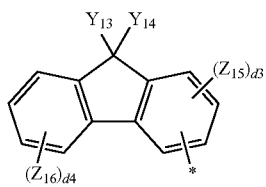

In Formulae 2-1 to 2-12, and Formulae 4-1 to 4-3, $Z_{11}$ to $Z_{28}$, and $Y_{11}$ to $Y_{16}$ may be each independently selected from i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 may be each independently an integer from 0 to 2, and

* may indicate a binding site to $L_1$ or an anthracene core.

As still another example, $R_{11}$ to $R_{13}$ in Formula 1 may be each independently selected from the groups represented by Formulae 3-1 to 3-14 and Formulae 5-1 to 5-4 below:

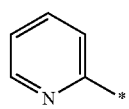

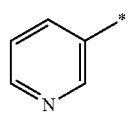

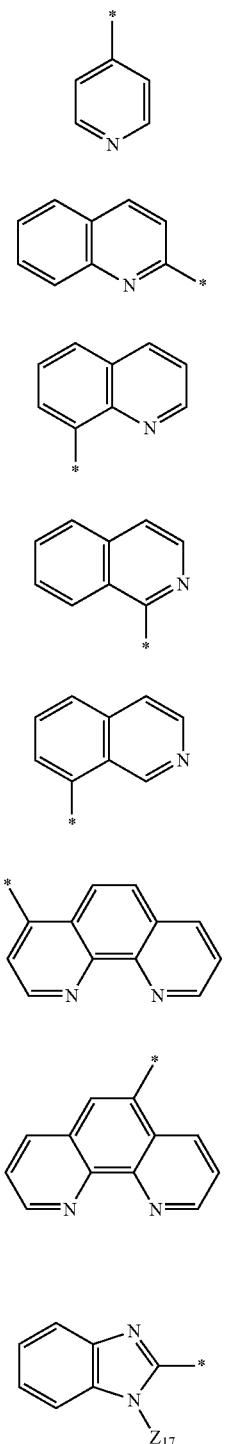
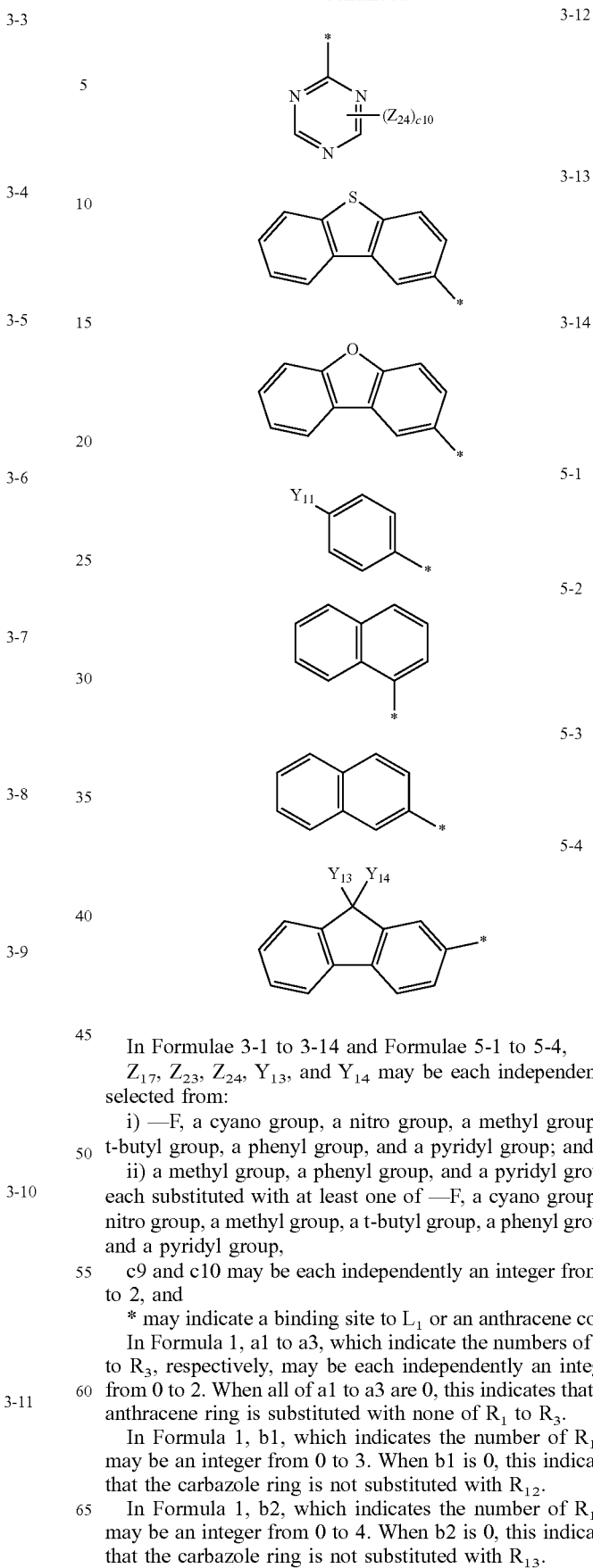

In Formulae 3-1 to 3-14 and Formulae 5-1 to 5-4, $Z_{17}$, $Z_{23}$, $Z_{24}$, $Y_{13}$, and $Y_{14}$ may be each independently selected from:

i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c9 and c10 may be each independently an integer from 0 to 2, and

* may indicate a binding site to $L_1$ or an anthracene core.

In Formula 1, a1 to a3, which indicate the numbers of $R_1$ to $R_3$, respectively, may be each independently an integer from 0 to 2. When all of a1 to a3 are 0, this indicates that an anthracene ring is substituted with none of $R_1$ to $R_3$.

In Formula 1, b1, which indicates the number of $R_{12}$s, may be an integer from 0 to 3. When b1 is 0, this indicates that the carbazole ring is not substituted with $R_{12}$.

In Formula 1, b2, which indicates the number of $R_{13}$s, may be an integer from 0 to 4. When b2 is 0, this indicates that the carbazole ring is not substituted with $R_{13}$.

For example, b1 and b2 in Formula 1 may be each independently an integer of 0 or 1.

In Formula 1 above, $L_1$ and $L_2$ may be each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted $C_2$-$C_{10}$ heterocycloalkylene group, a substituted or unsubstituted $C_2$-$C_{10}$ heterocycloalkenylene group, and a substituted or unsubstituted $C_2$-$C_{60}$ heteroarylene group.

For example, $L_1$ and $L_2$ in Formula 1 above may be each independently selected from a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted cinnolinylene group, a substituted or unsubstituted carbazolylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzoxazolylene group, a substituted or unsubstituted benzimidazolylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene group, a substituted or unsubstituted oxadiazolylene group, a substituted or unsubstituted triazinylene group, a substituted or unsubstituted benzoxazolylene group, a substituted or unsubstituted dibenzopuranylene group, a substituted or unsubstituted dibenzothiophenylene group, and a substituted or unsubstituted benzocarbazolylene group, but are not limited thereto.

In some embodiments, $L_1$ and $L_2$ in Formula 1 above may be each independently selected from:

i) a phenylene group, a naphthylene group, an anthracenyl group, a chrysenylene group, and a pyrenylene group; and ii) a phenylene group, a naphthylene group, an anthracenyl group, a chrysenylene group, and a pyrenylene group, each substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, and a $C_1$-$C_{10}$ alkyl group; a $C_1$-$C_{10}$ alkyl group substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a $C_6$-$C_{16}$ aryl group, and a $C_2$-$C_{16}$ heteroaryl group; and a $C_6$-$C_{16}$ aryl group, and a $C_2$-$C_{16}$ heteroaryl group, each substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In some other embodiments, $L_1$ and $L_2$ in Formula 1 may be each independently selected from i) a phenylene group, an anthracenyl group, a chrysenylene group, and a pyrenylene group; and ii) a phenylene group, an anthracenyl group, a chrysenylene group, and a pyrenylene group, each substituted with at least one selected from a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group; a phenyl group, a naphthyl group, a pyridyl group, and a triazinyl group; and a phenyl group, a naphthyl group, a pyridyl group, and a triazinyl group, each substituted with at least one of a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group.

In some other embodiments, $L_1$ and $L_2$ in Formula 1 may be each independently selected from a phenylene group, an anthracenyl group, a chrysenylene group, and a pyrenylene group, but are not limited thereto.

In Formula 1 above, n1 and n2, which indicate the numbers of $L_1$s and $L_2$s, respectively, may be each independently an integer from 0 to 3.

For example, n1 and n2 in Formula 1 may be each independently an integer of 0 or 1, but are not limited thereto.

As another example, n1 and n2 in Formula 1 may be both an integer of 0, but are not limited thereto.

In Formula 1 above, m1 and m2, which each indicates the number of CN groups, may be each independently an integer from 0 to 3, wherein m1+m2 may be an integer of 1 or greater. In Formula 1, both m1 and m2 may not be 0, which means that the carbazole ring is substituted with at least one CN group.

For example, m1 in Formula 1 may be an integer of 1, and m2 may be an integer of 0, but embodiments of the preset invention are not limited thereto.

For another embodiment, m1 in Formula 1 may be an integer of 0, and m2 may be an integer of 1, but embodiments are not limited thereto.

In Formula 1, m1+b1 may be equal to 4, and m2+b2 may be equal to 3.

In Formula 1 above, o1 and o2 may be each independently an integer from 1 to 3.

For example, o1 and o2 in Formula 1 may be each independently an integer of 1 or 2.

As another example, o1 and o2 in Formula 1 may both be an integer of 1.

In some embodiments, the anthracene-based compound of Formula 1 above may be a compound represented by one of Formulae 1a(1) to 1a(5), 1b(1) to 1b(3), 1c(1), and 1c(2) below:

<Formula 1a(1)>
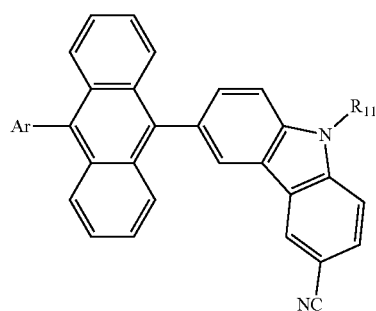

<Formula 1a(2)>
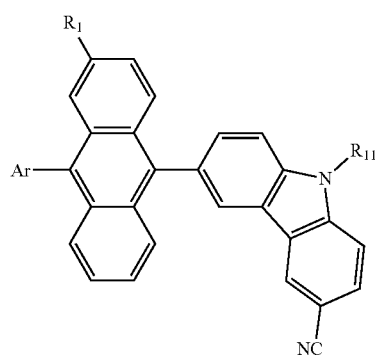

<Formula 1a(3)>
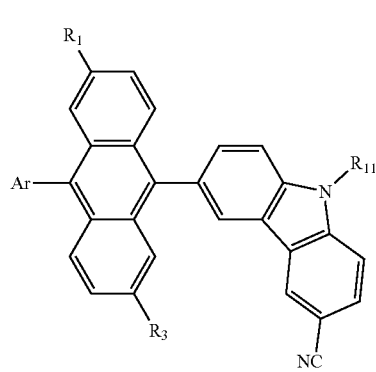

-continued

<Formula 1a(4)>
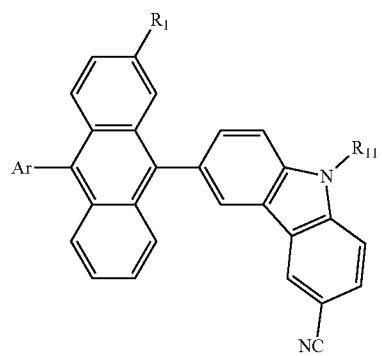

<Formula 1a(5)>
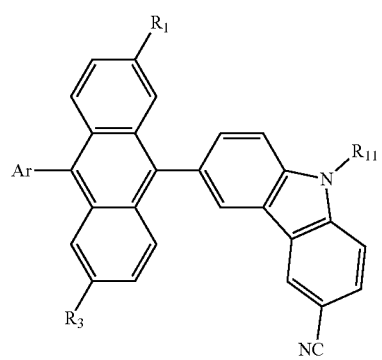

<Formula 1b(1)>

<Formula 1b(2)>
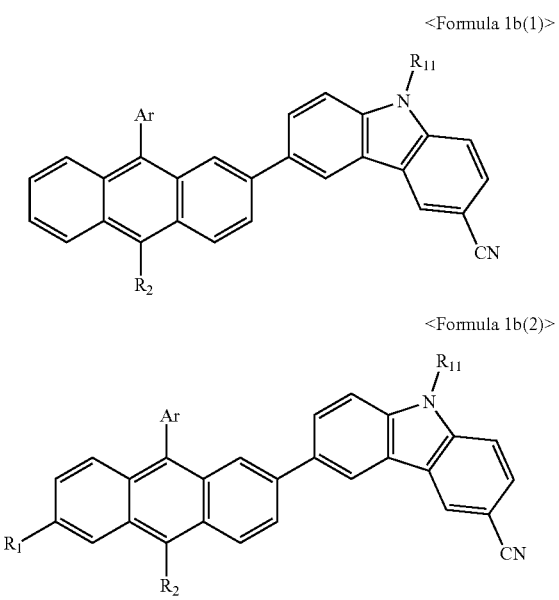

<Formula 1b(3)>
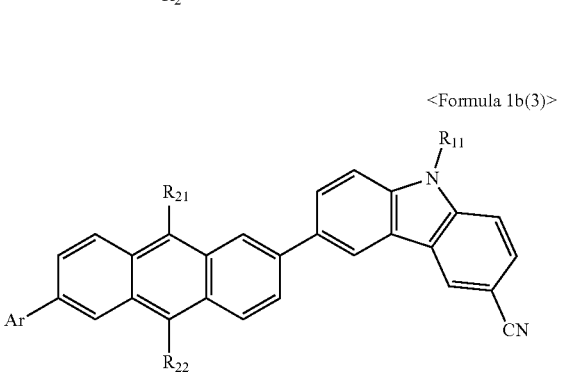
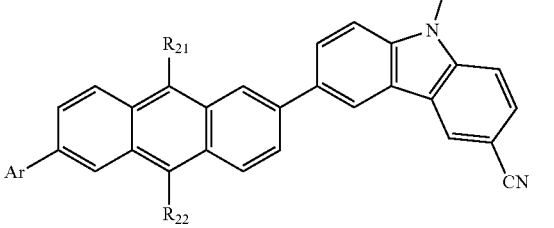

<Formula 1c(1)>
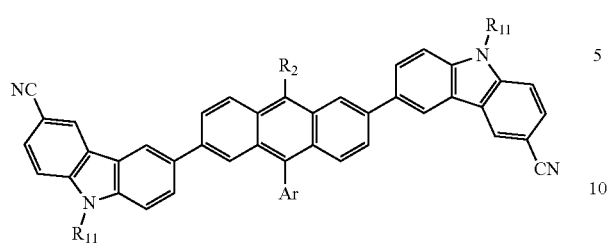
<Formula 1c(2)>
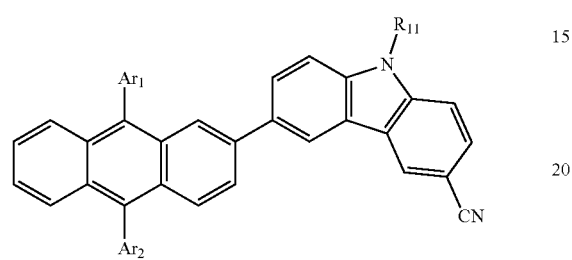
<Formula 1c(3)>
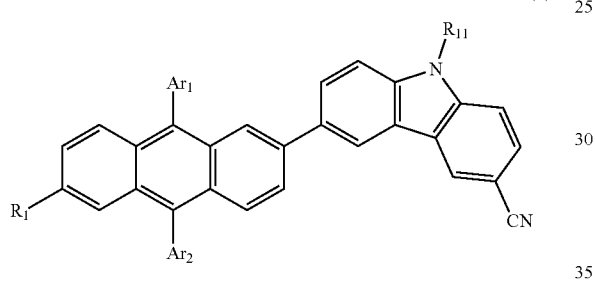
<Formula 1d(1)>
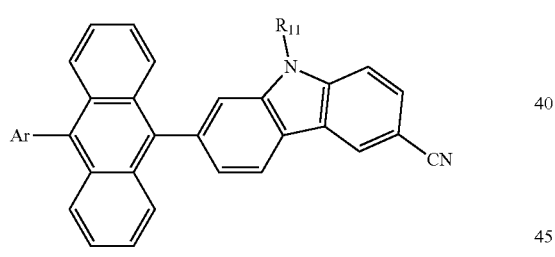
In Formulae 1a(1) to 1a(5), 1b(1) to 1b(3), 1c(1) to 1c(3), and 1d(1),
$Ar$, $Ar_1$, and $Ar_2$ may be each independently selected from groups represented by one of Formulae 3-1 to 3-14:
3-1
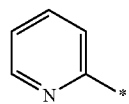
3-2
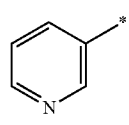
3-3
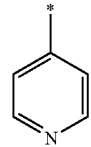
3-4
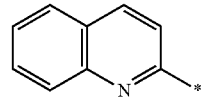
3-5
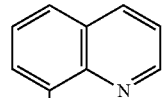
3-6
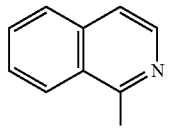
3-7
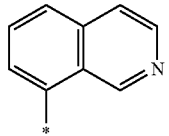
3-8
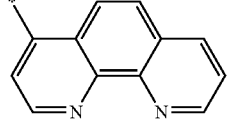
3-9
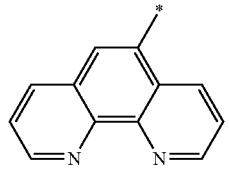
3-10
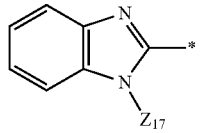
3-11
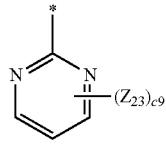
3-12
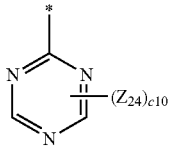

-continued 3-13
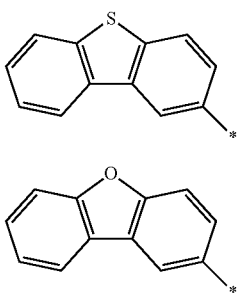

3-14
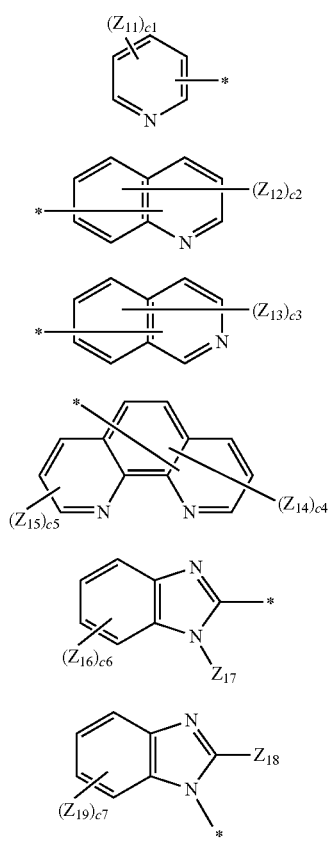

In Formulae 3-1 to 3-14, $Z_{17}$, $Z_{23}$, and $Z_{24}$ may be each independently selected from i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with a phenyl group, c9 and c10 may be each independently an integer from 0 to 2,

* may indicate a binding site to an anthracene core, $R_1$ to $R_3$, $R_{21}$, and $R_{22}$ may be each independently selected from a deuterium atom, —F, a cyano group, a nitro group, a methyl group, a t-butyl group, a phenyl group, a naphthyl group, a pyridyl group, and a quinolinyl group, and $R_{11}$ may be selected from the groups represented by Formulae 2-1 to 2-12, and Formulae 4-1 to 4-3 below:

-continued 2-7
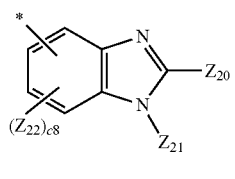

2-8
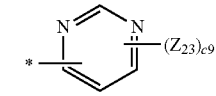

2-9
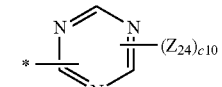

2-11
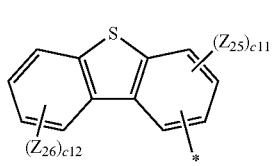

2-12
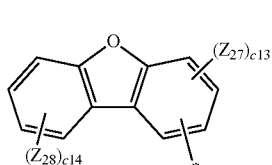

4-1
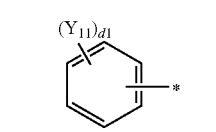

4-2
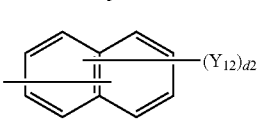

4-3
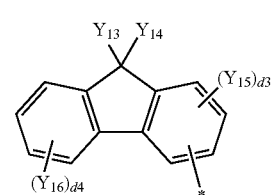

In Formulae 2-1 to 2-12, and Formulae 4-1 to 4-3, $Z_{11}$ to $Z_{28}$, and $Y_{11}$ to $Y_{16}$ may be each independently selected from i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 may be each independently an integer from 0 to 2, and

* may indicate a binding site to an anthracene core.

In some other embodiments, the anthracene-based compound of Formula 1 above may be one selected from Compounds 1 to 102 below, but is not limited thereto:

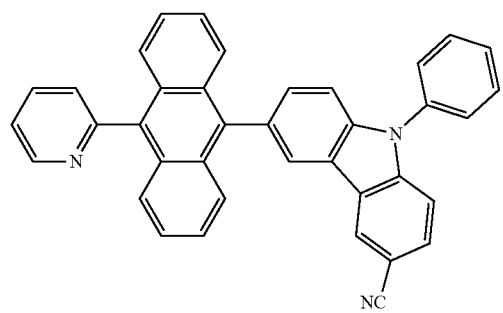
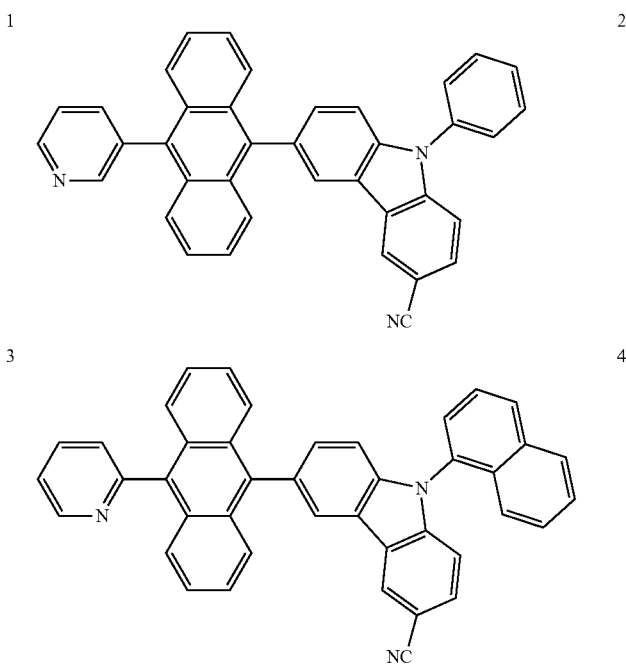
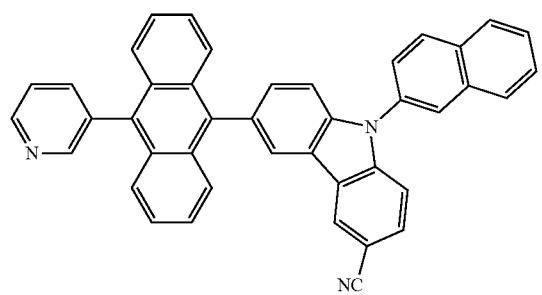
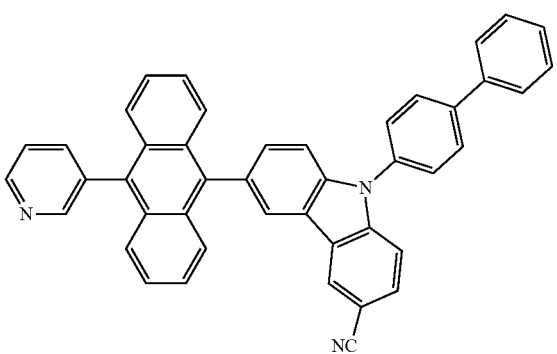
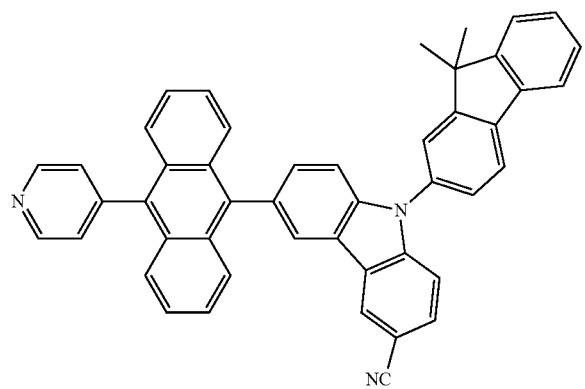
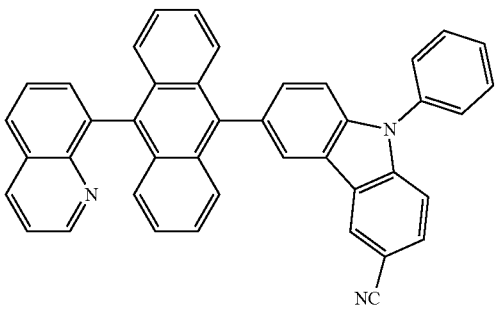

-continued
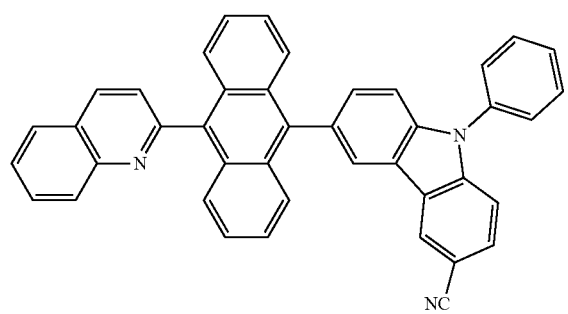
9
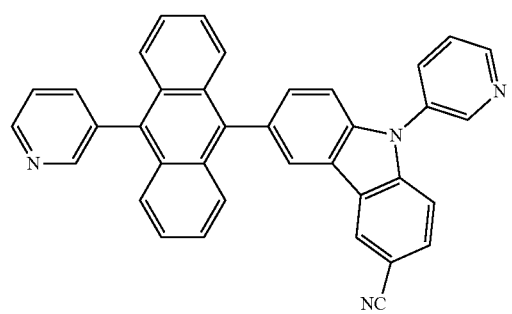
10
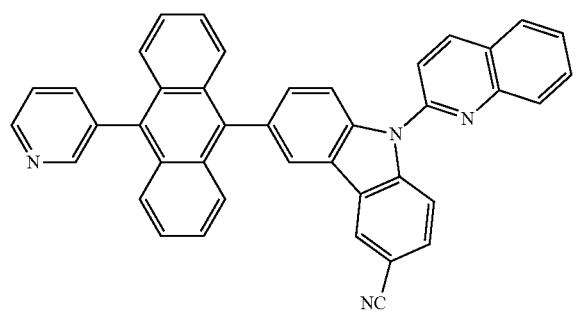
11
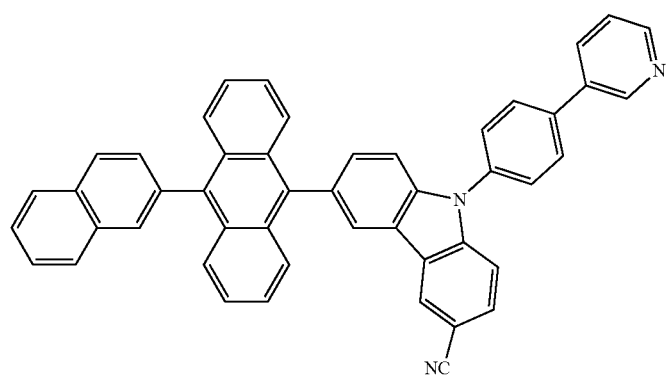
12
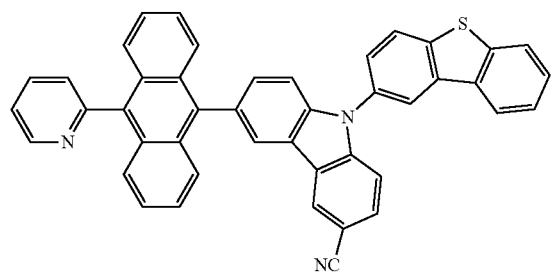
13
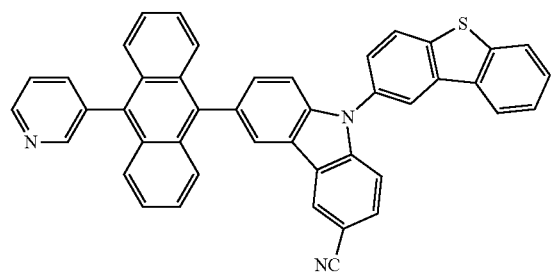
14
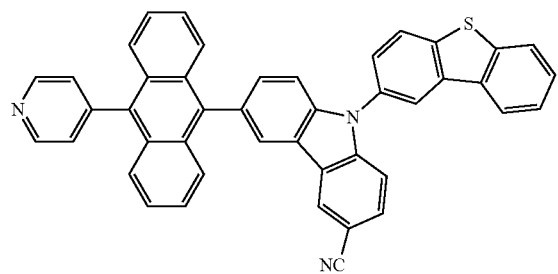
15
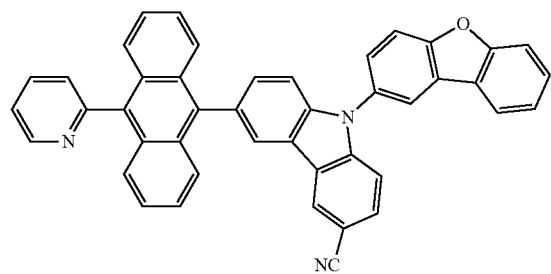
16

-continued
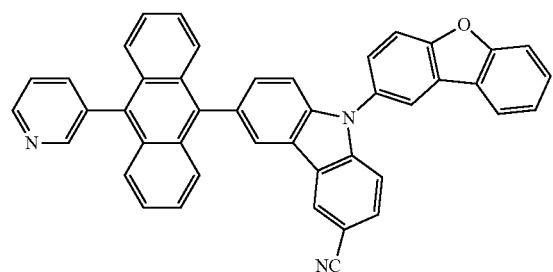
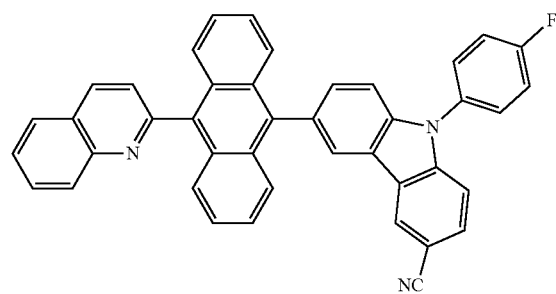
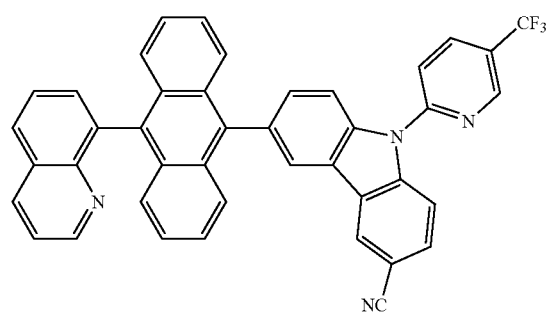
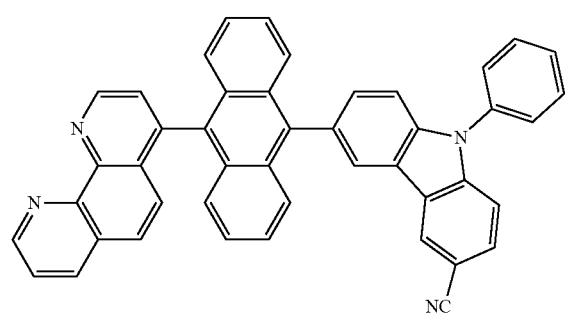
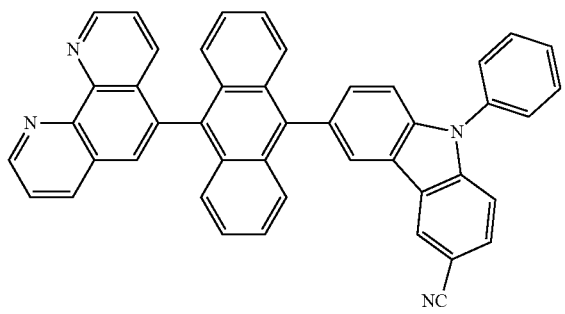

25
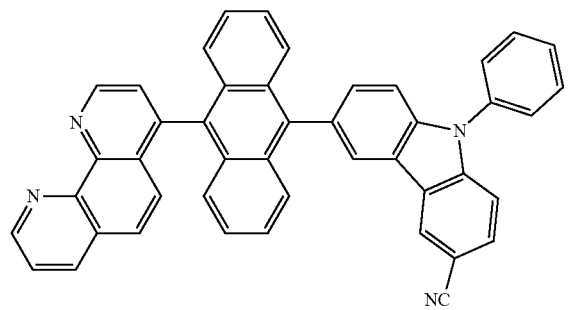
26
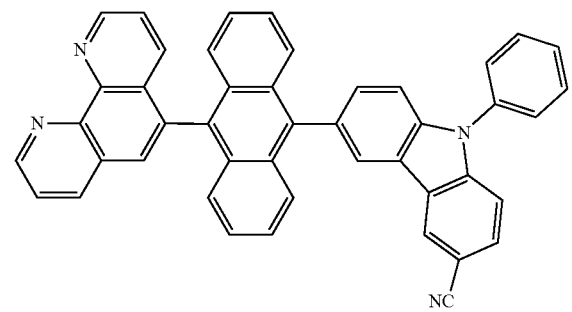
27
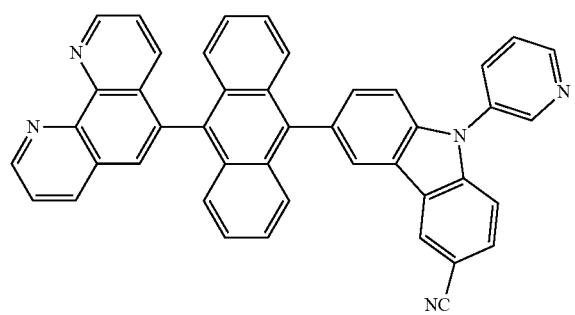
28
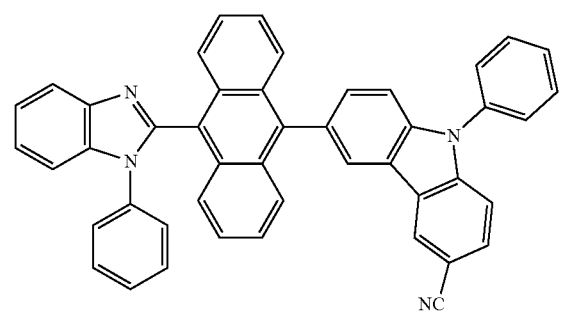
29
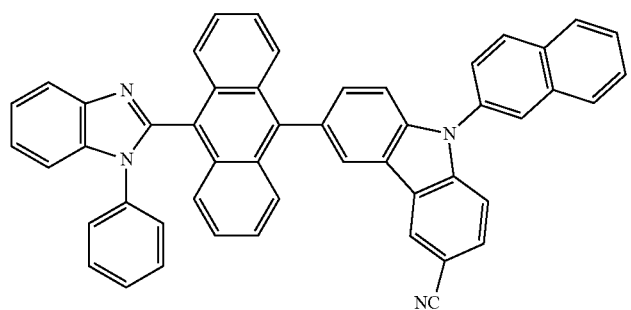
30
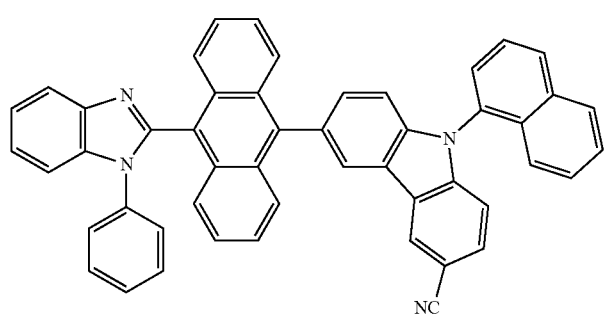

31
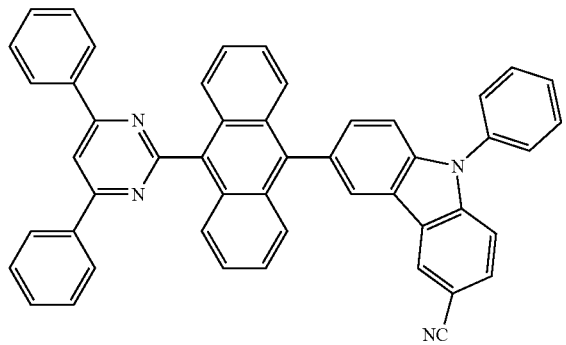
32
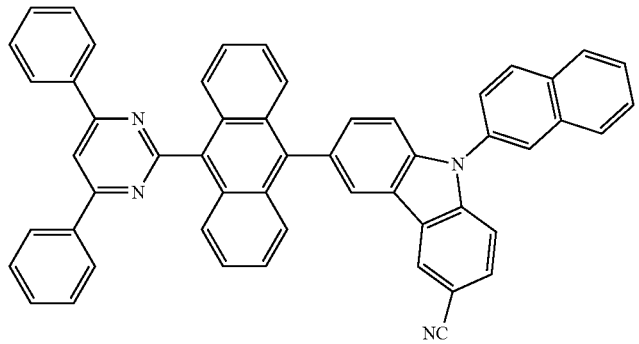
33
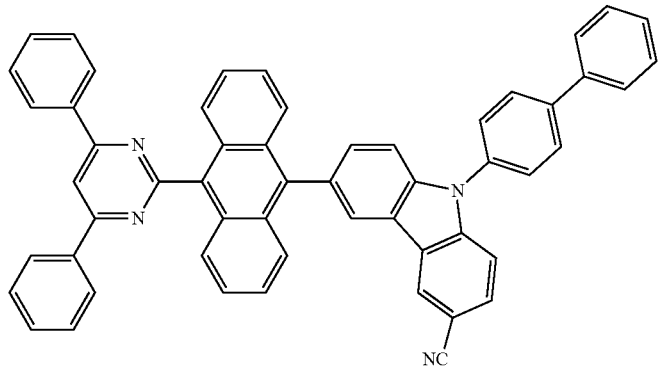
34
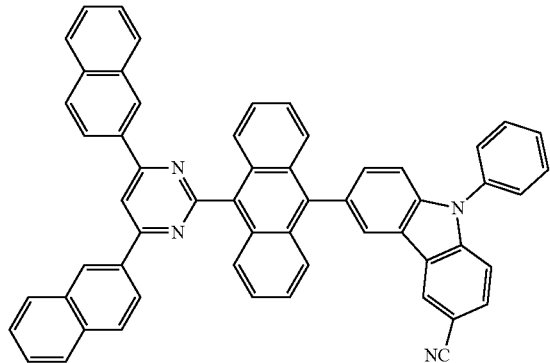
35
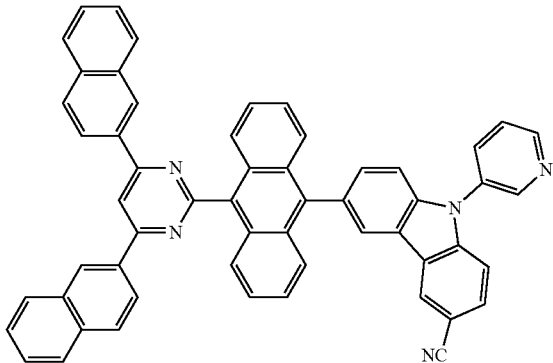

-continued
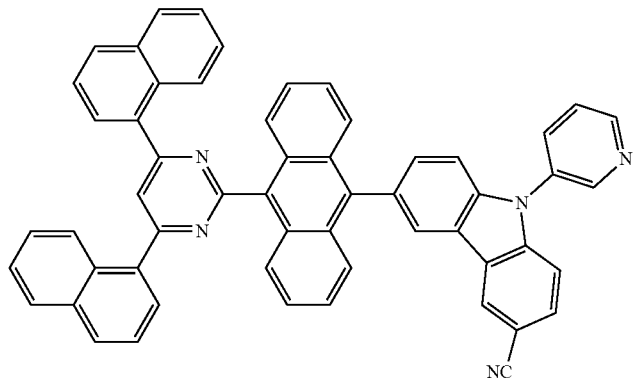
36
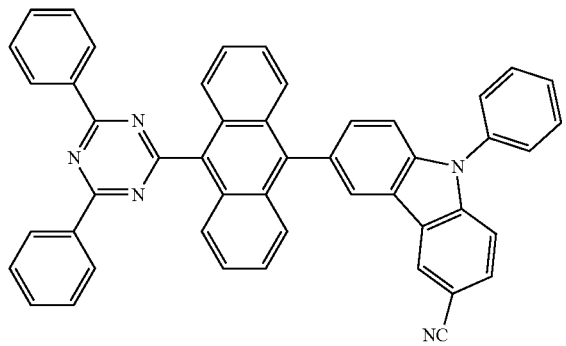
37
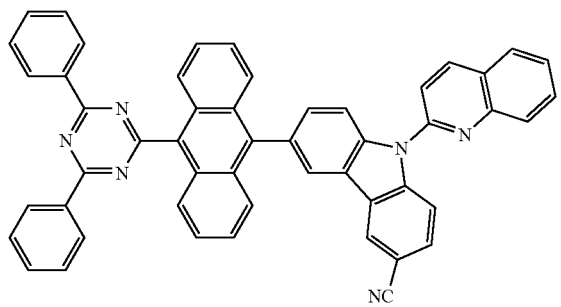
38
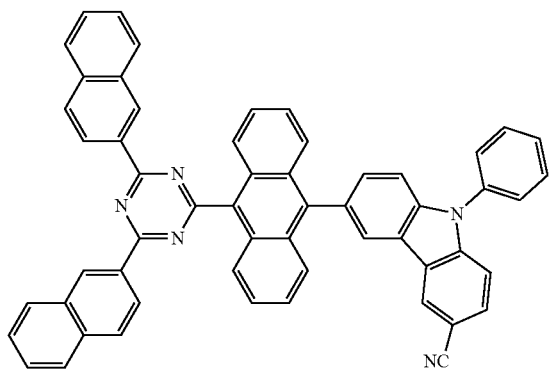
39
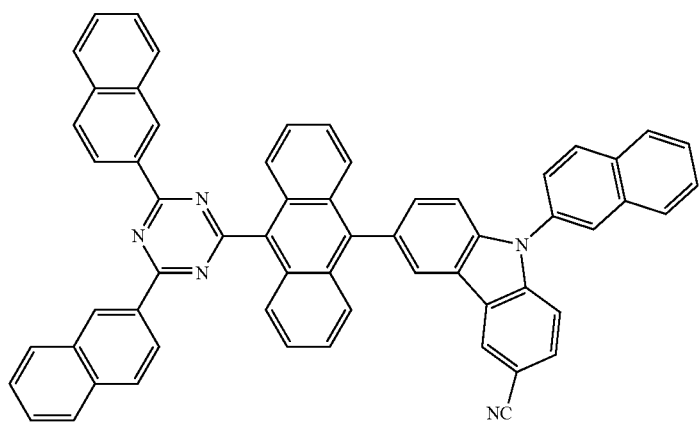
40

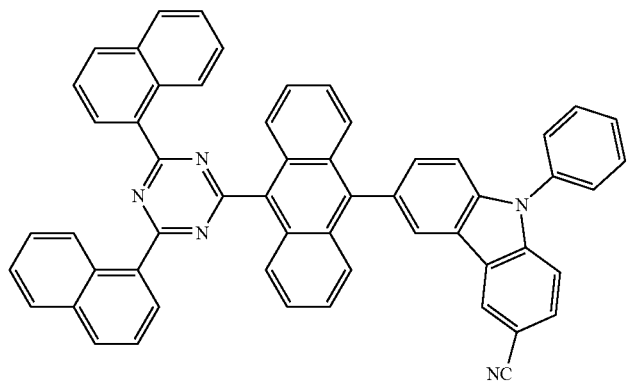
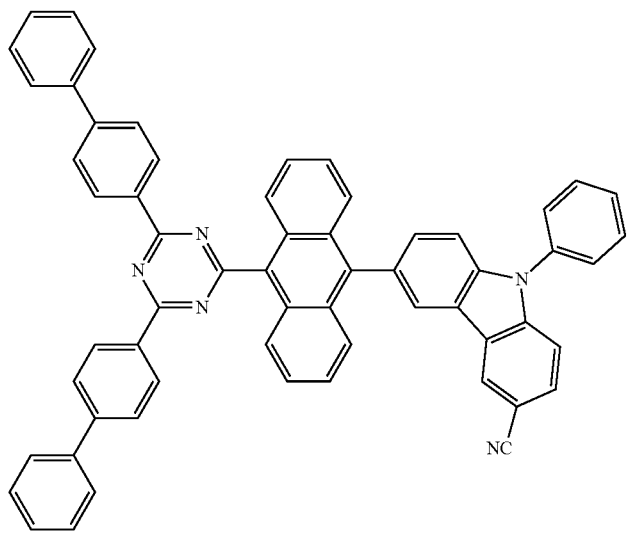
41
42
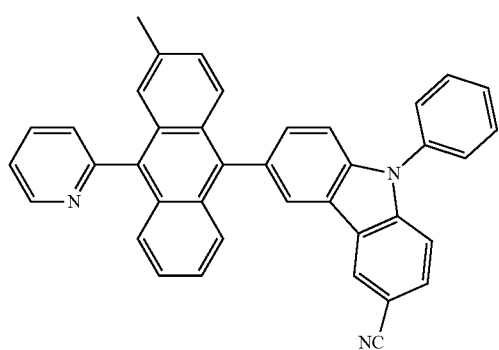
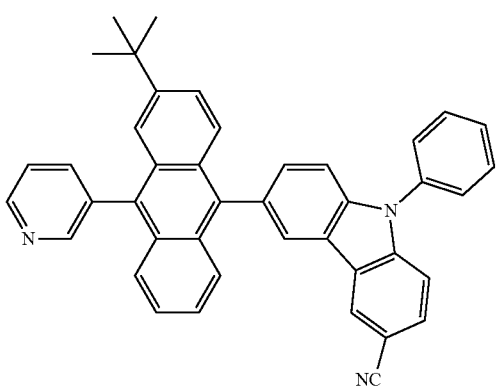
43
44

-continued
45
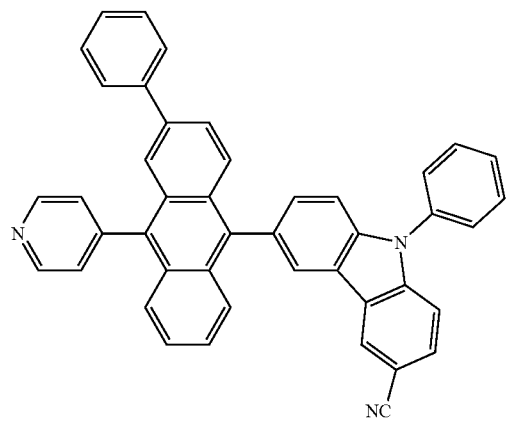
46
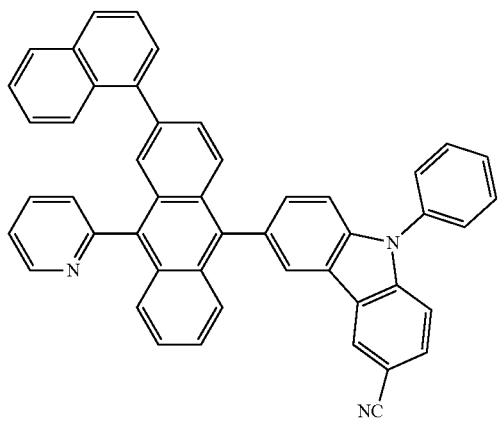
47
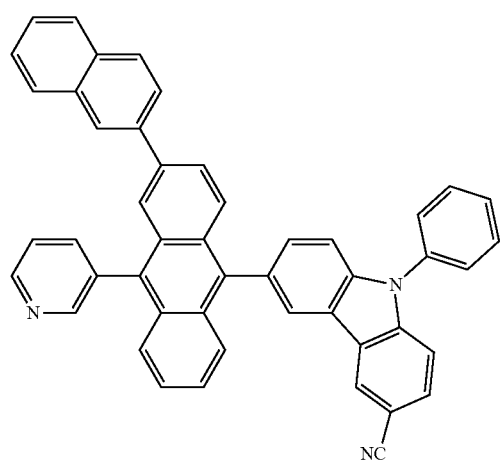
48
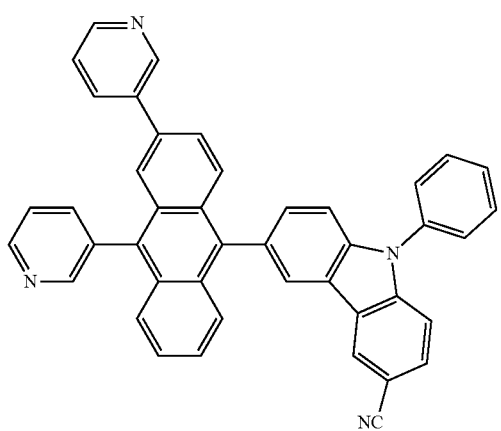
49
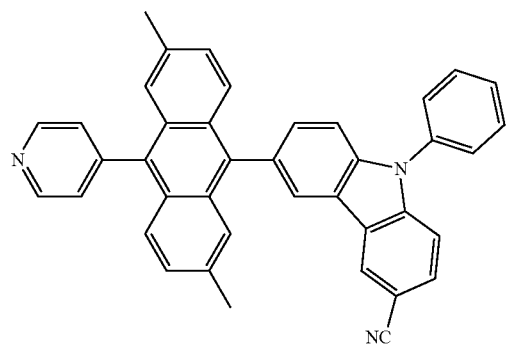
50
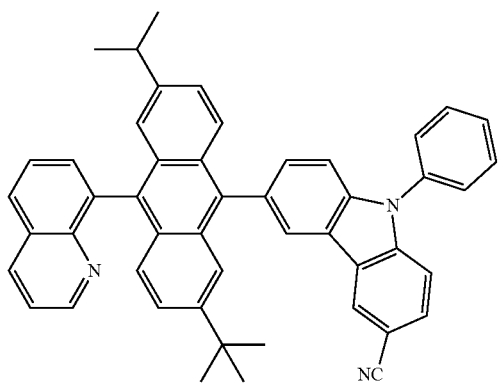

-continued
51
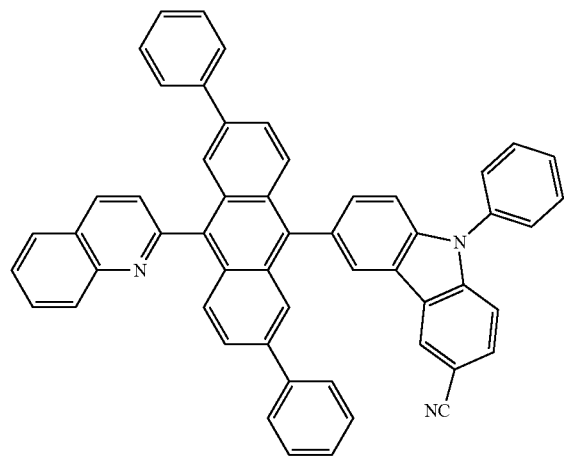
52
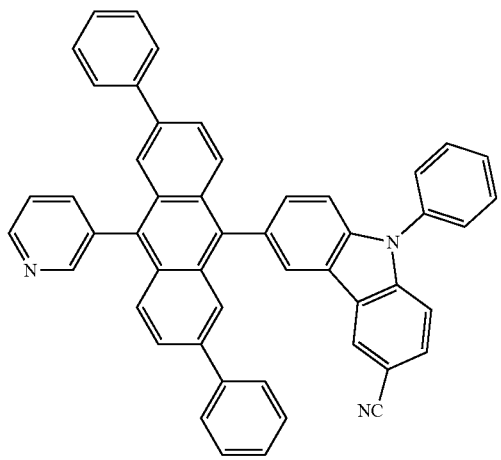
53
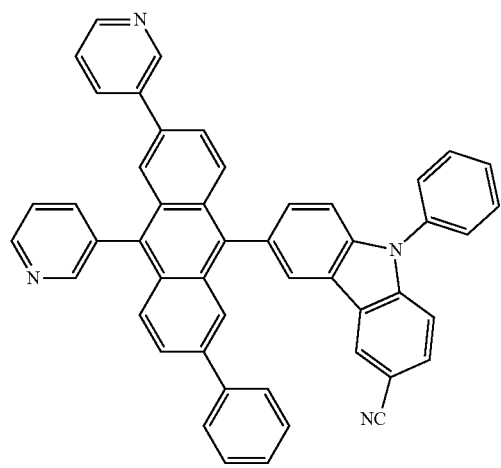
54
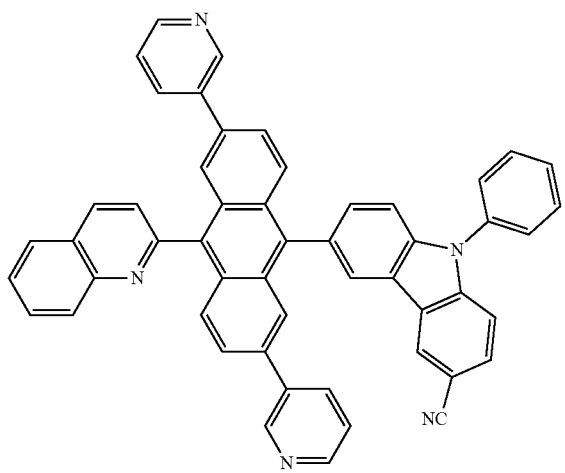
55
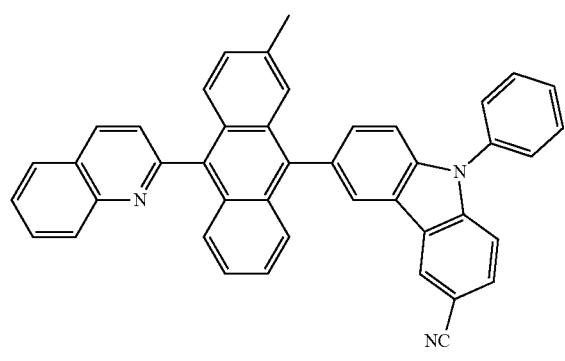
56
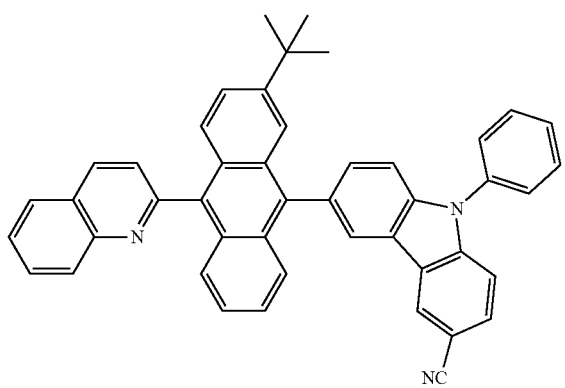

-continued
57
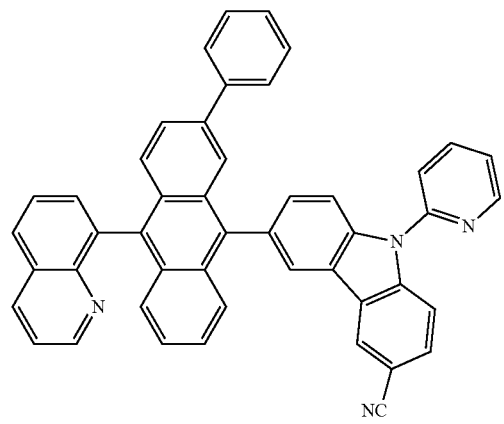
58
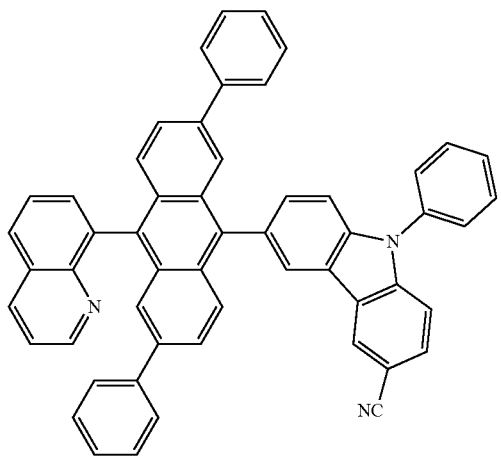
59
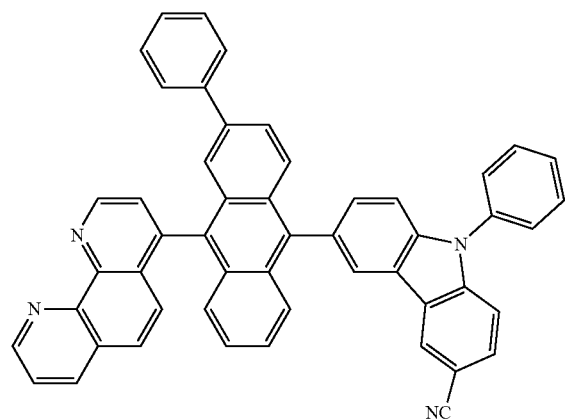
60
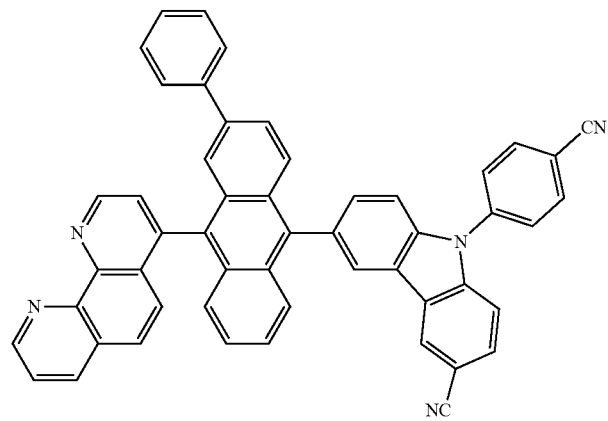

-continued
61
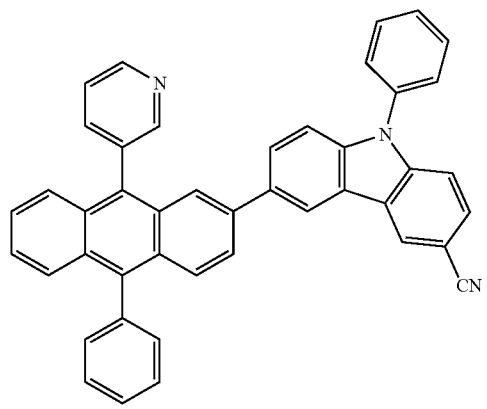
62
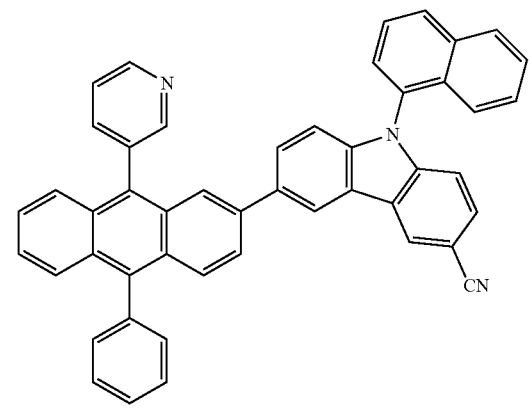
63
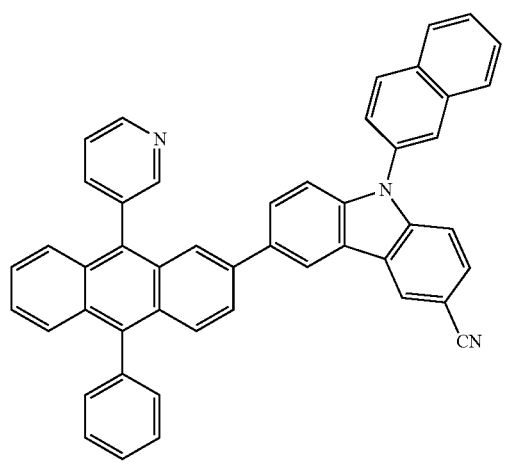
64
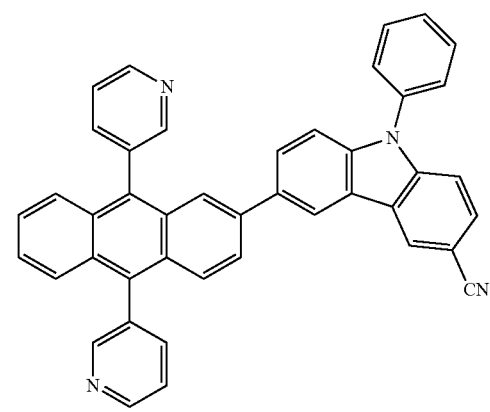
65
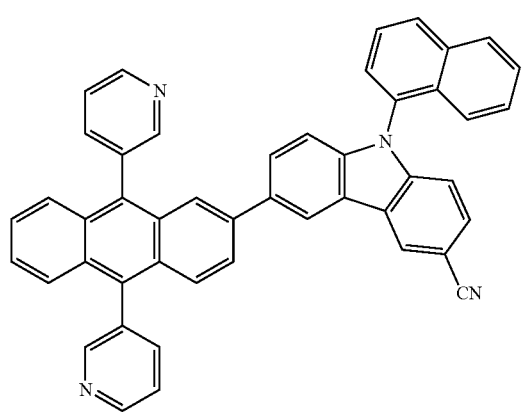
66
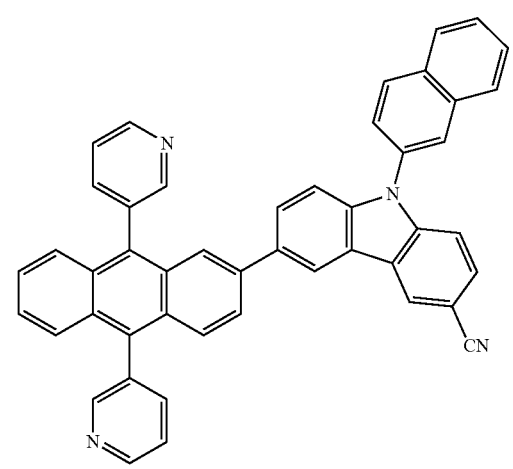

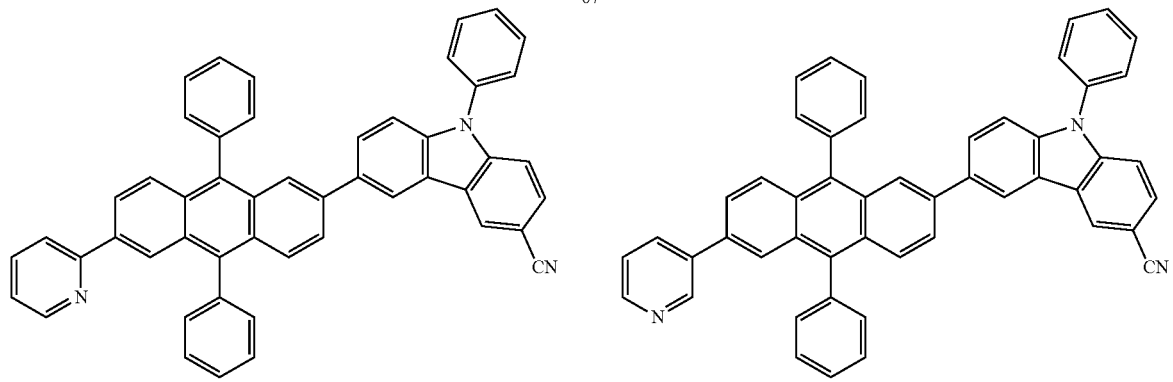
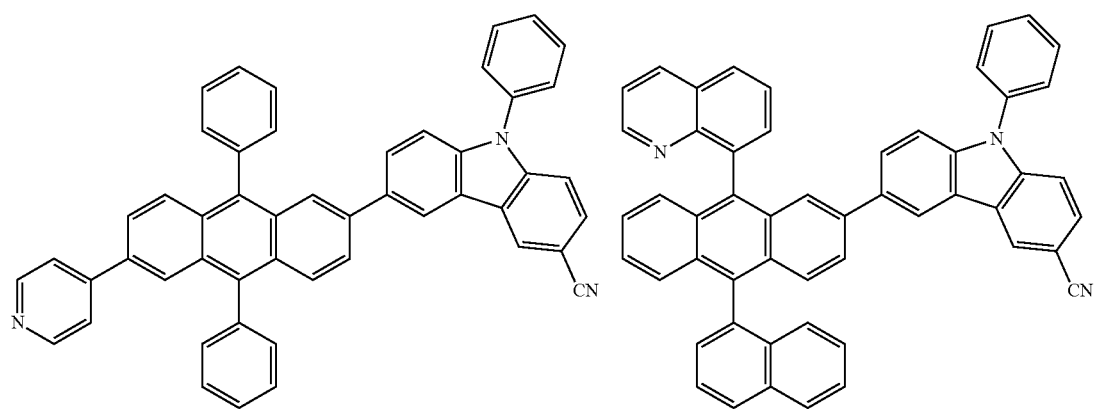
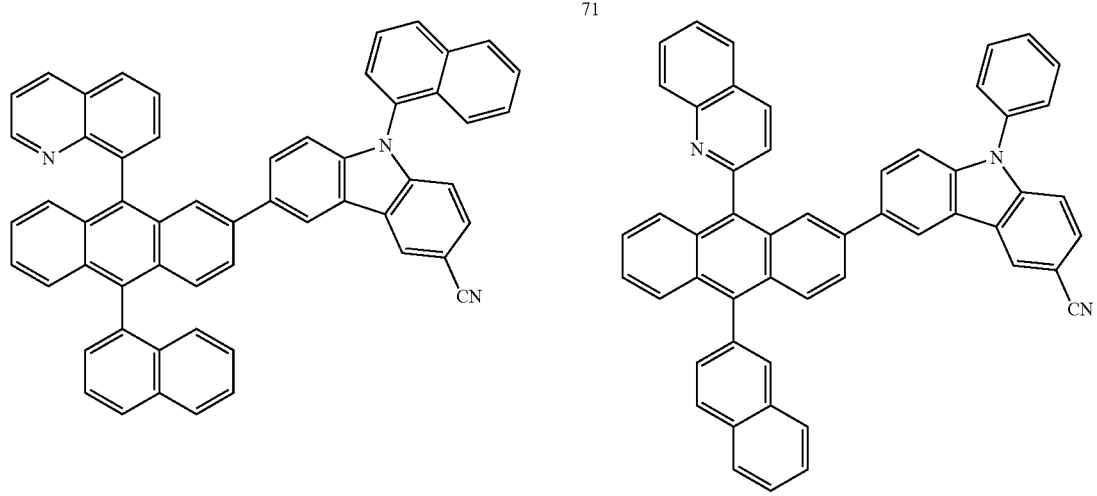

-continued
73
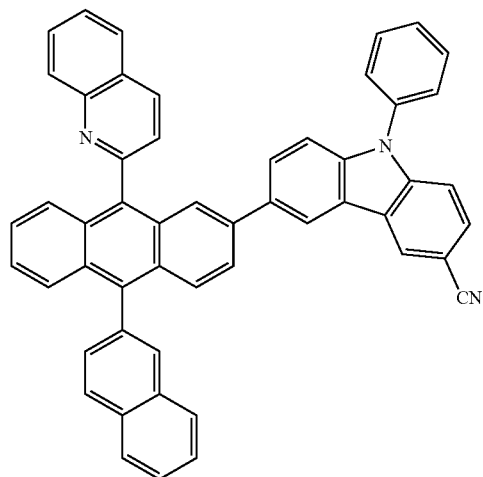
74
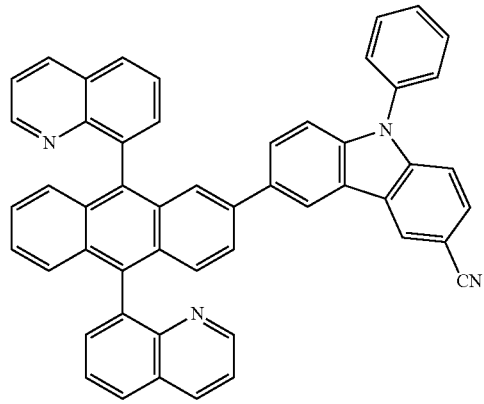
75
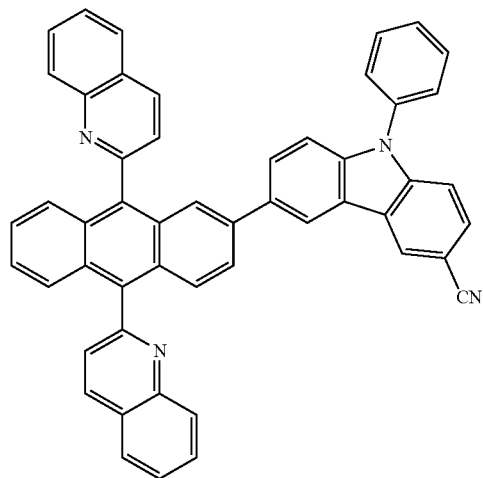
76
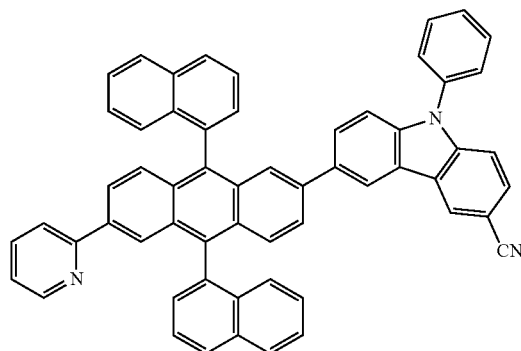
77
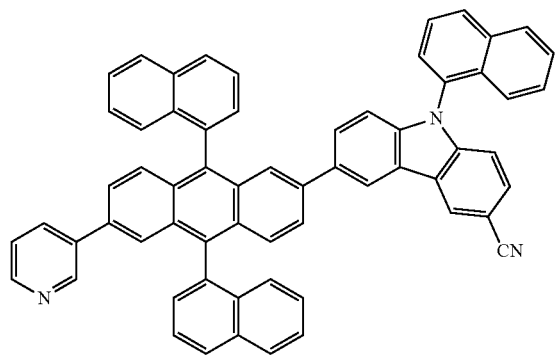

-continued
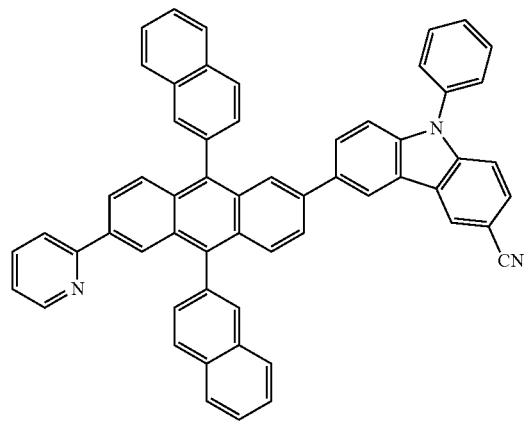
78
79
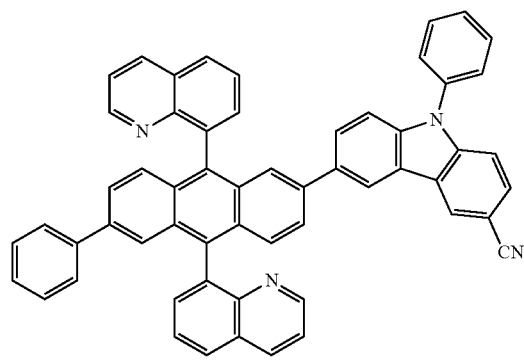
80
81
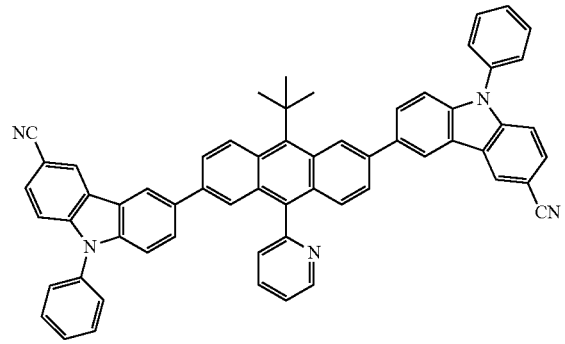
82
83
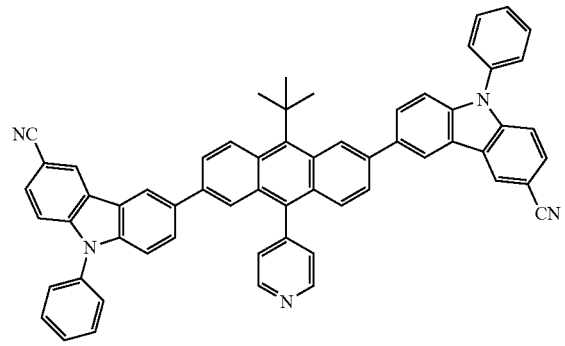
84
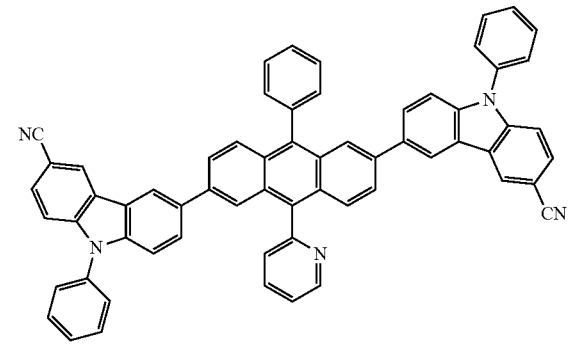
85

-continued
86
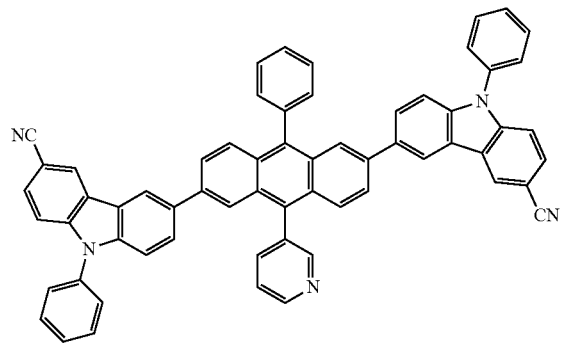
87
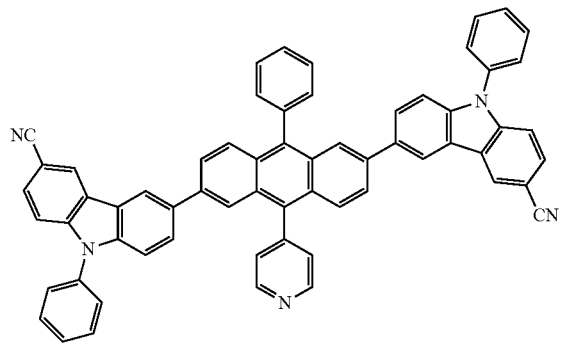
88
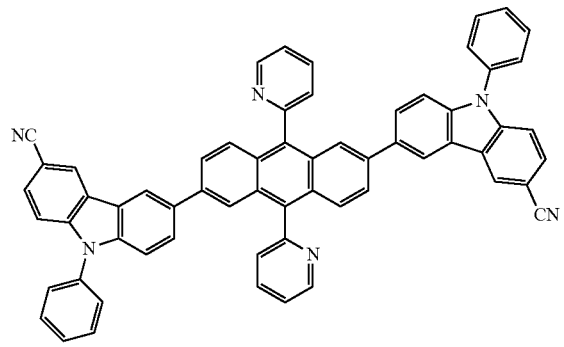
89
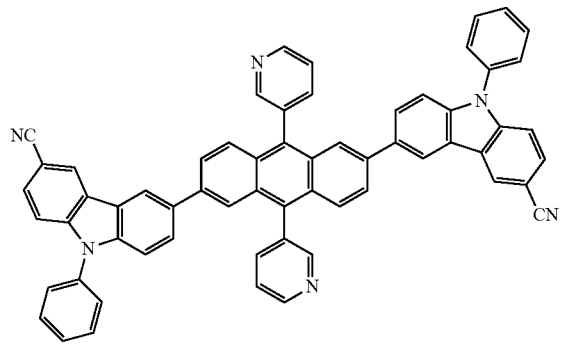
90
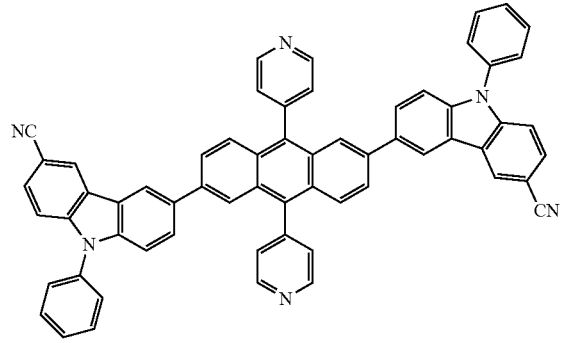
91
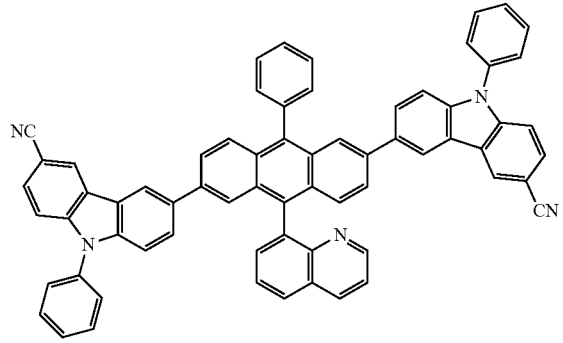
92
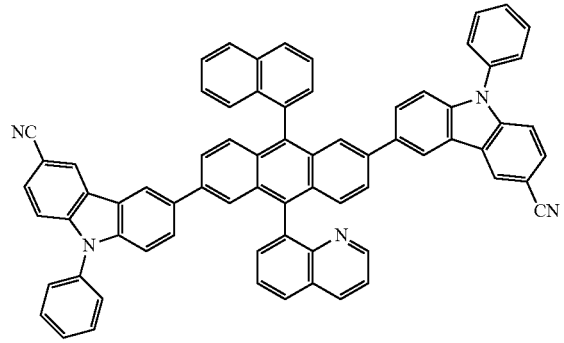
93
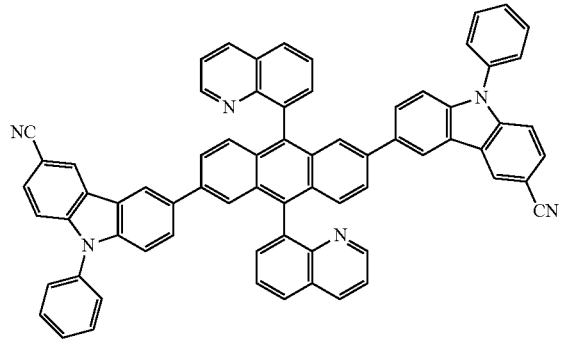

-continued
94
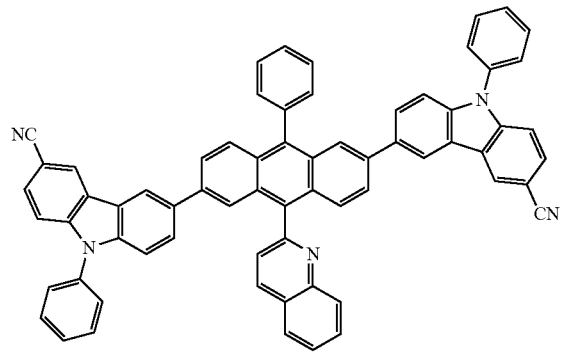
95
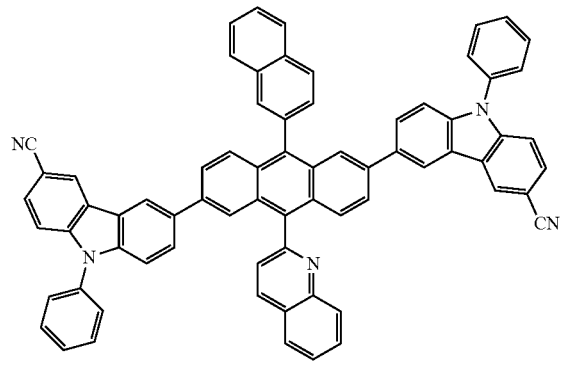
96
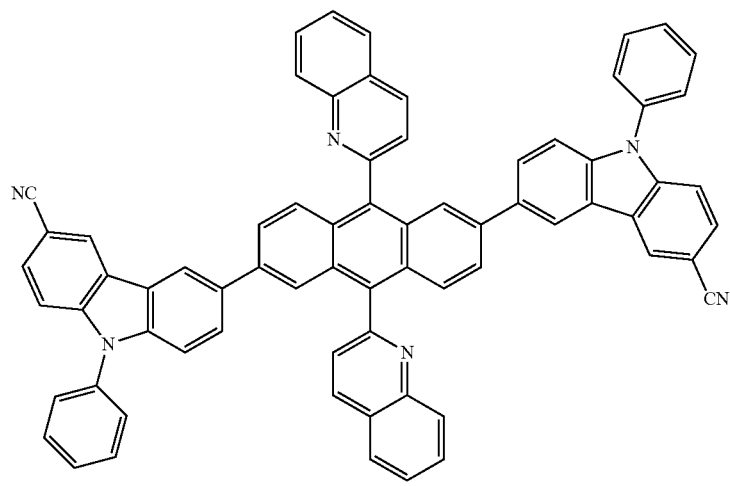
97
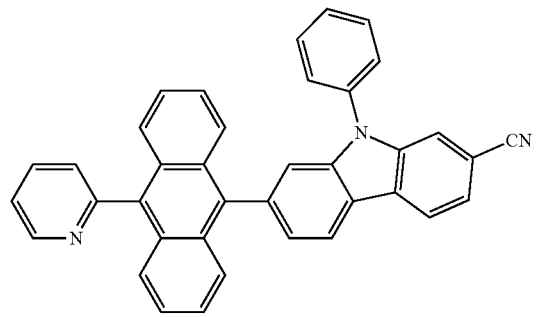
98
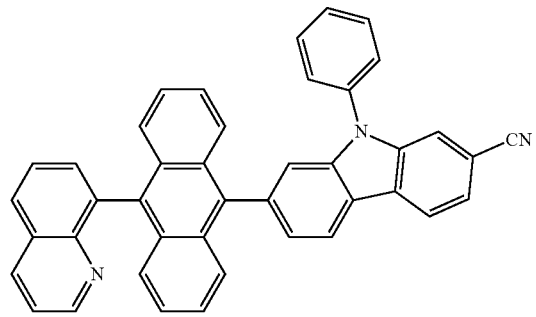
99
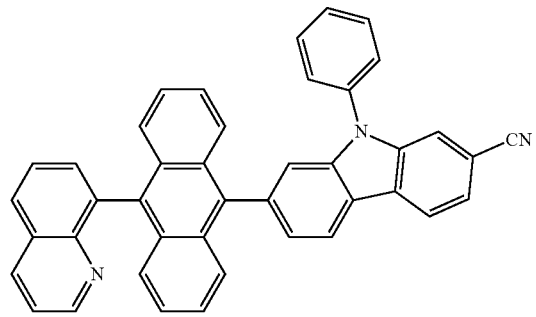
100
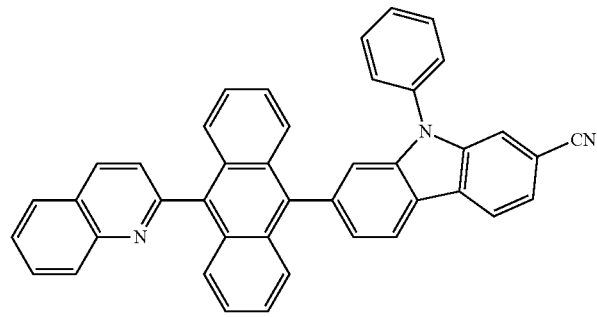

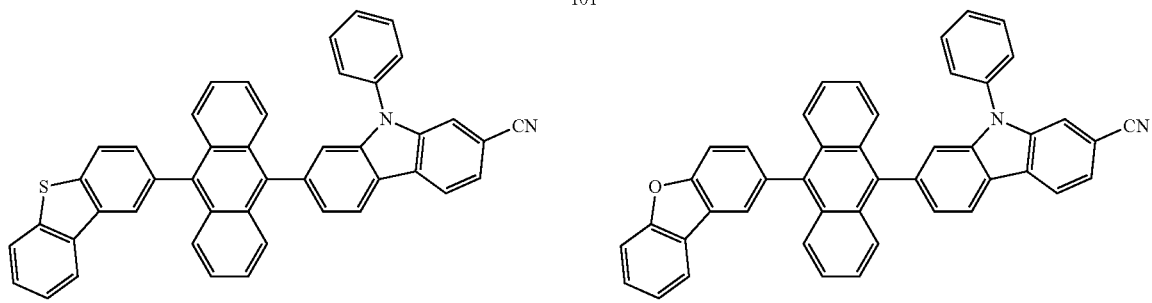

The anthracene-based compound of Formula 1 above may have effective electron transport and injection capabilities. An organic light-emitting device including the anthracene-based compound of Formula 1 as an electron transport material may have an improved efficiency and an improved lifetime.

In particular, the anthracene-based compound of Formula 1 above may include at least one —CN substituted in a carbazole ring, as illustrated in Formula 1' below. The —CN group may induce a string dipole moment in a direction indicated by a double arrow in Formula 1'. The nitrogen atom in the —CN group may form a coordinate bond with a metal ion present in an electron injection layer. In an organic light-emitting device including the anthracene-based compound of Formula 1 above, electrons may be more effectively injected from a cathode to an emission layer.

9-position of the carbazole ring, a conjugate structure between the anthracene ring and the carbazole ring might not be maintained, such that the carbazole ring might not serve as an electron donor.

The anthracene-based compound of Formula 1 above may include a heterogeneous atom such as N, O, or S with higher electronegativity than a carbon (C) atom. Accordingly, the anthracene-based compound of Formula 1 above may have high electrical stability when electrons are transported from a cathode to an emission layer, due to the high electronegativity of the heterogeneous atom.

The anthracene-based compound of Formula 1 above may have a low-symmetric structure, and thus may form a more amorphous organic layer, and consequently may improve the stability of the organic light-emitting device.

<Formula 1'>

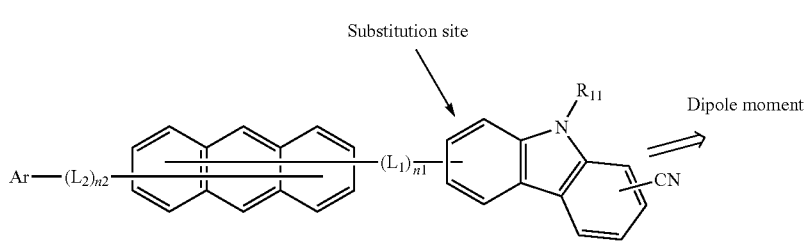

In the anthracene-based compound of Formula 1 above, an anthracene ring may be linked to a position of a carbazole ring other than the 9-position of the carbazole ring, and thus may maintain a conjugate structure with the carbazole ring. The carbazole ring may serve as an electron donor. If the anthracene ring were to be linked to the nitrogen atom at the The carbon atom at the 6-position of the carbazole electronically may be prone to form radicals. However, due to the substitution of —CN at the 6-position of the carbazole ring as illustrated in Formula 1" below, the anthracene-based compound of Formula 1 may be electronically stable.

<Formula 1">

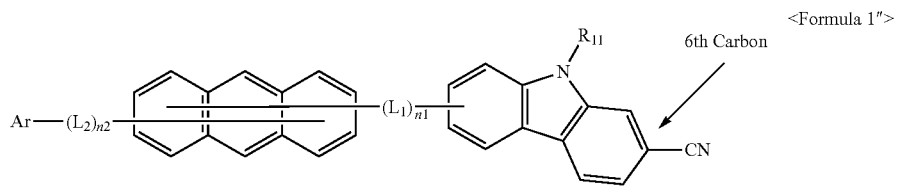

The anthracene-based compound of Formula 1 above may be synthesized using an organic synthesis method. A synthesis method of the anthracene-based compound of Formula 1 above may be understood by those of skill in the art with reference to the examples that will be described below.

At least one of the anthracene-based compounds of Formula 1 above may be used between a pair of electrodes in an organic light-emitting device, for example, in a hole transport region of the organic light-emitting device. For example, at least one of the anthracene-based compounds of Formula 1 above may be used as an electron transport material.

According to another embodiment, an organic light-emitting device may include a first electrode, a second electrode disposed opposite to the first electrode, and an organic layer disposed between the first electrode and the second electrode, wherein the organic layer includes at least one of the anthracene-based compounds of Formula 1 described above.

As used herein, the phrase "wherein the organic layer includes at least one anthracene-based compound" refers to the organic layer including one of the anthracene-based compounds of Formula 1 above, or the organic layer including at least two different anthracene-based compounds of Formula 1 above.

In some implementations, the organic layer may include only Compound 1 above, as an example, as the anthracene-based compound. In this regard, Compound 1 may be present in the electron transport layer of the organic light-emitting device. In other implementations, the organic layer may include Compounds 1 and 2, as examples, as the anthracene-based compound. In this regard, Compound 1 and Compound 2 may be present in the same layer (for example, an ETL) or in different layers (for example, a first ETL and a second ETL, respectively).

The organic layer may include a hole transport region between the first electrode and the emission layer, and an electron transport region between the emission layer and the second electrode. The hole transport region may include at least one of a hole injection layer, a hole transport layer, a functional layer (hereinafter, a "H-functional layer") having both hole injection and hole transport capabilities, a buffer layer, and an electron blocking layer. The electron transport region may include at least one of a hole blocking layer, an electron transport layer, and an electron injection layer.

The term "organic layer" as used herein refers to a single layer and/or a plurality of layers disposed between the first and second electrodes of the organic light-emitting device.

FIG. 1 illustrates a schematic sectional view of an organic light-emitting device 100 according to an embodiment. Hereinafter, a structure of an organic light-emitting device according to an embodiment and a method of manufacturing the same will now be described with reference to FIG. 1.

Referring to FIG. 1, the organic light-emitting device 100 includes a first electrode 120, an organic layer 130, and a second electrode 140. The organic light-emitting device 100 may further include a substrate 110.

The substrate 110, which may be a suitable substrate for use in OLEDs. For example, the substrate 110 may be a glass substrate or a transparent plastic substrate with excellent mechanical strength, thermal stability, transparency, surface smoothness, ease of handling, and water resistance.

The first electrode 120 may be formed by depositing or sputtering a first electrode-forming material on the substrate 110. When the first electrode 120 constitutes an anode, a material having a high work function may be used as the first electrode-forming material to facilitate hole injection. The first electrode 120 may be a reflective electrode or a transmissive electrode. Transparent and conductive materials such as ITO, IZO, $SnO_2$, and ZnO may be used to form the first electrode. The first electrode 120 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 120 may have a single-layer structure or a multi-layer structure including at least two layers. For example, the first electrode 120 may have a three-layered structure of ITO/Ag/ITO.

The organic layer 130 may be disposed on the first electrode 120. The organic layer 130 may include an emission layer (EML) 133.

The organic layer 130 may include a hole transport region between the first electrode 120 and the EML 133. The hole transport region may include at least one layer selected from a hole injection layer (HIL) 131, a hole transport layer (HTL) 132, a functional layer having both hole injection and transport capabilities (hereinafter, referred to as a H-functional layer), and an electron blocking layer.

The organic layer 130 may include an electron transport region between the EML 133 and the second electrode 140. The electron transport region may include at least one layer selected from an electron transport layer 134, an electron injection layer 130, and a hole blocking layer.

The HIL 131 may be formed on the first electrode 120 by a suitable method, for example, including vacuum deposition, spin coating, casting, Langmuir-Blodgett (LB) deposition, or the like.

When the HIL 131 is formed using vacuum deposition, vacuum deposition conditions may vary depending on the compound that is used to form the HIL and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec.

When the HIL 131 is formed using spin coating, the coating conditions may vary depending on the compound that is used to form the HIL and the desired structure and thermal properties of the HIL to be formed. For example, the coating rate may be in the range of about 2,000 rpm to about 5,000 rpm. A temperature at which heat treatment is performed to remove a solvent after coating may be in the range of about 80° C. to about 200° C.

A material for forming the HIL 131 may be a suitable hole injecting material. Examples of the hole injecting material include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris(N,N-diphenylamino)triphenylamine (TDATA), 4,4',4''-tris[2-naphthyl(phenyl)amino]triphenylamine) (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), or polyaniline/poly(4-styrenesulfonate (PANI/PSS).

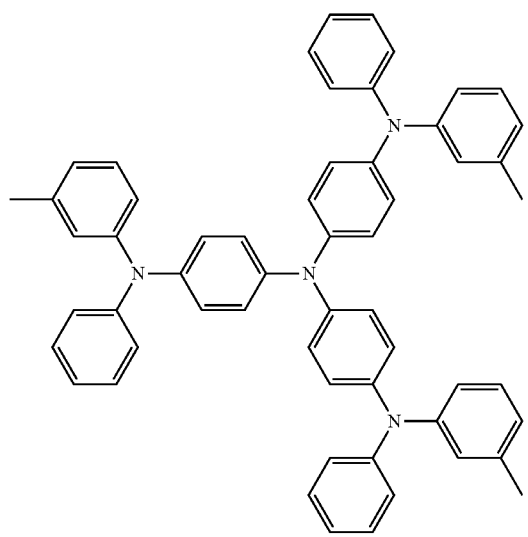

m-MTDATA

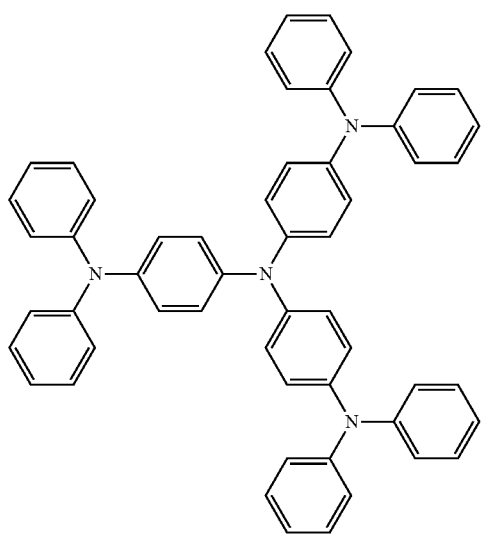

TDATA

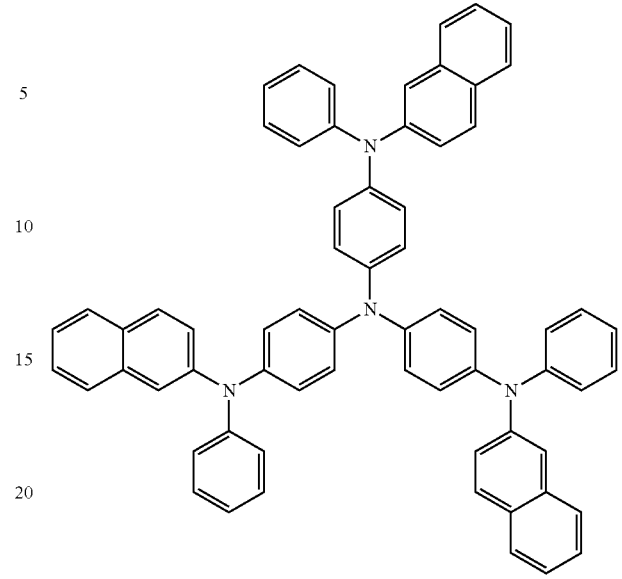

2-TNATA

The thickness of the HIL 131 may be about 100 Å to about 10,000 Å, and in some implementations, may be from about 100 Å to about 1,000 Å. When the thickness of the HIL 131 is within these ranges, the HIL may have good hole injecting ability without a substantial increase in driving voltage.

The HIL 131 may further include a p-dopant, in addition to such a HIL material as described above, to have improved conductivity. Examples of the p-dopant include quinone derivatives such as tetracyanoquinonedimethane (TCNQ), 2,3,5,6-tetrafluoro-tetracyano-1,4-benzoquinonedimethane (F4TCNQ), or the like; metal oxides such as tungsten oxide, molybdenum oxide, and the like; and cyano-containing compounds such as Compound 100 below.

<Compound 100>

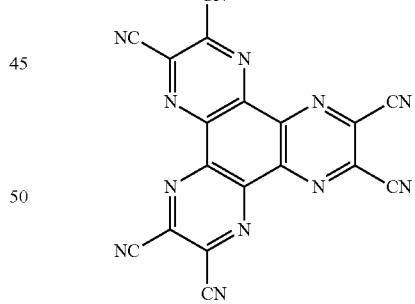

When the HIL 131 further includes such a p-dopant as described above, the p-dopant may be homogeneously dispersed or inhomogeneously distributed in the HIL 131.

Then, the HTL 132 may be formed on the HIL 131 by a suitable method, for example, vacuum deposition, spin coating, casting, Langmuir-Blodgett (LB) deposition, or the like. When the HTL 132 is formed using vacuum deposition or spin coating, the conditions for deposition and coating may be similar to those for the formation of the HIL 131, though the conditions for the deposition and coating may vary depending on the material that is used to form the HTL 132.

Examples of suitable hole transport materials include carbazole derivatives, such as N-phenylcarbazole or polyvinylcarbazole, N,N'-bis(3-methylphenyl)-N,N-diphenyl-[1,1-biphenyl]-4,4'-diamine, 4,4',4''-tris(N-carbazolyl)triphenylamine (TCTA), and N,N'-di(1-naphthyl)-N,N'-diphenylbenzidine) (NPB).

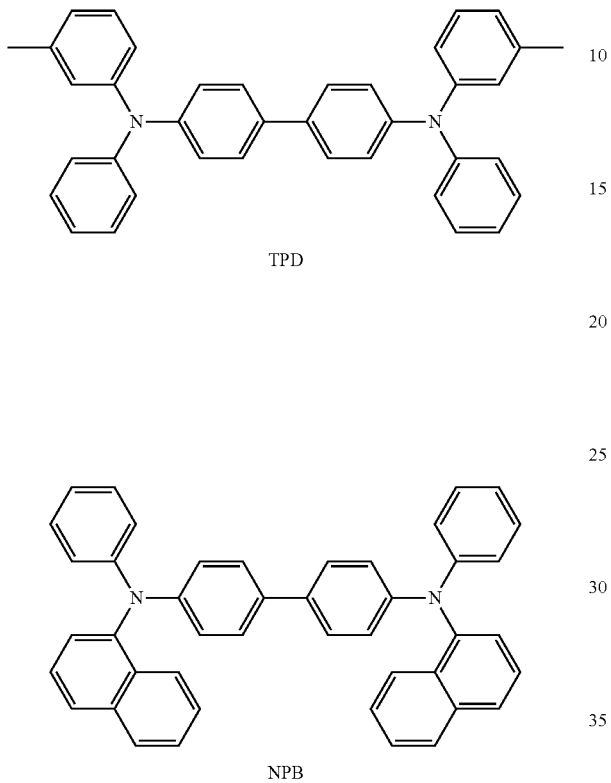

The thickness of the HTL 132 may be from about 50 Å to about 2,000 Å, and in some implementations, may be from about 100 Å to about 1,500 Å. When the thickness of the HTL 132 is within these ranges, the HTL 132 may have good hole transporting ability without a substantial increase in driving voltage.

The H-functional layer (having both hole injection and hole transport capabilities) may include at least one material from each group of the above-listed hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some implementations, at least one of the HIL 131, HTL 132, and H-functional layer may include at least one of a compound of Formula 300 below and a compound of Formula 350 below:

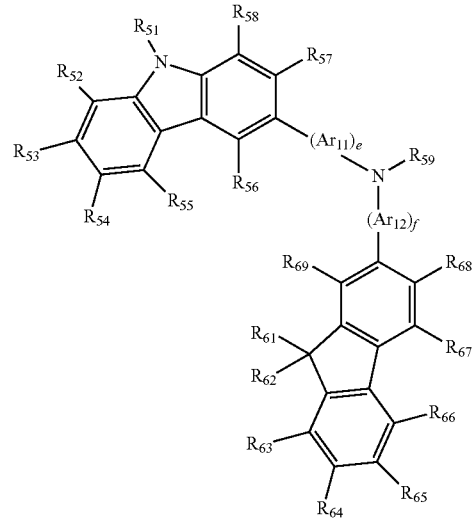

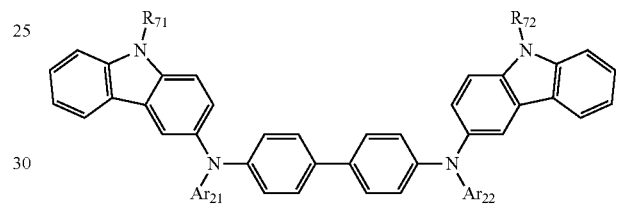

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. For example, e may be 1, and f may be 0.

In Formulae 300 and 350 above, $R_{51}$ to $R_{58}$, $R_{61}$ to $R_{69}$, and $R_{71}$ and $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

<Formula 300A>

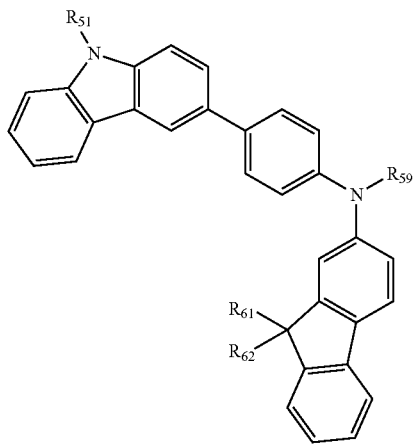

In Formula 300A, $R_{51}$, $R_{60}$, $R_{61}$, and $R_{59}$ may be as defined above.

In some non-limiting embodiments, at least one of the HIL, HTL, and H-functional layer may include at least one of compounds represented by Formulae 301 to 320 below:

301

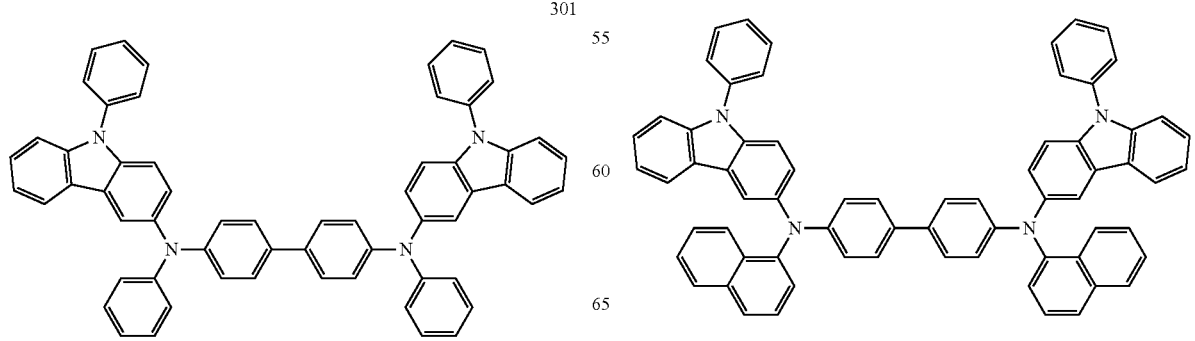

302

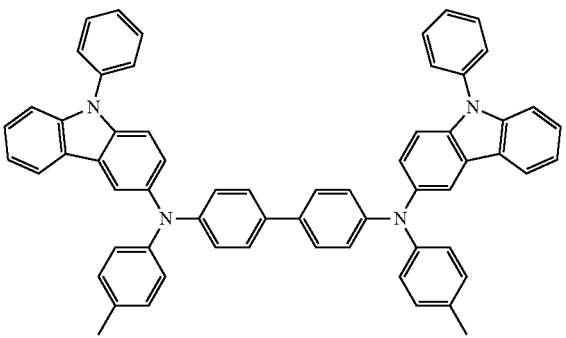

303

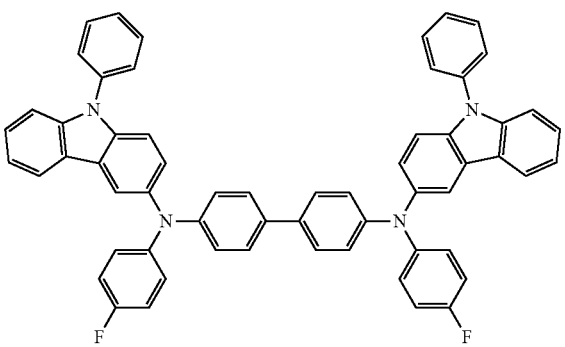

304

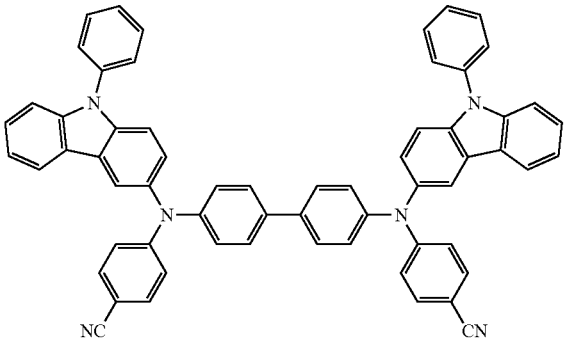

305

111
-continued
306
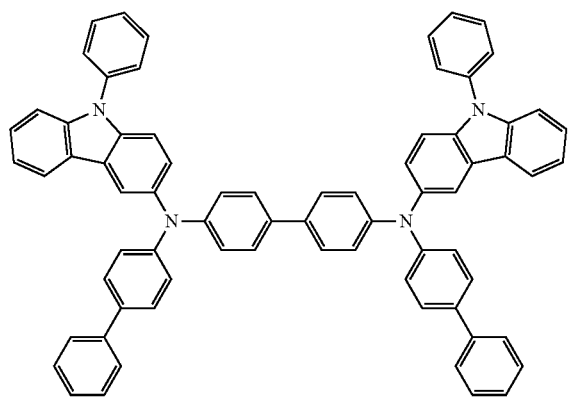
307
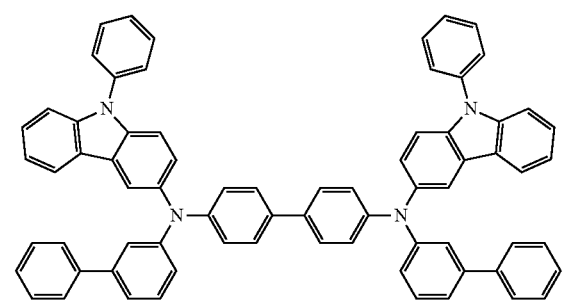
308
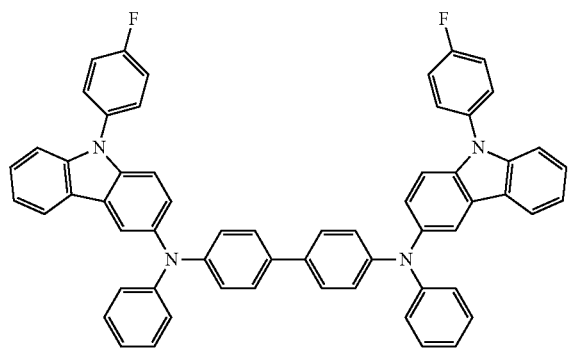
309
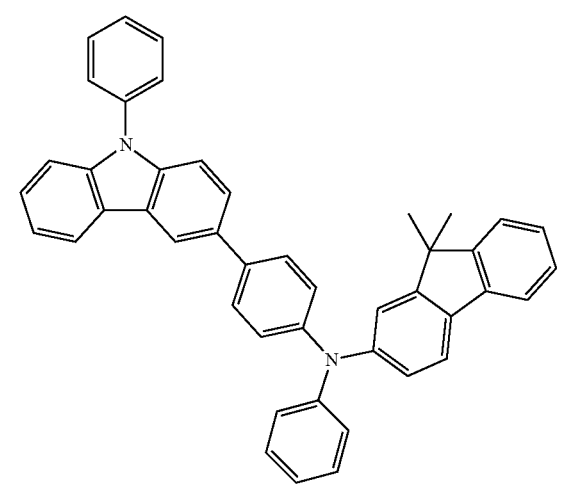
112
-continued
310
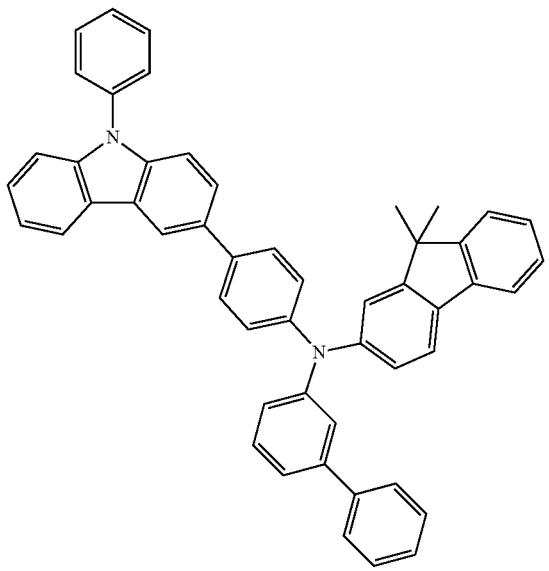
311
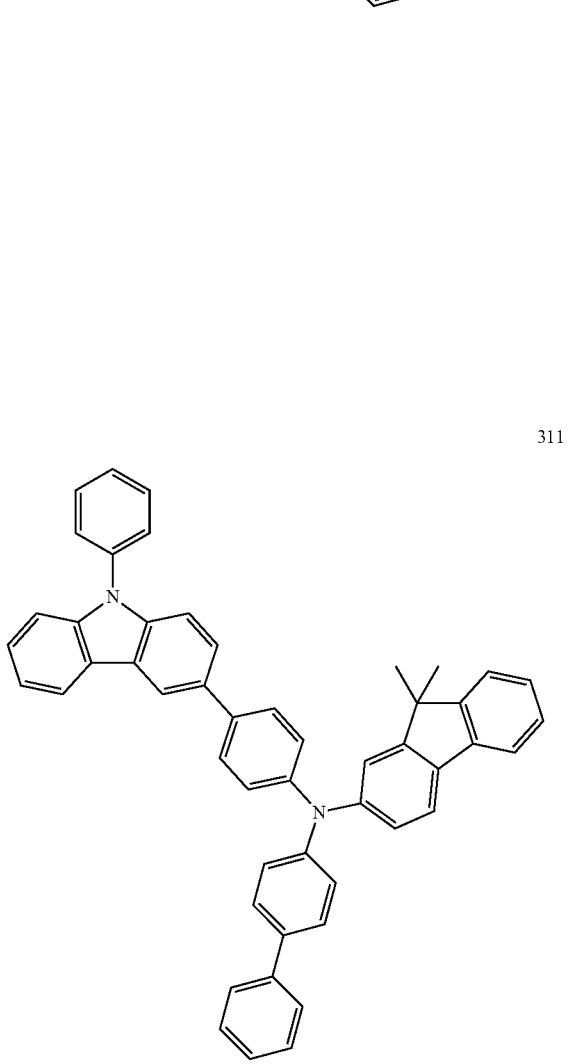

113
-continued
312
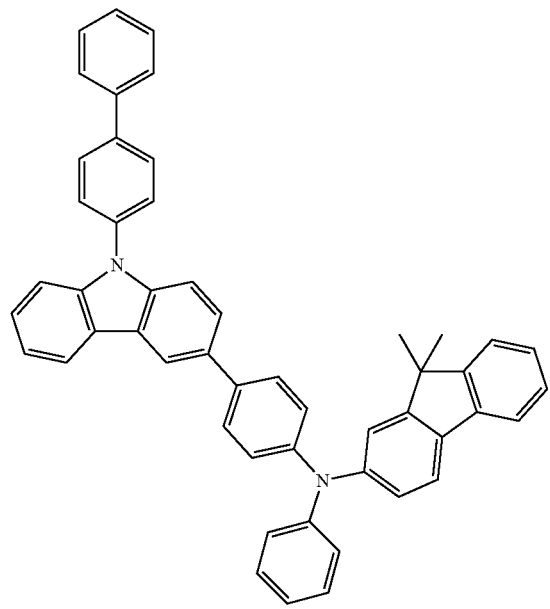
313
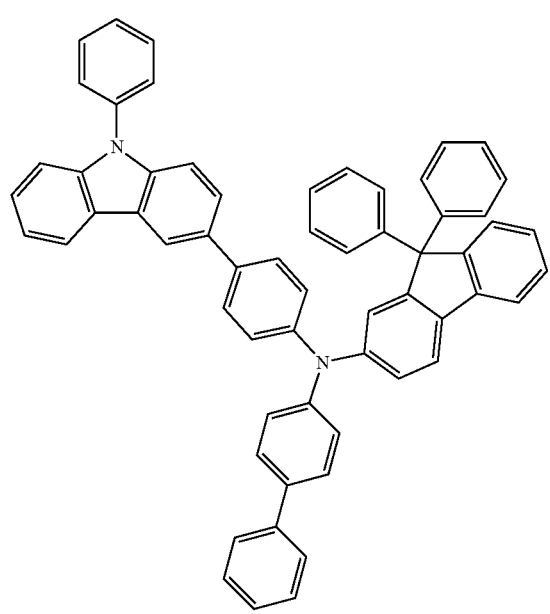
114
-continued
314
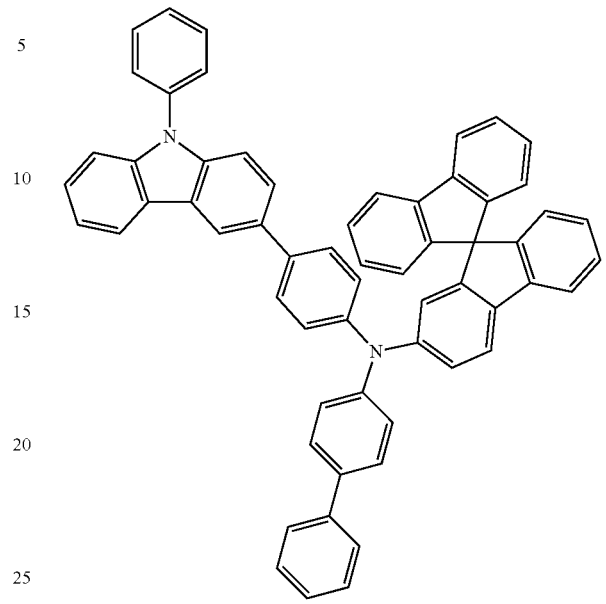
315
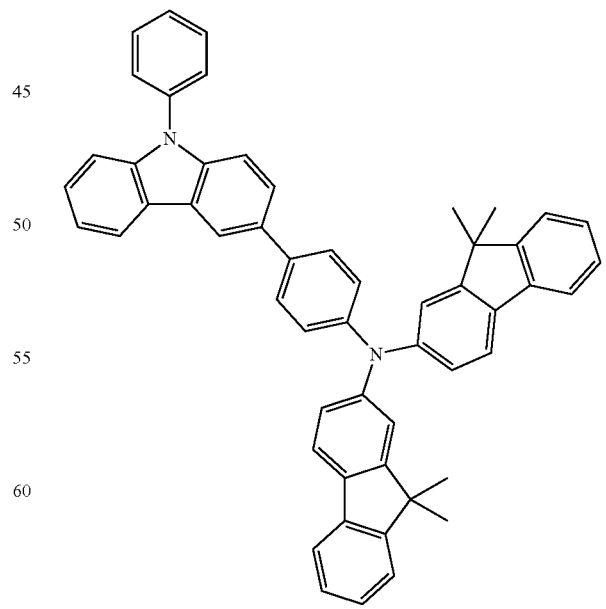

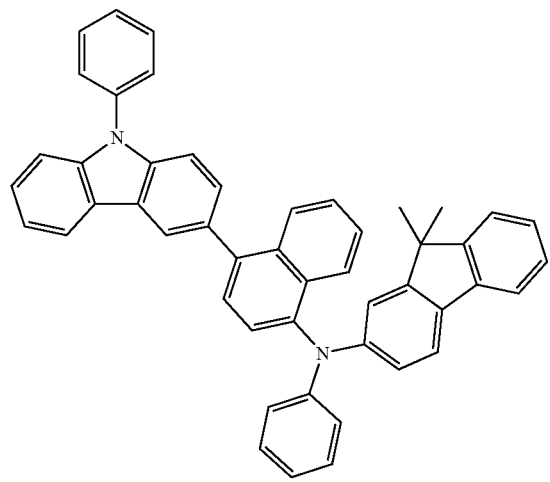

316

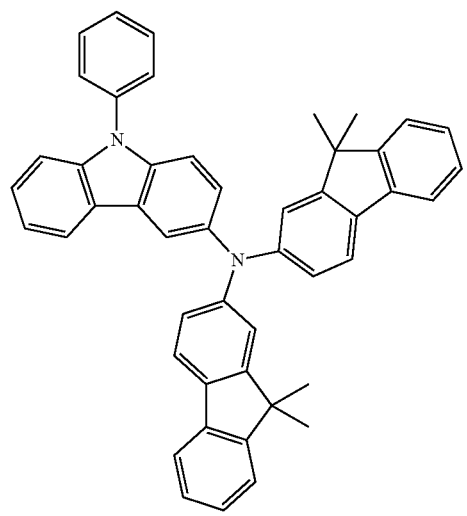

317

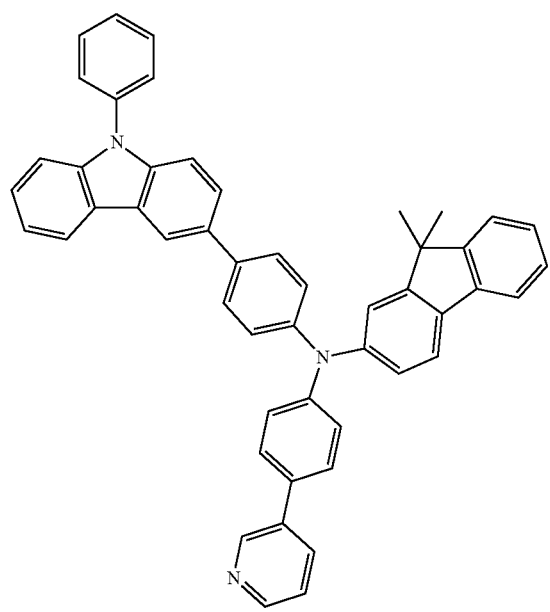

318

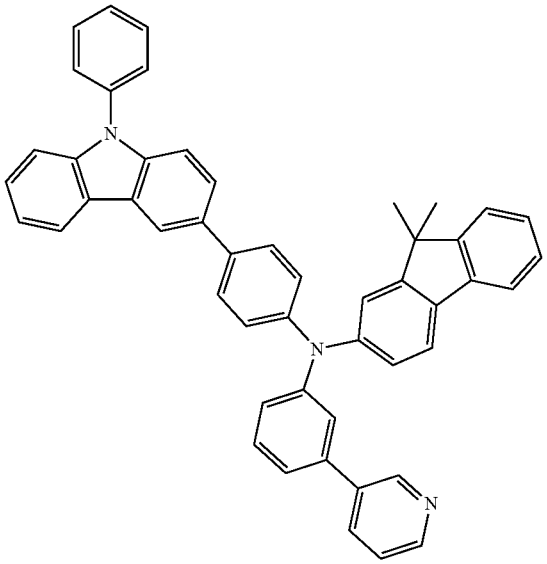

319

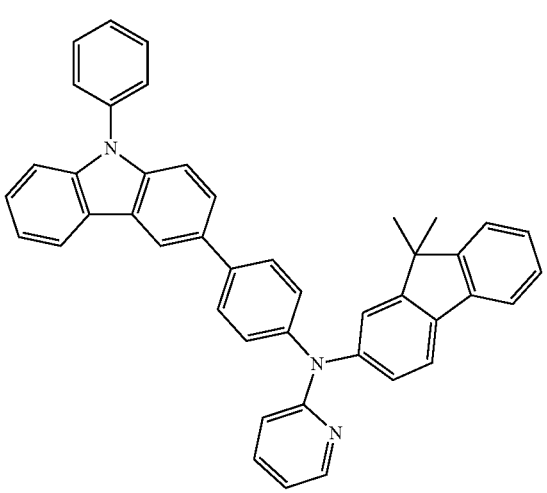

320

At least one of the HIL 131, HTL 132, and H-functional layer may further include a p-dopant to have improved conductivity, in addition to a suitable hole injecting material, hole transport material, and/or material having both hole injection and hole transport capabilities as described above.

For example, the p-dopant may be a quinine derivatives, a metal oxide, or compounds with a cyano group. Examples of the p-dopant are quinone derivatives such as tetracyano-quinonedimethane (TCNQ), 2,3,5,6-tetrafluoro-tetracyano-1,4-benzoquinonedimethane (F4-TCNQ), or the like; metal oxides such as tungsten oxide, molybdenum oxide, or the like; and cyano-containing compounds such as Compound 200 below.

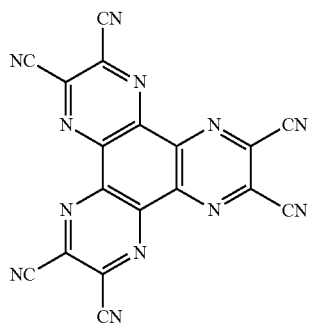

<Compound 200>

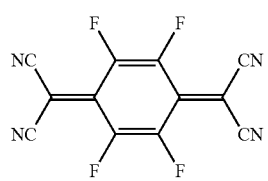

<F4-TCNQ>

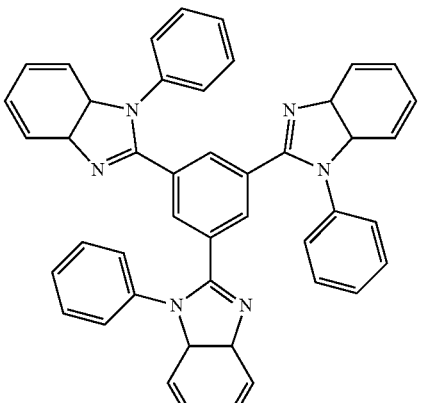

TPBI

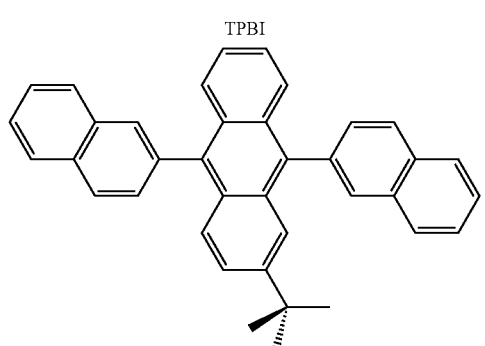

TBADN

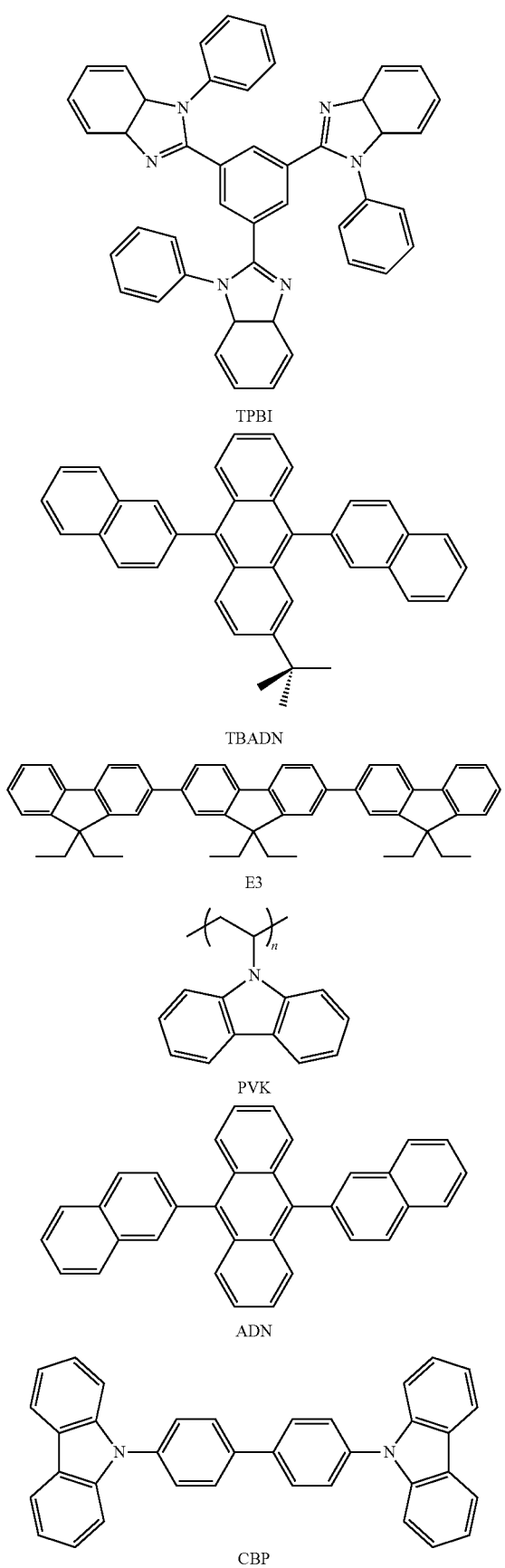

E3

PVK

ADN

CBP

When the HIL 131, HTL 132, or H-functional layer further includes a p-dopant, the p-dopant may be homogeneously dispersed or inhomogeneously distributed in the layer.

A buffer layer (not shown) may be disposed between at least one of the HIL 131, HTL 132, and H-functional layer, and the EML 133. The buffer layer may compensate for an optical resonance distance of light according to a wavelength of the light emitted from the EML 133, and thus may increase efficiency. The buffer layer may include a suitable hole injecting material or hole transporting material. In some other embodiments, the buffer layer may include the same material as one of the materials included in the HIL 131, HTL 132, and H-functional layer that underlie the buffer layer.

The EML 133 may be formed on the HTL 132, H-functional layer, or buffer layer by vacuum deposition, spin coating, casting, Langmuir-Blodget (LB) deposition, or the like. When the EML 133 is formed using vacuum deposition or spin coating, the deposition and coating conditions may be similar to those for the formation of the HIL 131, though the conditions for deposition and coating may vary depending on the material that is used to form the EML 133.

The EML 133 may include a suitable light-emitting material. For example, the EML 133 may include a suitable host and a suitable dopant.

Examples of a suitable host include $Alq_3$, 4,4'-N,N'-dicarbazole-biphenyl (CBP), poly(n-vinylcarbazole) (PVK), 9,10-di(naphthalene-2-yl)anthracene (DNA), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

119
-continued
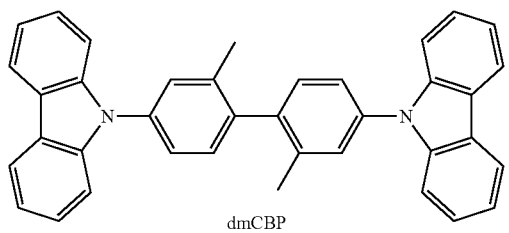
dmCBP
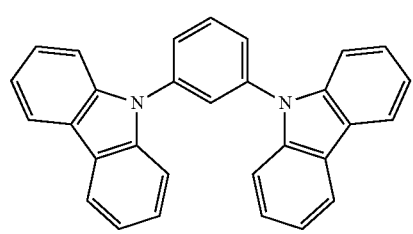
501
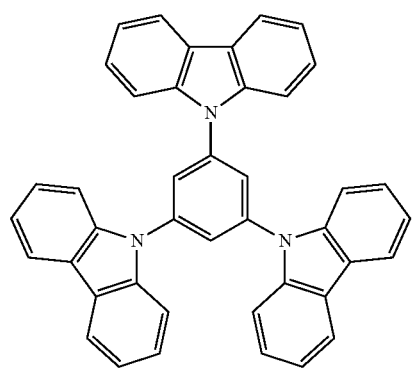
502
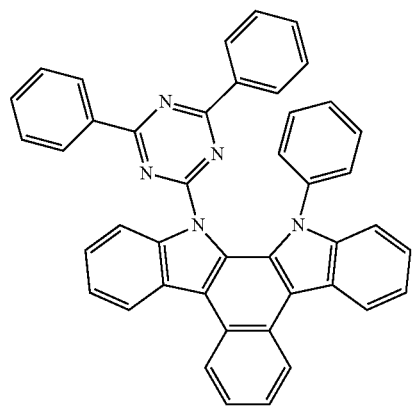
503
120
-continued
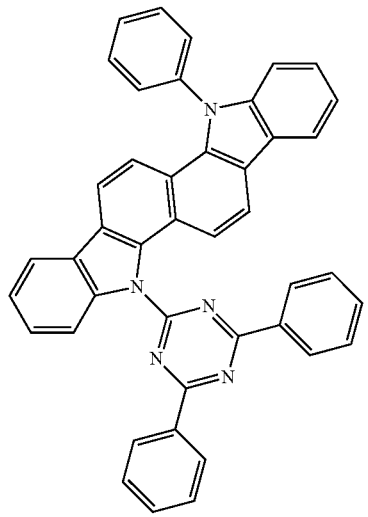
504
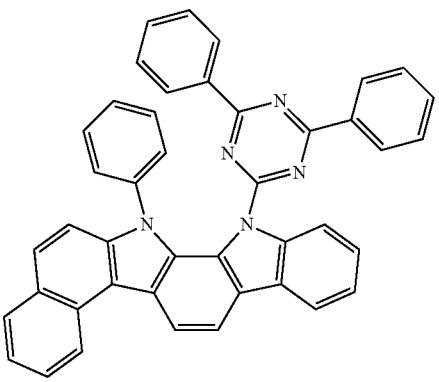
505
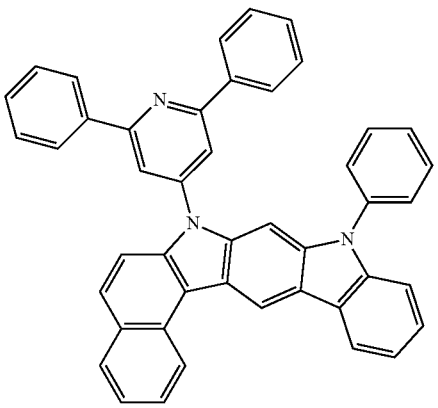
506

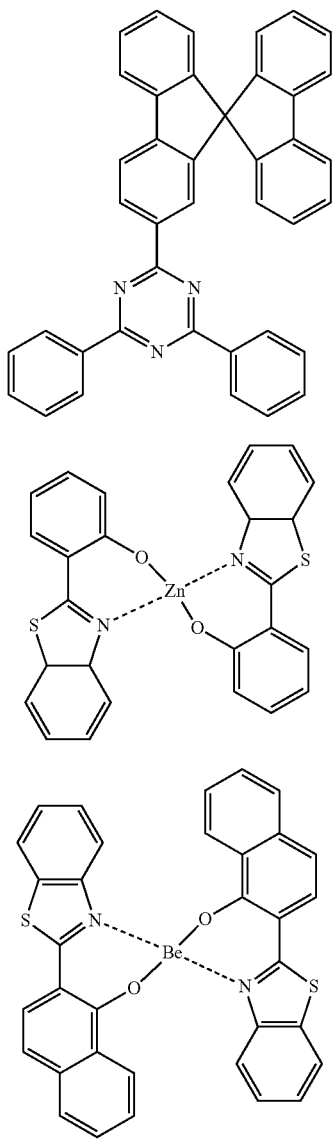

In some embodiments, an anthracene-based compound represented by Formula 400 below may be used as the host.

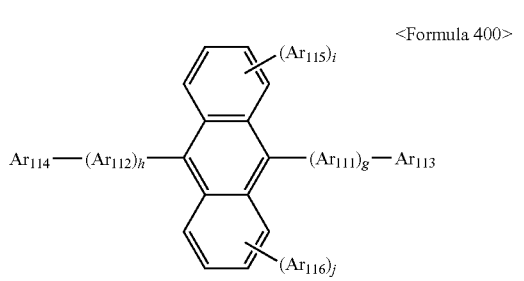

<Formula 400>

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_5$-$C_{60}$ aryl group; and g, h, I, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, and an anthryl group.

In Formula 400 above, g, h, I, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

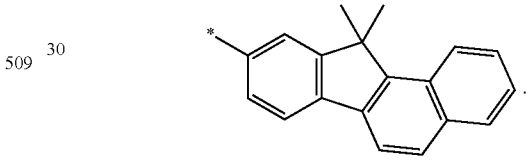

For example, the anthracene-based compound of Formula 400 above may be one of the compounds represented by the following formulae:

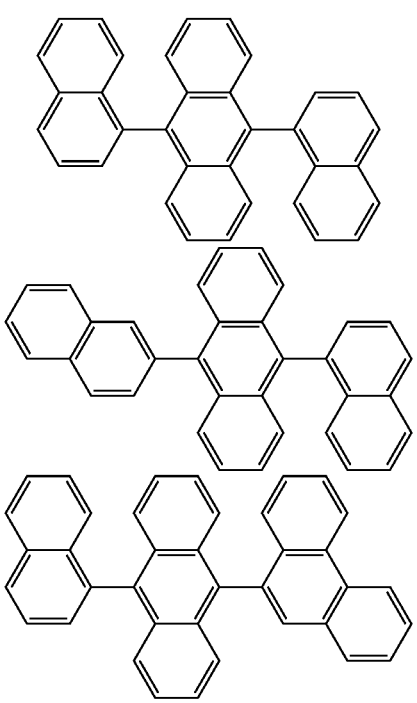

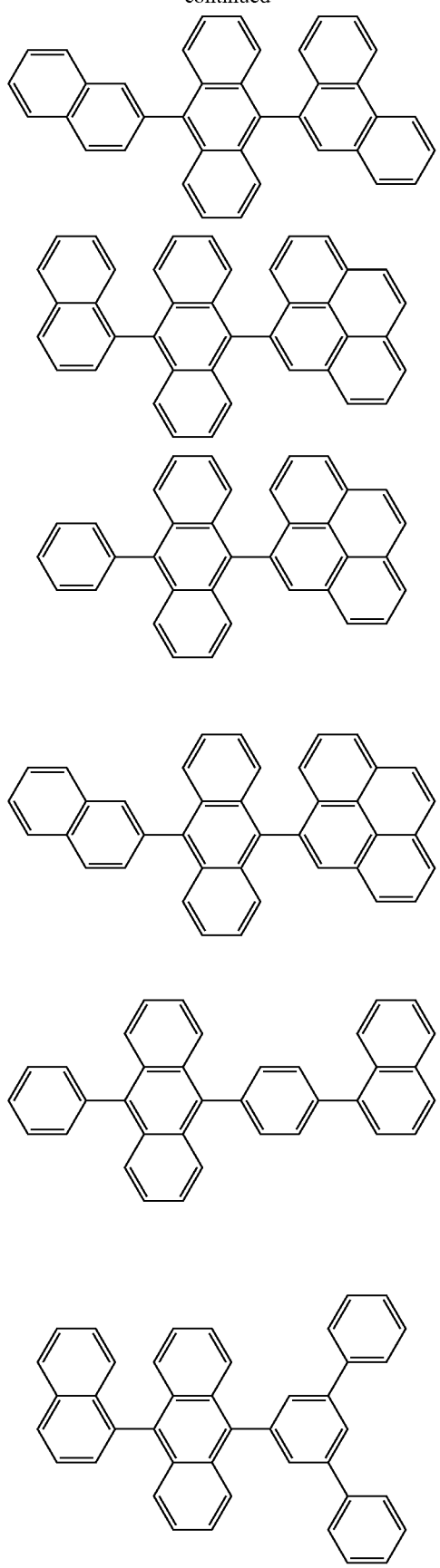
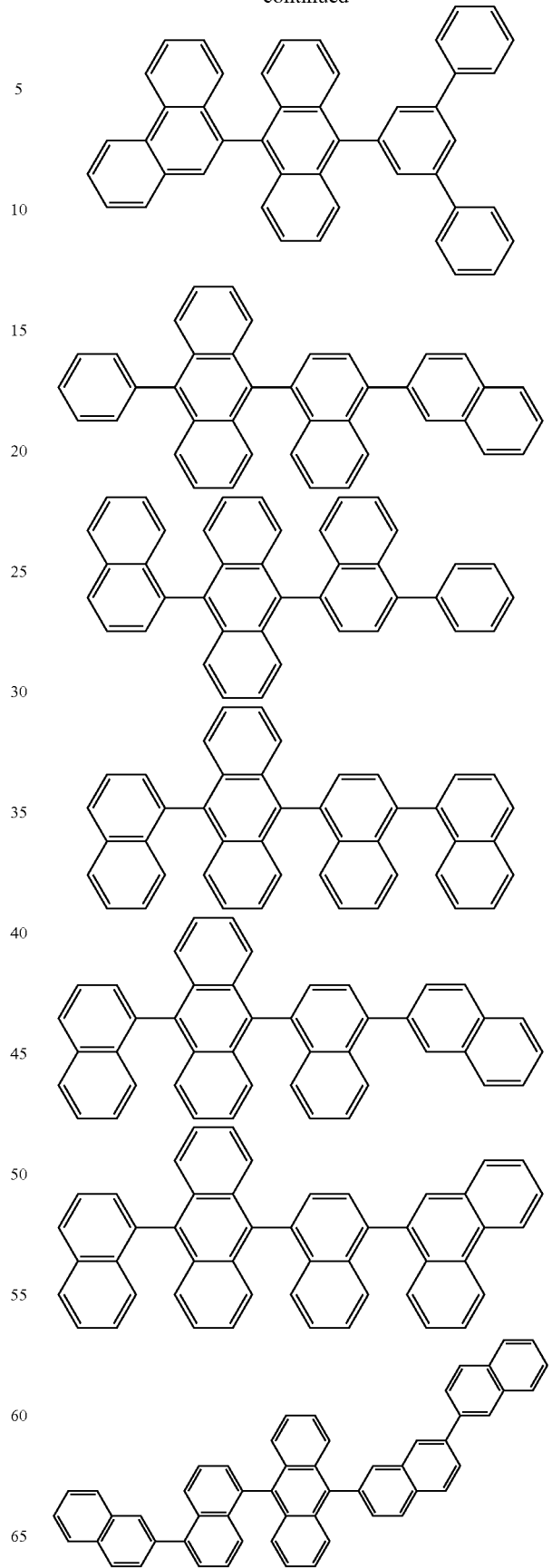

125
-continued
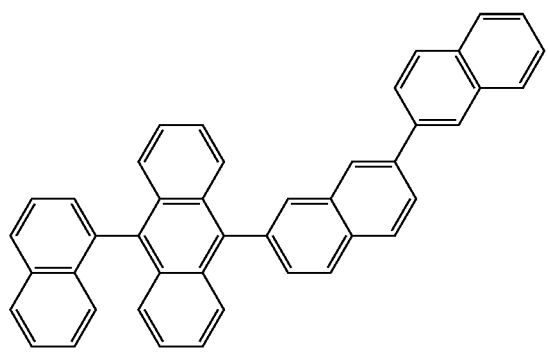
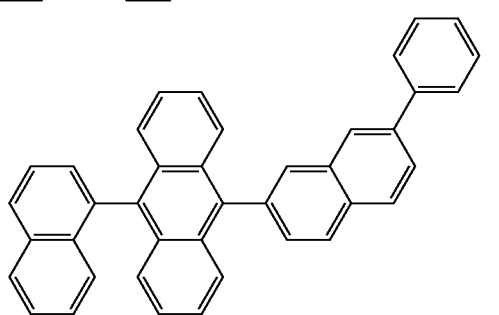
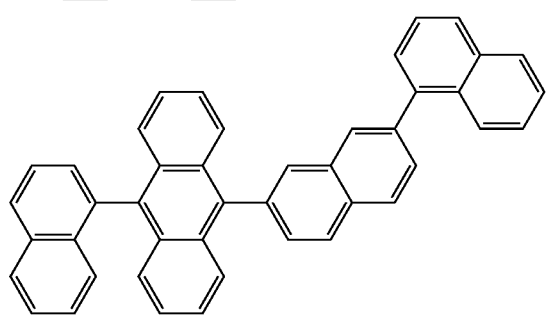
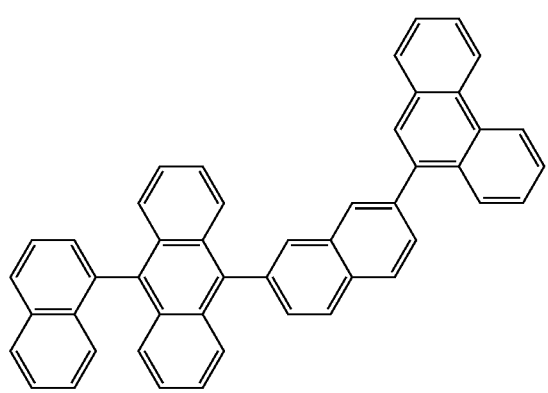
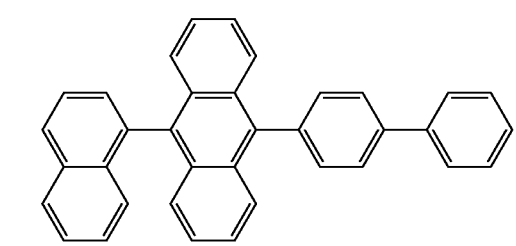
126
-continued
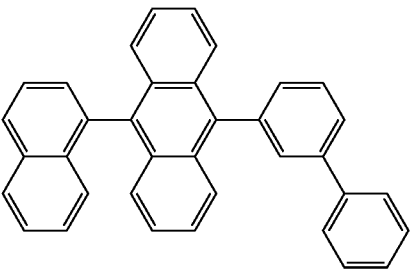
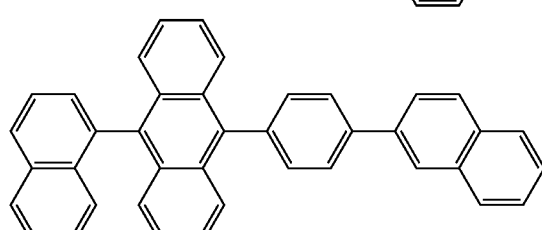
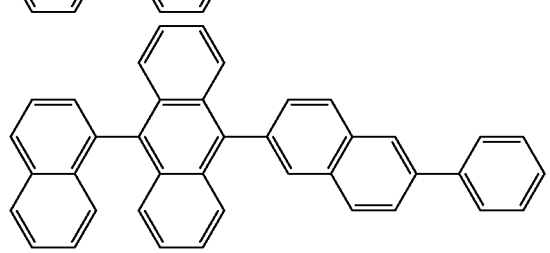
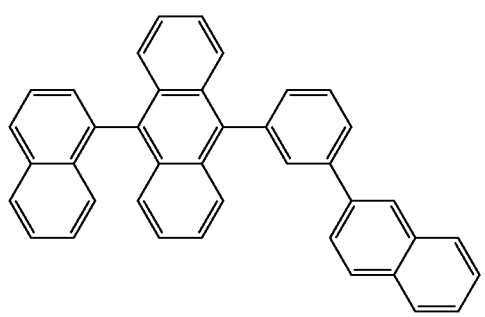
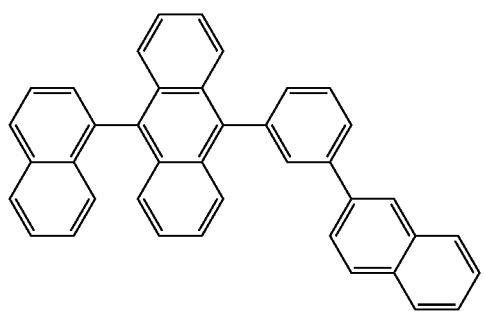
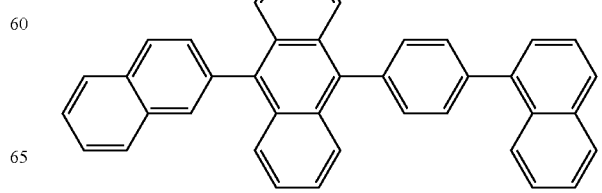

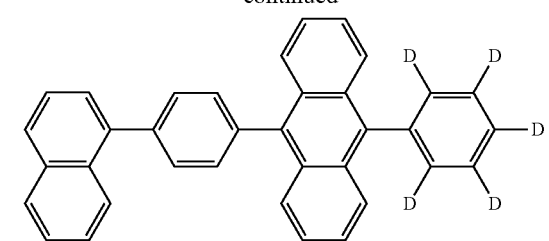
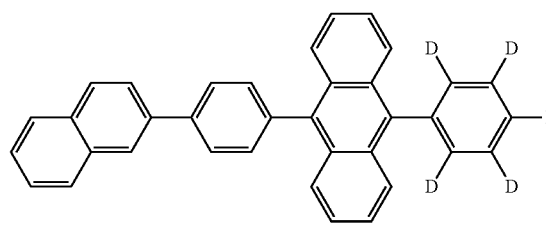
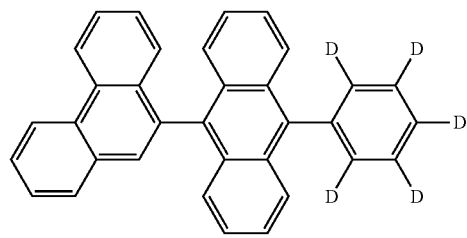
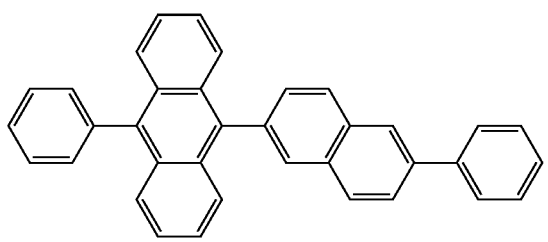
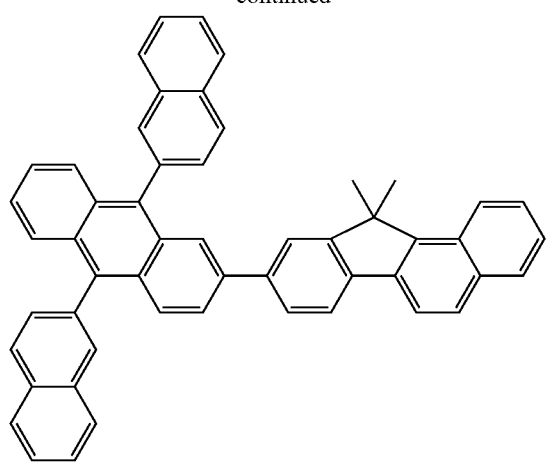
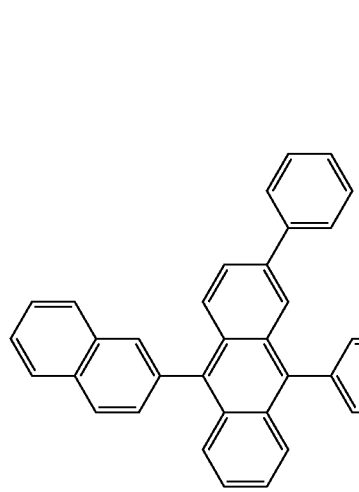
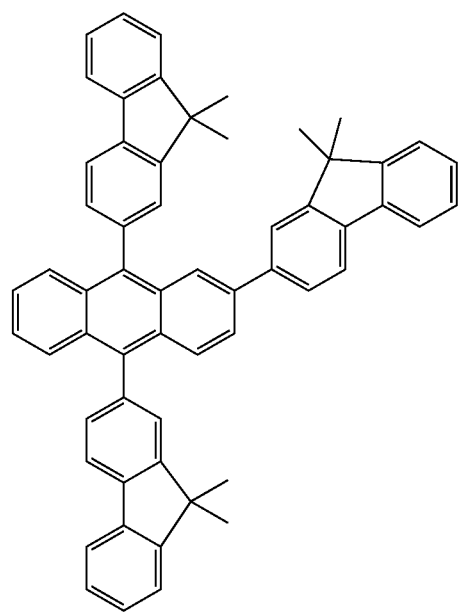

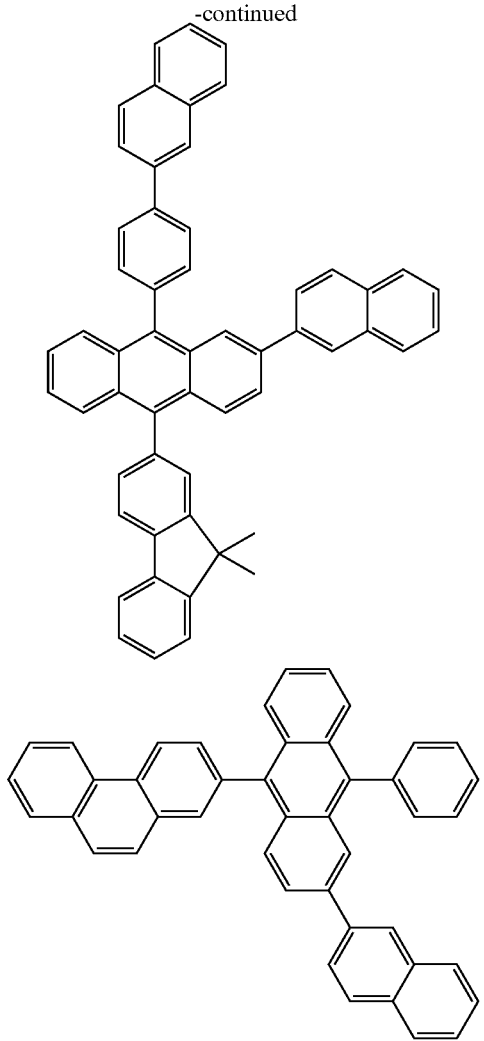

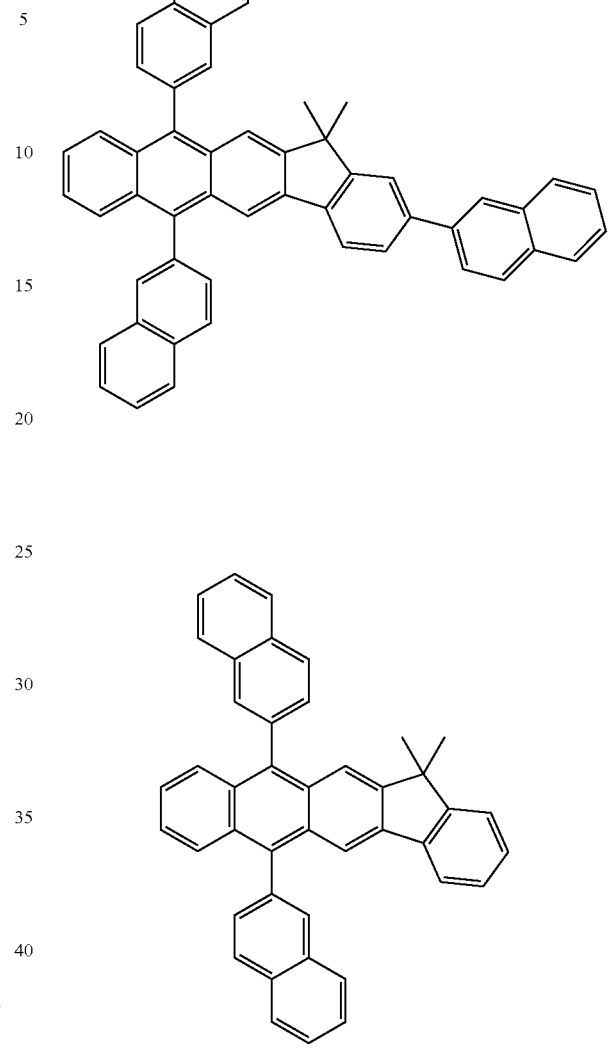

In some embodiments, an anthracene-based compound represented by Formula 401 below may be used as the host.

<Formula 401>

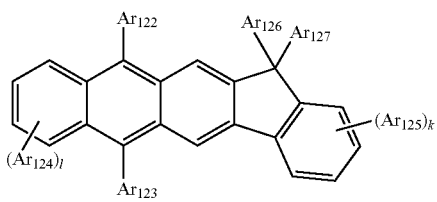

$Ar_{122}$ to $Ar_{125}$ in Formula 401 above have the same definition as $Ar_m$ of Formula 400 above, and thus detailed descriptions thereof will not be repeated here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae:

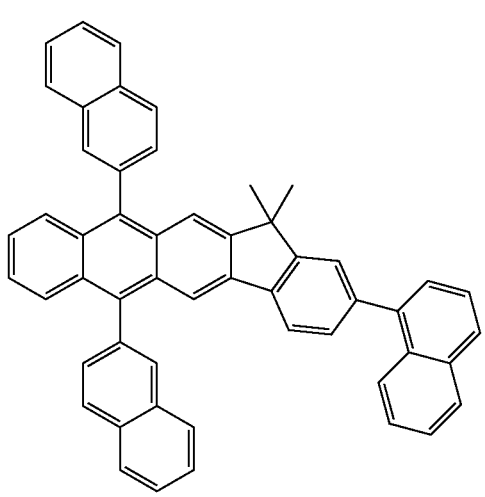

-continued

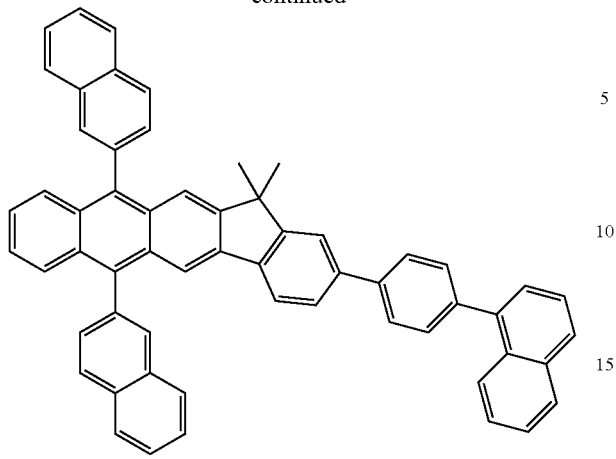

When the organic light-emitting device is a full color organic light-emitting device, the EML 133 may be patterned into a red emission layer, a green emission layer, and a blue emission layer.

At least one of the red EML, the green EML, and the blue EML may include a dopant below (ppy=phenylpyridine).

Examples of the blue dopant include compounds represented by the following formulae:

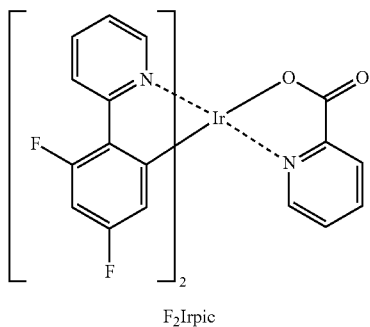
F₂Irpic

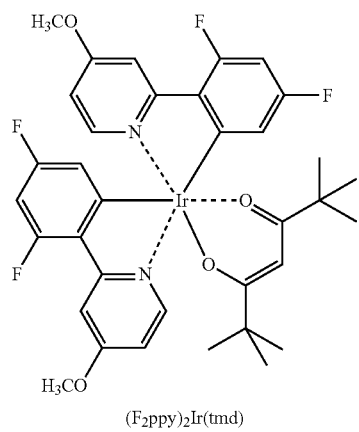
(F₂ppy)₂Ir(tmd)

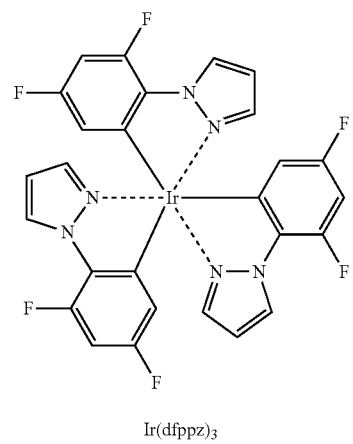
Ir(dfppz)₃

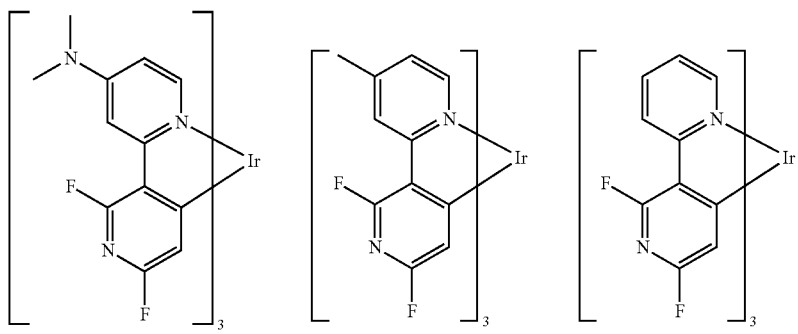

-continued
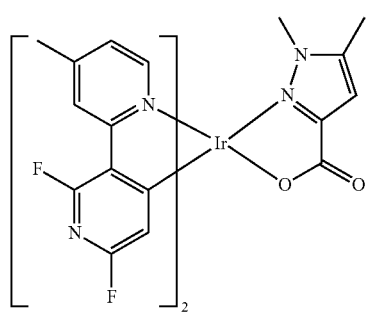
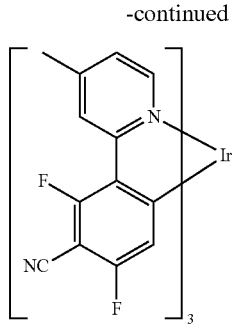
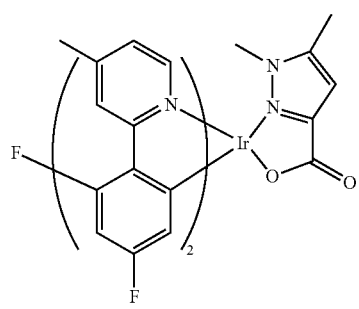
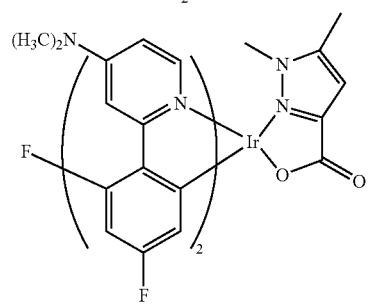
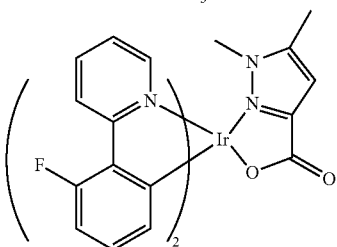
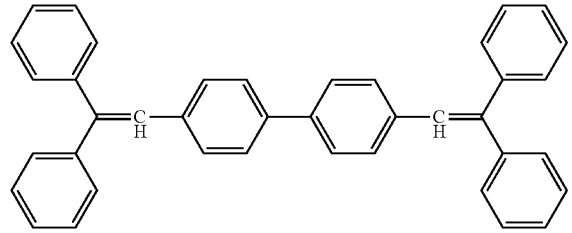
DPVBi
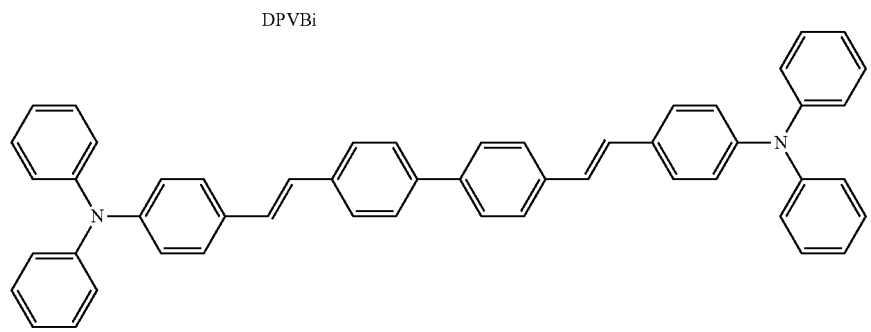
DPAVBi
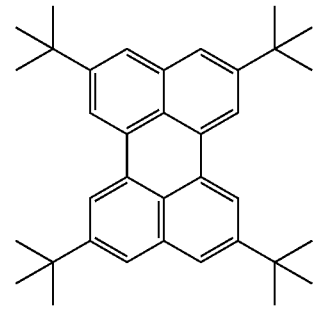
TBPe
Examples of the red dopant include compounds represented by the following formulae:
-continued
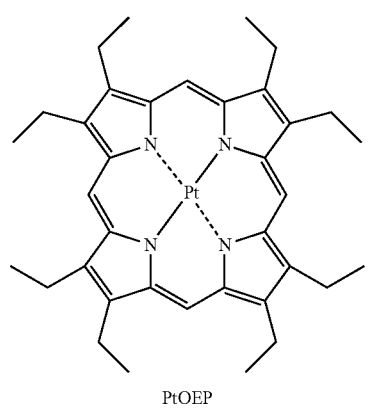
PtOEP
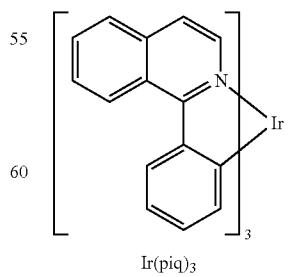
Ir(piq)₃
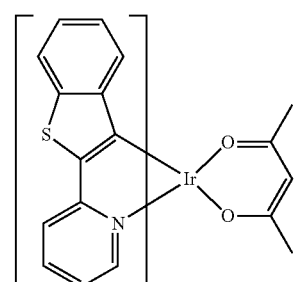
Btp₂Ir(acac)

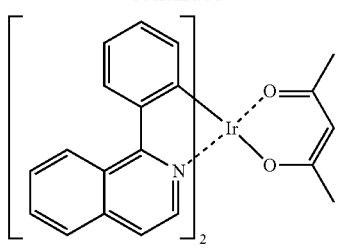
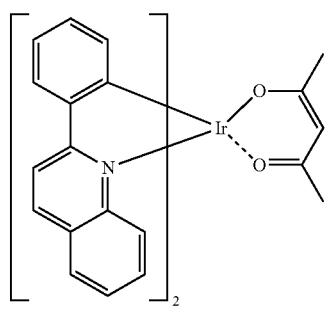
Ir(pq)₂(acac)
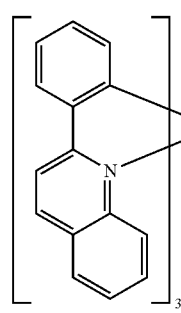
Ir(2-phq)₃
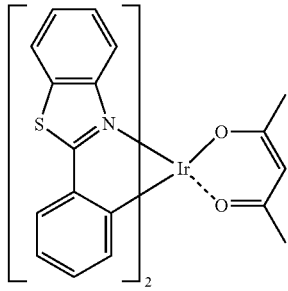
Ir(BT)₂(acac)
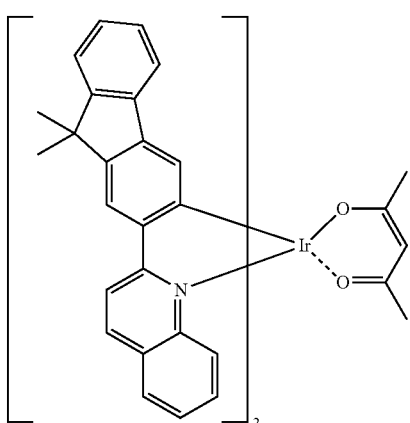
Ir(flq)₂(acac)
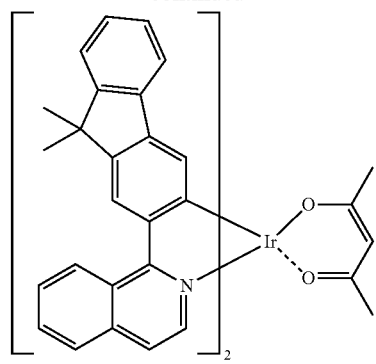
Ir(fliq)₂(acac)
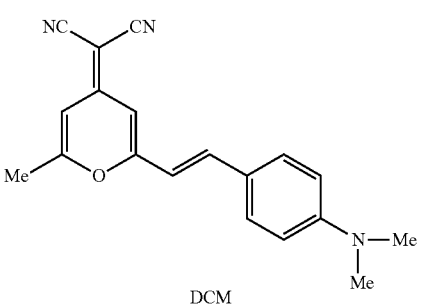
DCM
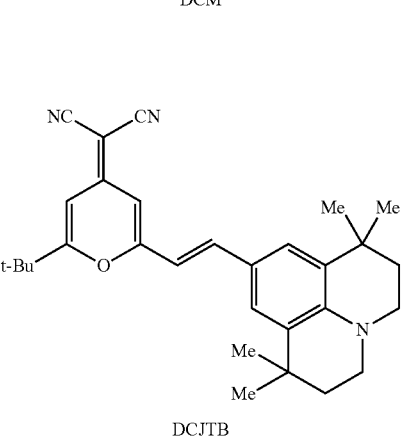
DCJTB
Examples of the green dopant include compounds represented by the following formulae:
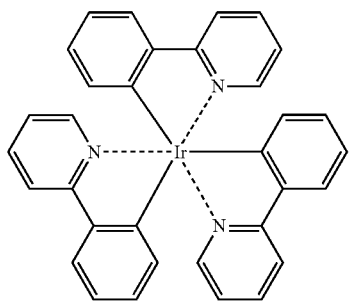
Ir(ppy)₃

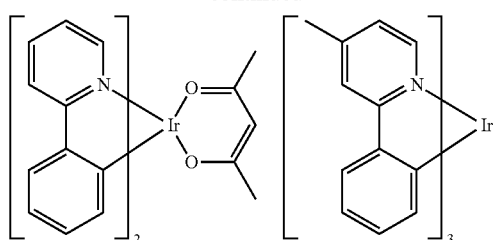
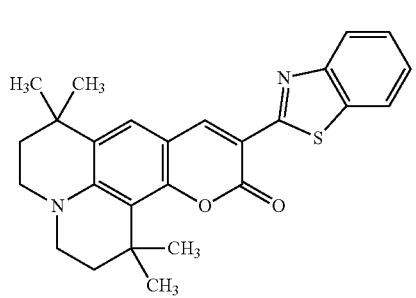
C545T
Examples of the dopant that may be used in the EML 133 include Pd complexes or Pt complexes represented by the following formulae:
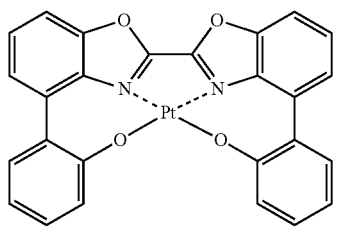
D1
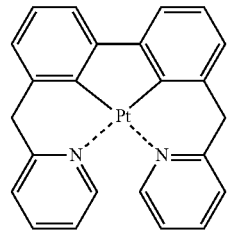
D2
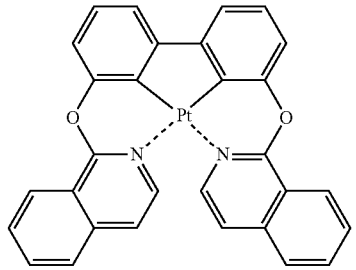
D3
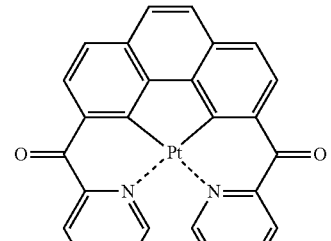
D4
D5
D6
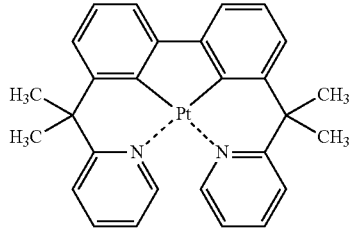
D7
D8
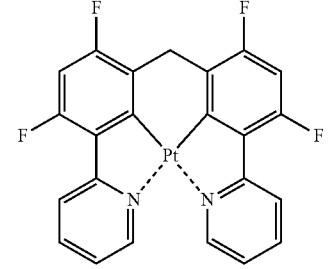
D9

139
-continued
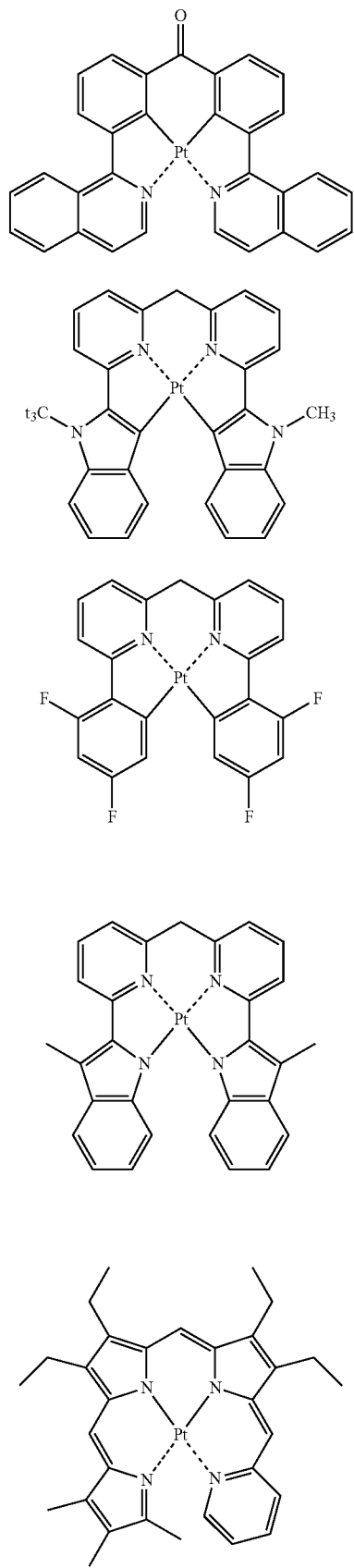
D10
D11
D12
D13
D14
140
-continued
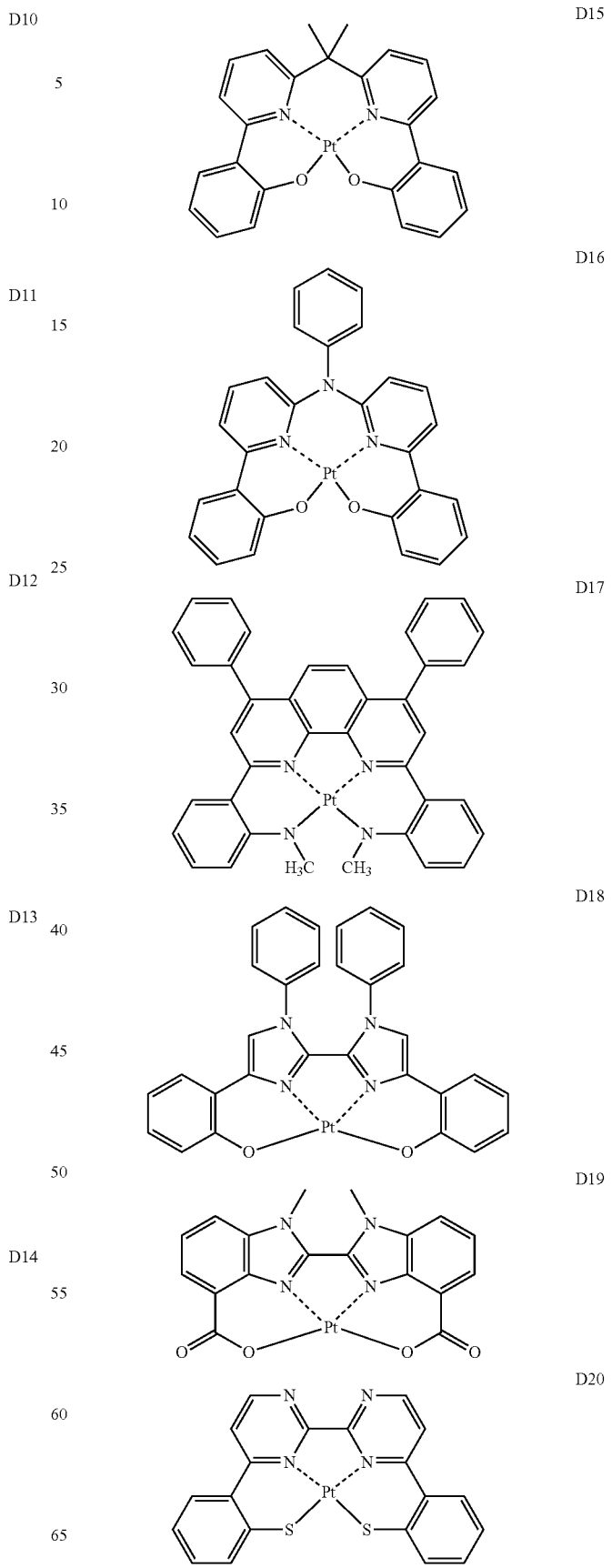
D15
D16
D17
D18
D19
D20

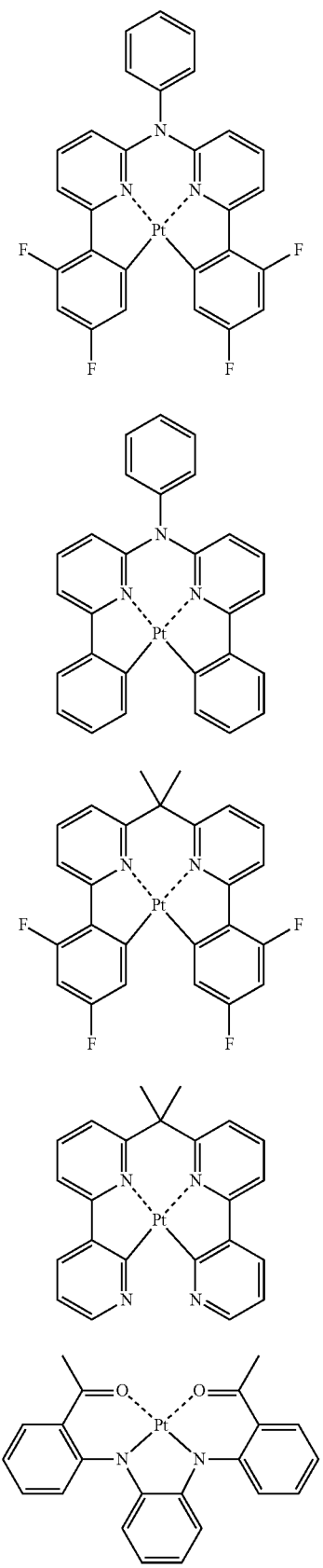
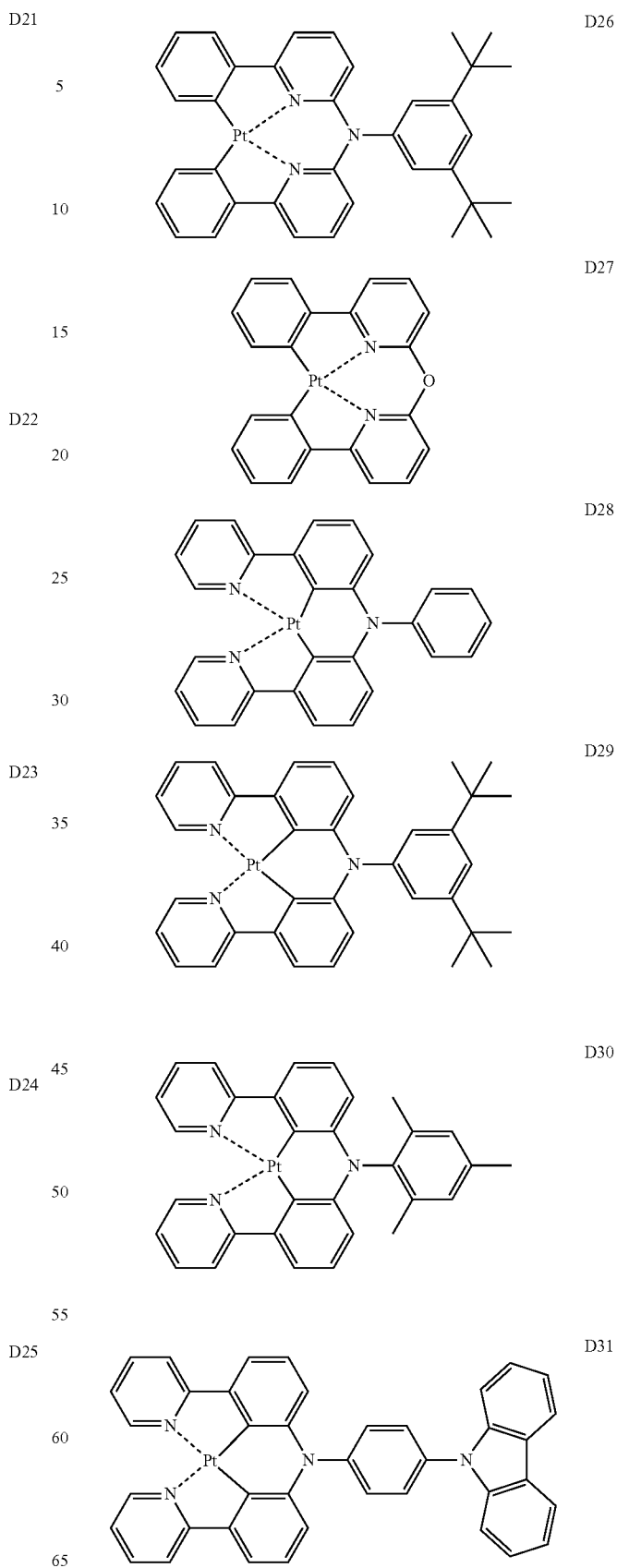

D32 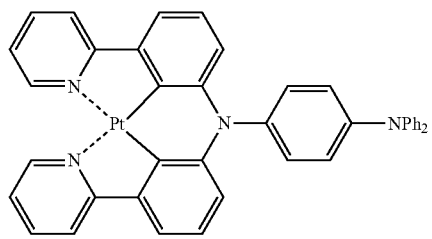
D33 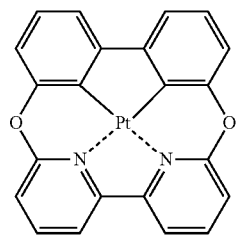
D34 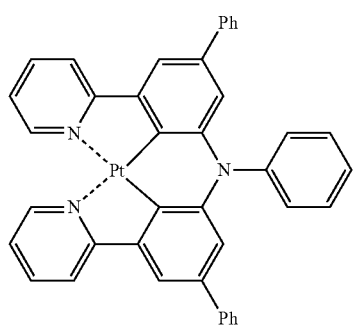
D35 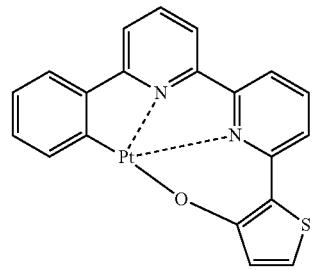
D36 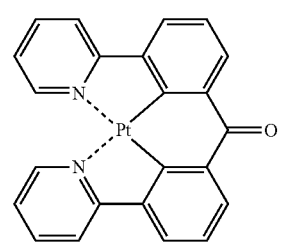
D37 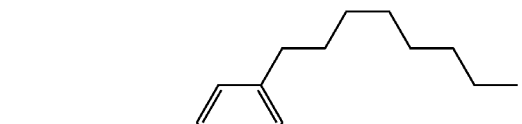
D38 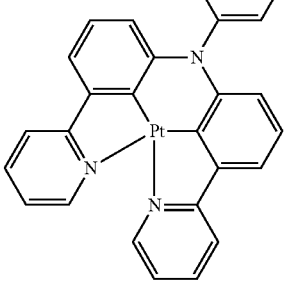
D39 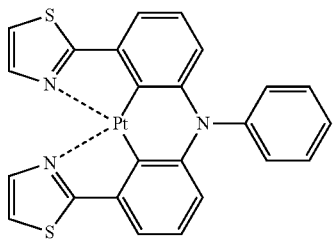
D40 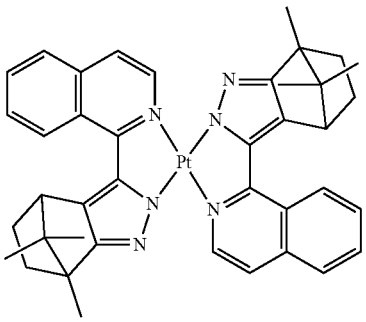
D41 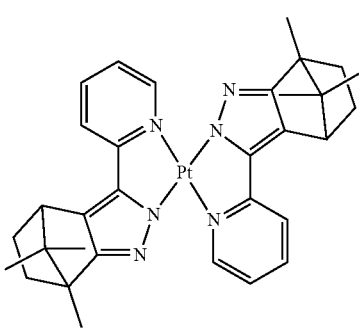

D42
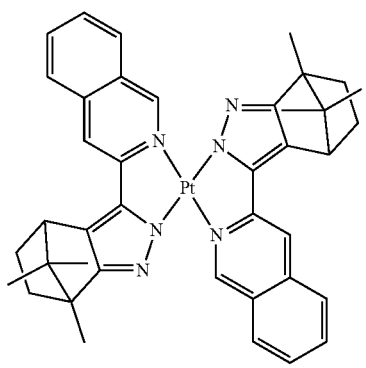
D43
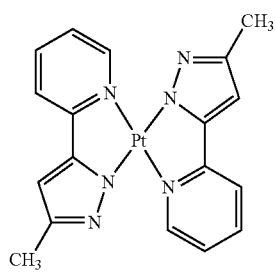
D44
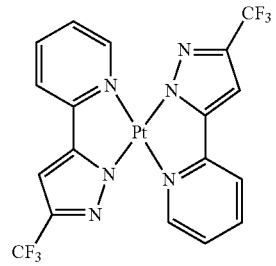
D45
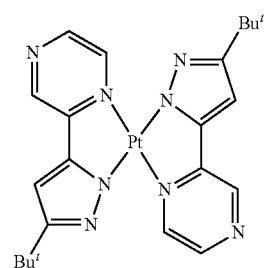
D46
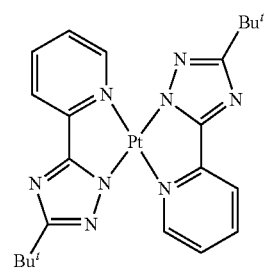
D47
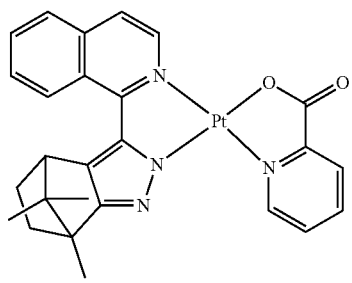
D48
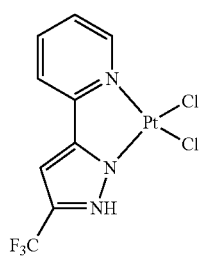
D49
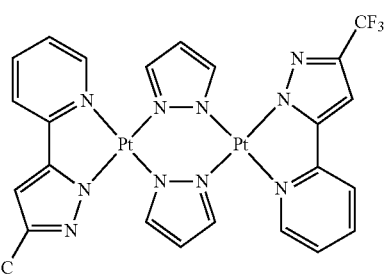
D50
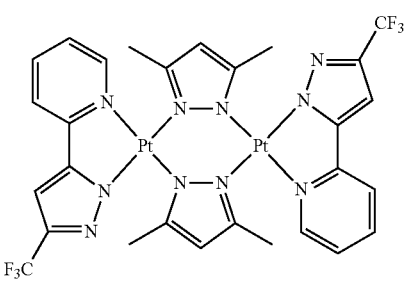
Examples of the dopant that may be used in the EML 133 include Os complexes represented by the following formulae:
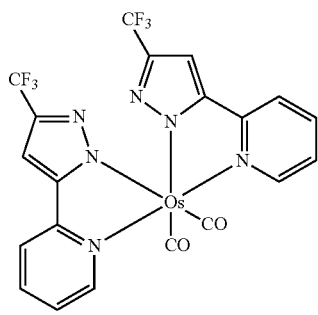
Os(fppz)$_2$(CO)$_2$

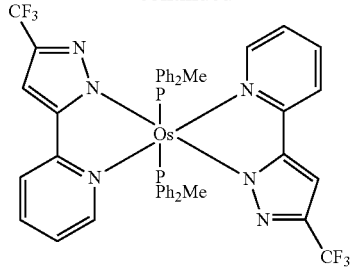

Os(fppz)₂(PPh₂Me)₂

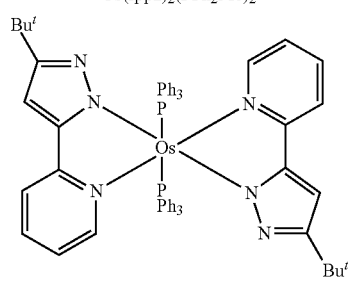

Os(bppz)₂(PPh₃)₂

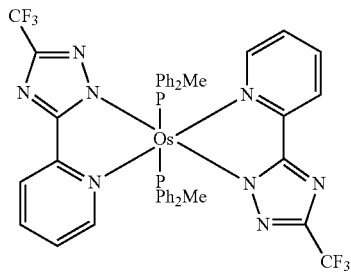

Os(fptz)₂(PPh₂Me)₂

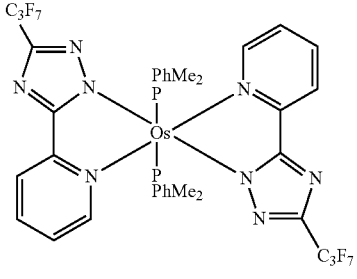

Os(hptz)₂(PPh₂Me₂)₂

When the EML 133 includes both a host and a dopant, an amount of the dopant may be from about 0.01 wt % to about 15 wt % based on 100 wt % of the EML, as an example.

A thickness of the EML 133 may be about 200 Å to about 700 Å. When the thickness of the EML 133 is within these ranges, the EML 133 may have good light emitting ability without a substantial increase in driving voltage.

When the organic light-emitting device is a full color organic light-emitting device, the EML 133 may be patterned into a red EML, a green EML, and a blue EML corresponding to red, green, and blue sub-pixels, respectively.

In some embodiments, the EML 133 may have a multi-layered structure including a red EML, a green EML, and a blue EML stacked upon one another to emit white light, or may have a single layer structure including a red light-emitting material, a green light-emitting material, and a blue light-emitting material. An organic light-emitting device including such an EML may further include a red color filter, a red color filter, and a blue color filter to emit full-color light.

The ETL 134 may be formed on the EML 133 by a suitable method, for example, vacuum deposition, spin coating, casting, or the like. When the ETL 134 is formed using vacuum deposition or spin coating, the deposition and coating conditions may be similar to those for the formation of the HIL 131, though the deposition and coating conditions may vary depending on the compound that is used to form the ETL 134. A material for forming the ETL 134 may be an anthracene-based compound of Formula 1 above able to stably transport electrons injected from an electron injecting electrode (cathode).

For example, the ETL 134 may further include a suitable electron transport material. Examples of materials for forming the ETL 134 include a quinoline derivative, such as tris(8-quinolinolate)aluminum (Alq₃), 3-(biphenyl-4-yl)-5-(4-tert-butylphenyl)-4-phenyl-4H-1,2,4-triazole (TAZ), bis(2-methyl-8-quinolinolato-N1,O8)-(1,1'-biphenyl) (Balq), beryllium bis(benzoquinolin-10-olate (Bebq₂), 9,10-di(naphthalene-2-yl)anthracene (ADN), Compound 101, Compound 102, and Bphen.

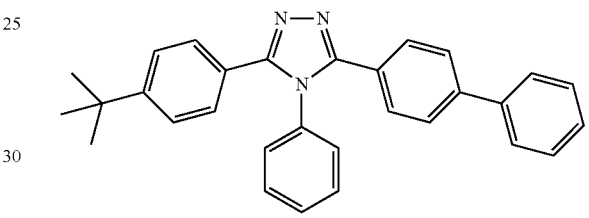

TAZ

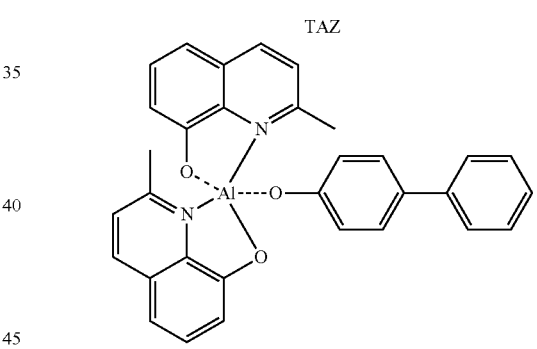

BAlq

<Compound 101>

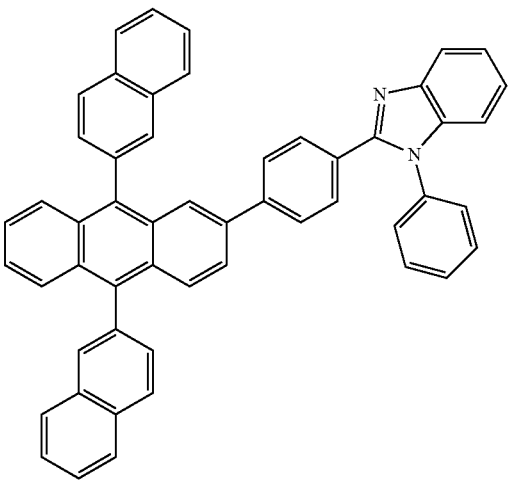

<Compound 102>

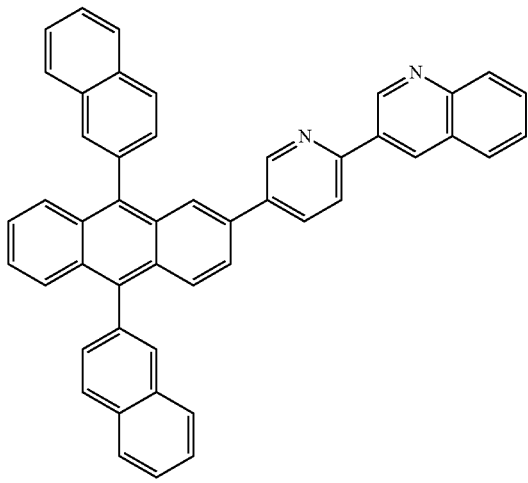

<Compound 203>

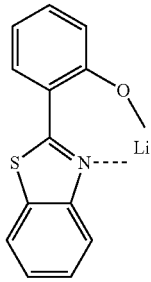

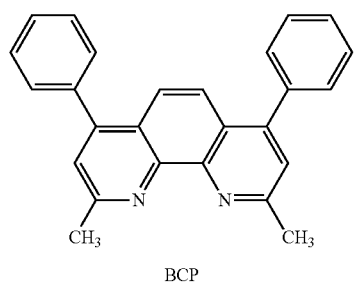

BCP

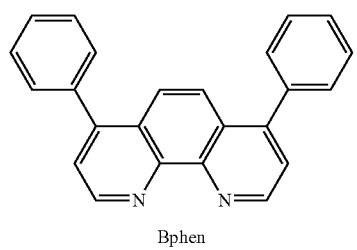

Bphen

The thickness of the ETL 134 may be from about 100 Å to about 1,000 Å, and in some implementations, may be from about 150 Å to about 500 Å. When the thickness of the ETL 134 is within these ranges, the ETL 134 may have satisfactory electron transport ability without a substantial increase in driving voltage.

In some embodiments the ETL 134 may further include a metal-containing material, in addition to a suitable electron-transporting organic compound. The metal-containing material may include a lithium (Li) complex. Examples of the Li complex include lithium quinolate (Liq) and Compound 203 below:

The EIL 135, which facilitates injection of electrons from the cathode, may be formed on the ETL 134. A suitable electron-injecting material may be used to form the EIL 135.

Examples of materials for forming the EIL 135 include LiF, NaCl, CsF, $Li_2O$, and BaO. The deposition and coating conditions for forming the EIL 135 may be similar to those for the formation of the HIL, though the deposition and coating conditions may vary depending on the material that is used to form the EIL 135.

The thickness of the EIL 135 may be from about 1 Å to about 100 Å, and in some embodiments, may be from about 3 Å to about 90 Å. When the thickness of the EIL 135 is within these ranges, the EIL 135 may have satisfactory electron injection ability without a substantial increase in driving voltage.

The second electrode 140 may be disposed on the organic layer 130. The second electrode 140 may be a cathode as an electron injection electrode. A material for forming the second electrode 140 may be a metal, an alloy, an electro-conductive compound that has a low work function, or a mixture thereof. The second electrode 140 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some implementations, to manufacture a top-emission light-emitting device, the transmission electrode may be formed of indium tin oxide (ITO) or indium zinc oxide (IZO).

When a phosphorescent dopant is used in the EML 133, a HBL may be formed between the HTL 132 and the EML 133 or between the H-functional layer and the EML 133 by using vacuum deposition, spin coating, casting, Langmuir-Blodgett (LB) deposition, or the like, in order to prevent diffusion of triplet excitons or holes into the ETL 134. When the HBL is formed using vacuum deposition or spin coating, the conditions for deposition and coating may be similar to those for the formation of the HIL 131, although the conditions for deposition and coating may vary depending on the material that is used to form the HBL. A suitable hole-blocking material may be used. Examples of hole-blocking materials include oxadiazole derivatives, triazole derivatives, and phenanthroline derivatives. For example, bathocuproine (BCP) represented by the following formula may be used as a material for forming the HBL.

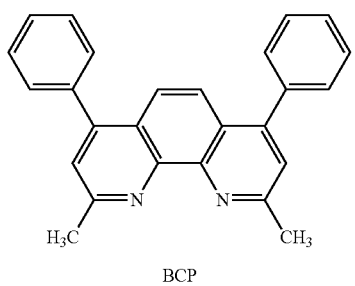 [SMILES: Cc1cc(-c2ccccc2)c2ccc3c(-c4ccccc4)cc(C)nc3c2n1 ; "BCP"]

BCP

The thickness of the HBL may be from about 20 Å to about 1,000 Å, and in some implementations, may be from about 30 Å to about 300 Å. When the thickness of the HBL is within these ranges, the HBL may have improved hole blocking ability without a substantial increase in driving voltage.

Although the organic light-emitting device of FIG. 1 is described above, embodiments are not limited thereto.

As used herein, the term "unsubstituted $C_1$-$C_{30}$ alkyl group" (or "$C_1$-$C_{30}$ alkyl group") refers to a linear or branched $C_1$-$C_{30}$ alkyl group, such as a methyl group, an ethyl group, a propyl group, an isobutyl group, a sec-butyl group, a pentyl group, an iso-amyl group, or a hexyl group. The substituted $C_1$-$C_{30}$ alkyl group may be a $C_1$-$C_{30}$ alkyl group of which at least one hydrogen atom is substituted with one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group, a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a phenyl group, a naphthyl group, an anthryl group, a fluorenyl group, dimethylfluorenyl group, a diphenylfluorenyl group, a carbazolyl group, a phenylcarbazolyl group, a pyridyl group, a pyrimidyl group, a pyrazinyl group, a pyridazinyl group, a triazinyl group, a quinolyl group, and an isoquinolyl group, and —N($Q_{11}$)($Q_{12}$), and —Si($Q_{13}$)($Q_{14}$)($Q_{15}$) (where $Q_{11}$ and $Q_{12}$ may be each independently a $C_6$-$C_{60}$ aryl group or a $C_2$-$C_{60}$ heteroaryl group; and $Q_{13}$ to $Q_{15}$ may be each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

As used herein, the term "unsubstituted $C_1$-$C_{30}$ alkoxy group" (or a "$C_1$-$C_{30}$ alkoxy group") refers to a group represented by —OA, wherein A is an unsubstituted $C_1$-$C_{30}$ alkyl group described above. Examples of the unsubstituted $C_1$-$C_{30}$ alkoxy group include a methoxy group, an ethoxy group, and an isopropyloxy group. At least one of the hydrogen atoms in the alkoxy group may be substituted with the substituents described above in conjunction with the substituted $C_1$-$C_{30}$ alkyl group.

As used herein, the term "unsubstituted $C_2$-$C_{30}$ alkenyl group" (or a "$C_2$-$C_{30}$ alkenyl group") refers to a $C_2$-$C_{30}$ alkyl group having at least one carbon-carbon triple bond in the center or at a terminal thereof. Examples of the alkenyl group include an ethenyl group, a propenyl group, a butenyl group, and the like. At least one hydrogen atom in the unsubstituted $C_2$-$C_{30}$ alkenyl group may be substituted with those substituents described above in conjunction with the substituted $C_1$-$C_{30}$ alkyl group.

As used herein, the term "unsubstituted $C_2$-$C_{30}$ alkynyl group" (or a "$C_2$-$C_{30}$ alkynyl group") refers to a $C_2$-$C_{30}$ alkyl group having at least one carbon-carbon triple bond in the center or at a terminal thereof. Examples of the unsubstituted $C_2$-$C_{60}$ alkynyl group (or a $C_2$-$C_{60}$ alkynyl group) include an ethenyl group, a propynyl group, and the like. At least one hydrogen atom in the alkynyl group may be substituted with those substituents described above in conjunction with the substituted $C_1$-$C_{30}$ alkyl group.

As used herein, the term "unsubstituted $C_3$-$C_{30}$ cycloalkyl group" refers to a cyclic, monovalent $C_3$-$C_{30}$ saturated hydrocarbon group. Examples of the unsubstituted $C_3$-$C_{30}$ cycloalkyl group include a cyclopropyl group, a cyclobutyl group, a cyclopentyl group, a cyclohexyl group, and a cyclooctyl group. At least one hydrogen atom in the cycloalkyl group may be substituted with those substituents described above in conjunction with the substituted $C_1$-$C_{30}$ alkyl group.

As used herein, the term "unsubstituted $C_3$-$C_{30}$ cycloalkenyl group" refers to a nonaromatic, cyclic unsaturated hydrocarbon group with at least one carbon-carbon double bond. Examples of the unsubstituted $C_3$-$C_{60}$ cycloalkenyl group include a cyclopropenyl group, a cyclobutenyl group, a cyclopentenyl group, a cyclohexcenyl group, a cycloheptenyl group, a 1,3-cyclohexadienyl group, a 1,4-cyclohexadienyl group, a 2,4-cycloheptadienyl group, and a 1,5-cyclooctadienyl group. At least one hydrogen atom in the cycloalkenyl group may be substituted with those substituents described above in conjunction with the substituted $C_1$-$C_{30}$ alkyl group.

As used herein, the term "unsubstituted $C_6$-$C_{60}$ aryl group" refers to a monovalent group having a carbocyclic aromatic system having 6 to 60 carbon atoms including at least one aromatic ring. The term "unsubstituted $C_6$-$C_{60}$ arylene group" refers to a divalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with those substituents described above in conjunction with the $C_1$-$C_{60}$ alkyl group.

Examples of the substituted or unsubstituted $C_6$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolinyl group, a methylanthracenyl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be inferred based on those of the unsubstituted $C_6$-$C_{60}$ aryl group and the substituted $C_1$-$C_{30}$ alkyl group described above. Examples of the substituted or unsubstituted $C_6$-$C_{60}$ arylene group may be inferred based on those examples of the substituted or unsubstituted $C_6$-$C_{60}$ aryl group described above.

As used herein, the term "$C_2$-$C_{10}$ heterocycloalkyl group" refers to a C2-C10 monovalent saturated cyclic hydrocarbon group including at least one of N, O, P, and S as a ring-forming atom. Examples of the $C_2$-$C_{10}$ heterocycloalkyl group include tetrahydrofuran and tetrahydropyran. At least one hydrogen atom in the heterocycloalkyl group may be substituted with those substituents described above in conjunction with the substituted $C_1$-$C_{30}$ alkyl group.

As used herein, the term "unsubstituted $C_2$-$C_{10}$ heterocycloalkenyl group" refers to a non-aromatic, cyclic unsaturated hydrocarbon group including at least one of N, O, P and S as a ring-forming atom and at least one carbon double bond. At least one hydrogen atom in the heterocycloalkenyl group may be substituted with those substituents described above in conjunction with the substituted $C_1$-$C_{30}$ alkyl group.

As used herein, the term "unsubstituted $C_2$-$C_{60}$ heteroaryl group" refers to a monovalent carbocyclic aromatic system having at least one aromatic ring and at least one of the heteroatoms selected from the group consisting of N, O, P, and S as a ring-forming atom. The unsubstituted $C_2$-$C_{60}$ heteroarylene group may be a divalent carbocyclic aromatic system having at least one aromatic ring and at least one of the heteroatoms selected from the group consisting of N, O, P, and S. When the heteroaryl group and the heteroarylene group have at least two rings, the two rings may be fused to each other via a single bond. At least one hydrogen atom in the heteroaryl group and the heteroarylene group may be substituted with those substituents described with reference to the $C_1$-$C_{60}$ alkyl group.

Non-limiting examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the substituted $C_2$-$C_{60}$ heteroarylene group may be inferred based on those examples of the substituted or unsubstituted $C_2$-$C_{60}$ arylene group described above.

As used herein, the term "substituted or unsubstituted $C_6$-$C_{30}$ aryloxy group" refers to —$OA_2$ (where $A_2$ is a substituted or unsubstituted $C_6$-$C_{30}$ aryl group described above). The term "substituted or unsubstituted $C_6$-$C_{30}$ arylthiol group" refers to —$SA_3$ (where $A_3$ is a substituted or unsubstituted $C_6$-$C_{30}$ aryl group described above).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 2

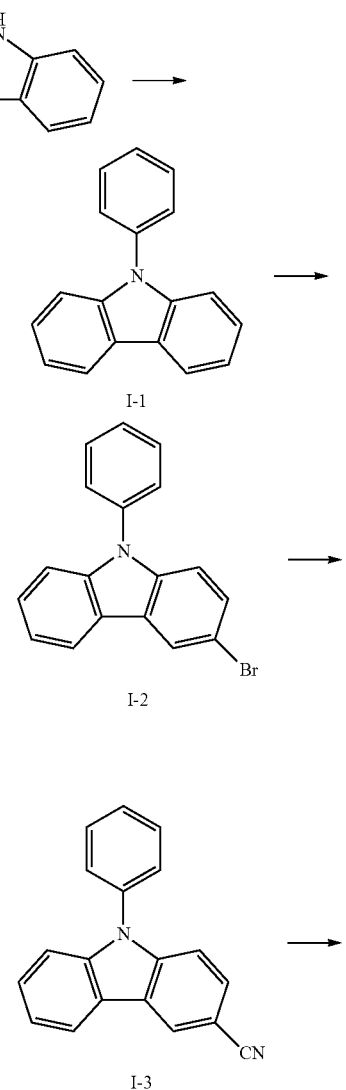

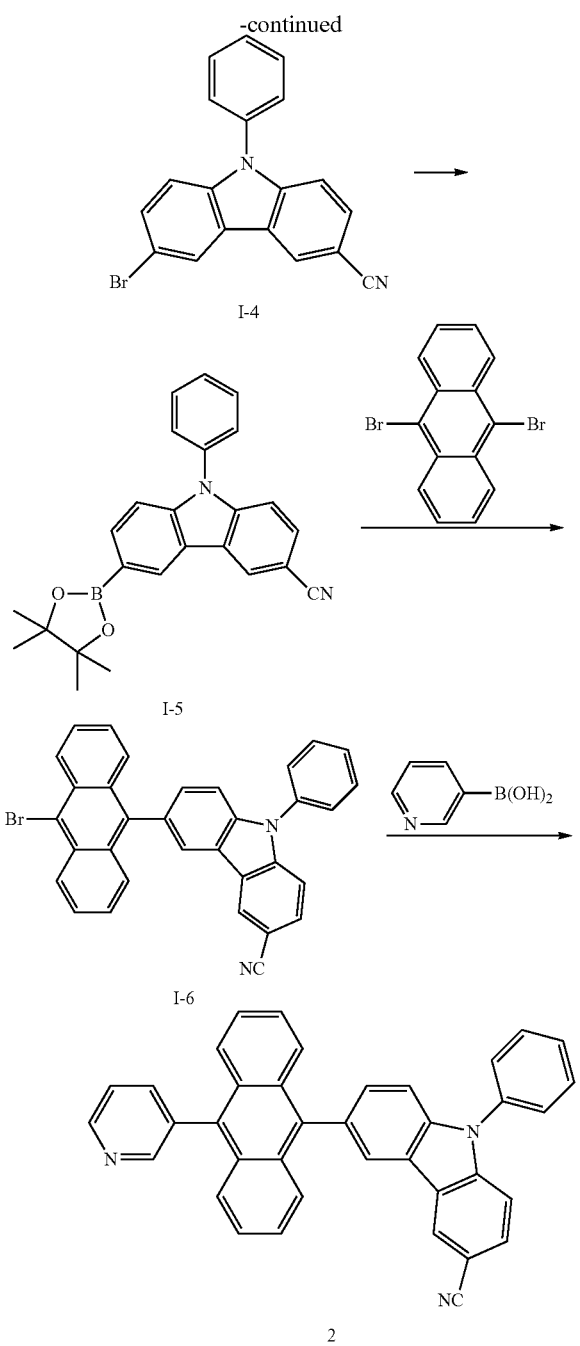

1) Synthesis of Intermediate I-1

5.02 g (30 mmol) of 9H-carbazole, 4.71 g (30 mmol) of bromobenzene, 1.14 g (18 mmol) of copper powder, and 6.22 g (45 mmol) of $K_2CO_3$ were dissolved in 80 mL of o-dichlorobenzene, and stirred at about 180° C. for about 24 hours. The resulting reaction solution was cooled down to room temperature, and 60 mL of water was added thereto, followed by extraction three times with 50 mL of ethyl acetate. An organic layer was collected and was dried using magnesium sulfate to evaporate the solvent. The residue was separated and purified using silica gel column chromatography to obtain 5.47 g of Intermediate I-1 (Yield: 75%). This compound was identified using liquid chromatography-mass spectroscopy (LC-MS).

$C_{18}H_{13}N$: $M^+$ 243.10

2) Synthesis of Intermediate I-2

After 5.47 g (22.5 mmol) of Intermediate I-1 was completely dissolved in 80 mL of $CH_2Cl_2$ to obtain a solution, 4.00 g (22.5 mmol) of N-bromosuccinimide was added thereto and stirred at room temperature for about 12 hours. The resulting reaction solution was cooled down to room temperature, and 60 mL of water was added thereto, followed by extraction three times with 50 mL of $CH_2Cl_2$. An organic layer was collected and was dried using magnesium sulfate to evaporate the solvent. The residue was recrystallized using methanol to obtain 6.16 g of Intermediate I-2 (Yield: 85%) This compound was identified using LC-MS.

$C_{18}H_{12}BrN$: $M^+$ 321.0

3) Synthesis of Intermediate I-3

6.16 g (19.1 mmol) of Intermediate I-2 and 2.57 g (28.7 mmol) of CuCN were dissolved in 70 mL of dimethylformamide (DMF) and stirred at about 150° C. for about 24 hours. The resulting reaction solution was cooled down to room temperature, and 60 mL of ammonia water and 60 mL of water were added thereto, followed by extraction three times with 50 mL of $CH_2Cl_2$. An organic layer was collected and was dried using magnesium sulfate to evaporate the solvent. The residue was separated and purified using silica gel column chromatography to obtain 4.71 g of Intermediate I-3 (Yield: 92%). This compound was identified using LC-MS.

$C_{19}H_{12}N_2$: $M^+$ 268.1

4) Synthesis of Intermediate I-4

After 4.71 g (17.6 mmol) of Intermediate I-3 was completely dissolved in 80 mL of $CH_2Cl_2$ to obtain a solution, 3.13 g (17.6 mmol) of N-bromosuccinimide was added thereto and stirred at room temperature for about 8 hours. 60 mL of water was added to the resulting reaction solution, followed by extraction three times with 50 mL of $CH_2Cl_2$. An organic layer was collected and was dried using magnesium sulfate to evaporate the solvent. The residue was recrystallized using methanol to obtain 5.81 g of Intermediate I-4 (Yield: 95%) This compound was identified using LC-MS.

$C_{19}H_{11}BrN_2$: $M^+$ 346.0

5) Synthesis of Compound I-5

5.81 g (16.7 mmol) of Intermediate I-4, 0.68 g (0.84 mmol) of $Pd(dppf)_2Cl_2$, and 4.92 g (50.1 mmol) of KOAc were dissolved in 80 mL of dimethyl sulfoxide (DMSO) and stirred at about 150° C. for about 24 hours. The resulting reaction solution was cooled down to room temperature, and 100 mL of water was added thereto, followed by extraction three times with 50 mL of $CH_2Cl_2$. An organic layer was collected and was dried using magnesium sulfate to evaporate the solvent. The residue was separated and purified using silica gel column chromatography to obtain 4.61 g of Intermediate I-5 (Yield: 70%). This compound was identified using LC-MS.

$C_{33}H_{19}BrN_2$: $M^+$ 522.1

6) Synthesis of Compound I-6

4.61 g (11.7 mmol) of Intermediate I-5, 5.90 g (17.6 mmol) of 9,10-dibromo-anthracene, 0.68 g (0.59 mmol) of $Pd(PPh_3)_4$, and 4.85 g (35.1 mmol) of $K_2CO_3$ were dissolved in 60 mL of THF and 30 mL of $H_2O$, and stirred at about 80° C. for about 12 hours. The resulting reaction solution was cooled down to room temperature, followed by extraction three times with 30 mL of water and 30 mL of ethyl acetate. An organic layer was collected and was dried using magnesium sulfate to evaporate the solvent. The residue was separated and purified using silica gel column chromatography to obtain 4.59 g of Compound I-6 (Yield: 75%). This compound was identified using LC-MS.

$C_{25}H_{23}BN_2O_2$: M+ 394.2

7) Synthesis of Compound 2

4.59 g (8.78 mmol) of Intermediate I-6, 1.08 g (8.78 mmol) of 3-pyridyl boronic acid, 0.51 g (0.44 mmol) of $Pd(PPh_3)_4$, and 3.64 g (26.3 mmol) of $K_2CO_3$ were dissolved in 60 mL of THF and 30 mL of $H_2O$, and stirred at about 80° C. for about 12 hours. The resulting reaction solution was cooled down to room temperature, followed by extraction three times with 30 mL of water and 30 mL of ethyl acetate. An organic layer was collected and was dried using magnesium sulfate to evaporate the solvent. The residue was separated and purified using silica gel column chromatography to obtain 3.21 g of Compound 2 (Yield: 70%). This compound was identified using mass spectroscopy/fast atom bombardment (MS/FAB) and $^1H$ nuclear magnetic resonance (NMR).

$C_{38}H_{23}N_3$ calcd: 521.19, found: 521.20
$^1H$ NMR δ=9.08 (d, 1H), 8.60 (dd, 1H), 8.45 (d, 1H), 8.27-8.24 (m, 1H), 8.01-7.90 (m, 6H), 7.65-7.58 (m, 2H), 7.52-7.47 (m, 4H), 7.39-7.27 (m, 7H)

Synthesis Example 2

Synthesis of Compound 9

3.41 g (Yield: 68%) of Compound 9 was obtained in the same manner as in the synthesis of Compound 2, except that 2-quinolyl boronic acid, instead of 3-pyridyl boronic acid used to obtain Compound 2, was used. This compound was identified using MS/FAB and $^1H$ NMR.

$C_{42}H_{25}N_3$ calcd: 571.20, found: 571.21
$^1H$ NMR δ=8.47-8.45 (m, 1H), 8.31 (d, 1H), 8.27-8.24 (m, 2H), 8.13-8.10 (m, 1H), 8.00-7.96 (m, 3H), 8.87 (d, 1H), 7.82-7.78 (m, 1H), 7.69-7.60 (m, 3H), 7.53-7.46 (m, 6H), 7.42-7.37 (m, 2H), 7.34-7.25 (m, 4H)

Synthesis Example 3

Synthesis of Compound 14

3.63 g (Yield: 66%) of Compound 14 was obtained in the same manner as in the synthesis of Compound 2, except that 2-bromo-dibenzothiophene, instead of bromobenzene used to obtain Intermediate I-1, was used. This compound was identified using MS/FAB and $^1H$ NMR.

$C_{44}H_{25}N_3S$ calcd: 627.18, found: 627.20

$^1H$ NMR δ=9.06 (d, 1H), 8.58 (dd, 1H), 8.50 (d, 1H), 8.25-8.22 (m, 1H), 8.12 (d, 1H), 8.05 (d, 1H), 7.99-7.91 (m, 5H), 7.86 (d, 1H), 7.81 (d, 1H), 7.70-7.54 (m, 4H), 7.46-7.30 (m, 8H)

Synthesis Example 4

Synthesis of Compound 18

3.76 g (Yield: 70%) of Compound 18 was obtained in the same manner as in the synthesis of Compound 2, except that 2-bromo-dibenzofuran, instead of bromobenzene used to obtain Intermediate I-1, was used. This compound was identified using MS/FAB and $^1H$ NMR.

$C_{44}H_{25}N_3O$ calcd: 611.20, found: 611.21
$^1H$ NMR δ=8.79 (dd, 2H), 8.50 (dd, 1H), 8.28 (dd, 1H), 7.92-7.85 (m, 4H), 7.79-7.75 (m, 2H), 7.71-7.62 (m, 7H), 7.53 (t, 1H), 7.40-7.27 (m, 7H)

Synthesis Example 5

Synthesis of Compound 24

3.66 g (Yield: 67%) of Compound 24 was obtained in the same manner as in the synthesis of Compound 2, except that 5-[1,10]-phenanthroline boronic acid, instead of 3-pyridyl boronic acid used to obtain Compound 2, was used. This compound was identified using MS/FAB and $^1H$ NMR.

$C_{45}H_{26}N_4$ calcd: 622.22, found: 622.23
$^1H$ NMR δ=9.12 (dd, 1H), 9.00 (d, 1H), 8.63 (d, 1H), 8.46-8.44 (m, 1H), 8.25-8.23 (m, 2H), 8.13 (s, 1H), 7.88-7.79 (m, 5H), 7.69-7.58 (m, 4H), 7.52-7.47 (m, 4H), 7.40-7.25 (m, 6H)

Synthesis Example 6

Synthesis of Compound 28

Compound 28 was obtained in the same manner as in the synthesis of Compound 2, except that 1-phenyl-1H-benzimidazole-2-yl boronic acid, instead of 3-pyridyl boronic acid used to obtain Compound 2, was used. This compound was identified using MS/FAB and $^1H$ NMR.

$C_{44}H_{24}N_4$ calcd: 636.23, found: 636.22
$^1H$ NMR δ=8.48-8.45 (m, 1H), 8.33 (d, 1H), 8.31 (d, 1H), 8.23-8.21 (m, 1H), 7.93 (dd, 2H), 7.87 (d, 1H), 7.81 (d, 1H), 7.63 (d, 1H), 7.60-7.43 (m, 14H), 7.40-7.34 (m, 1H), 7.32-7.21 (m, 4H)

Synthesis Example 7

Synthesis of Compound 32

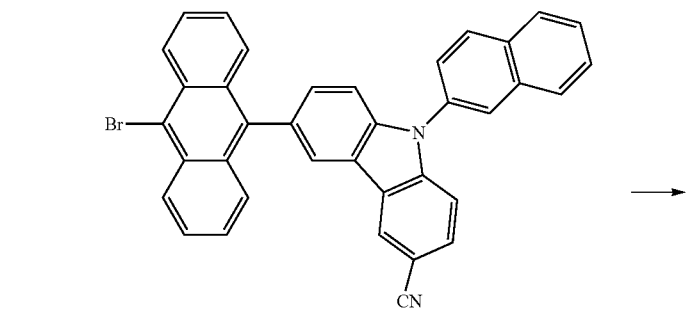

I-7

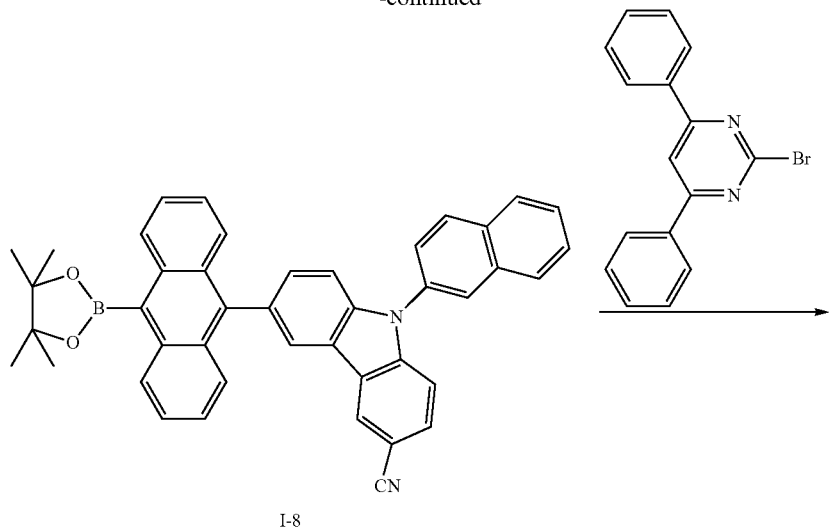

I-8

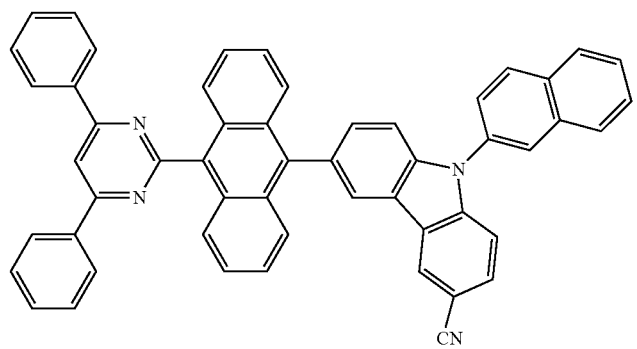

32

Synthesis of Intermediate I-7

5.30 g (Yield: 77%) of Compound I-7 was obtained in the same manner as in the synthesis of Compound I-6, except that 2-bromo naphthalene, instead of bromobenzene used to obtain Compound I-1, was used. This compound was identified using LC-MS.

$C_{37}H_{21}BrN_2$: M+ 572.1

2) Synthesis of Intermediate I-8

5.30 g (9.24 mmol) of Intermediate I-7, 0.38 g (0.46 mmol) of Pd(dppf)$_2$Cl$_2$, and 2.72 g (27.7 mmol) of KOAc were dissolved in 70 mL of dimethyl sulfoxide (DMSO), and stirred at about 150° C. for about 24 hours. The resulting reaction solution was cooled down to room temperature, and 100 mL of water was added thereto, followed by extraction three times with 50 mL of CH$_2$Cl$_2$. An organic layer was collected and was dried using magnesium sulfate to evaporate the solvent. The residue was separated and purified using silica gel column chromatography to obtain 4.13 g of Intermediate I-8 (Yield: 72%). This compound was identified using LC-MS.

$C_{43}H_{33}BN_2O_2$: M+ 620.3

3) Synthesis of Compound 32

3.33 g (Yield: 69%) of Compound 32 was obtained in the same manner as in the synthesis of Compound 2, except that Intermediate I-8 and 2-bromo-4,6-diphenyl pyrimidine, instead of Intermediate I-6 and 3-pyridyl boronic acid used to obtain Compound 2, respectively, were used. This compound was identified using MS/FAB and $^1$H NMR.

$C_{53}H_{32}N_4$ calcd: 724.26, found: 724.27

$^1$H NMR δ=8.51-8.49 (m, 1H), 8.35-8.32 (m, 4H), 8.28-8.24 (m, 3H), 7.98 (s, 1H), 7.90 (d, 1H), 7.86-7.83 (m, 2H), 7.68-7.48 (m, 16H), 7.44-7.41 (m, 1H), 7.31-7.27 (m, 3H)

Synthesis Example 8

Synthesis of Compound 39

3.36 g (Yield: 65%) of Compound 39 was obtained in the same manner as in the synthesis of Compound 32, except that bromobenzene, instead of 2-bromo naphthalene used to obtain Intermediate I-7, and 2-chloro-4,6-dinaphthalene-2-yl-[1,3,5]triazine, instead of 2-bromo-4,6-diphenyl pyrimidine used to obtain Compound 32, were used. This compound was identified using MS/FAB and $^1$H NMR.

$C_{56}H_{33}N_5$ calcd: 775.27, found: 775.25

$^1$H NMR δ=8.90 (d, 2H), 8.75 (d, 2H), 8.45 (dd, 1H), 8.25 (d, 2H), 8.23 (d, 1H), 8.16 (dd, 2H), 8.12 (d, 2H), 8.03 (dd, 2H), 7.88-7.86 (m, 3H), 7.70-7.46 (m, 14H), 7.34-7.25 (m, 2H)

Synthesis Example 9

Synthesis of Compound 45

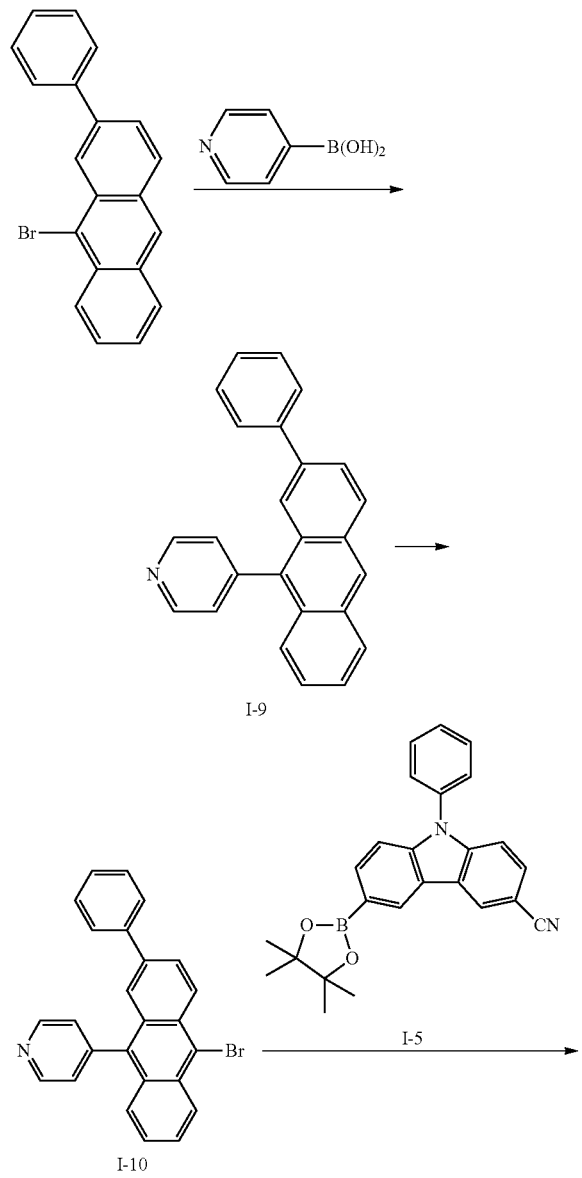

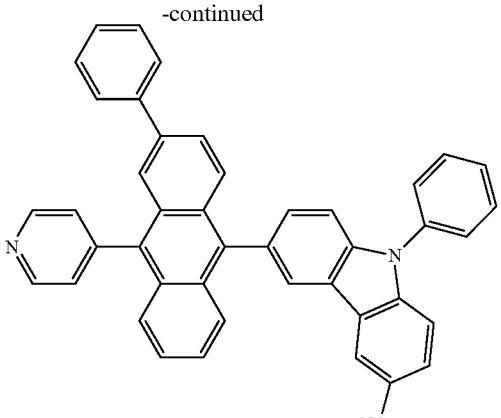

45

1) Synthesis of Intermediate I-9

5.00 g (15.0 mmol) of 9-bromo-2-phenyl-anthracene, 1.84 g (15.0 mmol) of 4-pyridyl boronic acid, 0.87 g (0.75 mmol) of Pd(PPh$_3$)$_4$, and 6.22 g (45.0 mmol) of K$_2$CO$_3$ were dissolved in 60 mL of THF and 30 mL of H$_2$O, and stirred at about 80° C. for about 12 hours. The resulting reaction solution was cooled down to room temperature, followed by extraction three times with 30 mL of water and 30 mL of ethyl acetate. An organic layer was collected and was dried using magnesium sulfate to evaporate the solvent. The residue was separated and purified using silica gel column chromatography to obtain 3.48 g of Compound I-9 (Yield: 70%). This compound was identified using LC-MS.

$C_{25}H_{17}N$: M$^+$ 331.1

2) Synthesis of Intermediate I-10

After 3.48 g (10.5 mmol) of Intermediate I-9 was completely dissolved in 80 mL of CH$_2$Cl$_2$ to obtain a solution, 1.87 g (10.5 mmol) of N-bromosuccinimide was added to the solution and stirred at room temperature for about 12 hours. 60 mL of water was added to the resulting reaction solution, followed by extraction three times with 50 mL of CH$_2$Cl$_2$. An organic layer was collected and was dried using magnesium sulfate to evaporate the solvent. The residue was recrystallized using methanol to obtain 3.75 g of Intermediate I-10 (Yield: 87%). This compound was identified using LC-MS.

$C_{25}H_{16}BrN$: M$^+$ 409.1

3) Synthesis of Compound 45

3.82 g (Yield: 70%) of Compound 457 was obtained in the same manner as in the synthesis of Intermediate I-6, except that Intermediate I-10, instead of 9,10-dibromo-anthracene to obtain Intermediate I-6, was used. This compound was identified using MS/FAB and $^1$H NMR.

$C_{44}H_{27}N_3$ calcd: 597.22, found: 597.23

$^1$H NMR δ=8.84-8.82 (m, 2H), 8.38-8.36 (m, 1H), 8.25-8.23 (m, 1H), 7.98 (dd, 1H), 7.89-7.85 (m, 2H), 7.80-7.72 (m, 6H), 7.65-7.61 (m, 3H), 7.52-7.47 (m, 6H), 7.42-7.26 (m, 5H)

Synthesis Example 10

Synthesis of Compound 64

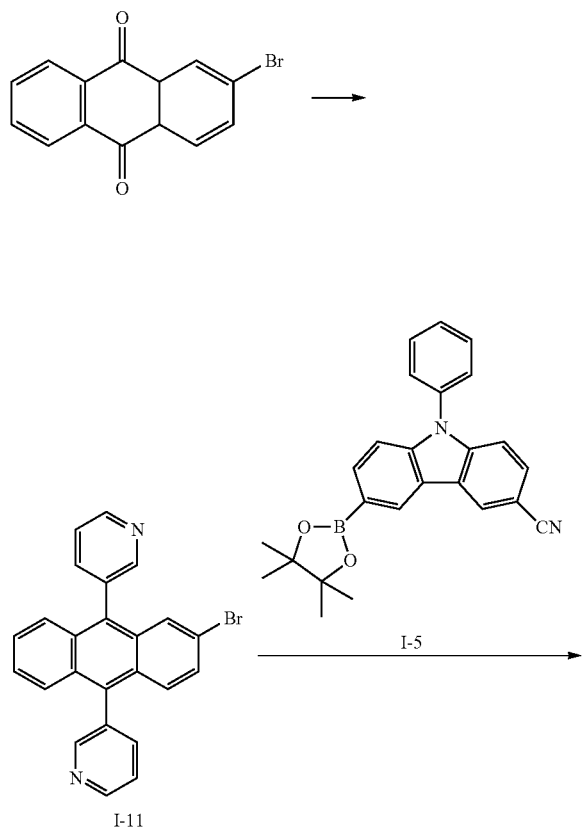

1) Synthesis of Intermediate I-11

After 5.45 g (34.5 mmol) of 3-bromo pyridine was dissolved in 60 mL of THF, 13.8 mL (34.5 mmol, 2.5M in hexane) of nBuLi was slowly dropwise added thereinto at about −78° C., and stirred for about 1 hour. 4.33 g (15.0 mmol) of 2-bromo-4a,9a-dihydro-anthraquinone was slowly dropwise added into the resulting reaction solution and stirred at room temperature for about 12 hours. 60 mL of water was added to the resulting reaction solution, followed by extraction three times with 50 mL of ethyl acetate. An organic layer was collected and was dried using magnesium sulfate to evaporate the solvent. The residue was mixed with 22.4 g (135 mmol) of KI, 21.3 g (165 mmol) of $Na_2H_2PO_2 \cdot H_2O$ and 50 mL of acetic acid, and stirred at about 120° C. for about 1 hour. The resulting reaction solution was cooled down to room temperature, and 60 mL of water was added thereto and filtered. The residue was separated and purified using silica gel column chromatography to obtain 5.05 g of Intermediate I-11 (Yield: 82%). This compound was identified using LC-MS.

$C_{24}H_{15}BrN_2$: $M^+$ 410.1

2) Synthesis of Compound 64

4.57 g (Yield: 62%) of Compound 64 was obtained in the same manner as in the synthesis of Intermediate I-6, except that Intermediate I-11, instead of 9,10-dibromo anthracene used to obtain Intermediate I-6, was used. This compound was identified using MS/FAB and $^1$H NMR.

$C_{43}H_{26}N_4$ calcd: 598.22, found: 598.21

$^1$H NMR δ=9.10-9.08 (d, 2H), 8.61-8.59 (m, 2H), 8.31-8.22 (m, 4H), 8.16 (dd, 1H), 8.00-7.90 (m, 3H), 7.85 (d, 1H), 7.74-7.71 (m, 2H), 7.63 (d, 1H), 7.52-7.47 (m, 4H), 7.42-7.35 (m, 4H), 7.32-7.26 (m, 2H)

Synthesis Example 11

Synthesis of Compound 68

Compound 68 was obtained in the same manner as in the synthesis of Compound 64, except that Intermediate A-1, instead of Intermediate I-11 used to obtain Compound 64, was used.

$C_{44}H_{31}N_3$ calcd: 673.25, found: 673.26

$^1$H NMR δ=9.02 (dd, 1H), 8.64 (dd, 1H), 8.31-8.28 (m, 2H), 8.15 (d, 1H), 8.09-8.05 (m, 2H), 7.98 (d, 1H), 7.91 (d, 1H), 7.87 (d, 1H), 7.83-7.80 (m, 5H), 7.72 (dd, 1H), 7.65-7.59 (m, 2H), 7.52-7.47 (m, 9H), 7.41-7.37 (m, 2H), 7.32-7.25 (m, 2H)

Synthesis Example 12
Synthesis of Compound 76
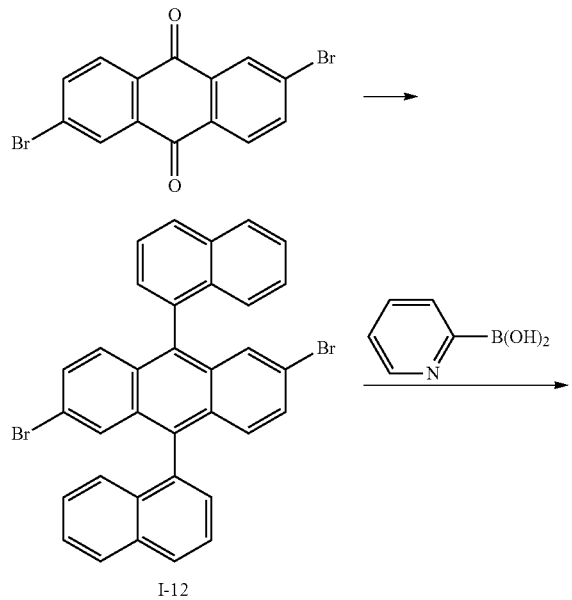
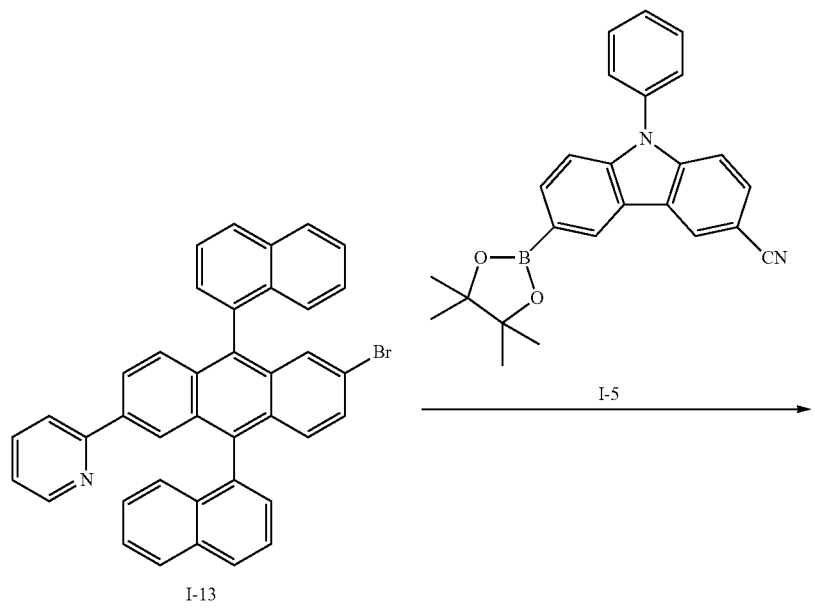

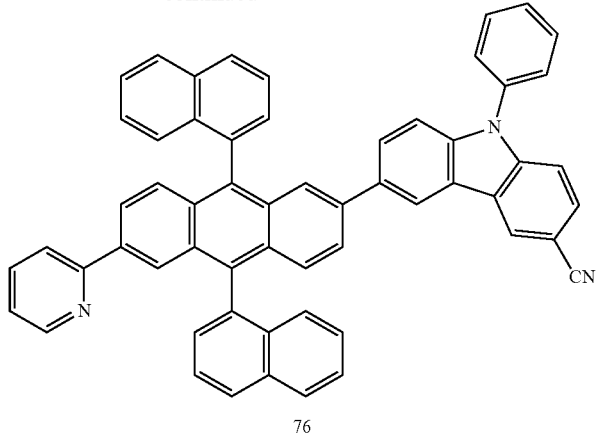

76

1) Synthesis of Intermediate I-12

6.18 g (Yield: 70%) of Intermediate I-10 was obtained in the same manner as in the synthesis of Intermediate I-12, except that 2,6-dibromo-4a,9a-dihydro-anthraquinone and bromonaphthalene, instead of 2-bromo-4a,9a-dihydro-anthraquinone and 3-bromo pyridine used to obtain Intermediate I-11, respectively, were used. This compound was identified using LC-MS.

$C_{34}H_{20}Br_2$: M$^+$ 586.0

2) Synthesis of Intermediate I-13

6.18 g (10.5 mmol) of Intermediate I-12, 1.29 g (10.5 mmol) of 2-pyridyl boronic acid, 0.61 g (0.53 mmol) of Pd(PPh$_3$)$_4$, and 4.35 g (31.5 mmol) of K$_2$CO$_3$ were dissolved in 60 mL of THF and 30 mL of H$_2$O, and stirred at about 80° C. for about 12 hours. The resulting reaction solution was cooled down to room temperature, followed by extraction three times with 30 mL of water and 30 mL of ethyl acetate. An organic layer was collected and was dried using magnesium sulfate to evaporate the solvent. The residue was separated and purified using silica gel column chromatography to obtain 4.19 g of Compound I-13 (Yield: 68%). This compound was identified using LC-MS.

$C_{39}H_{24}BrN$: M$^+$ 585.1

3) Synthesis of Compound 76

3.59 g (Yield: 65%) of Compound 76 was obtained in the same manner as in the synthesis of Compound 64, except that Intermediate I-13, instead of Intermediate I-11 used to obtain Compound 64, was used. This compound was identified using MS/FAB and $^1$H NMR.

$C_{58}H_{35}N_3$ calcd: 773.28, found: 773.26
$^1$H NMR δ=9.04 (d, 1H), 8.72 (dd, 1H), 8.40 (d, 2H), 8.35 (d, 1H), 8.31-8.26 (m, 3H), 8.18 (d, 1H), 8.06 (d, 1H), 7.95 (d, 1H), 7.86-7.82 (m, 3H), 7.77-7.68 (m, 7H), 7.63 (d, 1H), 7.57 (dd, 2H), 7.50-7.47 (m, 4H), 7.36-7.25 (m, 4H), 7.20-7.15 (m, 1H), 7.06-7.02 (m, 2H)

Synthesis Example 13

Synthesis of Compound 79

Compound 79 was obtained in the same manner as in the synthesis of Compound 64, except that Intermediate A-2 represented by the following formula, instead of Intermediate I-11 used to obtain Compound 64, was used. This compound was identified using MS/FAB and $^1$H NMR.

<Intermediate A-2>

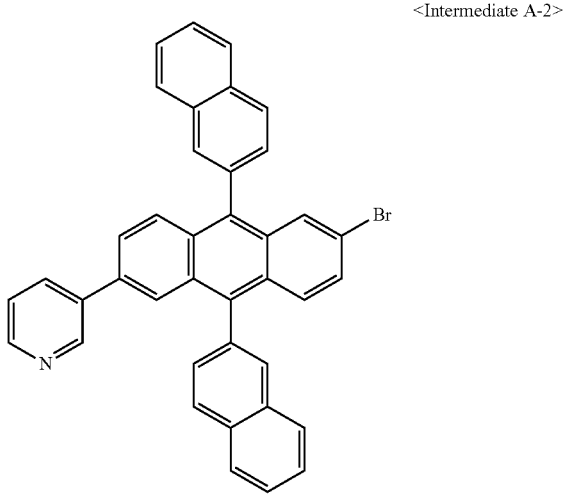 [SMILES: Brc1ccc2c(-c3ccc4ccccc4c3)c3cc(-c4cccnc4)ccc3c(-c3ccc4ccccc4c3)c2c1]

$C_{58}H_{35}N_3$ calcd: 773.28, found: 773.30
$^1$H NMR δ=9.01 (dd, 1H), 8.64 (dd, 1H), 8.31-8.22 (m, 3H), 8.09-8.07 (m, 4H), 7.97-7.83 (m, 11H), 7.72 (d, 1H), 7.65-7.47 (m, 12H), 7.34-7.26 (m, 2H)

Synthesis Example 14

Synthesis of Compound 98

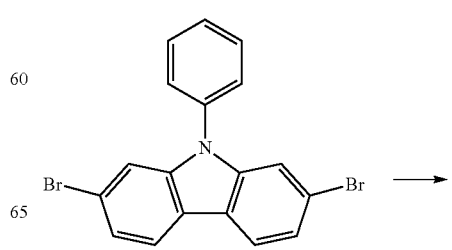

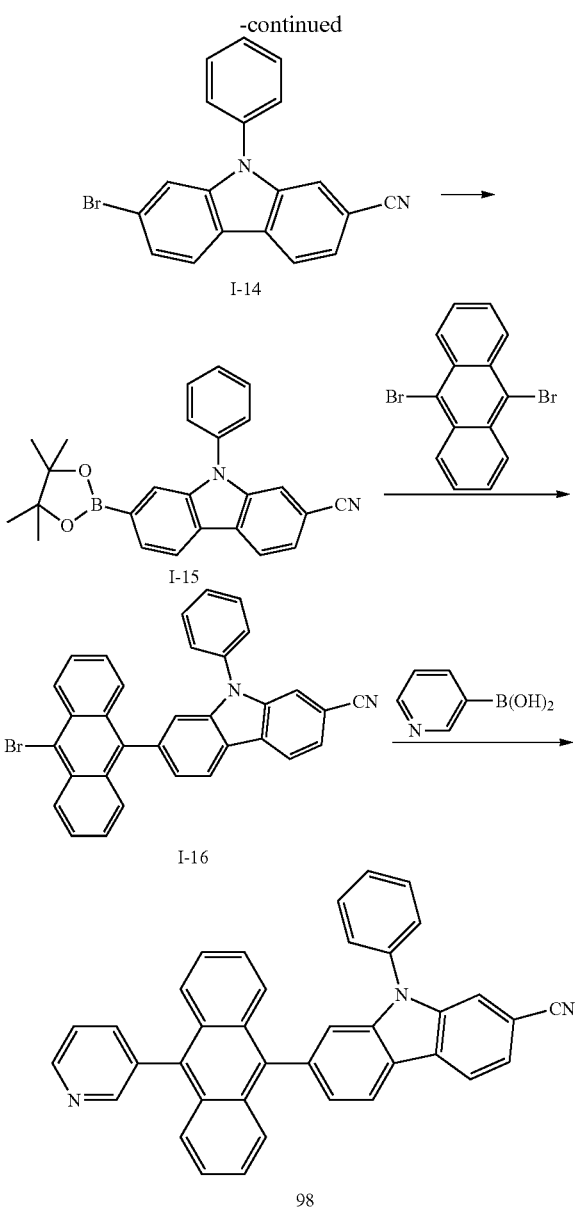

1) Synthesis of Intermediate I-14

20.0 g (50.0 mmol) of 2,7-dibromo-9-phenyl-9H-carbazole, and 4.48 g (50.0 mmol) of CuCN were dissolved in 120 mL of DMF, and stirred at about 150° C. for about 24 hours. The resulting reaction solution was cooled down to room temperature, and 60 mL of ammonia water and 60 mL of water were added thereto, followed by extraction three times with 60 mL of $CH_2Cl_2$. An organic layer was collected and was dried using magnesium sulfate to evaporate the solvent. The residue was separated and purified using silica gel column chromatography to obtain 6.08 g of Intermediate I-14 (Yield: 35%). This compound was identified using LC-MS.

$C_{19}H_{11}BrN_2$: M⁺ 346.0

2) Synthesis of Intermediate I-15

6.08 g (17.5 mmol) of Intermediate I-14, 0.71 g (0.88 mmol) of $Pd(dppf)_2Cl_2$, and 5.16 g (52.5 mmol) of KOAc were dissolved in 80 mL of DMSO, and stirred at about 150° C. for about 24 hours. The resulting reaction solution was cooled down to room temperature, and 100 mL of water was added thereto, followed by extraction three times with 50 mL of $CH_2Cl_2$. An organic layer was collected and was dried using magnesium sulfate to evaporate the solvent. The residue was separated and purified using silica gel column chromatography to obtain 5.17 g of Intermediate I-15 (Yield: 75%). This compound was identified using LC-MS.

$C_{25}H_{23}BN_2O_2$: M⁺ 394.2

3) Synthesis of Intermediate I-16

4.80 g (Yield: 70%) of Intermediate I-16 was obtained in the same manner as in the synthesis of intermediate I-6, except that Intermediate I-15, instead of Intermediate I-5 used to obtain Compound I-6, was used. This compound was identified using LC-MS.

$C_{33}H_{19}BrN_2$: M⁺ 522.1

4) Synthesis of Compound 98

3.44 g (Yield: 72%) of Compound 98 was obtained in the same manner as in the synthesis of Compound 2, except that Intermediate I-16, instead of Intermediate I-6 used to obtain Compound 2, was used. This compound was identified using MS/FAB and ¹H NMR.

$C_{38}H_{23}N_3$ calcd: 521.19, found: 521.18

¹H NMR δ=9.00 (dd, 1H), 8.48-8.43 (m, 2H), 8.33-8.28 (m, 2H), 8.22 (dd, 1H), 8.03-7.99 (m, 3H), 7.90-7.86 (m, 2H), 7.68 (d, 1H), 7.59 (d, 1H), 7.54-7.52 (m, 5H), 7.47-7.43 (m, 2H), 7.39-7.37 (m, 4H), 7.31-7.27 (m, 1H)

Synthesis Example 15

Synthesis of Compound 99

Compound 99 was obtained in the same manner as in the synthesis of Compound 2, except that Intermediate I-16 and 8-quinolinyl boronic acid, instead of Intermediate I-6 and 3-pyridyl boronic acid used to obtain Compound 2, respectively, were used. This compound was identified using MS/FAB and ¹H NMR.

$C_{42}H_{25}N_3$ calcd: 571.20, found: 571.21

¹H NMR δ=9.00 (dd, 1H), 8.48-8.43 (m, 2H), 8.33-8.28 (m, 2H), 8.22 (dd, 1H), 8.03-7.99 (m, 3H), 7.90-7.86 (m, 2H), 7.68 (d, 1H), 7.59 (d, 1H), 7.54-7.52 (m, 5H), 7.47-7.43 (m, 2H), 7.39-7.37 (m, 4H), 7.31-7.27 (m, 1H)

Synthesis Example 16

Synthesis of Compound 102

Compound 102 was obtained in the same manner as in the synthesis of Compound 2, except that Intermediate I-16 and 2-dibenzofuranyl boronic acid, respectively instead of Intermediate I-6 and 3-pyridyl boronic acid used to obtain Compound 2, were used. This compound was identified using MS/FAB and ¹H NMR.

$C_{44}H_{26}N_2O$ calcd: 610.20, found: 610.19

¹H NMR δ=8.39-8.37 (m, 1H), 8.03-8.95 (m, 4H), 7.93-7.90 (m, 2H), 7.80 (dd, 1H), 7.76-7.73 (m, 2H), 7.71-7.67 (m, 3H), 7.59 (d, 1H), 7.55-7.51 (m, 5H), 7.43 (dd, 1H), 7.37-7.27 (m, 6H)

Example 1

To manufacture an anode, a Corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone for about 10 minutes. The resulting glass substrate was loaded into a vacuum deposition device.

Then, 4,4',4"-tris[2-naphthyl(phenyl)amino]triphenylamine (2-TNATA) was vacuum-deposited on the ITO glass substrate to form a HIL having a thickness of 600 Å, and 4,4'-bis[N-(1-naphthyl)-N-phenylamino]biphenyl (NPB) was then vacuum-deposited on the HIL to form a HTL having a thickness of 300 Å.

Subsequently, 9,10-di-naphthalene-2-yl-anthracene (ADN) as a host and 4,4'-bis[2-(4-(N,N-diphenylamino)phenyl)vinyl]biphenyl (DPAVBi) as a dopant were co-deposited on the HTL in a weight ratio of 98:2 to form an EML having a thickness of about 300 Å.

Then, Compound 2 was vacuum-deposited on the EML to form an ETL having a thickness of about 300 Å, and then LiF was vacuum-deposited on the ETL to form an EIL having a thickness of about 10 Å. Then, Al was vacuum-deposited on the EIL to form a cathode having a thickness of about 3000 Å, thereby completing the manufacture of an organic light-emitting device.

Example 2

An organic light-emitting device was manufactured in the same manner as in Example 1, except that Compound 9, instead of Compound 2, was used to form the ETL.

Example 3

An organic light-emitting device was manufactured in the same manner as in Example 1, except that Compound 14, instead of Compound 2, was used to form the ETL.

Example 4

An organic light-emitting device was manufactured in the same manner as in Example 1, except that Compound 18, instead of Compound 2, was used to form the ETL.

Example 5

An organic light-emitting device was manufactured in the same manner as in Example 1, except that Compound 24, instead of Compound 2, was used to form the ETL.

Example 6

An organic light-emitting device was manufactured in the same manner as in Example 1, except that Compound 32, instead of Compound 2, was used to form the ETL.

Example 7

An organic light-emitting device was manufactured in the same manner as in Example 1, except that Compound 39, instead of Compound 2, was used to form the ETL.

Example 8

An organic light-emitting device was manufactured in the same manner as in Example 1, except that Compound 45, instead of Compound 2, was used to form the ETL.

Example 9

An organic light-emitting device was manufactured in the same manner as in Example 1, except that Compound 64, instead of Compound 2, was used to form the ETL.

Example 10

An organic light-emitting device was manufactured in the same manner as in Example 1, except that Compound 76, instead of Compound 2, was used to form the ETL.

Example 11

An organic light-emitting device was manufactured in the same manner as in Example 1, except that Compound 98, instead of Compound 2, was used to form the ETL.

Comparative Example 1

An organic light-emitting device was manufactured in the same manner as in Example 1, except that Alq$_3$, instead of Compound 2, was used to form the ETL.

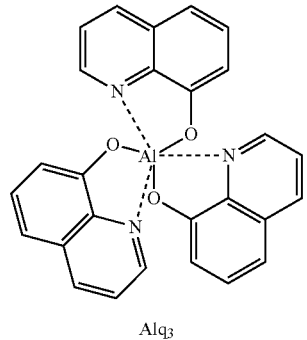

Alq$_3$

Comparative Example 2

An organic light-emitting device was manufactured in the same manner as in Example 1, except that Compound X below, instead of Compound 2, was used to form the ETL.

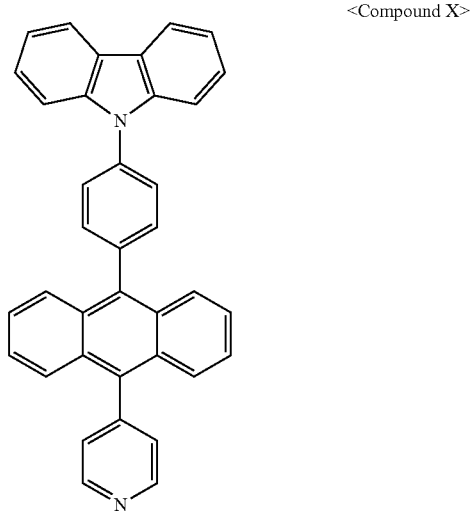 [SMILES: c1ccc2c(-c3ccc(-n4c5ccccc5c5ccccc54)cc3)c3ccccc3c(-c3ccncc3)c2c1]

<Compound X>

Comparative Example 3

An organic light-emitting device was manufactured in the same manner as in Example 1, except that Compound Y below, instead of Compound 2, was used to form the ETL.

<Compound Y>

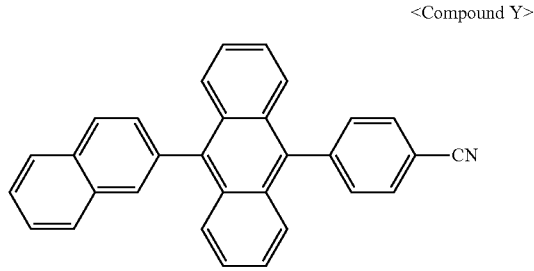 [SMILES: N#Cc1ccc(-c2c3ccccc3c(-c3ccc4ccccc4c3)c3ccccc23)cc1]

Evaluation Example

Driving voltages, current densities, luminance, efficiency, and emission colors of the organic light-emitting devices of Examples 1 to 9 and Comparative Examples 1 and 3 were measured using a PR650 (Spectroscan) Source Measurement Unit (available from Photo Research, Inc.). The results are shown in Table 1. In Table 1, half lifetime indicates the time in hours (hr) taken until an initial luminance (assumed as 100%) measured at a current density of about 100 mA/cm$_2$ was reduced to 50%.)

TABLE 1

| Example | ETL material | Driving voltage (V) | Current density (mA/cm$^2$) | Luminance (cd/m$^2$) | Efficiency (cd/A) | Emission color | Half lifetime (hr @ 100 mA/cm$^2$) |
|---|---|---|---|---|---|---|---|
| Example 1 | Compound 2 | 4.70 | 50 | 3,820 | 7.95 | blue | 650 hr |
| Example 2 | Compound 9 | 4.95 | 50 | 3,505 | 7.76 | blue | 617 hr |
| Example 3 | Compound 14 | 5.50 | 50 | 3,570 | 6.76 | blue | 585 hr |
| Example 4 | Compound 18 | 5.06 | 50 | 3,600 | 7.60 | blue | 622 hr |
| Example 5 | Compound 24 | 5.32 | 50 | 3,315 | 6.83 | blue | 562 hr |
| Example 6 | Compound 32 | 5.46 | 50 | 3.260 | 6.97 | blue | 596 hr |
| Example 7 | Compound 39 | 5.63 | 50 | 3,570 | 6.72 | blue | 625 hr |
| Example 8 | Compound 45 | 5.18 | 50 | 3,685 | 7.50 | blue | 598 hr |
| Example 9 | Compound 64 | 5.07 | 50 | 3,720 | 7.85 | blue | 638 hr |
| Example 10 | Compound 76 | 5.25 | 50 | 3,610 | 7.19 | blue | 603 hr |
| Example 11 | Compound 98 | 5.02 | 50 | 3,480 | 7.64 | blue | 617 hr |
| Comparative Example 1 | Alq3 | 7.35 | 50 | 2,065 | 4.13 | blue | 145 hr |
| Comparative Example 2 | Compound X | 5.70 | 50 | 3,380 | 7.05 | blue | 230 hr |
| Comparative Example 3 | Compound Y | 5.36 | 50 | 3,060 | 6.35 | blue | 527 hr |

Referring to Table 1, the organic light-emitting devices of Examples 1 to 9 were found to have lower driving voltages, higher luminance, and improved efficiency characteristics, compared to the organic light-emitting devices of Comparative Examples 1 to 3. The organic light-emitting devices of Examples 1 to 9 were also found to have improved lifetime characteristics, compared to the organic light-emitting devices of Comparative Examples 1 to 3.

By way of summation and review, one or more embodiments include an anthracene-based compound, and a high-quality organic light-emitting device including the anthracene-based compound. As described above, according to the one or more of the above embodiments an anthracene-based compound having improved stability, electrical characteristics, and chemical characteristics is provided. An organic light-emitting device including the anthracene-based compound of Formula 1 may have high efficiency, low driving voltage, high luminance, and long lifetime.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

What is claimed is:

1. An anthracene-based compound represented by Formula 1 below:

<Formula 1>

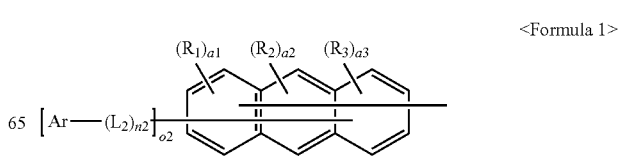

-continued

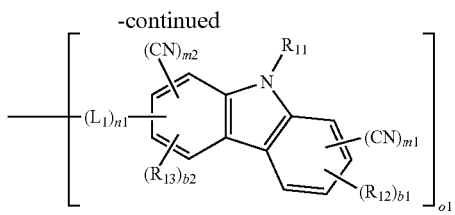

wherein, in Formula 1,

Ar is an electron transport moiety selected from a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{60}$ heteroaryl group, excluding a substituted or unsubstituted carbazolyl group;

$R_1$ to $R_3$, and $R_{11}$ to $R_{13}$ are each independently selected from a hydrogen atom, a deuterium atom, a halogen atom, a hydroxyl group, a cyano group, a nitro group, an amino group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{10}$ heterocycloalkyl group, a substituted or unsubstituted $C_2$-$C_{10}$ heterocycloalkenyl group, and a substituted or unsubstituted $C_2$-$C_{30}$ heteroaryl group;

a1 to a3 are each independently an integer of 0 or 2;

b1 is an integer from 0 to 3;

b2 is an integer from 0 to 4;

$L_1$ and $L_2$ are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, a substituted or unsubstituted $C_2$-$C_{10}$ heterocycloalkylene group, a substituted or unsubstituted $C_2$-$C_{10}$ heterocycloalkenylene group, and a substituted or unsubstituted $C_2$-$C_{60}$ heteroarylene group;

n1 and n2 are each independently an integer from 0 to 3;

m1 and m2 are each independently an integer from 0 to 3, where m1+m2 is equal to an integer of 1 or greater;

m1+b1=4, and m2+b2=3; and o1 and o2 are each independently an integer from 1 to 3.

2. The anthracene-based compound as claimed in claim 1, wherein Ar is selected from:

i) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group;

ii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a deuterium atom, —F, a hydroxyl group, a cyano group, a nitro group, a methyl group, an ethyl group, an n-propyl group, and a t-butyl group;

iii) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group; and iv) a pyridyl group, a pyrazinyl group, a pyrimidyl group, a quinolinyl group, an isoquinolinyl group, a benzoquinolinyl group, a phenanthridinyl group, an acridinyl group, a phenanthrolinyl group, a phenazinyl group, a benzoimidazolyl group, a benzofuranyl group, a dibenzofuranyl group, a benzothiophenyl group, a dibenzothiophenyl group, and a triazinyl group, each substituted with at least one of a phenyl group, a naphthyl group, a pyridyl group, and a quinolinyl group that are substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group.

3. The anthracene-based compound as claimed in claim 1, wherein Ar is selected from:

i) a pyridyl group, a pyrimidyl group, a quinolinyl group, a phenanthrolinyl group, a benzoimidazolyl group, a dibenzofuranyl group, a dibenzothiophenyl group, and a triazinyl group;

ii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group; and iii) a pyridyl group, a pyrimidyl group, a quinolinyl group, a phenanthrolinyl group, a benzoimidazolyl group, a dibenzofuranyl group, a dibenzothiophenyl group, and a triazinyl group, each substituted with at least one of a phenyl group, a naphthyl group, a pyridyl group, and a quinolinyl group that are substituted with at least one of a phenyl group, a naphthyl group, a pyridyl group, and a quinolinyl group.

4. The anthracene-based compound as claimed in claim 1, wherein Ar is selected from the groups represented by Formulae 2-1 to 2-12 below:

2-1

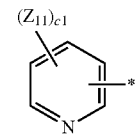

2-2

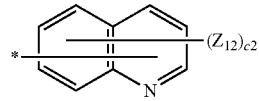

2-3

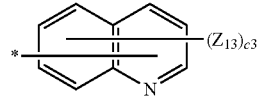

-continued 2-4
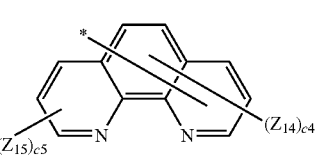

2-5
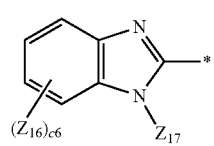

2-6
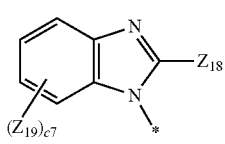

2-7
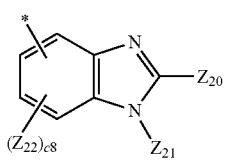

2-8
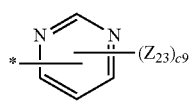

2-9
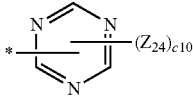

2-11
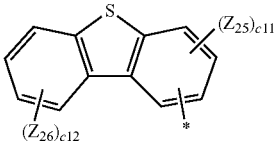

2-12
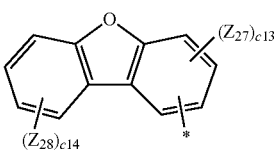

wherein, in Formulae 2-1 to 2-12, $Z_{11}$ to $Z_{28}$ are each independently selected from:

i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with at least one of a phenyl group, a 1-naphthyl group, a 2-naphthyl group, a pyridyl group, and a quinolinyl group, c1 to c14 are each independently an integer from 0 to 2, and

* indicates a binding site to $L_2$ or an anthracene core.

5. The anthracene-based compound as claimed in claim 1, wherein Ar is selected from the groups represented by Formulae 3-1 to 3-14 below:

3-1
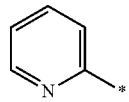

3-2
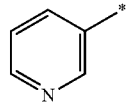

3-3
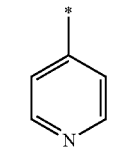

3-4
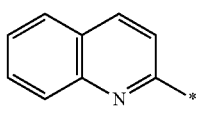

3-5
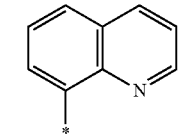

3-6
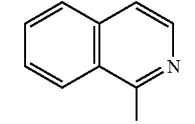

3-7
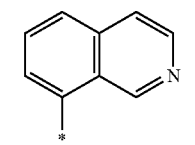

3-8
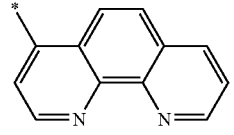

3-9
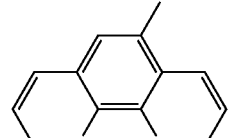

3-10
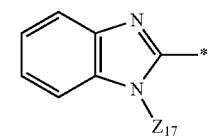

3-11
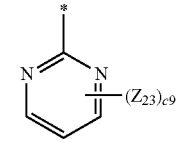

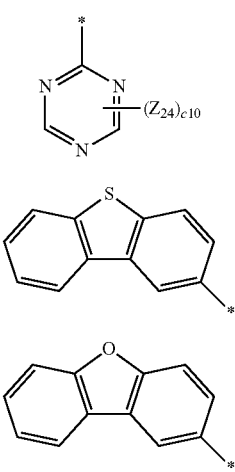

3-12

3-13

3-14 wherein, in Formulae 3-1 to 3-14, $Z_{17}$, $Z_{23}$, and $Z_{24}$ are each independently selected from:

i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with a phenyl group, c9 and c10 are each independently an integer from 0 to 2, and

* indicates a binding site to $L_2$ or an anthracene core.

6. The anthracene-based compound as claimed in claim 1, wherein $R_1$ to $R_3$ in Formula 1 are each independently selected from:

i) a hydrogen atom, a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and ii) a phenyl group, a naphthyl group, a pyridyl group, and a quinolinyl group, each substituted with at least one of a deuterium atom, —F, a hydroxyl group, a cyano group, a nitro group, a methyl group, an ethyl group, an n-propyl group, and a t-butyl group.

7. The anthracene-based compound as claimed in claim 1, wherein $R_1$ to $R_3$ in Formula 1 are each independently selected from a deuterium atom, —F, a cyano group, a nitro group, a methyl group, a t-butyl group, a phenyl group, a naphthyl group, a pyridyl group, and a quinolinyl group.

8. The anthracene-based compound as claimed in claim 1, wherein $R_{11}$ to $R_{13}$ in Formula 1 are each independently selected from:

i) a phenyl group, a naphthyl group, a fluorenyl group, a pyridyl group, a quinolinyl group, an isoquinolinyl group, a dibenzofuranyl group, and a dibenzothiophenyl group;

ii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a deuterium atom, —F, a hydroxyl group, a cyano group, a nitro group, a methyl group, an ethyl group, an n-propyl group, a t-butyl group, a phenyl group, a naphthyl group, a pyridyl group, and a quinolinyl group; and iii) a phenyl group, a naphthyl group, a fluorenyl group, a pyridyl group, a quinolinyl group, an isoquinolinyl group, a dibenzofuranyl group, and a dibenzothiophenyl group, each substituted with at least one of a methyl group, a t-butyl group, a phenyl group, a naphthyl group, a pyridyl group, and a quinolinyl group that are substituted with at least one of a deuterium atom, —F, a hydroxyl group, a cyano group, a nitro group, a methyl group, and a t-butyl group.

9. The anthracene-based compound as claimed in claim 1, wherein $R_{11}$ to $R_{13}$ in Formula 1 are each independently selected from the groups represented by Formulae 2-1 to 2-12 and Formulae 4-1 to 4-3 below:

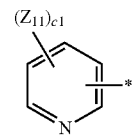

2-1

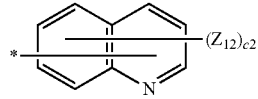

2-2

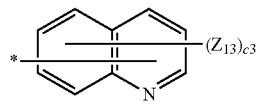

2-3

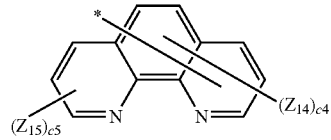

2-4

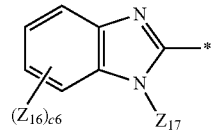

2-5

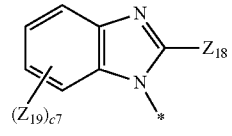

2-6

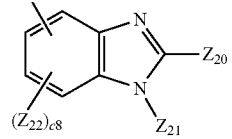

2-7

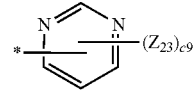

2-8

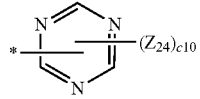

2-9

-continued 2-11
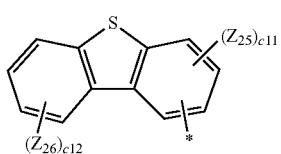

2-12
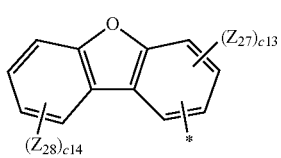

4-1
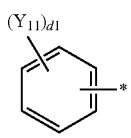

4-2
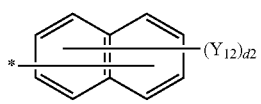

4-3
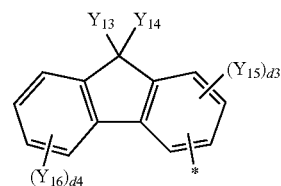

wherein, in Formulae 2-1 to 2-12, and Formulae 4-1 to 4-3, $Z_{11}$ to $Z_{28}$, and $Y_{11}$ to $Y_{16}$ are each independently selected from:

i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 are each independently an integer from 0 to 2, and

* indicates a binding site to $L_1$ or an anthracene core.

10. The anthracene-based compound as claimed in claim 1, wherein $R_{11}$ to $R_{13}$ in Formula 1 are each independently selected from groups represented by Formulae 3-1 to 3-14 and Formulae 5-1 to 5-4 below:

3-1
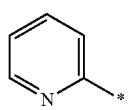

3-2
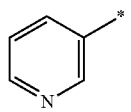

-continued 3-3
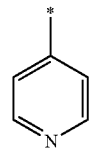

3-4
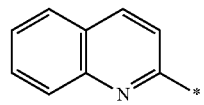

3-5
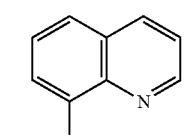

3-6
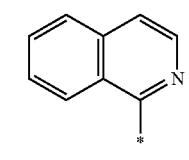

3-7
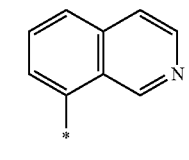

3-8
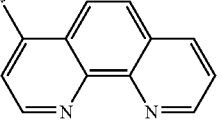

3-9
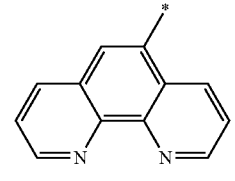

3-10
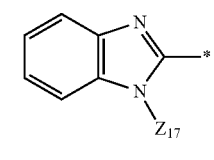

3-11
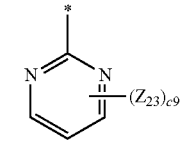

3-12
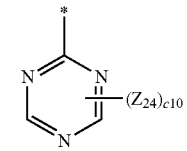

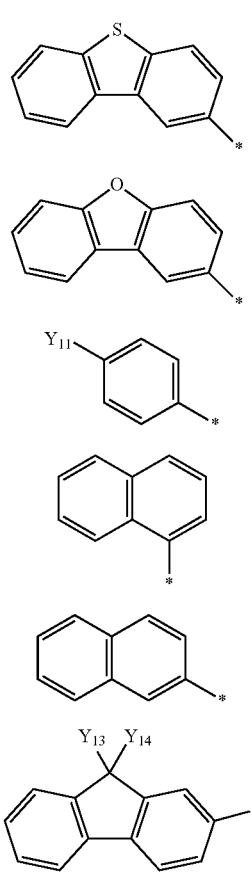

3-13

3-14

5-1

5-2

5-3

5-4 wherein, in Formulae 3-1 to 3-14 and Formulae 5-1 to 5-4, $Z_{17}$, $Z_{23}$, $Z_{24}$, $Y_{13}$, and $Y_{14}$ are each independently selected from:
i) —F, a cyano group, a nitro group, a methyl group, a t-butyl group, a phenyl group, and a pyridyl group; and
ii) a methyl group, a phenyl group, and a pyridyl group, each substituted with at least one of —F, a cyano group, a nitro group, a methyl group, a t-butyl group, a phenyl group, and a pyridyl group,
c9 and c10 are each independently an integer from 0 to 2, and
* indicates a binding site to $L_1$ or an anthracene core.

11. The anthracene-based compound as claimed in claim 1, wherein $L_1$ and $L_2$ in Formula 1 are each independently selected from:
i) a phenylene group, a naphthylene group, an anthracenyl group, a chrysenylene group, and a pyrenylene group; and
ii) a phenylene group, a naphthylene group, an anthracenyl group, a chrysenylene group, and a pyrenylene group, each substituted with at least one selected from:
a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, and a $C_1$-$C_{10}$ alkyl group;
a $C_1$-$C_{10}$ alkyl group substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof;
a $C_6$-$C_{16}$ aryl group, and a $C_2$-$C_{16}$ heteroaryl group; and
a $C_6$-$C_{16}$ aryl group, and a $C_2$-$C_{16}$ heteroaryl group, each substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

12. The anthracene-based compound as claimed in claim 1, wherein $L_1$ and $L_2$ in Formula 1 are each independently selected from:
i) a phenylene group, an anthracenyl group, a chrysenylene group, and a pyrenylene group; and
ii) a phenylene group, an anthracenyl group, a chrysenylene group, and a pyrenylene group, each substituted with at least one selected from:
a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group; a phenyl group, a naphthyl group, a pyridyl group, and a triazinyl group; and a phenyl group, a naphthyl group, a pyridyl group, and a triazinyl group, each substituted with at least one of a deuterium atom, a halogen atom, a hydroxyl group, a cyano group, a nitro group, a methyl group, an ethyl group, an n-propyl group, an iso-propyl group, an n-butyl group, a sec-butyl group, an iso-a butyl group, and a tert-butyl group.

13. The anthracene-based compound as claimed in claim 1, wherein n1 and n2 are both 0.

14. The anthracene-based compound as claimed in claim 1, wherein m1 is 1, and m2 is 0.

15. The anthracene-based compound as claimed in claim 1, wherein o1 and o2 are each independently 1 or 2.

16. The anthracene-based compound as claimed in claim 1, wherein the anthracene-based compound of Formula 1 is a compound represented by one of Formulae 1a(1) to 1a(5), 1b(1) to 1b(3), 1c(1) to 1c(3) and 1d(1) below:

<Formula 1a(1)>

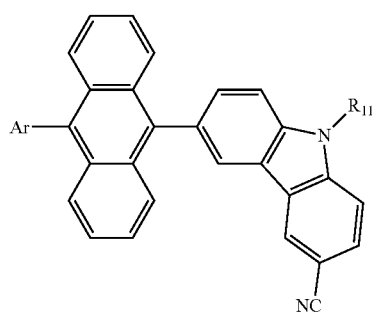

<Formula 1a(2)>
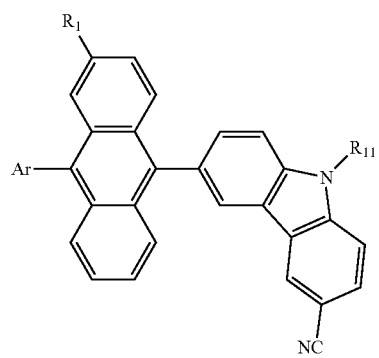
<Formula 1a(3)>
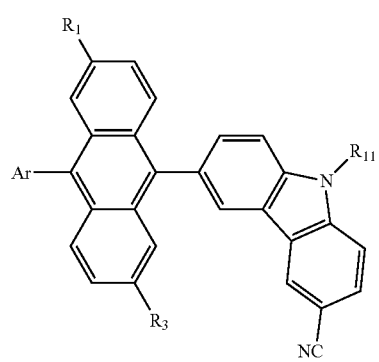
<Formula 1a(4)>
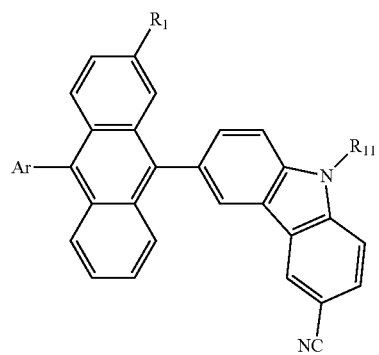
<Formula 1a(5)>
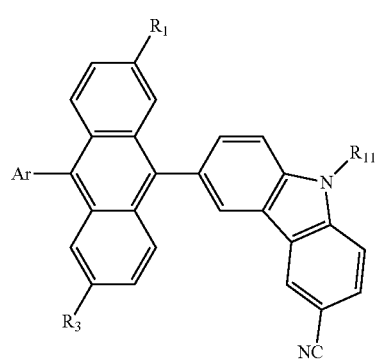
<Formula 1b(1)>
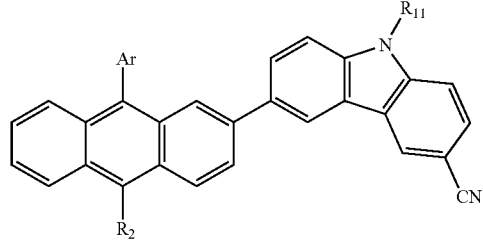
<Formula 1b(2)>
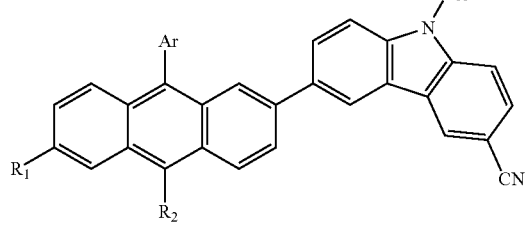
<Formula 1b(3)>
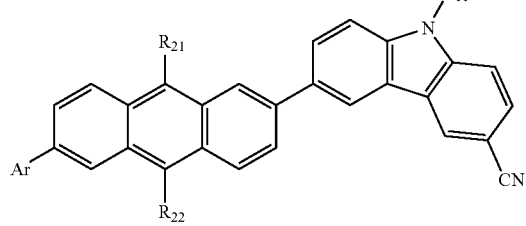
<Formula 1c(1)>
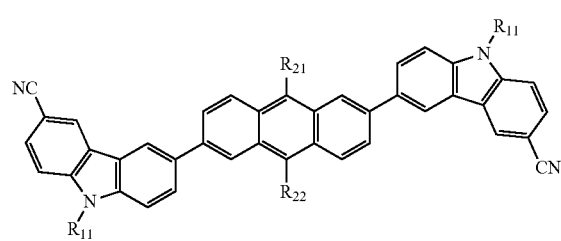
<Formula 1c(2)>
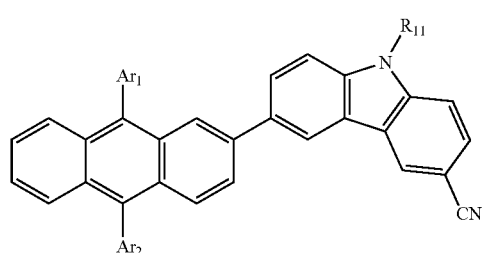
<Formula 1c(3)>
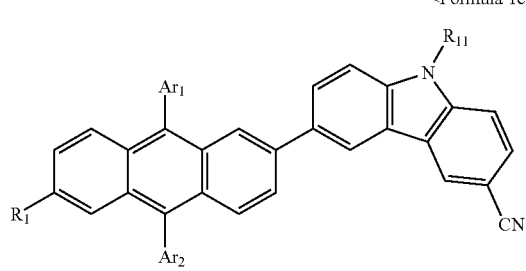

<Formula 1d(1)>

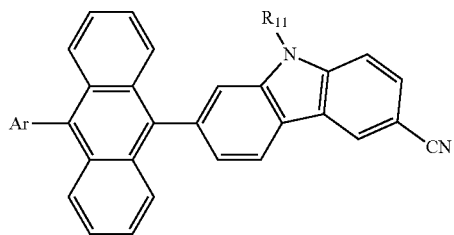

wherein, in Formulae 1a(1) to 1a(5), 1b(1) to 1b(3), 1c(1) to 1c(3), and 1d(1),

Ar, $Ar_1$, and $Ar_2$ are each independently selected from the groups represented by Formulae 3-1 to 3-14:

3-1

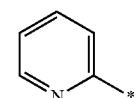

3-2

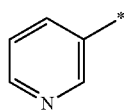

3-3

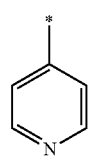

3-4

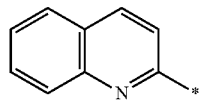

3-5

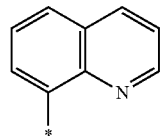

3-6

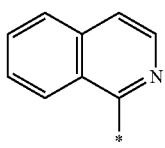

3-7

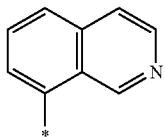

3-8

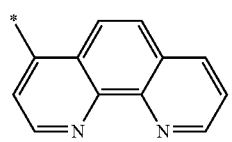

3-9

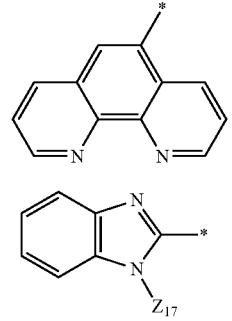

3-10

3-11

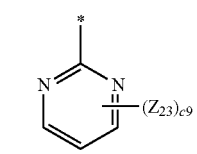

3-12

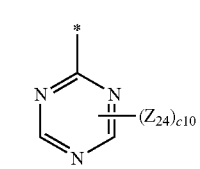

3-13

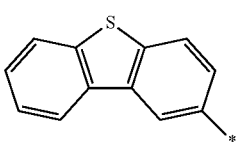

3-14

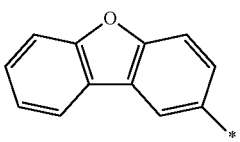

wherein, in Formulae 3-1 to 3-14, $Z_{17}$, $Z_{23}$, and $Z_{24}$ are each independently selected from:

i) a phenyl group, a 1-naphthyl group, a 2-naphthyl group, a pyridyl group, and a quinolinyl group; and ii) a phenyl group, a 1-naphthyl group, a 2-naphthyl group, a pyridyl group, and a quinolinyl group, each substituted with a phenyl group, c9 and c10 are each independently an integer from 0 to 2,

* indicates a binding site to an anthracene core, $R_1$ to $R_3$, $R_{21}$, and $R_{22}$ are each independently selected from a deuterium atom, —F, a cyano group, a nitro group, a methyl group, a t-butyl group, a phenyl group, a naphthyl group, a pyridyl group, and a quinolinyl group, and $R_{11}$ is selected from the groups represented by Formulae 2-1 to 2-12, and Formulae 4-1 to 4-3 below:

2-1

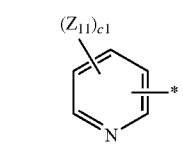

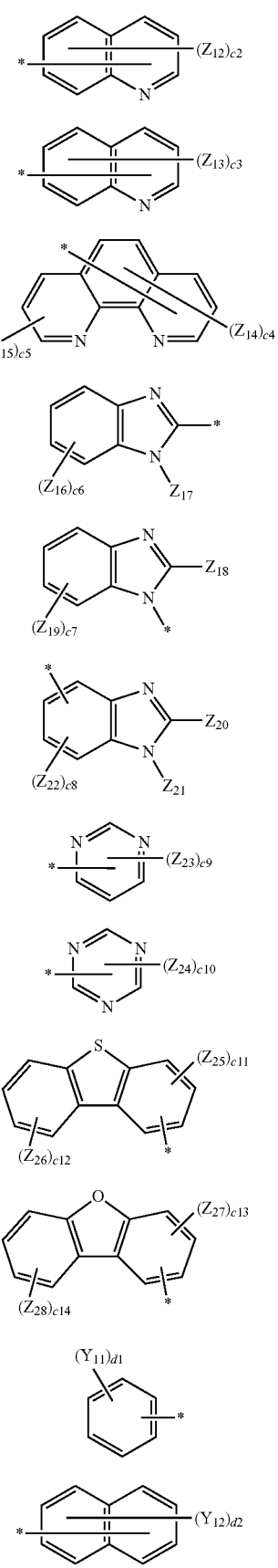

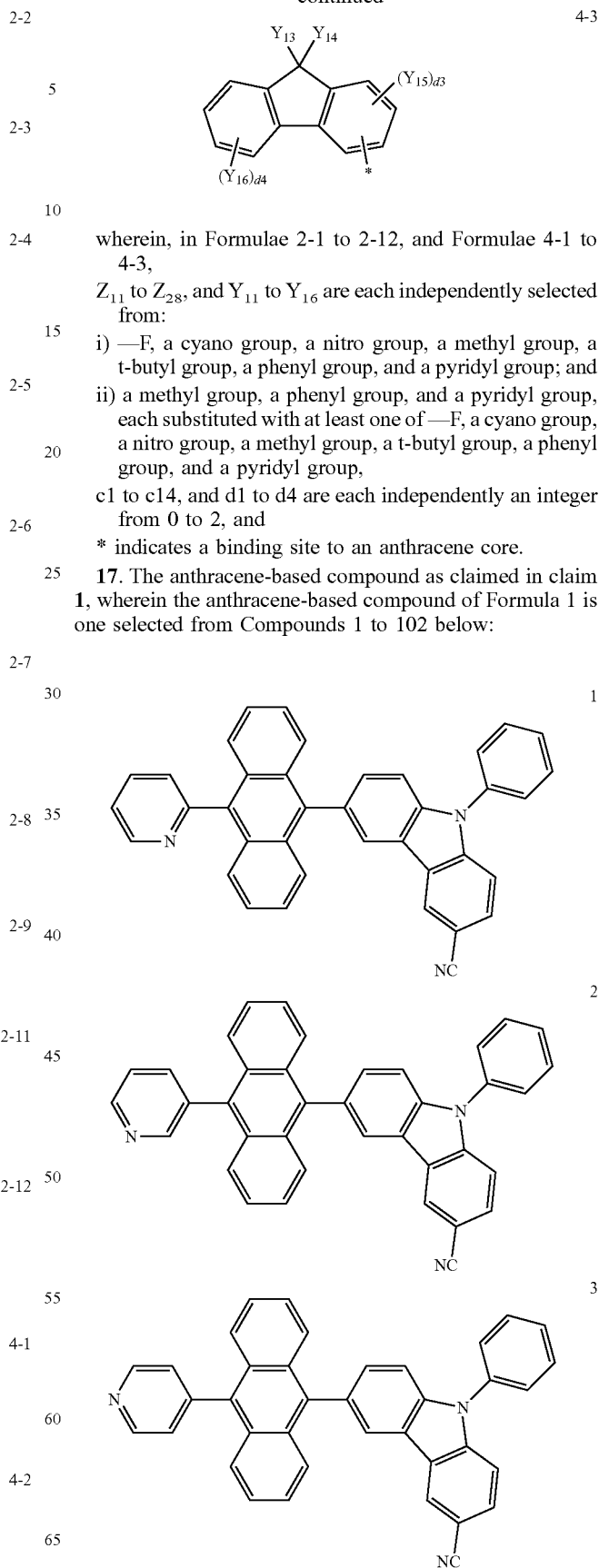

wherein, in Formulae 2-1 to 2-12, and Formulae 4-1 to 4-3, $Z_{11}$ to $Z_{28}$, and $Y_{11}$ to $Y_{16}$ are each independently selected from:

i) —F, a cyano group, a nitro group, a methyl group, a t-butyl group, a phenyl group, and a pyridyl group; and ii) a methyl group, a phenyl group, and a pyridyl group, each substituted with at least one of —F, a cyano group, a nitro group, a methyl group, a t-butyl group, a phenyl group, and a pyridyl group, c1 to c14, and d1 to d4 are each independently an integer from 0 to 2, and

* indicates a binding site to an anthracene core.

17. The anthracene-based compound as claimed in claim 1, wherein the anthracene-based compound of Formula 1 is one selected from Compounds 1 to 102 below:

-continued
4
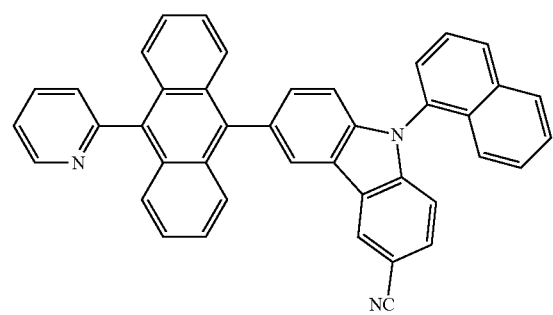
5
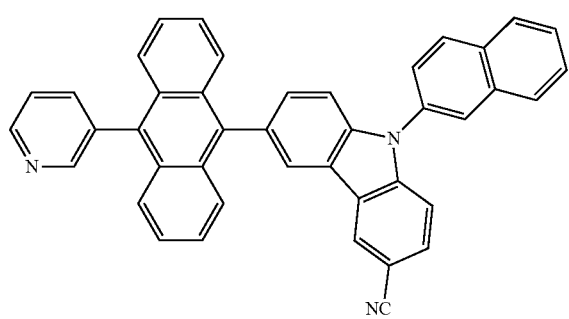
6
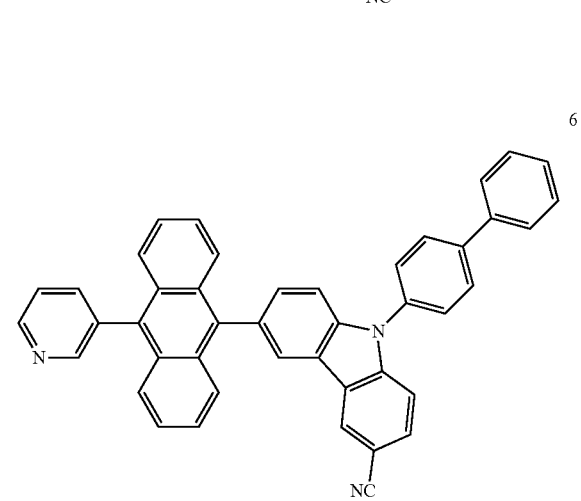
7
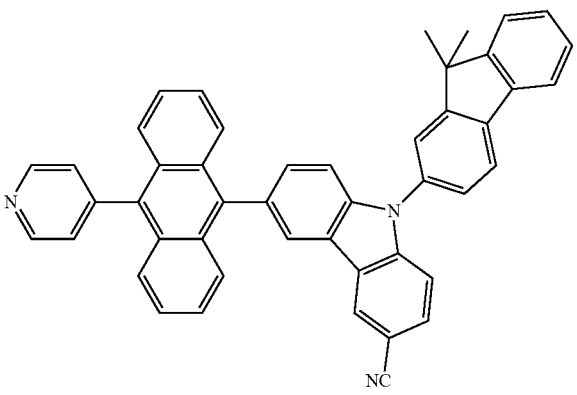
-continued
8
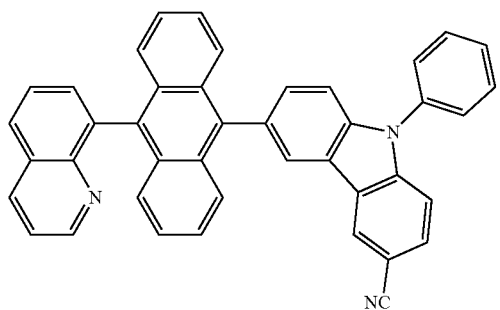
9
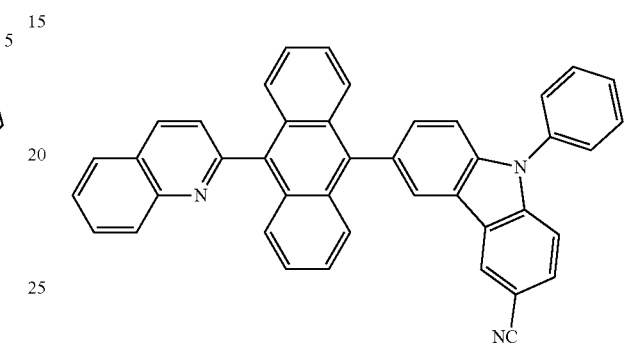
10
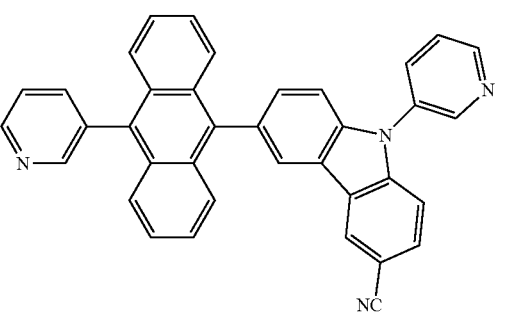
11
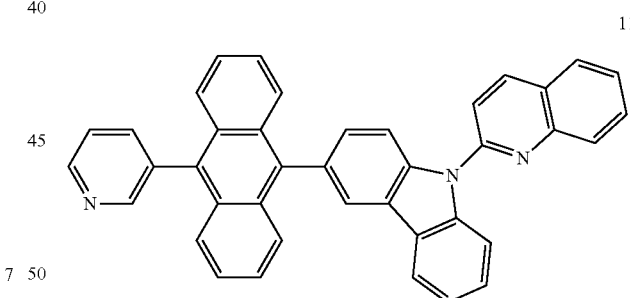
12
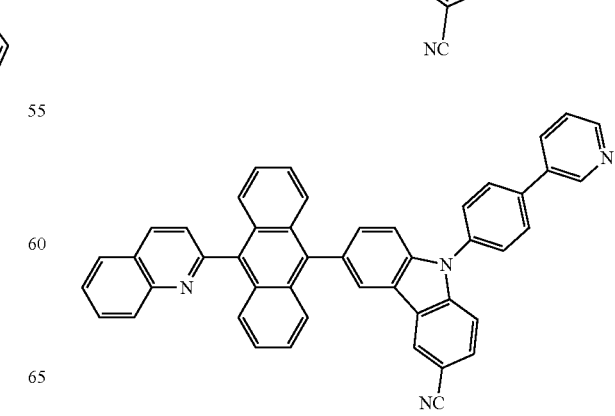

-continued

23
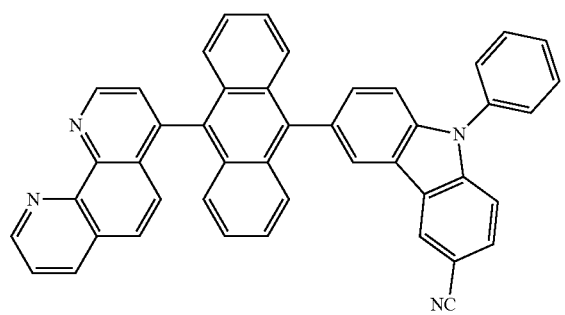
24
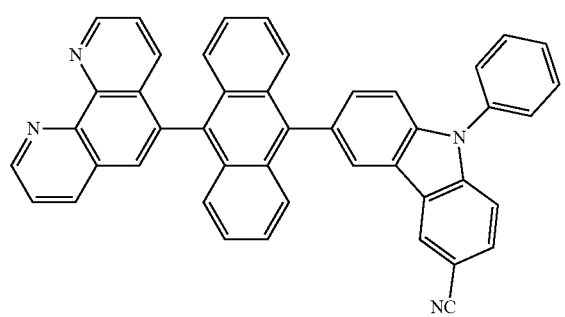
25
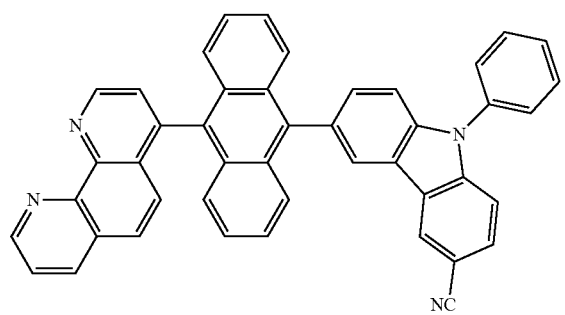
26
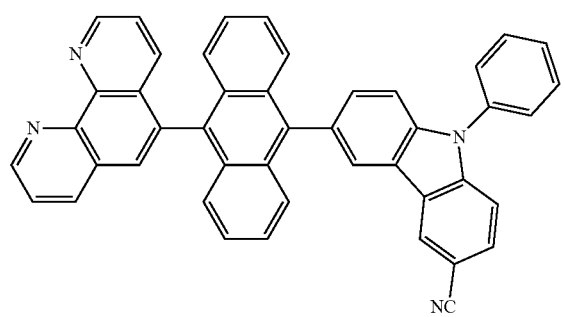
27
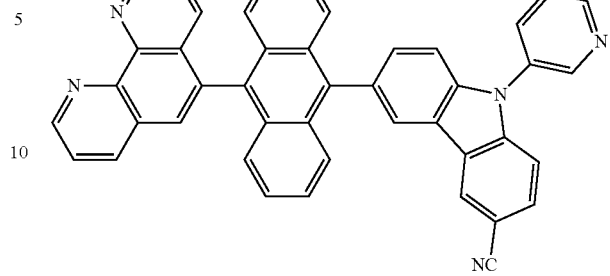
28
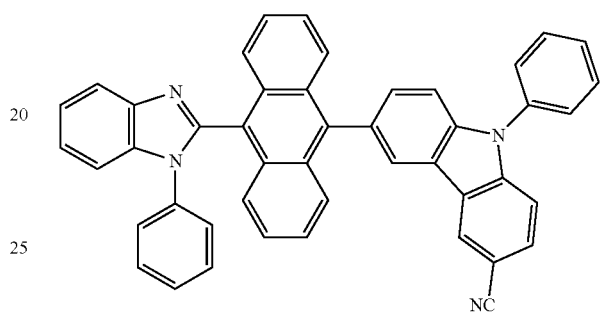
29
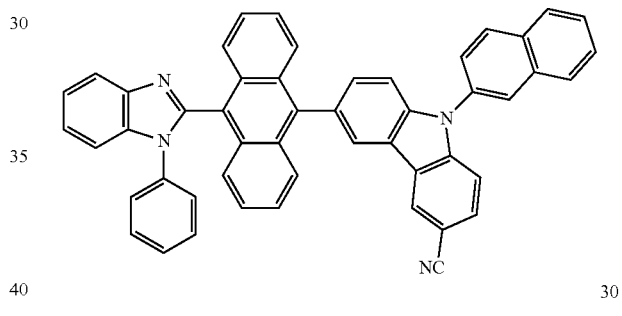
30
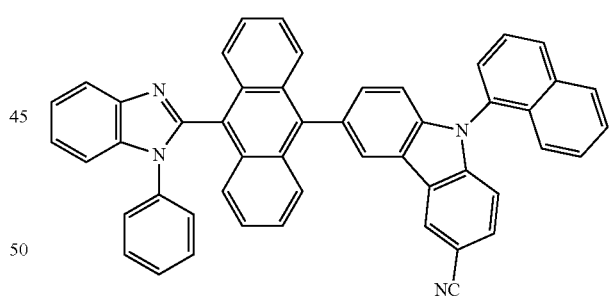
31
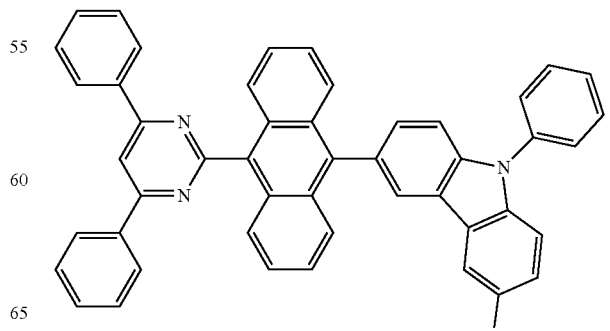

32
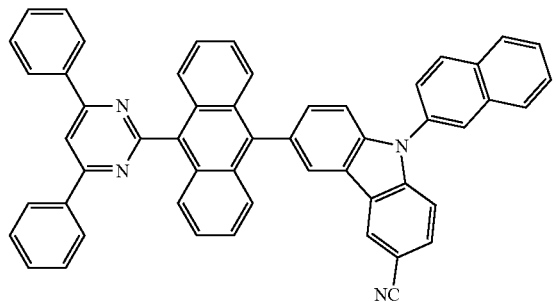
33
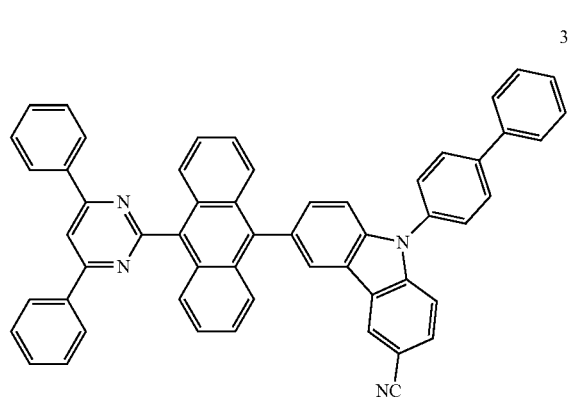
34
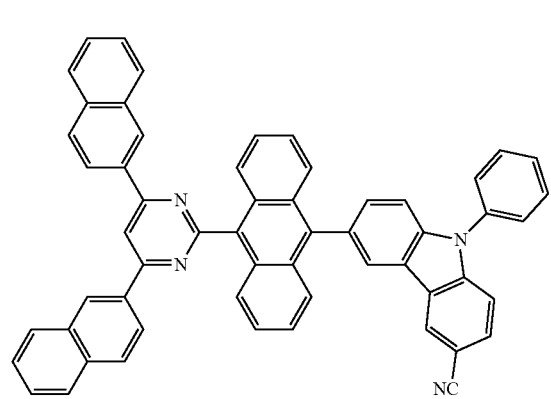
35
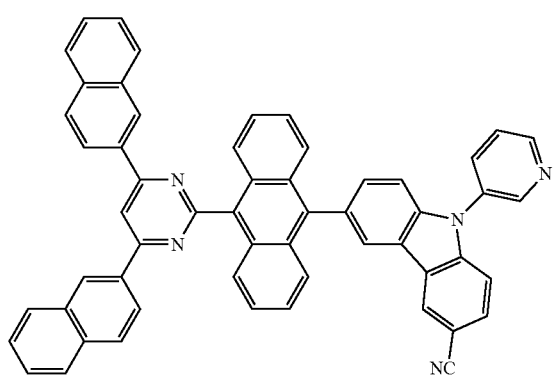
36
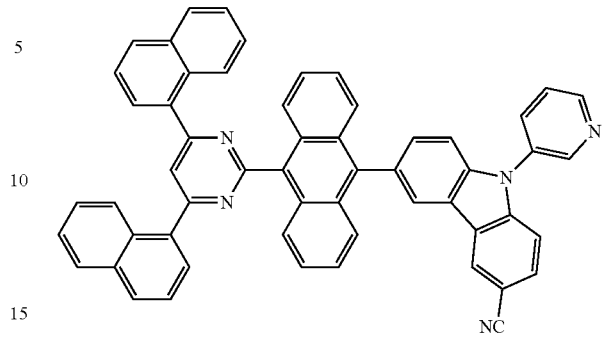
37
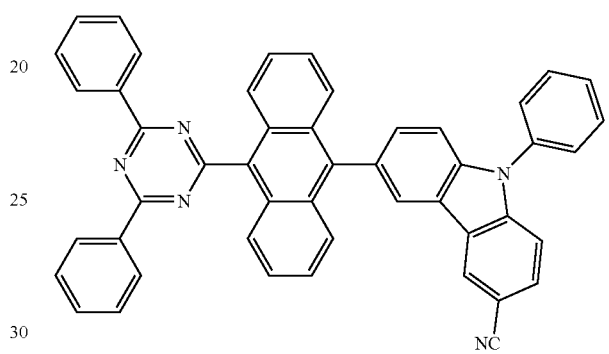
38
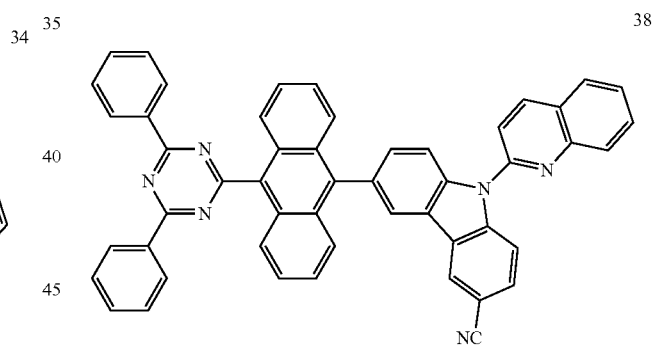
39
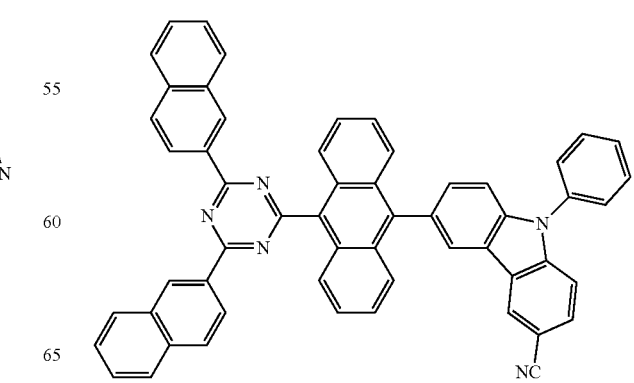

199
-continued
| 40 |
|---|
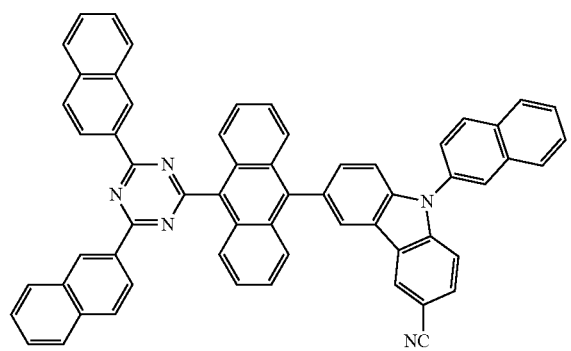
41
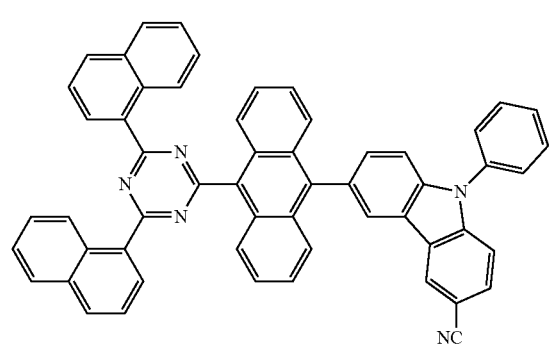
42
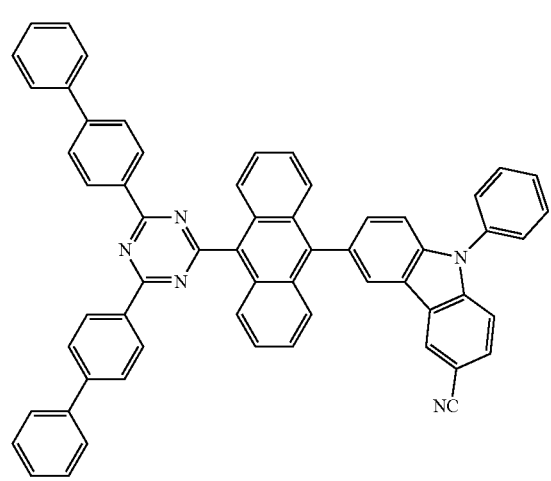
43
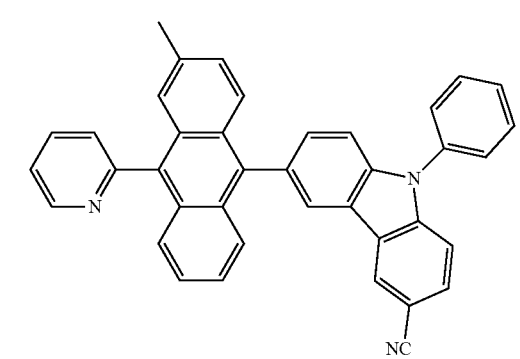
200
-continued
44
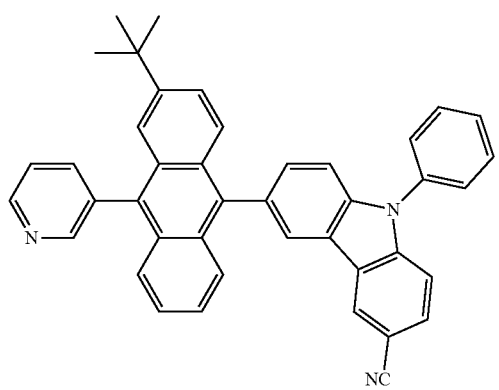
45
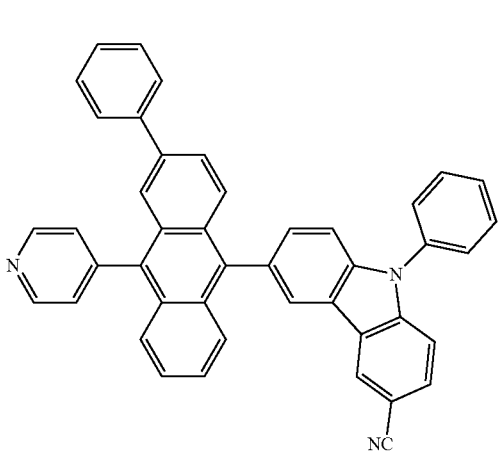
46
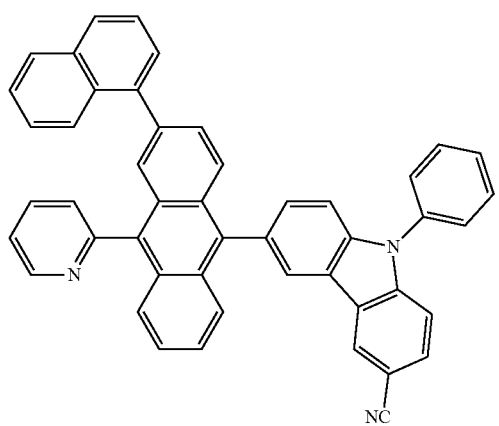

47
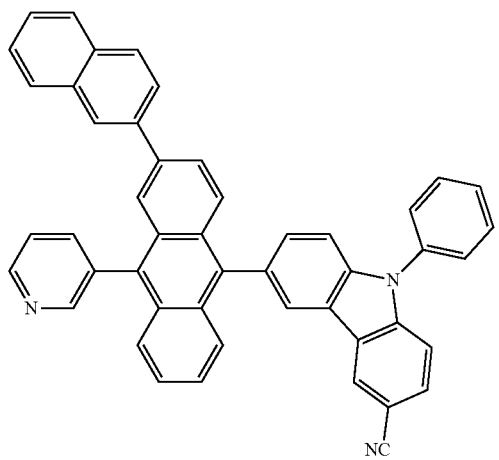
48
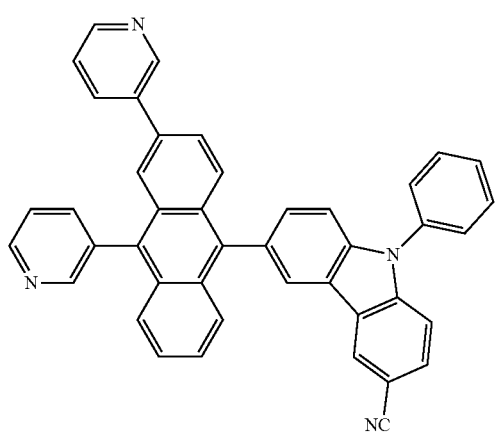
49
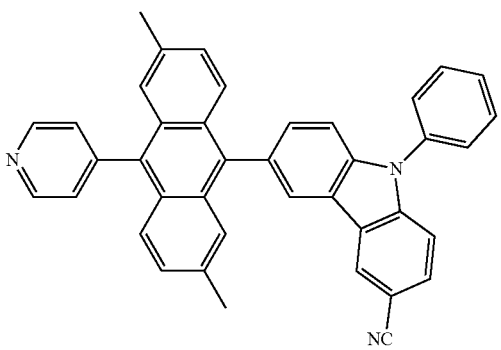
50
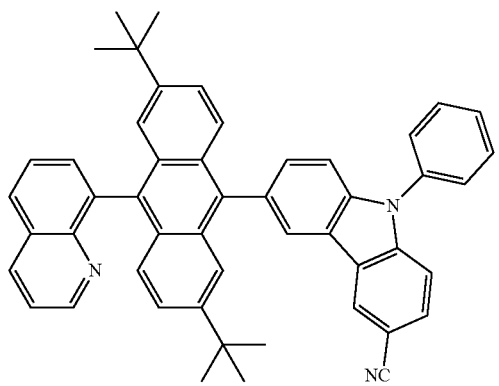
51
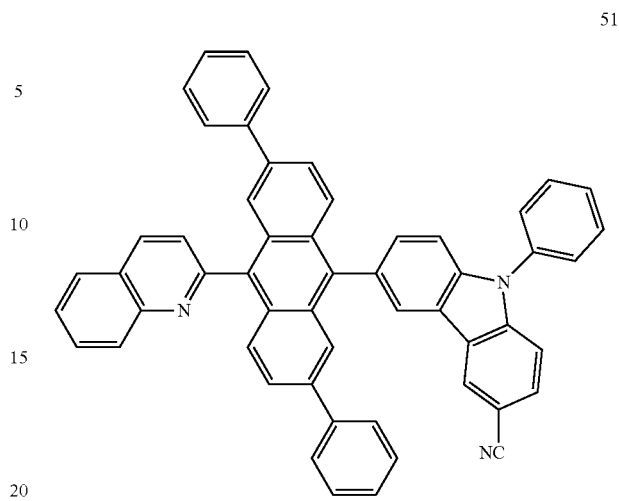
52
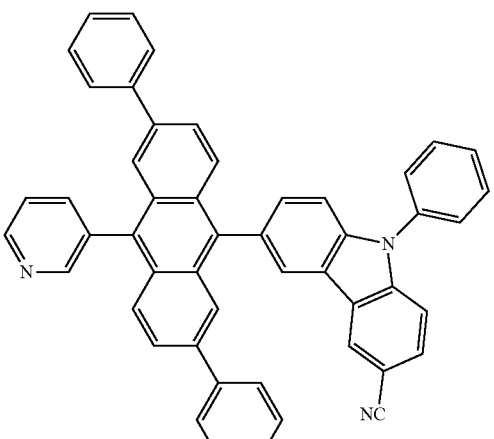
53
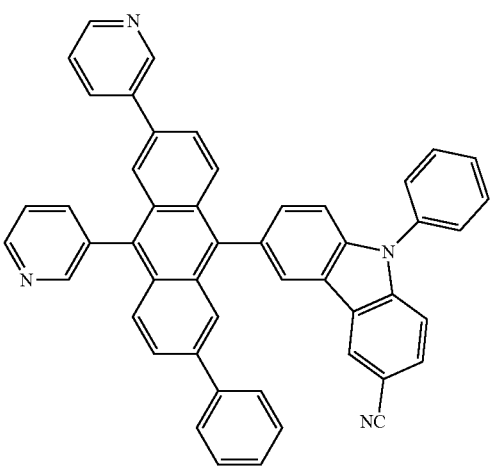

203
-continued
54
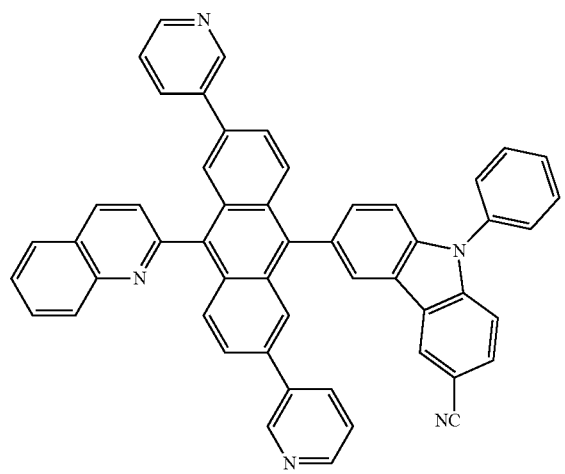
55
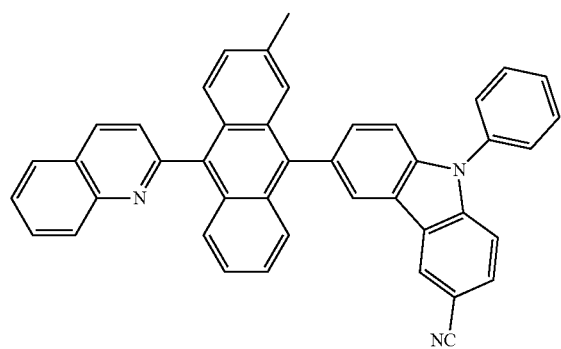
56
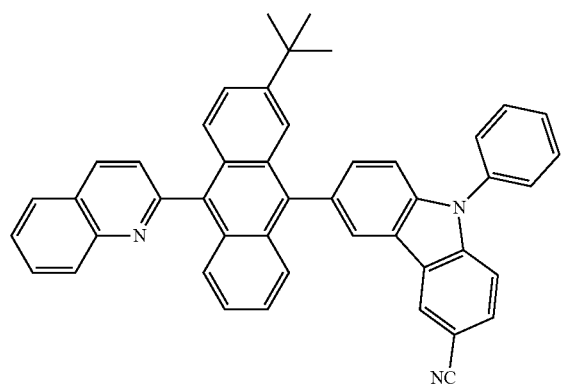
204
-continued
57
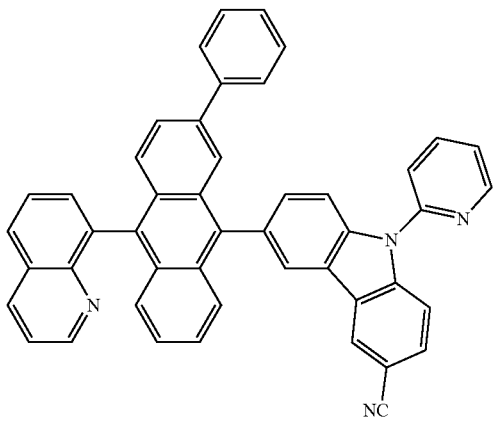
58
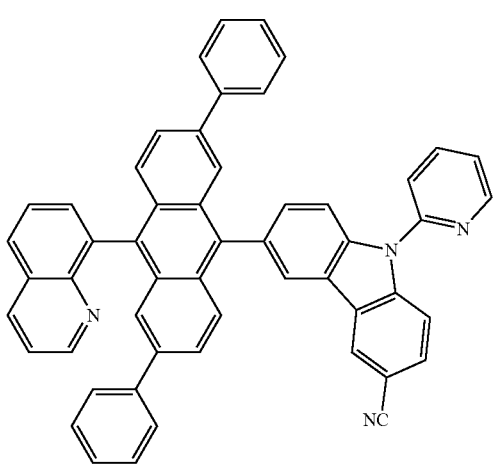
59
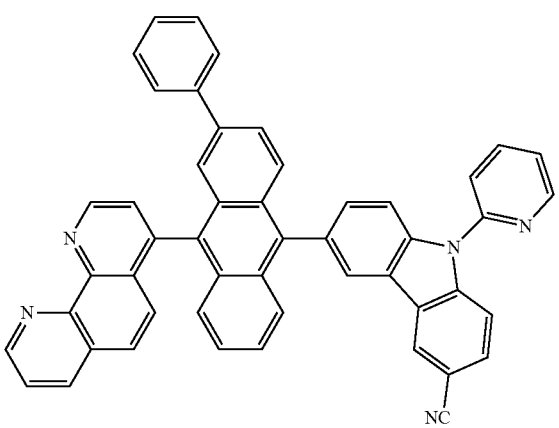

60
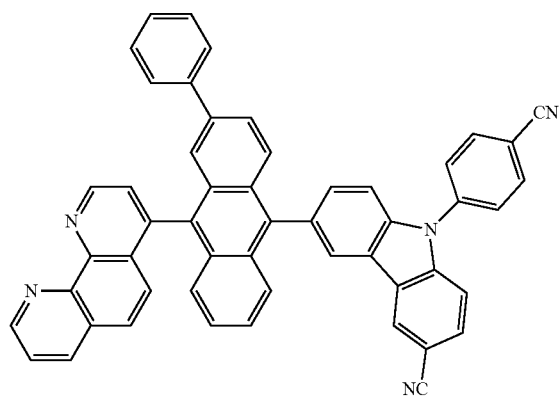
61
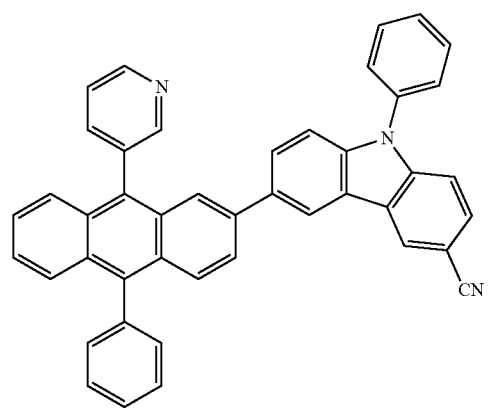
62
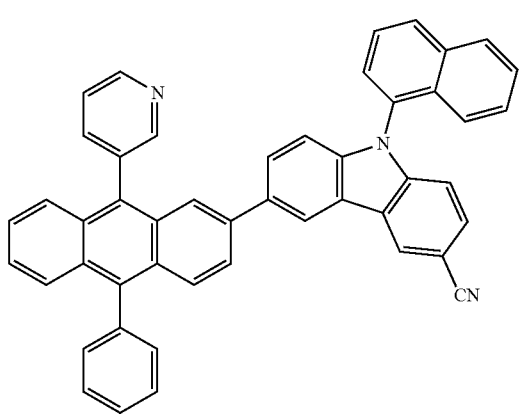
63
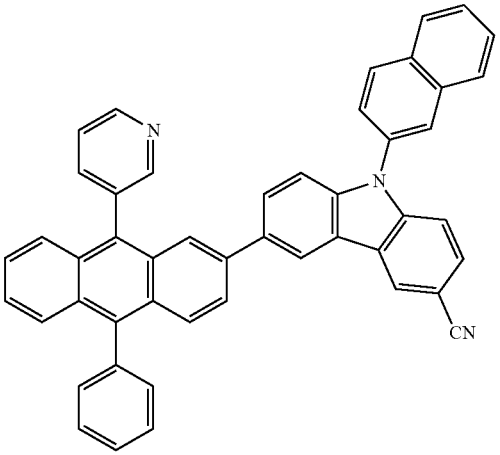
64
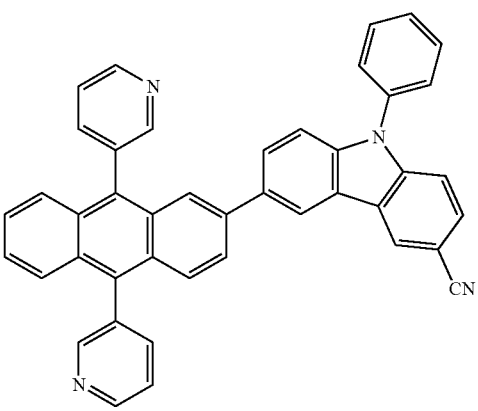
65
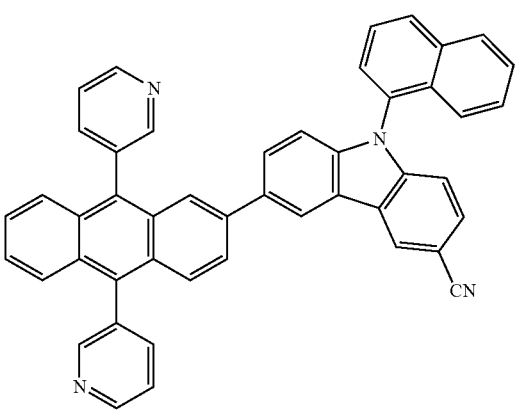

66
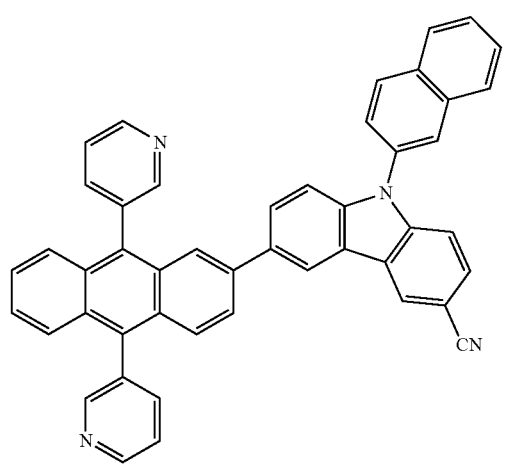
67
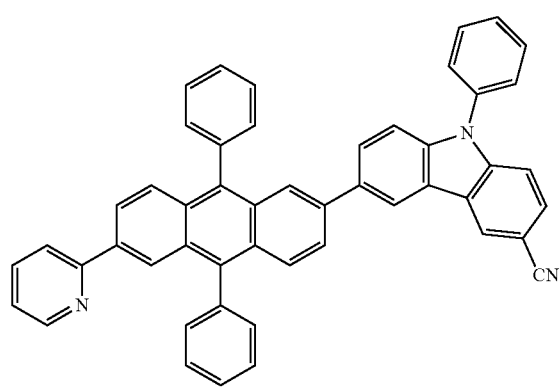
68
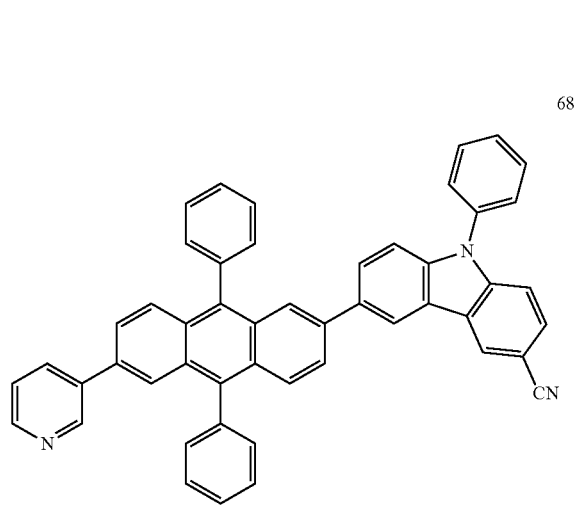
69
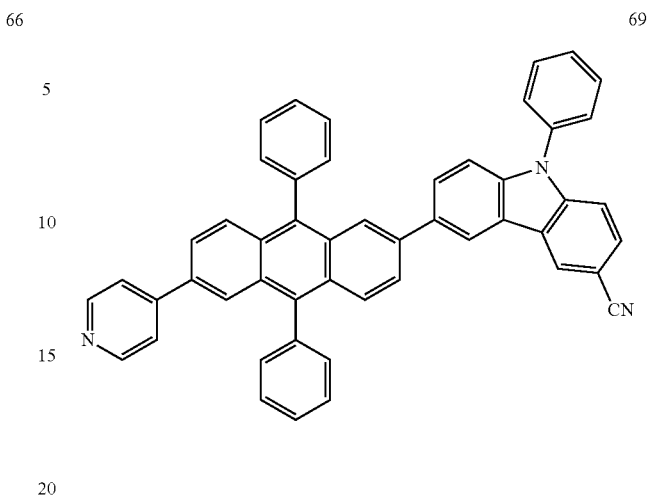
70
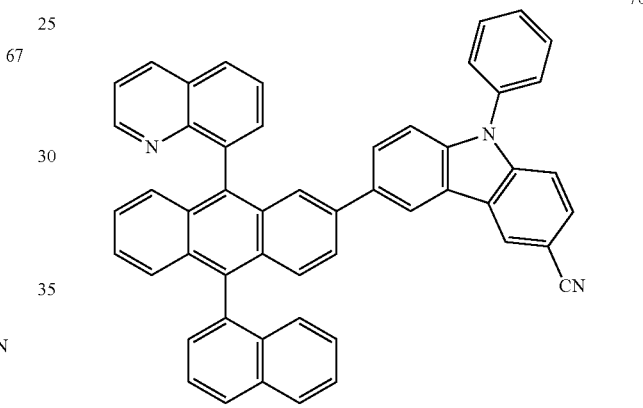
71
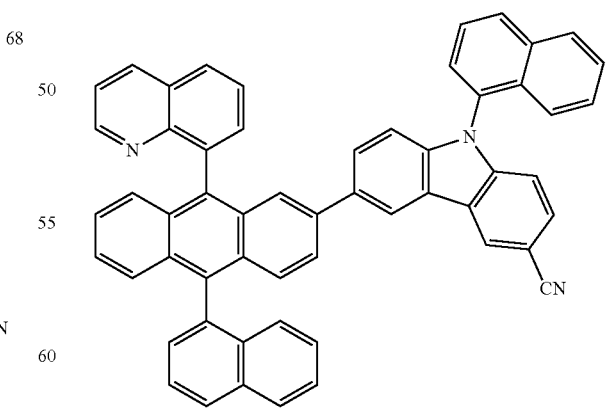

209
-continued
72
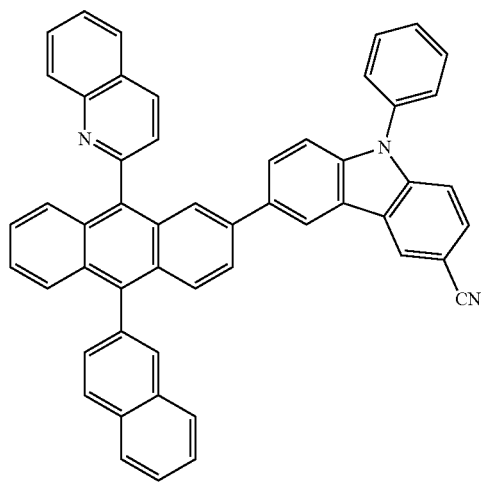
73
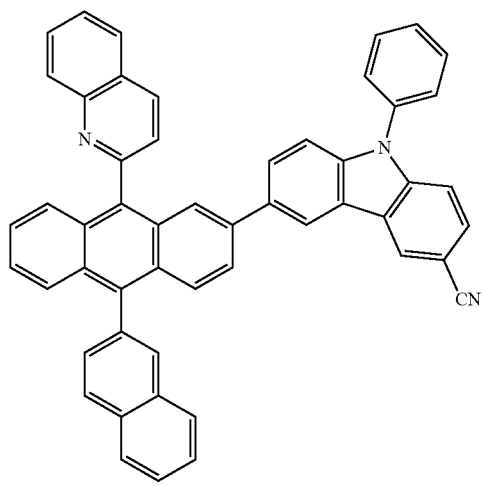
74
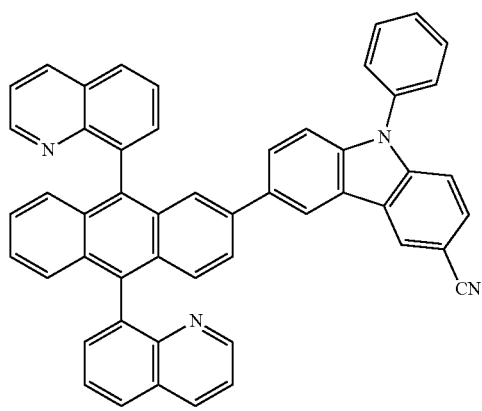
210
-continued
75
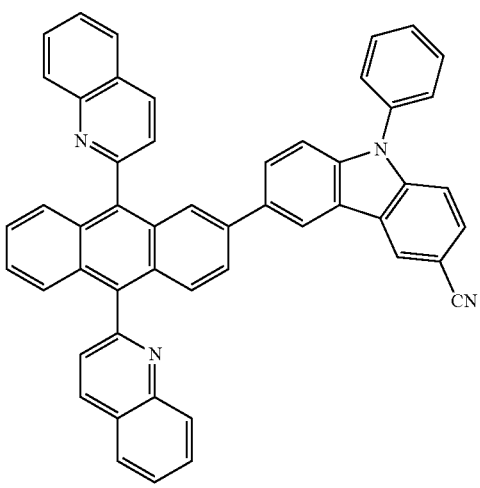
76
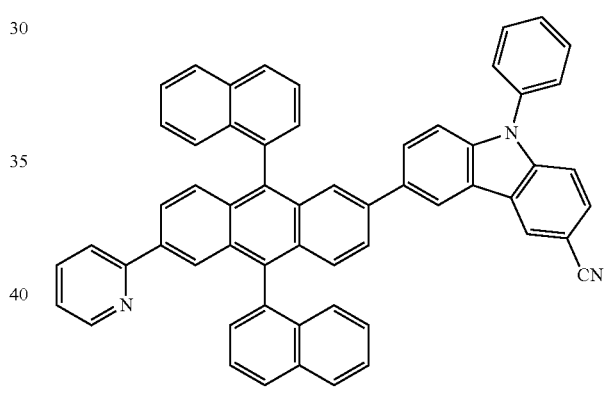
77
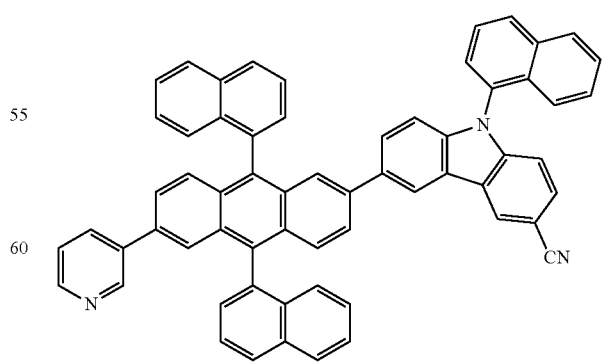

211
-continued
78
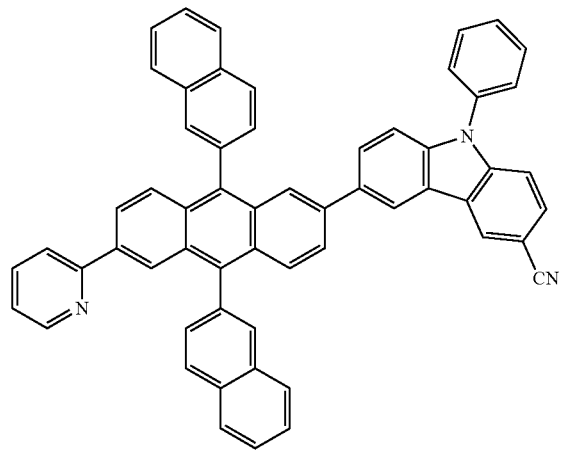
79
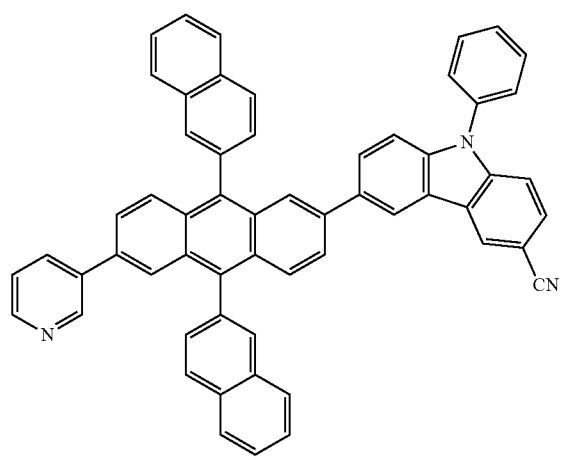
80
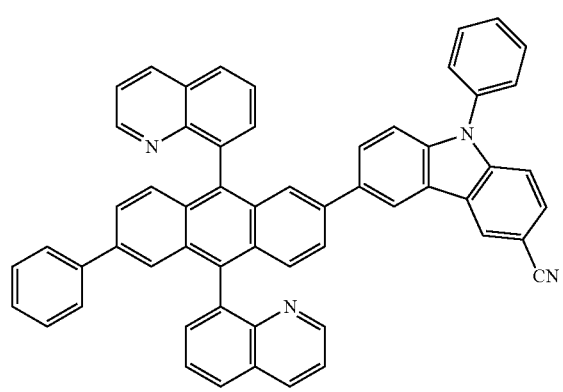
212
-continued
81
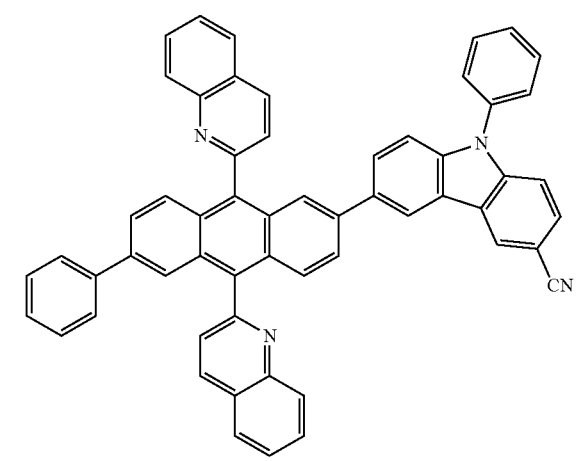
82
83
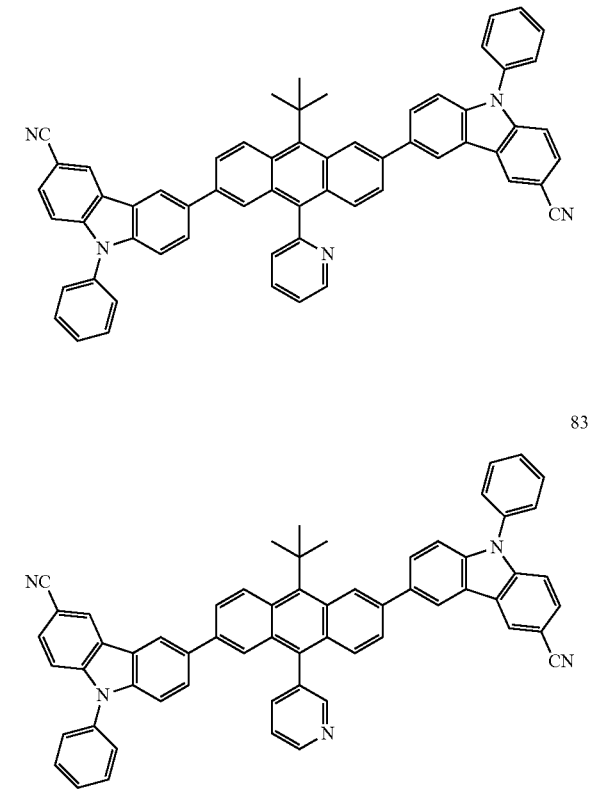
84
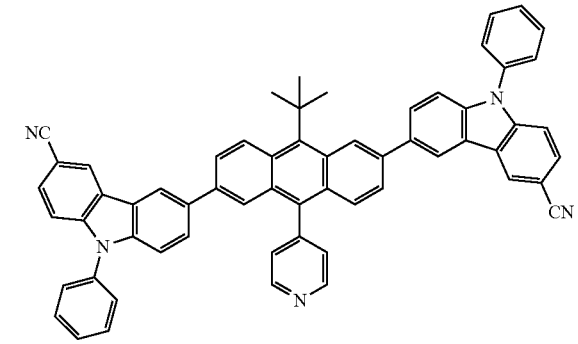

213
-continued
85
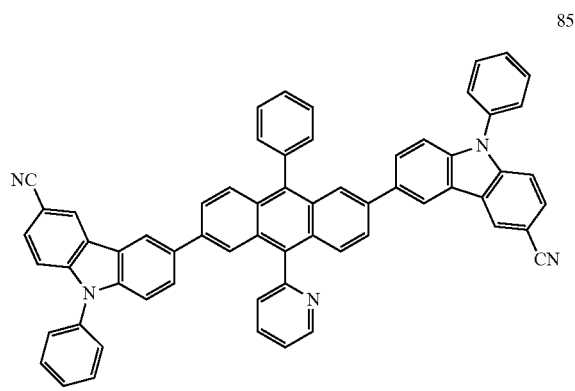
86
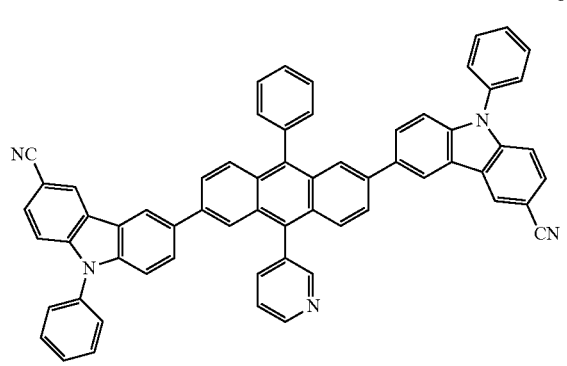
87
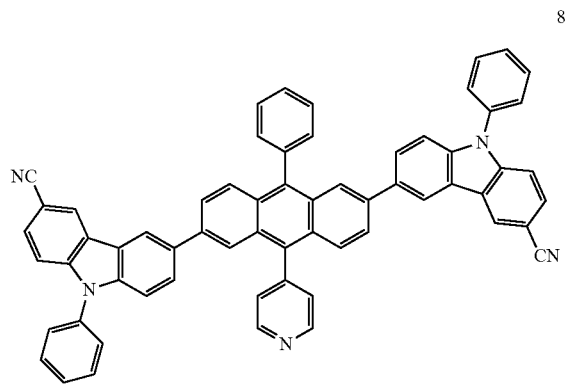
88
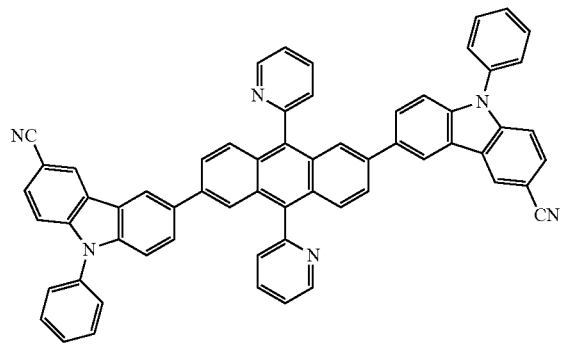
214
-continued
89
90
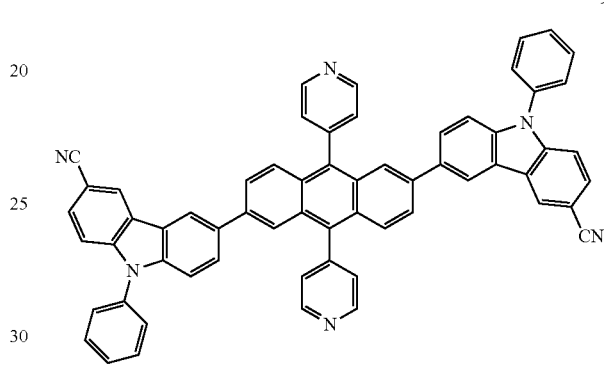
91
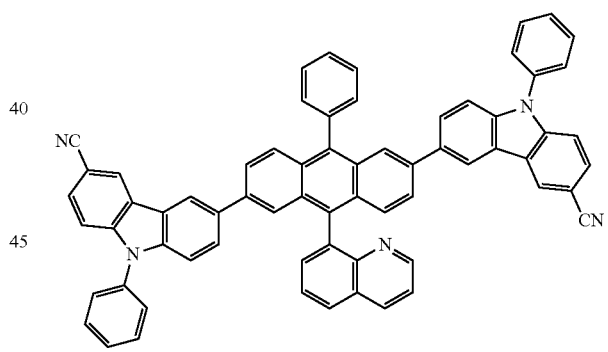
92
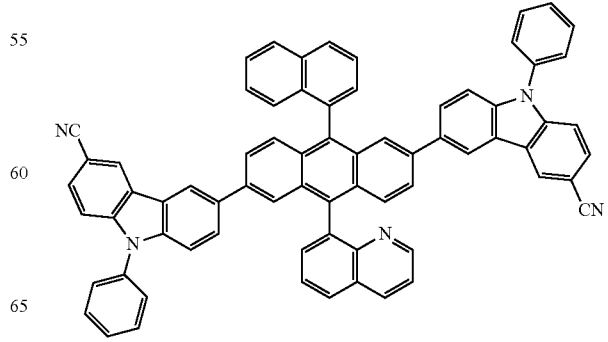

215
-continued
93
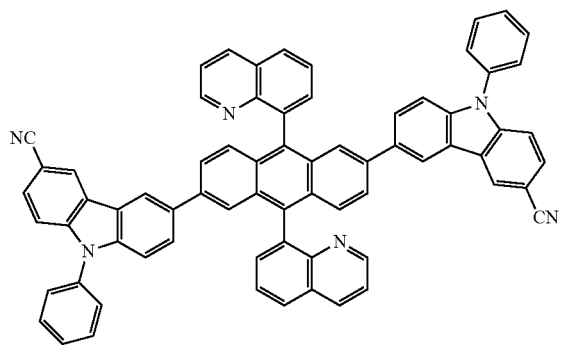
94
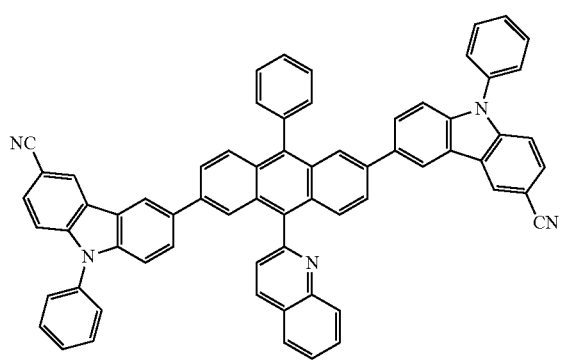
95
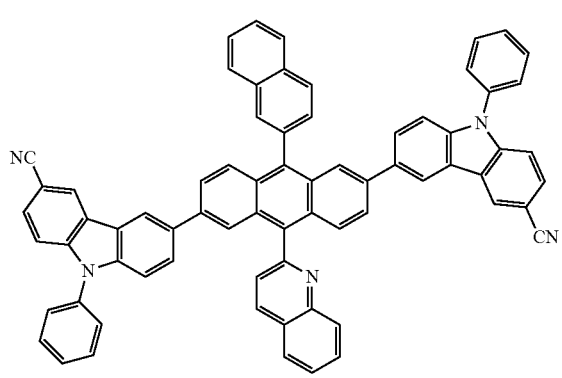
96
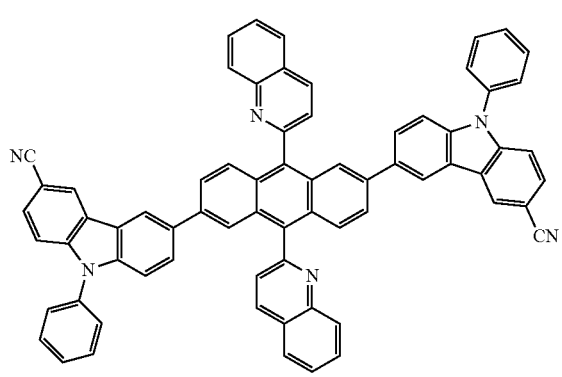
216
-continued
97
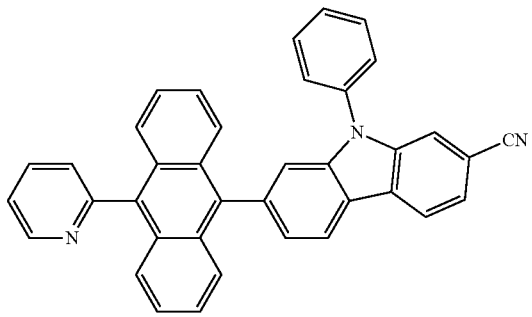
98
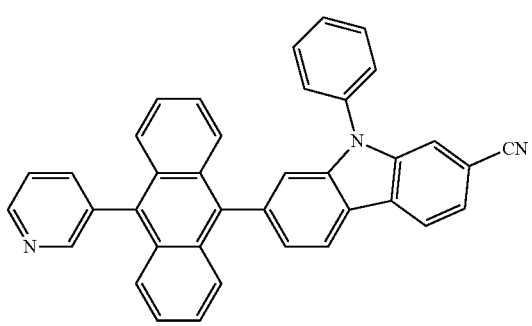
99
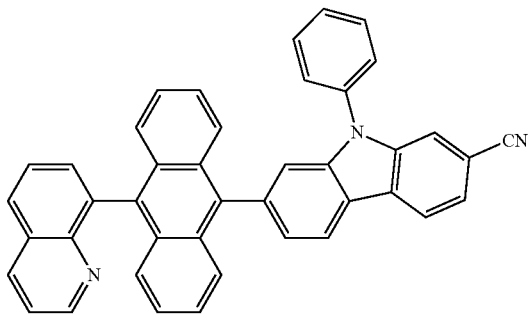
100
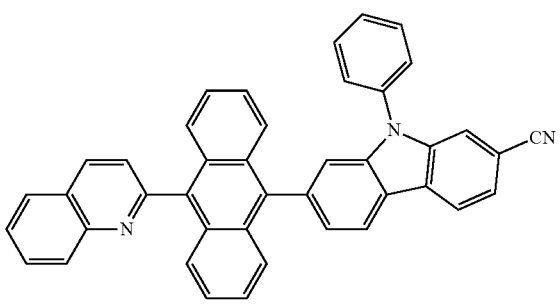

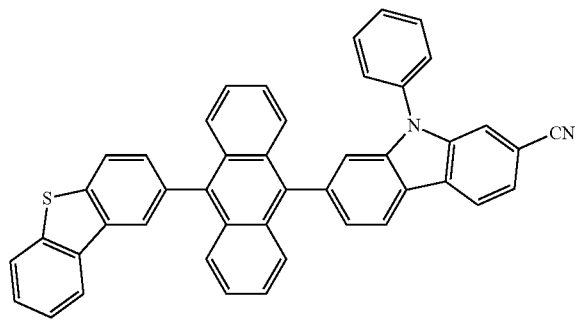

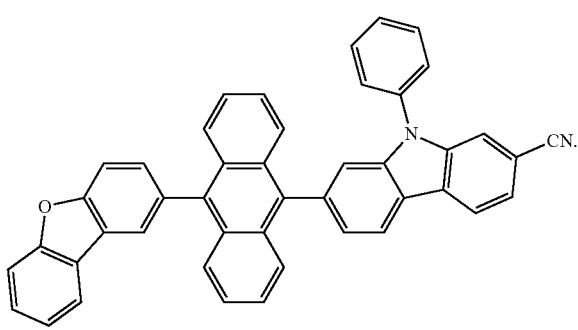

18. An organic light-emitting device comprising: a first electrode; a second electrode opposite to the first electrode; and an organic layer between the first electrode and the second electrode, the organic layer including an emission layer, wherein the organic layer includes at least one anthracene-based compound as claimed in claim 1.

19. The organic light-emitting device as claimed in claim 18, wherein:

the organic layer includes a hole transport region between the first electrode and the emission layer, and an electron transport region between the emission layer and the second electrode, the hole transport region includes at least one of a hole injection layer, a hole transport layer, a functional layer having both hole injection and hole transport capabilities, a buffer layer, an electron blocking layer, and the electron transport region includes at least one of a hole blocking layer, an electron transport layer, and an electron injection layer.

20. The organic light-emitting device as claimed in claim 19, wherein the anthracene-based compound is present in the electron transport region.

* * * * *